(12) United States Patent
Sinclair et al.

(10) Patent No.: US 7,544,497 B2
(45) Date of Patent: Jun. 9, 2009

(54) COMPOSITIONS FOR MANIPULATING THE LIFESPAN AND STRESS RESPONSE OF CELLS AND ORGANISMS

(75) Inventors: David A. Sinclair, Chestnut Hill, MA (US); Konrad T. Howitz, Allentown, PA (US); Robert E. Zipkin, Wynnewood, PA (US); Kevin J. Bitterman, Boston, MA (US); Dudley W. Lamming, Somerville, MA (US)

(73) Assignees: President and Fellows of Harvard College, Cambridge, MA (US); Biomol International LP, Plymouth Meeting, PA (US)

( * ) Notice: Subject to any disclaimer, the term of this patent is extended or adjusted under 35 U.S.C. 154(b) by 7 days.

(21) Appl. No.: 10/884,879

(22) Filed: Jul. 1, 2004

(65) Prior Publication Data

US 2005/0136537 A1    Jun. 23, 2005

Related U.S. Application Data

(60) Provisional application No. 60/483,949, filed on Jul. 1, 2003, provisional application No. 60/532,158, filed on Dec. 23, 2003.

(51) Int. Cl.
    *C12N 9/00*    (2006.01)
(52) U.S. Cl. ........................... 435/183; 435/366
(58) Field of Classification Search .................. 514/2, 514/9, 80, 733; 435/366, 183
    See application file for complete search history.

(56) References Cited

U.S. PATENT DOCUMENTS

| | | | |
|---|---|---|---|
| 4,591,600 A | 5/1986 | Creuzet et al. | |
| 5,500,367 A | 3/1996 | Hain et al. | |
| 5,689,046 A | 11/1997 | Schroder et al. | |
| 5,689,047 A | 11/1997 | Hain et al. | |
| 5,747,536 A | 5/1998 | Cavazza | |
| 5,827,898 A | 10/1998 | Khandwala et al. | |
| 5,874,399 A | 2/1999 | Samal | |
| 5,874,444 A | 2/1999 | West | |
| 5,945,106 A | 8/1999 | Sinnott | |
| 5,985,647 A | 11/1999 | Schroder et al. | |
| 6,008,260 A * | 12/1999 | Pezzuto et al. | 514/733 |
| 6,020,129 A | 2/2000 | Schroder et al. | |
| 6,022,901 A | 2/2000 | Goodman | |
| 6,048,903 A | 4/2000 | Toppo | |
| 6,063,820 A | 5/2000 | Cavazza | |
| 6,063,988 A | 5/2000 | Hain et al. | |
| 6,080,701 A | 6/2000 | Jeandet et al. | |
| 6,124,125 A | 9/2000 | Kemper et al. | |
| 6,132,740 A | 10/2000 | Hu | |
| 6,147,121 A * | 11/2000 | Breton et al. | 514/726 |
| 6,184,248 B1 | 2/2001 | Lee et al. | |
| 6,190,716 B1 | 2/2001 | Galbreath, Jr. | |
| 6,197,834 B1 | 3/2001 | Docherty | |
| 6,211,247 B1 | 4/2001 | Goodman | |
| 6,245,814 B1 | 6/2001 | Nag et al. | |
| 6,264,995 B1 | 7/2001 | Newmark et al. | |
| 6,270,780 B1 | 8/2001 | Carson et al. | |
| 6,300,377 B1 | 10/2001 | Chopra | |
| 6,319,523 B1 | 11/2001 | Zhou | |
| 6,331,633 B1 | 12/2001 | Neogi et al. | |
| 6,333,441 B1 | 12/2001 | Sato et al. | |
| 6,355,692 B2 * | 3/2002 | Docherty | 514/733 |
| 6,358,517 B1 | 3/2002 | Pillai et al. | |
| 6,361,815 B1 | 3/2002 | Zheng et al. | |
| 6,368,617 B1 | 4/2002 | Hastings et al. | |
| 6,387,416 B1 | 5/2002 | Newmark et al. | |
| 6,410,596 B1 | 6/2002 | Hopp et al. | |
| 6,414,037 B1 | 7/2002 | Pezzuto et al. | |
| 6,416,806 B1 | 7/2002 | Zhou | |
| 6,423,747 B1 | 7/2002 | Lanzendorfer et al. | |
| 6,426,061 B1 | 7/2002 | Li et al. | |
| 6,440,433 B1 | 8/2002 | Breton et al. | |
| 6,448,450 B1 | 9/2002 | Nag et al. | |
| 6,469,055 B2 | 10/2002 | Lee et al. | |
| 6,475,530 B1 | 11/2002 | Kuhrts | |
| 6,479,466 B1 | 11/2002 | Redfield et al. | |
| 6,486,203 B1 | 11/2002 | Dannenberg | |
| 6,500,451 B2 | 12/2002 | Adams | |

(Continued)

FOREIGN PATENT DOCUMENTS

DE      102 30 961     2/2004

(Continued)

OTHER PUBLICATIONS

Borra, MT et al., Mechanism of human SIRT1 activation by resveratrol, J Biol Chem. Apr. 29, 2005; 280(17): 17187-95. Epub Mar. 4, 2005.

(Continued)

*Primary Examiner*—Ruth A Davis
(74) *Attorney, Agent, or Firm*—Wolf, Greenfield & Sacks, P.C.

(57) ABSTRACT

Provided herein are methods and compositions for modulating the activity of sirtuin deacetylase protein family members; p53 activity; apoptosis; lifespan and sensitivity to stress of cells and organisms. Exemplary methods comprise contacting a cell with an activating compound, such as a flavone, stilbene, flavanone, isoflavone, catechin, chalcone, tannin or anthocyanidin; or an inhibitory compound, such as a sphingolipid, e.g., sphingosine.

12 Claims, 42 Drawing Sheets

U.S. PATENT DOCUMENTS

| | | |
|---|---|---|
| 6,515,020 B1 | 2/2003 | Cavazza |
| 6,537,969 B1 | 3/2003 | Blass |
| 6,541,522 B2 | 4/2003 | Inman et al. |
| 6,544,564 B1 | 4/2003 | Farley |
| 6,552,085 B2 | 4/2003 | Inman et al. |
| 6,552,213 B1 | 4/2003 | Deshpande et al. |
| 6,572,882 B1 | 6/2003 | Vercauteren et al. |
| 6,573,299 B1 | 6/2003 | Petrus |
| 6,576,660 B1 | 6/2003 | Liao et al. |
| 6,605,296 B1 | 8/2003 | Stuckler |
| 6,615,843 B2 | 9/2003 | Pera |
| 6,624,197 B1 | 9/2003 | Nag et al. |
| 6,638,543 B2 * | 10/2003 | Kang et al. .................. 424/757 |
| 6,638,545 B1 | 10/2003 | Rombi |
| 6,656,925 B2 | 12/2003 | Petrus |
| 6,844,163 B1 | 1/2005 | Matsuzawa et al. |
| 2001/0020043 A1 | 9/2001 | Docherty |
| 2001/0039296 A1 | 11/2001 | Bagchi et al. |
| 2001/0056071 A1 | 12/2001 | Pelliccia et al. |
| 2002/0002200 A1 | 1/2002 | Nag et al. |
| 2002/0009482 A1 | 1/2002 | Adams |
| 2002/0028852 A1 | 3/2002 | Ghai et al. |
| 2002/0051799 A1 | 5/2002 | Pruche et al. |
| 2002/0052407 A1 | 5/2002 | Lee et al. |
| 2002/0058701 A1 | 5/2002 | Inman et al. |
| 2002/0058707 A1 | 5/2002 | Hopp et al. |
| 2002/0091087 A1 | 7/2002 | Zhang et al. |
| 2002/0110604 A1 * | 8/2002 | Babish et al. ............... 424/725 |
| 2002/0111383 A1 | 8/2002 | Hassen |
| 2002/0119952 A1 | 8/2002 | Petrus |
| 2002/0120008 A1 | 8/2002 | Benzer et al. |
| 2002/0142017 A1 | 10/2002 | Simonnet |
| 2002/0146424 A1 | 10/2002 | Benza et al. |
| 2002/0146472 A1 | 10/2002 | Chen et al. |
| 2002/0148478 A1 | 10/2002 | Pera |
| 2002/0155075 A1 | 10/2002 | Collington |
| 2002/0164385 A1 | 11/2002 | Dannenberg et al. |
| 2002/0173472 A1 | 11/2002 | Pezzuto et al. |
| 2002/0173549 A1 | 11/2002 | Wurtman et al. |
| 2002/0182196 A1 | 12/2002 | McCleary |
| 2002/0192310 A1 | 12/2002 | Bland et al. |
| 2003/0004142 A1 | 1/2003 | Prior et al. |
| 2003/0004143 A1 | 1/2003 | Prior et al. |
| 2003/0031693 A1 | 2/2003 | Breton et al. |
| 2003/0044474 A1 | 3/2003 | C. Tao et al. |
| 2003/0044946 A1 | 3/2003 | Longo |
| 2003/0054053 A1 | 3/2003 | Young et al. |
| 2003/0054357 A1 | 3/2003 | Young et al. |
| 2003/0055108 A1 | 3/2003 | Young |
| 2003/0055114 A1 | 3/2003 | Young |
| 2003/0064913 A1 | 4/2003 | Sonis |
| 2003/0078212 A1 | 4/2003 | Li et al. |
| 2003/0082116 A1 | 5/2003 | Badejo et al. |
| 2003/0082203 A1 | 5/2003 | Farley |
| 2003/0082597 A1 | 5/2003 | Cannon et al. |
| 2003/0082647 A1 | 5/2003 | Reenan et al. |
| 2003/0084912 A1 | 5/2003 | Pera |
| 2003/0086986 A1 | 5/2003 | Bruijn et al. |
| 2003/0118536 A1 | 6/2003 | Rosenbloom |
| 2003/0118617 A1 | 6/2003 | Soby et al. |
| 2003/0124101 A1 | 7/2003 | Gu et al. |
| 2003/0124161 A1 | 7/2003 | Biatry et al. |
| 2003/0129247 A1 | 7/2003 | Ju et al. |
| 2003/0133992 A1 | 7/2003 | Bagchi et al. |
| 2003/0145354 A1 | 7/2003 | Milkowski et al. |
| 2003/0149261 A1 | 8/2003 | Schramm et al. |
| 2003/0152617 A1 | 8/2003 | Yatvin |
| 2003/0161830 A1 | 8/2003 | Jackson et al. |
| 2003/0161902 A1 | 8/2003 | Duncan |
| 2003/0165854 A1 | 9/2003 | Cunningham et al. |
| 2003/0180719 A1 | 9/2003 | Herget et al. |
| 2003/0182302 A1 | 9/2003 | Li |
| 2003/0185912 A1 | 10/2003 | Rosenbloom |
| 2003/0186898 A1 | 10/2003 | Maurya et al. |
| 2003/0190337 A1 | 10/2003 | Bissett |
| 2003/0190381 A1 | 10/2003 | Bland et al. |
| 2003/0191064 A1 | 10/2003 | Kopke |
| 2003/0199581 A1 | 10/2003 | Seligson et al. |
| 2003/0203973 A1 | 10/2003 | Cooper et al. |
| 2003/0207325 A1 | 11/2003 | Guarente et al. |
| 2003/0224077 A1 | 12/2003 | Mahe et al. |
| 2003/0228269 A1 | 12/2003 | DeRosa et al. |
| 2003/0232782 A1 | 12/2003 | Escalante-Semerena et al. |
| 2004/0002499 A1 | 1/2004 | Aggarwal |
| 2004/0005574 A1 | 1/2004 | Guarente et al. |
| 2004/0009197 A1 | 1/2004 | DeRosa et al. |
| 2004/0014682 A1 | 1/2004 | Ravagnan et al. |
| 2004/0014721 A1 | 1/2004 | Hensley et al. |
| 2004/0015020 A1 | 1/2004 | Deshpande et al. |
| 2004/0018987 A1 | 1/2004 | Hoffman et al. |
| 2004/0028607 A1 | 2/2004 | Verdin et al. |
| 2004/0067894 A1 | 4/2004 | Carola et al. |
| 2004/0209952 A1 | 10/2004 | Kim et al. |
| 2004/0249938 A1 | 12/2004 | Bunch |
| 2004/0259938 A1 | 12/2004 | Nag et al. |
| 2004/0265861 A1 | 12/2004 | Goldfarb |
| 2005/0020511 A1 | 1/2005 | Li et al. |
| 2005/0038125 A1 | 2/2005 | Smit et al. |
| 2005/0049208 A1 | 3/2005 | Kaufmann et al. |
| 2005/0070470 A1 | 3/2005 | Coy et al. |
| 2005/0096256 A1 | 5/2005 | Sinclair |
| 2005/0136429 A1 | 6/2005 | Guarente et al. |
| 2005/0136537 A1 | 6/2005 | Sinclair et al. |
| 2005/0171027 A1 | 8/2005 | Sinclair et al. |
| 2005/0267023 A1 | 12/2005 | Sinclair et al. |
| 2006/0002914 A1 | 1/2006 | Milbrandt et al. |
| 2006/0014705 A1 | 1/2006 | Howitz et al. |
| 2006/0025337 A1 | 2/2006 | Sinclair et al. |
| 2006/0084085 A1 | 4/2006 | Sinclair et al. |
| 2006/0084135 A1 | 4/2006 | Howitz et al. |
| 2006/0111435 A1 | 5/2006 | Sinclair et al. |
| 2006/0229265 A1 | 10/2006 | Milburn et al. |
| 2006/0257502 A1 | 11/2006 | Liu |
| 2006/0276393 A1 | 12/2006 | Milburn et al. |
| 2006/0276416 A1 | 12/2006 | Sinclair et al. |
| 2007/0160586 A1 | 7/2007 | Alt et al. |

FOREIGN PATENT DOCUMENTS

| | | |
|---|---|---|
| DE | 10230961 | 2/2004 |
| EP | 1 064 931 | 1/2001 |
| EP | 1064931 | 1/2001 |
| EP | 1440688 | 7/2004 |
| JP | 2004-18376 | 1/2004 |
| WO | 97/07790 | 3/1997 |
| WO | 98/41113 | 9/1998 |
| WO | 98/57928 | 12/1998 |
| WO | WO-99/59561 | 11/1999 |
| WO | 00/21526 | 4/2000 |
| WO | WO 00/53176 | 9/2000 |
| WO | 00/59522 | 10/2000 |
| WO | 00/69430 | 11/2000 |
| WO | WO 01/98291 | 12/2001 |
| WO | WO 02/13811 | 2/2002 |
| WO | WO 02/14252 | 2/2002 |
| WO | WO 02/17959 | * 3/2002 |
| WO | WO-02/17959 | 3/2002 |
| WO | 02/49575 | 6/2002 |
| WO | 02/49994 | 6/2002 |
| WO | WO-02/102981 | 12/2002 |
| WO | 03/031404 | 4/2003 |
| WO | 03/039535 | 5/2003 |
| WO | WO 03/039535 | 5/2003 |
| WO | WO-03/103583 | 12/2003 |

| WO | 2004/016726 | 2/2004 |
| WO | 2004/041758 | 5/2004 |
| WO | 2004/105517 | 12/2004 |
| WO | 2005/002527 | 1/2005 |
| WO | 2005/002555 | 1/2005 |
| WO | 2005/002672 | 1/2005 |
| WO | WO-2005/004814 | 1/2005 |
| WO | 2005/026112 | 3/2005 |
| WO | 2005/053609 | 6/2005 |
| WO | 2005/065667 | 7/2005 |

OTHER PUBLICATIONS

Lacey, J., Paul F. Glenn launches labs for aging research, Harvard Medical School Communications, Harvard University Gazette, Mar. 17, 2005.
GenBank Accession No. NP_877591. Oct. 27, 2004. pre-B-Cell colony enhancing factor 1 isoform b.
GenBank Accession No. NP_005737. Oct. 28, 2004. pre-B-cell colony enhancing factor 1 isoform a.
Wu, Z. et al., Ginkgo biloba extract EGb 761 increases stress resistance and extends life span of Caenorhabditis elegans, Cell Mol Biol (Noisy-le-grand). 2002; 48(6):725-31.
Sun, Ay et al., The "French Paradox" and beyond: neuroprotective effects of polyphenols, Free Radic Biol Med. 2002; 15;32(4):314-8.
GenBank Accession No. BC020691. Jun. 29, 2004. Homo sapiens pre-B-cell colony enhancing factor 1.
Sinclair, D., Sirtuins for healthy neurons, Nat Genet. Apr. 2005; 37(4):339-40.
Lamming, D.W. et al., Small molecules that regulate lifespan: evidence for xenohormesis, Mol Microbiol. 2004; 53(4):1003-9.
Wood, J.G. et al., Sirtuin activators mimic caloric restriction and delay ageing in metazoans, Nature. Aug. 5, 2004;430(7000):686-9. Epub Jul. 14, 2004.
Anderson R.M. et al., Nicotinamide and PNC1 govern lifespan extension by caloric restriction in Saccharomyces cerevisiae, Nature. May 8, 2003:423(6936):181-5.
Anderson, R.M. et al., Manipulation of a nuclear NAD+ salvage pathway delays aging without altering steady-state NAD+ levels, J Biol Chem. May 24, 2002(21):18881-90. Epub Mar. 7, 2002.
Sawada, M. et al., Cytoprotective membrane-permable peptides designed from the Bax-binding domain of Ku70, Nat Cell Biol. Apr. 2003;5(4):352-7.
Anderson, R.M. et al., Yeast life-span extension by calorie restriction is independent of NAD fluctuation, Science. Dec. 19, 2003;302(5653):2124-6. Epub Nov. 6, 2003.
Bitterman, K.J. et al., Longevity regulation in Saccharomyces cerevisia: linking metabolism, genome stability, and heterochromatin, Microbiol Mol Biol Rev. Sep. 2003;6793):376-99.
Bitterman, K.J. et al., Inhibition of silencing and accelerated aging by nicotinamide, a putative negative regulator of yeast sir2 and human SIRT1, J Biol Chem. Nov. 22, 2002;277(47):45099-107. Epub Sep. 23, 2002.
Luo, J. et al., Negative control of p53 by Sir2alpha promotes cell survival under stress, Cell. Oct. 19, 2001;107(2):137-48.
Sawada, M. et al., Ku70 suppresses the apoptotic translocation of Bax to mitochondria, Nat Cell Biol. Apr. 2003;5(4):320-9 (Abstract only).
Bieganowski, P. et al., Discoveries of Nicotinamide Riboside as a Nutrient and Conserved NRK Genes Establish a Preiss-Handler Independent Route to NAD+ in Fungi and Humans, Cell, May 4, 2004;117:495-502.
Brunet, A. et al., Stress-dependent regulation of FOXO transcription factors by the SIRT1 deacetylase, Science. Mar. 26, 2004;303(5666):2011-5. Epub Feb. 19, 2004.
Cohen, H.Y. et al., Acetylation of the C Terminus of Ku70 by CBP and PCAF Controls Bax-Mediated Apoptosis, Mol Cell. Mar. 12, 2004;13:627-638.
Marcotte, P.A. et al., Fluorescence Assay of SIRT protein deacetylases using an acetylated peptide substrate and a secondary trypsin reaction, Analytical Biochemistry 332(2004):90-99.
Bedalov, A. et al., NAD to the Rescue, Science Aug. 12, 2004;305-954-955.

Araki, T. et al., Increased Nuclear NAD Biosynthesis and SIRT1 Activation Prevent Axonal Degeneration, Science, Aug. 13, 2004;305:1010-1013.
Grozinger, C.M. et al., Identification of a Class of Small Molecule Inhibitors of the Sirtuin Family of a NAD-dependent Deacetylases by Phenotype Screening, J Biol. Chem. Oct. 19, 2001;276(42):38837-38843.
Bedalov, A. et al., Identification of a small molecule inhibitor of Sir2p, PNAS, Dec. 18, 2001;98:15113-15118.
Hirao, M. et al., Identification of Selective Inhibitors of $NAD^+$-dependent Deacetylases Using Phenotypic Screens in Yeast, J Biol. Chem. Dec. 26, 2003;278(52):52773-58782.
Zhao, K. et al., Structural basis for nicotinamide cleavage and ADP-ribose transfer by $NAD^+$-dependant Sir2 histone/protein deacetylases, PNAS, Jun. 8, 2004;101(23):8563-8. Epub May 18, 2004.
Rogina, B. et al., Longevity Regulation by Drosophila Rpd3 Deacetylase and Caloris Restriction, Science, Nov. 29, 2002;298:1745.
Aging Research's Family Feud, Science, Feb. 27, 2004;303:1276-1279.
Kimura, Y. et al., Pharmacological Studies on Resveratrol, Methods Find Exp Clin Pharmacol, 2003;25(4):297-310.
De Cabo, R. et al., An in vitro model of caloric restriction, Experimental Gerontology, 2003;38:631-639.
Nemoto, S. et al., Nutrient Availability Regulates SIRT1 Through a Forkhead-Dependent Pathway, Science, Dec. 17, 2004;306:2105-2108.
Porcu, M. et al., The emerging therapeutic potential of sirtuin-interacting drugs: from cell death to lifespace extension, Trends in Pharmacological Sciences, Feb. 2005;26(2): 94-103.
Ignatowicz, E. et al., Resveratrol, A Natural Chemopreventive Agent Against Degenerative Diseases, Pol J Pharmacol, 2001;53:557-569.
Motta C.M. et al., Mammalian SIRT-1 Represses Forkhead Transcription Factors, Cell, Feb. 20, 2004;116(4):551-63. Epub Feb. 5, 2004.
Campisi, J., Aging, Chromatin, and Food Restriction-Connecting the Dots, Science, Sep. 22, 2000;289:2062-2063.
Lin, Su-Ju et al., Requirement of NAD and SIR2 for Life-Span Extension by Calorie Restriction in Saccharomyces cerevisiae, Science, Sep. 22, 2000;289:2126-2128.
Pugh, T.D. et al., Controlling caloric consumption: protocols for rodents and rhesus monkeys, Neurobiology of Aging, Apr. 20, 1999:157-165.
Subramanian, C. et al., Ku70 acetylation mediates neuroblastoma cell death induced by histone deacetylase inhbitors, PNAS, Mar. 29, 2005;102(13):4842-4847.
Cohen, H.Y. et al., Calorie Restriction Promotes Mammalian Cell Survival by Inducing the SIRT1 Deacetylase, Science, Jul. 16, 2004;305:390-392.
Mai, A. et al., Histone Deacetylation in Eipgenetics: An Attractive Target for Anticancer Therapy, Medicinal Research Reviews, 2005;25:261-309.
Johnstone, R.W. et al., Histone deacetylase inhibitors in cancer therapy: Is transcription the primary target? Cancer Cell, Jul. 2003;4:13-18.
Yoshida, M. et al., Histone deacetylase as a new target for cancer chemotherapy, Cancer Chemother Pharmacol, 2001;48(1):520-526.
Kaeberlein, M. et al., The SIR2/3/4 complex and SIR2 alone promote longevity in Saccharomyces cerevisiae by two different mechanisms, Genes & Development, 1999;13:2570-2580.
Aiston, S. et al., Glucose 6-phosphate cause translocation of phosphorylase in hepatocytes and inactivates the enzyme synergistically with glucose, Biochem J., 2004;377:195-204.
Bergeron, R. et al., Effect of 5-Aminoimidazole-4-Carboxamide-1-β-D-Ribofuranoside Infusion on In Vivo Glucose and Lipid Metabolism in Lean and Obese Zucker Rats, Diabetes, May 2001;50:1076-1082.
Zhou, G. et al., Role of AMP-activated protein kinase in mechanism of metformin action, The Journal of Clinical Investigation, Oct. 2001;108(8):1167-1174.

Zern, T. et al., Grape Polyphenols Decrease Plasma Triglycerides and Cholesterol Accumulation in the Aorta of Ovariectomized Guinea Pigs[1], J. Nutr., 2003;133:2268-2272.

Howitz, K. et al., Small molecule activators of sirtuins extend *Sacdharomyces cerevisiae* lifespan, Nature, Sep. 11, 2003;425:191-196.

Picard, F. et al., Sirt1 promotes fat mobilization in white adipocytes by repressing PPAR-, Nature, Jun. 17, 2004;429(6993):771-6. Epub Jun. 2, 2004.

Guarente Describes Investigation into Longevity Gene at Dean's Distinguished Lecture Series, Harvard Public Health Now, Feb. 20, 2004:1-3.

Brehm, D., The skinny of fat: MIT researchers establish first link between eating and aging, Massachusetts Institute of Technology, Jun. 2, 2004.

Flam, F., PA Scientists may be on to antiaging compound, Philadelphia Inquirer; Sep. 10, 2003.

Sampson, M.T., Compound Identified in Grapes May Fight Cancer and Diabetes, htt://prohealth.com;May 27, 2002.

Michael, L., Compound in Blueberries May Prevent Heart Disease and Type 2 Diabetes, Healthy Living NYC; 2005.

American Federation for Aging Research, The Latest Research on Caloric Restriction and Animal and Human Longevity, Jul. 8, 2003.

Harvard Medical School, Molecules Discovered That Extend Life In Yeast, Human Cells, Science Blog, Aug. 2003.

Nicholas Wade, Study Spurs Hope of Finding Way to Increase Human Life, The New York Times, Aug. 25, 2003.

Study Sheds Light on Wine's Benefits, Reuters, Aug. 25, 2003.

Stephen Smith, In Lab, seeking secret of youth, Chemical abundant in red wine appears to slow aging in study, The Boston Globe, Aug. 25, 2003.

Michael LaSalandra, Wine, less dine: Age study eyes low-calorie diet . . . and a glass of red, Boston Herald, Aug. 25, 2003.

Rick Weiss, Enzymes Found to Delay Aging Process, The Washington Post, Aug. 25, 2003.

To Red Wine, Long Life, Newsday.com, Aug. 26, 2003.

Lydia Polgreen, Selling Red Wine as Good (and Good for You), The New York Times, Aug. 26, 2003.

Grape Expections, The Boston Globe Editorial, Aug. 29, 2003.

Rowland, Nethaway, Do life spans of biblical proportions await us?, The Atlanta Journal Constitution, Sep. 2, 2003.

Lidia Wasowicz, Red wine ingredient may extend life, United Press International, Aug. 28, 2003.

Hildebrandt, H., Pschyrembel Klinisches Woerterbuch, 1998, XP002141063:47-49.

Parfit et al., Antineoplastics and Immunosuppressants, Pharmaceutical Press, London, 1995, XP002329271, Martindale 32nd ed.

Bagchi et al., Phytoestrogen, Resveratrol and Women's Health, Research Communications in Pharmacology and Toxicology, vol. 5., Nos. 1&2, 2000 XP-001018765.

Berkow R. et al., Merck Manual of Diagnosis and Therapy, 1987, Merck Manual of Diagnosis and Therapy, Rahway, Merck & Co., US, XP002141064:pp. 2392.

Sandmeier, J. et al., Telomeric and rNDA Silencing in *Saccharomyces cerevisiae* Are Dependent on a Nuclear NAD+ Salvage Pathway, Genetics, Mar. 2002;160:877-889.

Smith, J. et al., A phylogenetically conserved NAD+-dependent protein deacetylase activity in the Sir2 protein family, Proc. Natl. Acad. Sci. USA, Jun. 6, 2000;97(12):6658-6663.

Zhang, H. et al:, Crystal Structures of *E. coli* Nicotinate Mononucleotide Adenylyltransferase and Its Complex with Deamido-NAD, Structure, Jan. 2002;10:69-79.

Raffaelli, N. et al., Identification of a novel human nicotinamide mononucleotide adenylyltransferease, Biochem Biophys Res Commun Oct. 4, 2002;297 (Abstract only).

Vaziri, H. et al., hSIR2SIRT1 Functions as an NAD-Dependent p53 Deacetylase, Cell, 2001 Oct. 2001;107:149-159.

Mills, K. et al., *MEC1*-Dependent Redistribution of the Sir3 Silencing Protein from Telomeres to DNA Double-Strand Breaks, Cell. May 28, 1999;(97):609-620.

Khanna, S. et al., Dermal Would Healing Properties of Redox-Active Grape Seed Proanthocyanidins, Free Radical Biology & Medicine, 2002;33(8):1089-1096.

Regev-Shoshani, G. et al., Glycosylation of resveratrol protects it from enzymatic oxidation, Biochemical Journal Aug. 15, 2003;374:157. e-pub Apr. 16, 2003.

Brandolini, V. et al., Capillary Electrophoresis Determination, Synthesis, and Stability of Resveratrol and Related 3-*O-B-D*-Glucopyranosides, Journal of Agricultural and Food Chemistry, 2002;50:7407-7411.

South, James, Resveratrol & Quercetin—pro Heart & anti-Cancer, Offshore Pharmacy, Jun. 26, 2003 or earlier.

Perez, J. et al., Synthesis and characterization of complexes of *p*-isopropyl benzaldehyde and methyl 2-pyridyl ketone thiosemicarbazones with Zn(II) and Cd(II) metallic centers. Cytotoxic activity and induction of apoptosis in Pam-*ras* cells, J. of Inorganic Biochemistry, 1999;75:255-261.

Koubova, J. et al, How does calorie restriction work? Genes & Development, 2003;17:313-321.

Kaeberlein, M. et al., High Osmolarity Extends Life Span in *Saccharomyces cerevisiae* by a Mechanism Related to Calorie Restriction, Molecular and Cellular Biology, Nov. 2002;22(22):8056-8066.

Bastianetto, S. et al, Reversatrol and Red Wine Constituents: Evaluation of Their Neuroprotective Properties, Pharmaceutical News, 2001:8(5):33-38.

Fukuhara, A. et al, Vistafin: A Protein Secreted by Visceral Fat that Mimics the Effects of Insulin, Sciencexpress/www.sciencexpress.org/2004 December 16:1/10.1126.

Jai, S. H. et al, Pre-B cell colony-enhancing factor inhibits neutrophil apoptosis in experimental inflammation and clinical sepsis, J. Clin. Invest., 2004;113:1318-1327.

Revollo, J. et al, The NAD Biosynthesis Pathway Mediated by Nicotinamide Phosphoribosyltransferase Regulates Sir2 Activity in Mammalian Cells*, The Journal of Biological Chemistry, Dec. 3, 2004;279(49):50754-50763.

Samal, B. et al., Cloning and Characterization of the cDNA Encoding a novel Human Pre-B-Cell Colony-Enhancing Factor, Molecular and Cellular Biology, Feb. 1994;14(2):1431-1437.

Ognjanovic, S. et al., Genomic organization of the gene coding for human pre-B-cell colony enhancing factor and expression in human fetal membranes, Journal of Molecular Endocrinology, 2001;16:107-117.

Hendrickson, Dyke, A dietary magic? Harvard team says pill will fight effects of high-fat eating, The Journal of New England Technology, Mass. High Tech, Dec. 8-14, 2003.

Dajas, F. et al., Cell culture protection and in vivo neuroprotective capacity of flavonoids, Neurotox Res. 2003;5(6):425-32. (Abstract only).

Lui, M. et al., Antimalarial Alkoxylated and Hydroxylated Chalones: Structure—Activity Relationship Analysis, J. Med. Chem. 2004;(4):4443-4452.

Kris-Etherton P. et al., Bioactive Compounds in Foods: Their Role in the Prevention of Cardiovascular Disease and Cancer, Am. J. Med. 2002;113(9B):71S-88S.

Hu, H.L. et al., Antioxidants may contribute in the fight against ageing: an in vitro model, Mechanisms of Aging and Development, 2000;121:217-230.

Graefe, E. U. et al., Pharmacokinetics and bioavailability of the flavonol quercetin in humans, Intl. J. of Clin. Pharmacology and Therapeutics, 1999;37(5):219-233.

Morino, M. et al., Specific Regulation of HSPs in Human Tumor Cell Lines by Flavonoids, In Vivo, 1997;11:265-270.

Nothwehr, S. et al., A Retention factor keeps death at bay, Nature Cell Biology, Apr. 2003;5:281-283.

Chua, K.F. et al., Mammalian SIRT1 limits replicative life span in response to chronic genotoxic street, Cell Metabolism, Jul. 2005;2:67-76.

Aguilaniu et al., "Asymmetric Inheritance of Oxidatively Damaged Proteins During Cytokinesis", Science 2003 299:1751-1753.

Benguría et al., "Sir2p suppresses recombination of replication forks stalled at the replication fork barrier of ribosomal DNA in *Saccharomyces cerevisiae*", Nucleic Acids Research 2003 31(3):893-898.

Brachmann et al., "The *SIR2* gene family, conserved from bacteria to humans, functions in silencing, cell cycle progression, and chromosome stability", Genes & Development 1995 9:2888-2902.

Bryk et al., "Transcriptional silencing of Ty1 elements in the RDN1 locus of yeast", Genes & Development 1997 11:255-269.

Coronado et al., "Alfalfa Root Flavonoid Production Is Nitrogen Regulated", Plant Physiol. 1995 108:533-542.

Defossez et al., "Elimination of Replication Block Protein Fob1 Extends the Life Span of Yeast Mother Cells", Molecular Cell 1999 3:447-455.

Denu, M., "Linking chromatin function with metabolic networks-:Sir2 family of NAD$^+$-dependent deacetylases", Trends in Biochemical Sciences 2003 28(1):41-48.

Dong, Z., "Molecular mechanism of the chemopreventive effect of resveratrol", Mutation Research 2003 523-524:145-150.

Ferguson, R., "Role of plant polyphenols in genomic stability", Mutation Research 2002 475:89-111.

Frye, R.A., "Phylogenetic Classification of Prokaryotic and Eukaryotic Sir2-like Proteins", Biochemical and Biophysical Research Communications 2000 273:793-798.

Glossmann et al., "Quercetin Inhibits Tyrosine Phosphorylation by the Cyclic Nucleotide-Independent, Transforming Protein Kinase, pp60$^{src}$", Naunyn-Schmiedeberg's Arch Pharmacol 1981 317:100-102.

Gottlieb et al., "A New Role for a Yeast Transcriptional Silencer Gene, SIR2, in Regulation of Recombination in Ribosomal DNA", Cell 1989 56:771-776.

Guarente et al., "Genetic pathways that regulate ageing in model organisms", Nature 2000 408:255-262.

Hekimi et al., "Genetics and the Specificity of the Aging Process", Science 2003 299:1351-1354.

Herzenberg et al., "The History and Future of the Fluorescence Activated Cell Sorter and Flow Cytometry:A View from Stanford", Clinical Chemistry 2002 48:10 1819-1827.

Holla et al., "New bis-aminomercaptotriazoles and bis-triazolothiadiazoles as possible anticancer agents", Eur. J. Med. Chem. 2002 37:511-517.

Holzenberger et al., "IGF-1 receptor regulates lifespan and resistance to oxidative stress in mice", Nature 2003 421:182-187.

Imai et al., "Transcriptional silencing and longevity protein Sir2 is an NAD-dependent histone deacetylase", Nature 2000 403:795-800.

Jang et al., "Cancer Chemopreventive Activity of Resveratrol, a Natural Product Derived from Grapes", Science 1997 275:218-220.

Jazwinski, S. M., "Metabolic Control and Gene Dysregulation in Yeast Aging", Annals New York Academy of Sciences 2000 908:21-30.

Kaeberlein et al., "The *SIR2/3/4* complex and *SIR2* alone promote longevity in *Saccharomyces cerevisiae* by two different mechanisms", Genes & Development 1999 13:2570-2580.

Kenyon, C., "A Conserved Regulatory System for Aging", Cell 2001 105:165-168.

Landry et al., "The silencing protein SIR2 and its homologs are NAD-dependent protein deacetylases", Proc. Natl. Acad. Sci. USA 2000 97(11):5807-5811.

Langley et al., "Human SIR2 deacetylates p53 and antagonizes PML/p53-induced cellular senescence", The EMBO Journal 2002 21(10):2383-2396.

Laurenson et al., "Silencers, Silencing, and Heritable Transcriptional States", Microbiological Reviews 1992 56(4):543-560.

Longo et al., "Evolutionary Medicine:From Dwarf Model Systems to Healthy Centenarians", Science 2003 299:1342-1346.

Middleton et al., "The Effects of Plant Flavonoids on Mammalian Cells:Implications for Inflammation, Heart Disease, and Cancer", Pharmacol Rev 2000 52:673-751.

Monod et al., "On the Nature of Allosteric Transitions:A Plausible Model", J. Mol. Biol. 1965 12:88-118.

Nicolini et al., "Anti-apoptotic effect of *trans*-resveratrol on paclitaxel-induced apoptosis in the human neuroblastoma SH-SY5Y cell line", Neuroscience Letters 2001 302:41-44.

Oliver et al., "Inhibition of Mast Cell Fc R1-mediated Signaling and Effector Function by the Syk-selective Inhibitor, Piceatannol", J. Biol. Chem. 1994 269(47):29697-29703.

Pandey et al., "Analysis of histone acetyltransferase and histone deacetylase families of *Arabidopsis thaliana* suggests functional diversification of chromatin modification among multicellular eukaryotes", Nucleic Acids Research 2002 30(23):5036-5055.

Park et al., "Effects of Mutations in DNA Repair Genes on Formation of Ribosomal DNA Circles and Life Span in *Saccharomyces cerevisiae*", Molecular and Cellular Biology 1999 19(5):3848-3856.

Pont et al., "Relation Between the Chemical Structure and the Biological Activity of Hydroxystilbenes Against *Botrytis cinerea*", J. Phytopathology 1990 130:1-8.

Shimokawa et al., "Life span extension by reduction of the growth hormone-insulin-like growth factor-1 axis:relation to caloric restriction", FASEB 2003 17:1108-1109.

Sinclair et al., "Extrachromosomal rDNA Circles-A Cause of Aging in Yeast", Cell 1997 91:1033-1042.

Sinclair, D.A., "Paradigms and pitfalls of yeast longevity research", Mechanisms of Ageing and Development 2002 123:857-867.

Smith et al., "An unusual form of transcriptional silencing in yeast ribosomal DNA", Genes & Development 1997 11:241-254.

Soleas et al., "Resveratrol:A Molecule Whose Time Has Come? And Gone?", Clinical Biochemistry 1997 30(2):91-113.

Stojanovi et al., "Efficiency and Mechanism of the Antioxidant Action of *trans*-Resveratrol and Its Analogues in the Radical Liposome Oxidation", Archives of Biochemistry and Biophysics 2001 391(1):79-89.

Tanner et al., "Silent information regulator 2 family of NAD-dependent histone/protein deacetylases generates a unique product, 1-0-acetyl-ADP-ribose", Proc. Natl. Acad. Sci. USA 2000 97(26):14178-14182.

Tanny et al., "Coupling of histone deacetylation to NAD breakdown by the yeast silencing protein Sir2:Evidence for acetyl transfer from substrate to an NAD breakdown product", Proc. Natl. Acad. Sci. USA 2001 98(2):415-420.

Tanny et al., "An Enzymatic Activity in the Yeast Sir2 Protein that Is Essential for Gene Silencing", Cell 1999 99:735-745.

Tatar et al., "The Endocrine Regulation of Aging by Insulin-like Signals", Science 2003 299:1346-1351.

Tissenbaum et al., "Increased dosage of a *sir-2* gene extends lifespan in *Caenorhabditis elegans*", Nature 2001 410:227-230.

Vergnes et al., "Cytoplasmic SIR2 homologue overexpression promotes survival of *Leishmania* parasites by preventing programmed cell death", Gene 2002 296:139-150.

Bauer, J. and Sinclair, D. Therapeutic potential of resveratrol: the in vivo evidence. Nature Reviews, vol. 5, Jun. 2006, pp. 493-506.

Bauer, J. A. et al. Resveratrol improves health and survival of mice on a high-calorie diet. Nature Articles. Nature Publishing Group, 2006. pp. 1-6.

Kaeberlein M. et al. Substrate-specific Activation of Sirtuins by Resveratrol. J. of Biol. Chem. vol. 280, No. 17, Apr. 29, 2005, pp. 17038-17045.

Kaeberlein, M. and Rabinovitch, P. Grapes versus gluttony. Nature News & Views. Nature Publishing Group, 2006. pp. 1-2.

Solomon, J. et al. Inhibition of SIRT1 Catalytic Activity Increases p53 Acetylation but Does Not Alter Cell Survival following DNA Damage. Mol. and Cell. Biol. vol. 26, No. 1, Jan. 2006, pp. 28-38.

International Search Report dated Jan. 2, 2007 from PCT/US2006/025318.

Office Action dated Jun. 15, 2007 for U.S. Appl. No. 10/884,062.

Office Action dated Jul. 2, 2007 for U.S. Appl. No. 10/074,374.

Kim, D. et al., "SIRT1 deacetylase protects against neurodegeneration in models for Alzheimer's disease and amyotrophic lateral sclerosis," *The EMBO Journal* 2007; 26: 3169-3179.

* cited by examiner

Figure 1
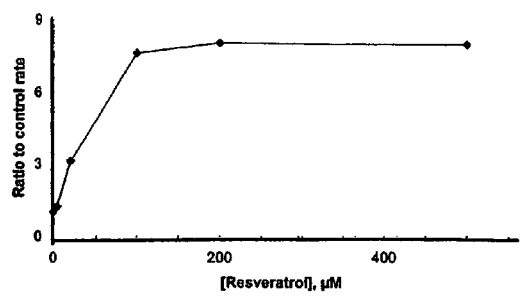
a
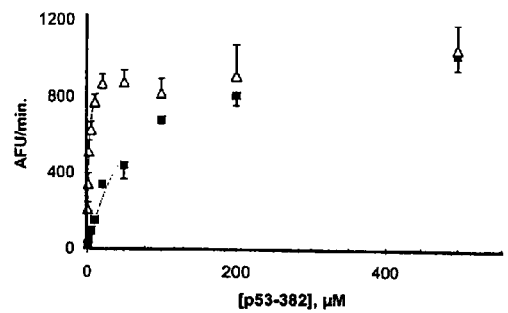
b
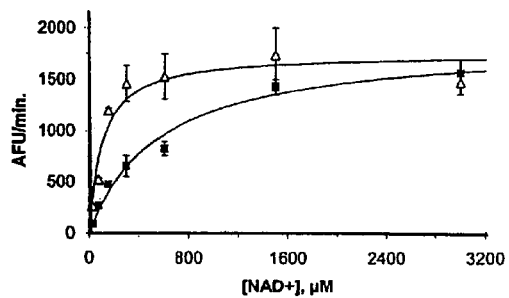
c
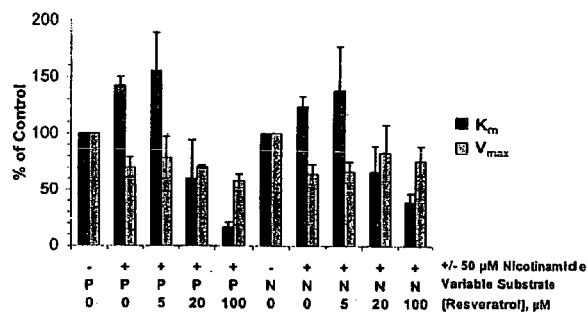
d

Figure 4
a
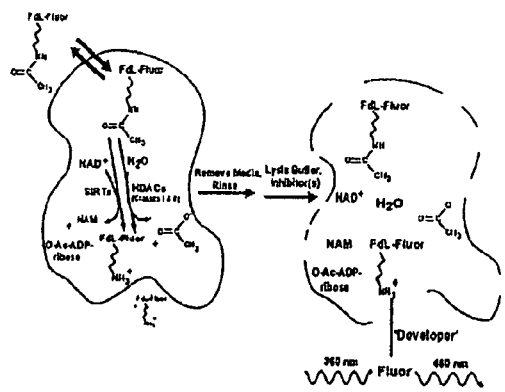
b
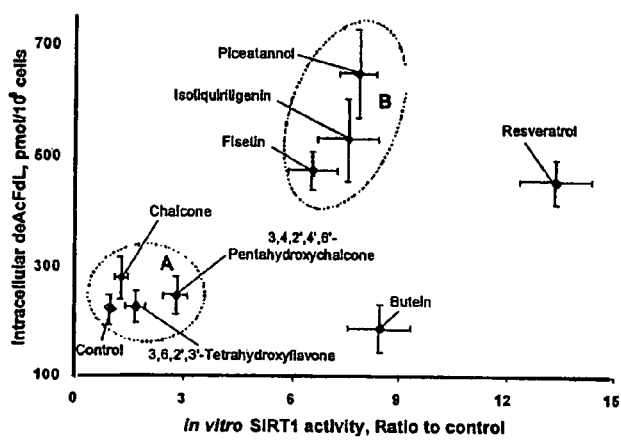
c, d
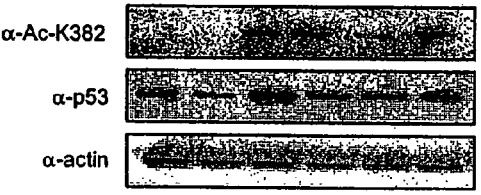
e

| Substrate Name Sequence Source-Residue #(s), (manufacturer's substrate name, (BIOMOL, Plymouth Meeting, PA) | Sequence |
|---|---|
| H3-4-9 | K(Ac)QTARK(Ac) |
| H3-9-14 | K(Ac)STGGK(Ac) |
| H3-9-14/pS | K(Ac)-S(PO3)-TGGK(Ac) |
| H3-14-18 | K(Ac)APRK(Ac) |
| H4-1-5 | SGRGK(Ac) |
| H4-12-16 (Fluor de Lys-H4-AcK16) | KGGAK(Ac) |
| H4-12-16/diAc | K(Ac)GGAK(Ac) |
| p53-320 (Fluor de Lys-SIRT2) | QPKK(Ac) |
| p53-373 | K(Ac)SKK(Ac) |
| p53-382 (Fluor de Lys-SIRT1) | RHKK(Ac) |
| p53-382/di-Ac (Fluor de Lys-HDAC8) | RHK(Ac)K(Ac) |
| ε-acetyl lysine (Fluor de Lys, FdL) | K(Ac) |

|  | AFU/min | SE |  | AFU/20 min | SD |
|---|---|---|---|---|---|
| 0 | 96.35835 | 7.819439 | | 1927.167 | 270.8733 |
| 2 | 105.3334 | 5.886086 | | 2106.667 | 203.9 |
| 5 | 98.15 | 13.63784 | | 1963 | 472.4288 |
| 20 | 98.575 | 4.85032 | | 1971.5 | 168.02 |
| 100 | 60.85835 | 9.009262 | | 1217.167 | 312.09 |
| 200 | 32.43335 | 1.127565 | | 648.667 | 39.06 |
| 500 | 5.33335 | 9.047656 | | 106.667 | 313.42 |

Figure 8

Figure 9
a
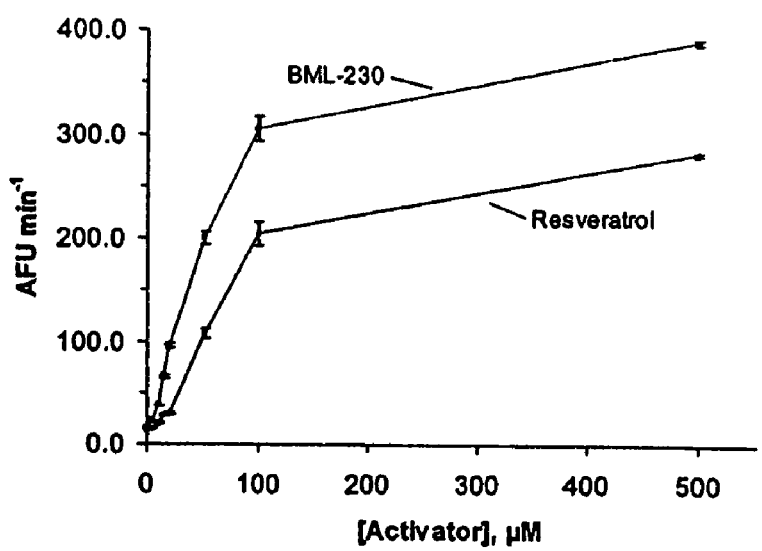
b
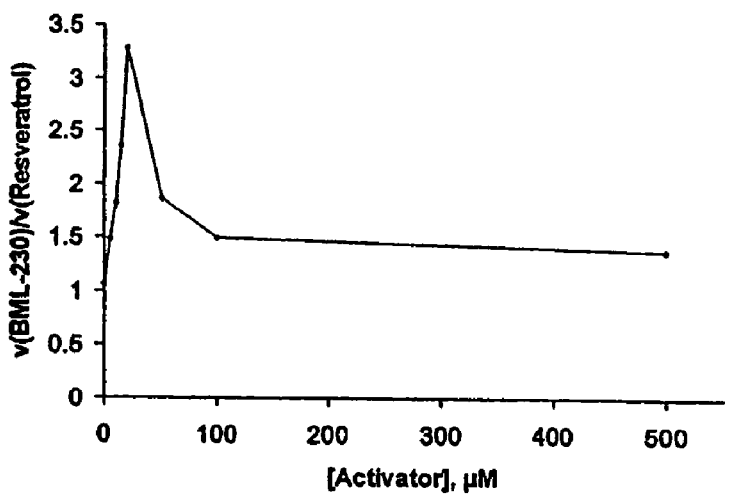

Table 1. Stimulation of SIRT1 Catalytic Rate by Plant Polyphenols (100 μM).

| Compound | Ratio to Control Rate Mean ± SE | Structure |
|---|---|---|
| Resveratrol (3,5,4'-Trihydroxy-*trans*-stilbene) | 13.4 ± 1.0 | 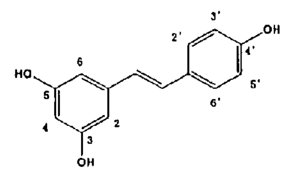 |
| Butein (3,4,2',4'-Tetrahydroxychalcone) | 8.53 ± 0.89 | 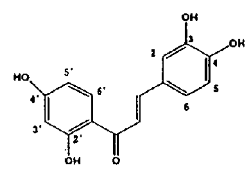 |
| Piceatannol (3,5,3',4'-Tetrahydroxy-*trans*-stilbene) | 7.90 ± 0.50 | 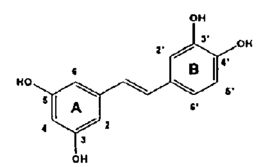 |
| Isoliquiritigenin (4,2',4'-Trihydroxychalcone) | 7.57 ± 0.84 | 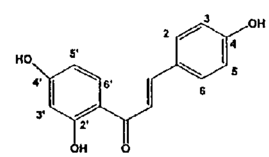 |
| Fisetin (3,7,3',4'-Tetrahydroxyflavone) | 6.58 ± 0.69 | 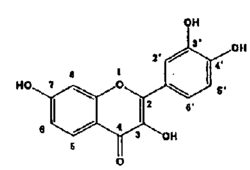 |
| Quercetin (3,5,7,3',4'-Pentahydroxyflavone) | 4.59 ± 0.47 | 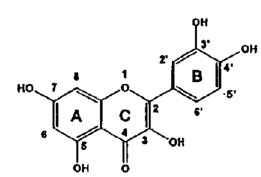 |

Abbreviation: SE, Standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

Figure 16

Supplementary Table 1. Effects of Stilbenes and Chalcones (100 µM) on SIRT1 Rate.

| Compound | Ratio to Control Rate Mean ± SE | Replicates | Structure Skeleton |
|---|---|---|---|
| Resveratrol (3,5,4'-Trihydroxy-trans-stilbene) | 13.4 ± 1.0 | 10 | 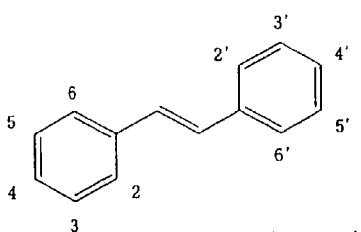 STILBENES (trans) |
| Piceatannol (3,5,3',4'-Tetrahydroxy-trans-stilbene) | 7.90 ± 0.50 | 7 | |
| Deoxyrhapontin (3,5-Dihydroxy-4'-methoxystilbene 3-O-β-D-glucoside) | 1.94 ± 0.21 | 6 | |
| trans-Stilbene | 1.48 ± 0.15 | 6 | |
| Rhapontin 3,3',5-Trihydroxy-4'-methoxystilbene 3-O-β-D-glucoside | 1.40 ± 0.37 | 6 | |
| cis-Stilbene | 1.14 ± 0.29 | 6 | |
| Butein (3,4,2',4'-Tetrahydroxychalcone) | 8.53 ± 0.89 | 6 | 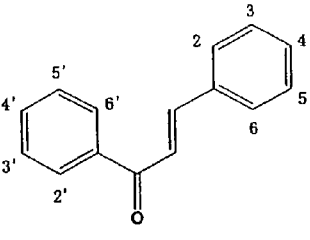 CHALCONES |
| 4,2',4'-Trihydroxychalcone | 7.57 ± 0.84 | 6 | |
| 3,4,2',4',6'-Pentahydroxychalcone | 2.80 ± 0.32 | 6 | |
| Chalcone | 1.34 ± 0.17 | 6 | |

Abbreviation: SE, Standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 17

Supplementary Table 2. Effects of Flavones (100 µM) on SIRT1 Rate (Part I).

| Compound | Ratio to Control Rate Mean ± SE | Replicates |
|---|---|---|
| Fisetin (3,7,3',4'-Tetrahydroxyflavone) | 6.58 ± 0.69 | 9 |
| 5,7,3',4',5'-Pentahydroxyflavone | 6.05 ± 0.98 | 6 |
| Luteolin (5,7,3',4'-Tetrahydroxyflavone) | 5.66 ± 0.80 | 6 |
| 3,6,3',4'-Tetrahydroxyflavone | 5.45 ± 0.57 | 12 |
| Quercetin (3,5,7,3',4'-Pentahydroxyflavone) | 4.59 ± 0.47 | 16 |
| 7,3',4',5'-Tetrahydroxyflavone | 3.62 ± 0.56 | 6 |
| Kaempferol (3,5,7,4'-Tetrahydroxyflavone) | 3.55 ± 0.56 | 6 |
| 6-Hydroxyapigenin (5,6,7,4'-Tetrahydroxyflavone; Scutellarein) | 3.06 ± 0.29 | 6 |
| Apigenin (5,7,4'-Trihydroxyflavone) | 2.77 ± 0.40 | 6 |
| 3,6,2',4'-Tetrahydroxyflavone | 2.10 ± 0.22 | 6 |
| 7,4'-Dihydroxyflavone | 1.91 ± 0.17 | 6 |

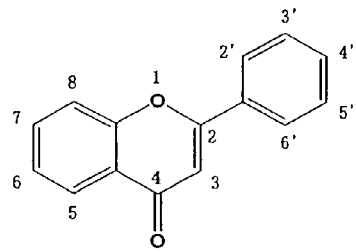

FLAVONES

Abbreviation: SE, Standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 18

Supplementary Table 3. Effects of Flavones (100 µM) on SIRT1 Rate (Part II).

| Compound | Ratio to Control Rate Mean ± SE | Replicates | Structure Skeleton |
|---|---|---|---|
| 7,8,3',4'-Tetrahydroxyflavone | 1.91 ± 0.39 | 6 | |
| 3,6,2',3'-Tetrahydroxyflavone | 1.74 ± 0.27 | 6 | |
| 4'-Hydroxyflavone | 1.73 ± 0.12 | 6 | |
| 5,4'-Dihydroxyflavone | 1.56 ± 0.15 | 6 | |
| 5,7-Dihydroxyflavone | 1.51 ± 0.18 | 6 | 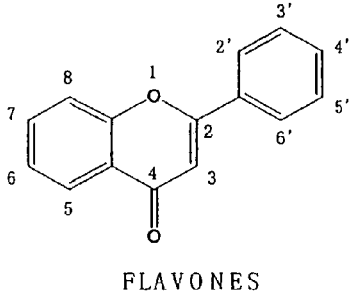 |
| Morin (3,5,7,2',4'-Pentahydroxyflavone) | 1.461 ± 0.071 | 6 | |
| Flavone | 1.41 ± 0.23 | 6 | FLAVONES |
| 5-Hydroxyflavone | 1.22 ± 0.19 | 6 | |
| Myricetin (Cannabiscetin; 3,5,7,3',4',5'-Hexahydroxyflavone) | 0.898 ± 0.070 | 12 | |
| 3,7,3',4',5'-Pentahydroxyflavone | 0.826 ± 0.074 | 12 | |
| Gossypetin (3,5,7,8,3',4'-Hexahydroxyflavone) | 0.723 ± 0.062 | 6 | |

Abbreviation: SE, Standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 19

Supplementary Table 4. Effects of Isoflavones, Flavanones and Anthocyanidins (100 µM) on SIRT1 Rate

| Compound | Ratio to Control Rate Mean ± SE | Replicates | Structure Skeleton |
|---|---|---|---|
| Daidzein (7,4'-Dihydroxyisoflavone) | 2.28 ± 0.74 | 2 | ISOFLAVONES |
| Genistein (5,7,4'-Trihydroxyisoflavone) | 1.109 ± 0.026 | 2 | |
| Naringenin (5,7,4'-Trihydroxyflavanone) | 2.10 ± 0.23 | 6 | FLAVANONES |
| 3,5,7,3',4'-Pentahydroxyflavanone | 1.97 ± 0.22 | 5 | |
| Flavanone | 1.92 ± 0.24 | 6 | |
| Pelargonidin chloride (3,5,7,4'-Tetrahydroxyflavylium chloride) | 1.586 ± 0.037 | 2 | ANTHOCYANIDINS (Flavylium Chloride Salts) |
| Cyanidin chloride (3,5,7,3',4'-Pentahydroxyflavylium chloride) | 0.451 ± 0.015 | 2 | |
| Delphinidin chloride (3,5,7,3',4',5'-Hexahydroxyflavylium chloride) | 0.4473 ± 0.0071 | 2 | |

Abbreviation: SE, Standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 20

Supplementary Table 5. Effects of Catechins (Flavan-3-ols) (100 µM) on SIRT1 Rate.

| Compound | Ratio to Control Rate Mean ± SE | Replicates | Structure Skeleton/Structure |
|---|---|---|---|
| (-)-Epicatechin (Hydroxy Sites: 3,5,7,3',4') | 1.53 ± 0.31 | 4 | CATECHINS (Flavan-3-ols) |
| (-)-Catechin (Hydroxy Sites: 3,5,7,3',4') | 1.41 ± 0.21 | 4 | |
| (-)-Gallocatechin (Hydroxy Sites: 3,5,7,3',4',5') | 1.35 ± 0.25 | 4 | |
| (+)-Catechin (Hydroxy Sites: 3,5,7,3',4') | 1.31 ± 0.19 | 4 | |
| (+)-Epicatechin (Hydroxy Sites: 3,5,7,3',4') | 1.26 ± 0.20 | 4 | |
| (-)-Epigallocatechin (Hydroxy Sites: 3,5,7,3',4',5') | 0.41 ± 0.11 | 4 | |
| (-)-Epigallocatechin Gallate (Hydroxy Sites: 3*,5,7,3',4',5'; *Position of gallate ester) | 0.32 ± 0.12 | 4 | (-)-EPIGALLOCATECHIN GALLATE |

Abbreviation: SE, Standard error of the mean. Rate measurements with 25 µM $NAD^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 21

Supplementary Table 6. Effects of Free Radical Protective Compounds (100 μM) on SIRT1 Rate.

| Compound | Ratio to Control Rate Mean ± SE | Replicates | Protective Mechanism |
|---|---|---|---|
| Hinokitiol (b-Thujaplicin; 2-hydroxy-4-isopropyl-2,4,6-cycloheptatrien-1-one) | 2.48 ± 0.15 | 2 | Iron Chelator |
| L-(+)-Ergothioneine ((S)-a-Carboxy-2,3-dihydro-N,N,N-trimethyl-2-thioxo-1H-imidazole-4-ethanaminium inner salt) | 2.06 ± 0.48 | 2 | Antioxidant, Peroxynitrite Scavenger |
| Caffeic Acid Phenyl Ester | 1.80 ± 0.16 | 2 | Iron Chelator |
| MCI-186 (3-Methyl-1-phenyl-2-pyrazolin-5-one) | 1.2513 ± 0.0080 | 2 | Radical Scavenger and Antioxidant |
| HBED (N,N'-Di-(2-hydroxybenzyl)ethylenediamine-N,N'-diacetic acid·HCl·H2O) | 1.150 ± 0.090 | 2 | Iron Chelator |
| Ambroxol (trans-4-(2-Amino-3,5-dibromobenzylamino)cyclohexane·HCl) | 1.075 ± 0.0026 | 2 | Radical Scavenger |
| U-83836E ((-)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol·2HCl) | 1.030 ± 0.055 | 2 | "Lazaroid" aminosteroid, Peroxidation inhibitor |
| Trolox (6-Hydroxy-2,5,7,8-tetramethylchroman-2-carboxylic acid) | 0.995 ± 0.019 | 2 | Antioxidant |

Abbreviation: SE, Standard error of the mean. Rate measurements with 25 μM $NAD^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

Figure 22

Supplementary Table 7. Effects of Miscellaneous Compounds (100 μM) on SIRT1 Catalytic Rate.

| Compound | Ratio to Control Rate Mean ± SE | Replicates | Structure & Activities |
|---|---|---|---|
| Dipyridamole (2,6-bis(Diethanolamino)-4,8-dipiperidino-pyrimido[5,4-d]pyrimidine) | 3.54 ± 0.20 | 2 | 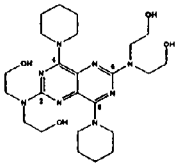 Inhibitor of Adenosine Transport, Phosphodiesterase, 5-Lipoxygenase |
| Nicotinamide | 0.428 ± 0.019 | 42 |  Sirtuin Reaction Product/Inhibitor |
| NF279 | 0.0035 ± 0.0011 | 3 | 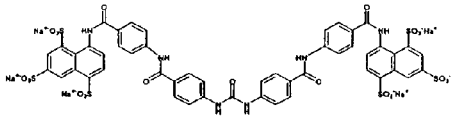 Purinergic Receptor Antagonist |
| NF023 | -0.0016 ± 0.0015 | 3 | 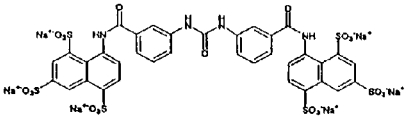 G-protein Antagonist |
| Suramin | -0.0002 ± 0.0010 | 3 | 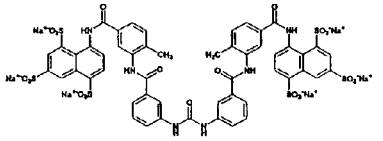 G-protein Antagonist, Reverse Transcriptase Inhibitor |

Abbreviation: SE, Standard error of the mean. Rate measurements with 25 μM NAD$^+$ and 25 μM p53-382 acetylated peptide substrate were performed as described in Methods. All ratio data were calculated from experiments in which the total deacetylation in the control reaction was 0.25-1.25 μM peptide or 1-5% of the initial concentration of acetylated peptide.

Figure 23

Supplementary Table 8. Effects of Various Modulators on SIRT1 Rate.

| Compound, (Concentration) | Ratio to Control Rate Mean ± SE | Replicates | Structure |
|---|---|---|---|
| ZM 336372, (100 µM) | 3.5 ± 1.1 | 3 | 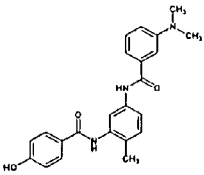 |
| Camptothecin, (10 µM) | 2.92 ± 0.41 | 3 | 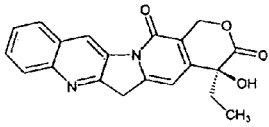 |
| Coumestrol, (10 µM) | 2.30 ± 0.31 | 2 | 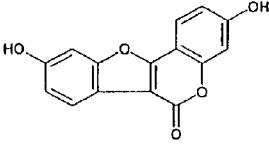 |
| NDGA, (100 µM) | 1.738 ± 0.088 | 3 | 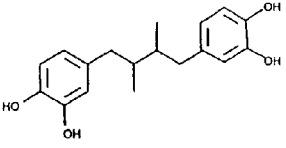 |
| Esculetin, (10 µM) | 1.737 ± 0.082 | 3 | 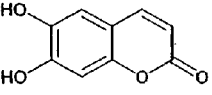 |
| Sphingosine | 0.069 ± 0.028 | 3 | 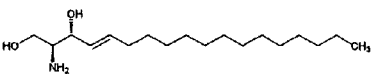 |

Abbreviation: SE, Standard error of the mean. Rate measurements with 25 µM NAD$^+$ and 25 µM p53-382 acetylated peptide substrate were performed as described in Methods. All ratio data were calculated from experiments in which the total deacetylation in the control reaction was 0.25-1.25 µM peptide or 1-5% of the initial concentration of acetylated peptide.

Figure 24

Table 9. SIRT1 Rate Effects of New Resveratrol Analogs (100 µM).

| Compound | Ratio to Control Rate Mean ± SE | N | Structure | Stability in Solution $t_{1/2}$, hrs. |
|---|---|---|---|---|
| BML-230 (3,5-Dihydroxy-4'-thiomethyl-*trans*-stilbene) | 11.8 ± 1.9 | 12 | 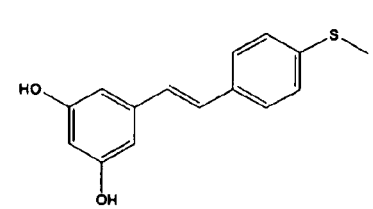 | |
| Resveratrol (3,5,4'-Trihydroxy-*trans*-stilbene) | 10.7 ± 0.4 | 49 | 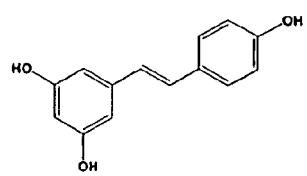 | 59 (ethanol), 20 (water) |
| BML-217 (3,5-Dihydroxy-4'-chloro-*trans*-stilbene) | 10.6 ± 0.4 | 3 | 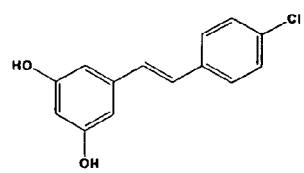 | |
| Pinosylvin (3,5-Dihydroxy-*trans*-stilbene) | 9.95 ± 0.45 | 3 | 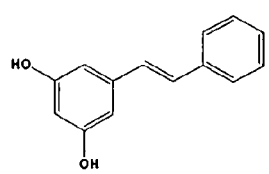 | |
| BML-225 (3,5-Dihydroxy-4'-ethyl-*trans*-stilbene) | 9.373 ± 0.014 | 3 | 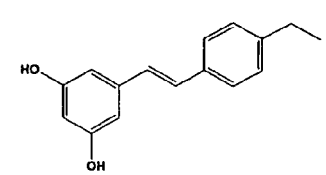 | |
| BML-212 (3,5-Dihydroxy-4'-fluoro-*trans*-stilbene) | 8.20 ± 0.69 | 3 | 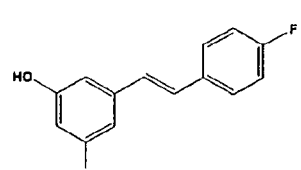 | 66 (ethanol) |

Figure 25

Table 10. SIRT1 Rate Effects of New Resveratrol Analogs (100 μM).

| Compound | Ratio to Control Rate Mean ± SE | N | Structure | Stability in Solution $t_{1/2}$, hrs. |
|---|---|---|---|---|
| BML-228 (3,5-Dihydroxy-4'-methyl-*trans*-stilbene) | 7.72 ± 0.12 | 3 | 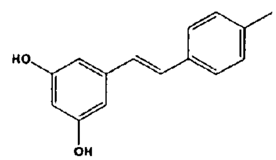 | |
| BML-232 (3,5-Dihydroxy-4'-azido-*trans*-stilbene) | 7.24 ± 0.12 | 3 | 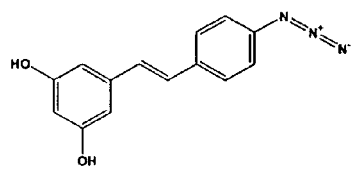 | |
| BML-229 (3,5-Dihydroxy-4'-nitro-*trans*-stilbene) | 6.78 ± 0.22 | 3 | 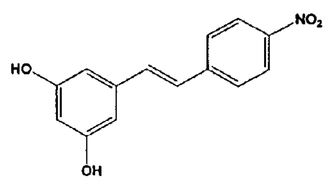 | |
| BML-231 (3,5-Dihydroxy-4'-isopropyl-*trans*-stilbene) | 6.01 ± 0.15 | 3 | 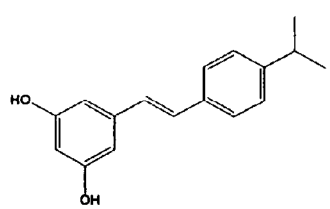 | |
| BML-233 3,5-Dihydroxy-4'-methoxy-*trans*-stilbene | 5.48 ± 0.33 | 6 | 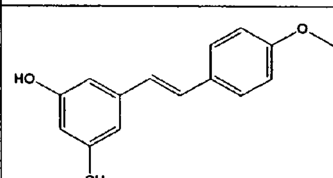 | |

Figure 26

Table 11. SIRT1 Rate Effects of New Resveratrol Analogs (100 μM).

| Compound | Ratio to Control Rate Mean ± SE | N | Structure | Stability in Solution $t_{1/2}$, hrs. |
|---|---|---|---|---|
| Rhapontin aglycone (3,5,3'Trihydroxy-4'-methoxy-*trans*-stilbene) | 4.060 ± 0.069 | 3 | 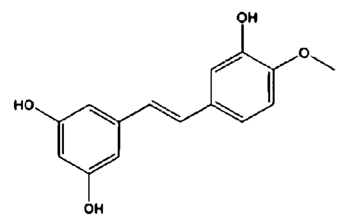 | |
| BML-227 (3,4'-Dihydroxy-5-acetoxy-*trans*-stilbene) | 3.340 ± 0.093 | 3 | 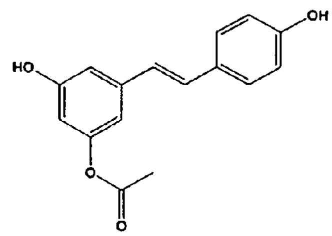 | |
| BML-221 (3,5-Dihydroxy-4'-acetoxy-*trans*-stilbene) | 3.05 ± 0.54 | 6 | 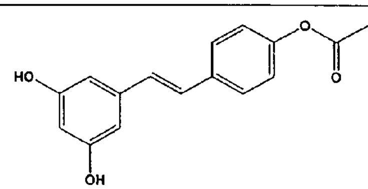 | 504 (ethanol) |
| BML-218 (E)-1-(3,5-Dihydroxyphenyl)-2-(2-napthyl) ethene | 3.05 ± 0.37 | 6 | 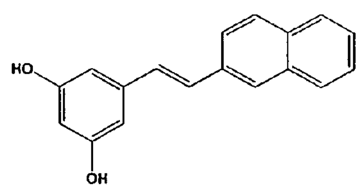 | |
| BML-216 3-Hydroxystilbene | 2.357 ± 0.074 | 3 | 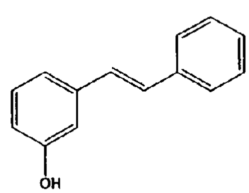 | |

Figure 27

Table 12. SIRT1 Rate Effects of New Resveratrol Analogs (100 µM).

| Compound | Ratio to Control Rate Mean ± SE | N | Structure | Stability in Solution $t_{1/2}$, hrs. |
|---|---|---|---|---|
| BML-226 (3,5-Dimethoxymethoxy-4'-thiomethyl-*trans*-stilbene) | 2.316 ± 0.087 | 3 | 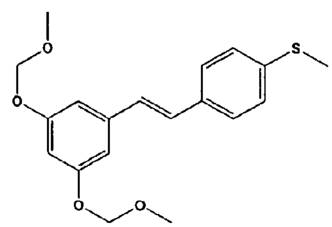 | |
| BML-222 (3,5-Dihydroxy-4'-acetamide-*trans*-stilbene) | 1.88 ± 0.11 | 3 | 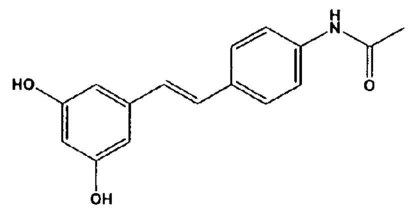 | |
| BML-215 3,4-Dihydroxy-*trans*-stilbene | 1.64 ± 0.10 | 6 | 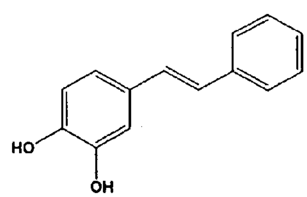 | |
| BML-224 (E)-1-(3,5-Dihydroxyphenyl)-2-(cyclohexyl)ethene | 1.297 ± 0.042 | 3 | 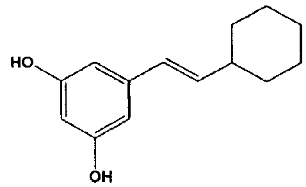 | |
| 3,4-Dimethoxy-*trans*-stilbene | 1.127 ± 0.019 | 3 | 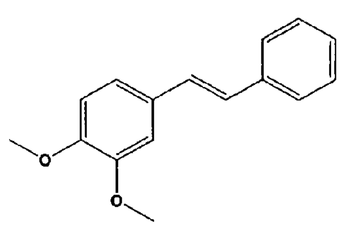 | |

Figure 28
Table 13. SIRT1 Rate Effects of New Resveratrol Analogs (100 µM).
| Compound | Ratio to Control Rate Mean ± SE | N | Structure | Stability in Solution $t_{1/2}$, hrs. |
|---|---|---|---|---|
| Dihydroresveratrol (1-(3,5-Dihydroxyphenyl)-2-(4-hydroxyphenyl) ethane) | 1.08 ± 0.14 | 4 | 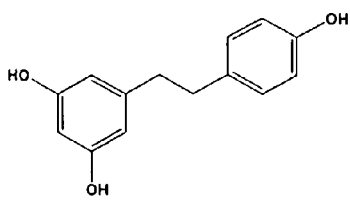 | |
| 4-Hydroxy-*trans*-stilbene | 0.943 ± 0.039 | 3 | 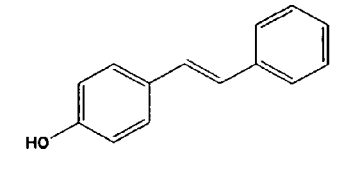 | |
| BML-219 *N*-phenyl-(3,5-dihydroxy)benzamide | 0.902 ± 0.014 | 3 | 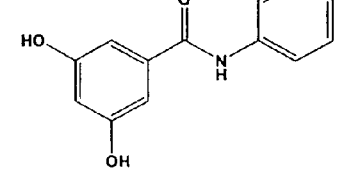 | |
| 3,5-Dihydroxy-4'-nitro-*trans*-stilbene | 0.870 ± 0.019 | 3 | 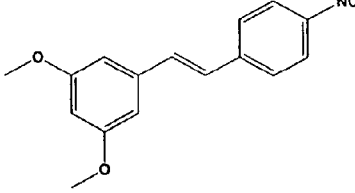 | |
| 4-Methoxy-*trans*-stilbene | 0.840 ± 0.089 | 3 | 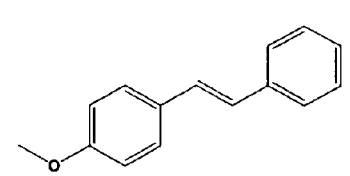 | |

Figure 29

Table 14. Resveratrol Analog Synthetic Intermediates

| Compound | Benzylphosphonate | Aldehyde | Structure |
|---|---|---|---|
| BML-217 (3,5-Dihydroxy-4'-chloro-*trans*-stilbene) | Diethyl 3-5-dimethoxybenzyl phosphonate | 4-Chlorobenzaldehyde | 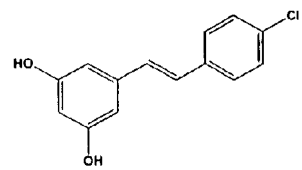 |
| Resveratrol (3,5,4'-Trihydroxy-*trans*-stilbene) | N/A | N/A | 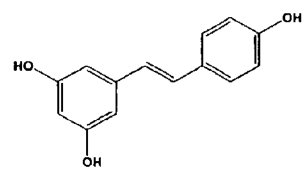 |
| Pinosylvin (3,5-Dihydroxy-*trans*-stilbene) | Diethyl benzyl phosphonate | 3,5-Dimethoxy benzaldehyde | 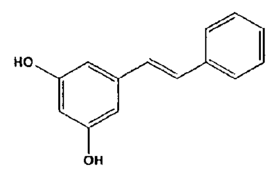 |
| BML-225 (3,5-Dihydroxy-4'-ethyl-*trans*-stilbene) | Diethyl 3-5-dimethoxybenzyl phosphonate | 4-Ethylbenzaldehyde | 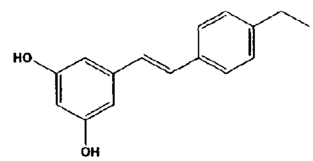 |
| BML-212 (3,5-Dihydroxy-4'-fluoro-*trans*-stilbene) | Diethyl 4-fluoro benzylphosphonate | 3,5-Dimethoxy benzaldehyde | 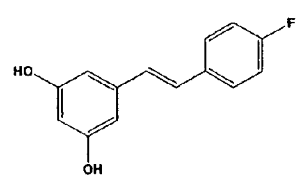 |
| BML-228 (3,5-Dihydroxy-4'-methyl-*trans*-stilbene) | Diethyl 3-5-dimethoxybenzyl phosphonate | 4-Methylbenzaldehyde | 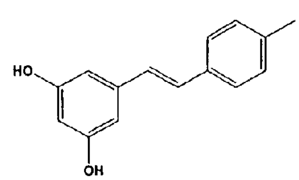 |

Figure 30

Table 15. Resveratrol Analog Synthetic Intermediates

| Compound | Benzylphosphonate | Aldehyde | Structure |
|---|---|---|---|
| BML-232 (3,5-Dihydroxy-4'-azido-*trans*-stilbene) | Diethyl 4-azido benzylphosphonate | 3,5-Dimethoxymethoxy benzaldehyde | 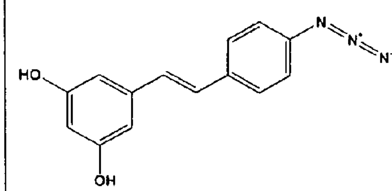 |
| BML-230 (3,5-Dihydroxy-4'-thiomethyl-*trans*-stilbene) | Diethyl 4-methylthio benzylphosphonate | 3,5-Dimethoxymethoxy benzaldehyde | 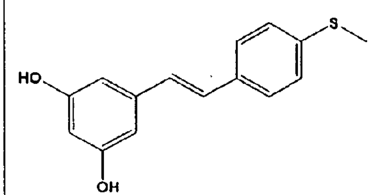 |
| BML-229 (3,5-Dihydroxy-4'-nitro-*trans*-stilbene) | Diethyl 3-5-dimethoxybenzyl phosphonate | 4-Nitrobenzaldehyde | 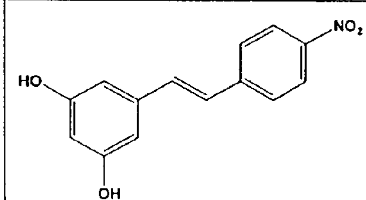 |
| BML-231 (3,5-Dihydroxy-4'-isopropyl-*trans*-stilbene) | Diethyl 3-5-dimethoxybenzyl phosphonate | 4-Isopropyl benzaldehyde | 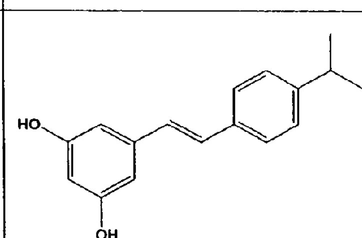 |
| 3,5-Dihydroxy-4'-methoxy-*trans*-stilbene | N/A | N/A | 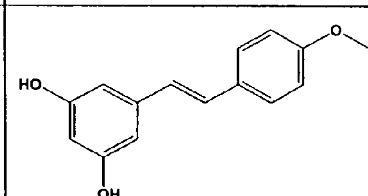 |

Figure 31

Table 16. Resveratrol Analog Synthetic Intermediates

| Compound | Benzylphosphonate | Aldehyde | Structure |
|---|---|---|---|
| Rhapontin aglycone (3,5,3'Trihydroxy-4'-methoxy-trans-stilbene) | N/A | N/A | 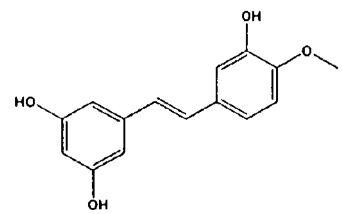 |
| BML-227 (3,4'-Dihydroxy-5-acetoxy-trans-stilbene) | N/A | N/A | 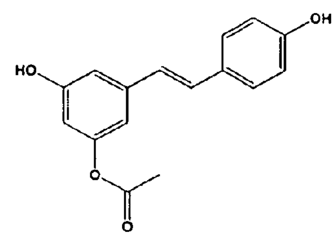 |
| BML-221 (3,5-Dihydroxy-4'-acetoxy-trans-stilbene) | N/A | N/A | 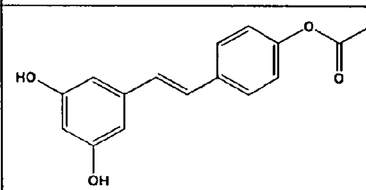 |
| BML-218 (E)-1-(3,5-Dihydroxyphenyl)-2-(2-napthyl) ethene | Diethyl 3-5-dimethoxybenzyl phosphonate | 2-Naphthaldehyde | 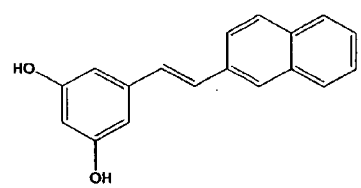 |
| BML-216 3-Hydroxystilbene | Benzylphosphonate | 3-Methoxy benzaldehyde | 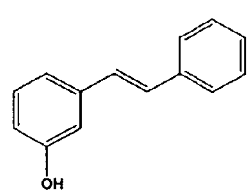 |

Figure 32

Table 17. Resveratrol Analog Synthetic Intermediates

| Compound | Benzylphosphonate | Aldehyde | Structure |
|---|---|---|---|
| BML-226 (3,5-Dimethoxymethoxy-4'-thiomethyl-*trans*-stilbene) | Diethyl 4-methylthio benzylphosphonate | 3,5dimethoxymethoxy benzaldehyde | 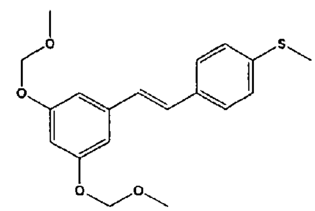 |
| BML-222 (3,5-Dihydroxy-4'-acetamide-*trans*-stilbene) | Diethyl 4-acetamido benzylphosphonate | 3,5-dimethoxymethoxy benzaldehyde | 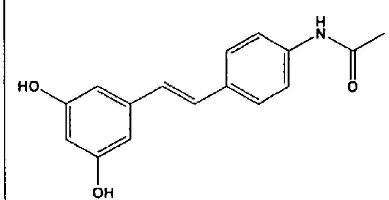 |
| BML-215 3,4-Dihydroxy-*trans*-stilbene | Benzylphosphonate | 3,4-Dimethoxy benzaldehyde | 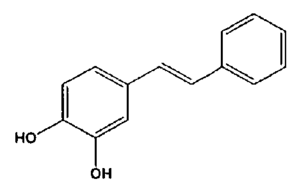 |
| BML-224 (E)-1-(3,5-Dihydroxyphenyl)-2-(cyclohexyl) ethene | 3,5-Dimethoxy benzylphosphonate | Cyclohexane carboxaldehyde | 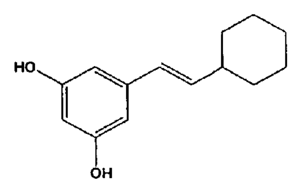 |
| 3,4-Dimethoxy-*trans*-stilbene | Benzylphosphonate | 3,4-Dimethoxy benzaldehyde | 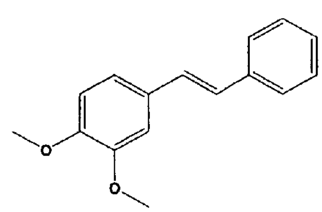 |

Figure 37

Table 18. Resveratrol Analog Synthetic Intermediates

| Compound | Benzylphosphonate | Aldehyde | Structure |
|---|---|---|---|
| Dihydroresveratrol (1-(3,5-Dihydroxyphenyl)-2-(4-hydroxyphenyl)ethane) | N/A | N/A | 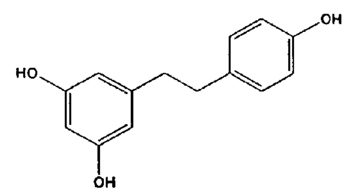 |
| BML-214 4-Hydroxy-*trans*-stilbene | Benzylphosphonate | 4-Methoxy benzaldehyde | 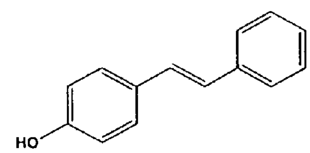 |
| BML-219 N-phenyl-(3,5-dihydroxy)benzamide | N/A | N/A | 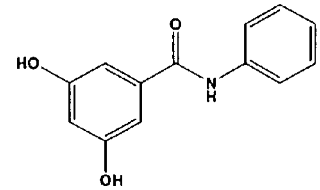 |
| 3,5-Dihydroxy-4'-nitro-*trans*-stilbene | 3,5-Dimethoxy benzylphosphonate | 4-Nitrobenzaldehdye | 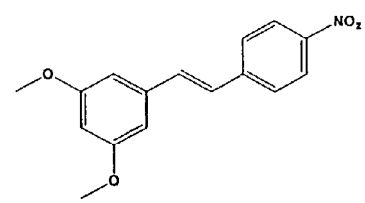 |
| 4-Methoxy-*trans*-stilbene | Benzylphosphonate | 4-Methoxy benzaldehyde | 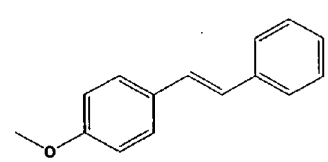 |

Figure 34

Table 20

| Trial | Genotype | Diet | Treatment | Female N(0) | Median lifespan days | Median lifespan % change† | Mean lifespan days | Mean lifespan s.e. | Log-rank Test χ2 | Log-rank Test prob | Male N(0) | Median lifespan days | Median lifespan % change† | Mean lifespan days | Mean lifespan s.e. | Log-rank Test χ2 | Log-rank Test prob |
|---|---|---|---|---|---|---|---|---|---|---|---|---|---|---|---|---|---|
| 1 | Canton-S | 15% SY | control | 189 | 35 | | 34.5 | 0.83 | | | 189 | 52 | | 47.4 | 0.51 | | |
| | | | 10µM Resv | 203 | 45 | 28.6 | 43.2 | 0.73 | 53.8 | <0.0001 | 182 | 56 | 7.7 | 53.9 | 0.11 | 17.8 | <0.0001 |
| | | | 100µMResv | 189 | 41 | 17.1 | 41.8 | 0.75 | 34.2 | <0.0001 | 188 | 53 | 1.9 | 50.8 | 0.9 | 0.8 | 0.383 |
| | | | 200µM Resv | 189 | 36 | 2.9 | 36.6 | 0.65 | 0.14 | 0.71 | 198 | 49 | -5.8 | 47.9 | 0.95 | 0.0 | 0.838 |
| | | 5% SY | control | 198 | 66 | | 63.6 | 0.93 | | | 180 | 67 | | 67.9 | 0.93 | | |
| | | | 10µM Resv | 203 | 63 | -4.5 | 60 | 0.9 | 11.2 | 0.0008 | 180 | 66 | -1.5 | 63.8 | 1.1 | 7.0 | 0.0081 |
| | | | 100µM Resv | 194 | 60 | -9.1 | 60.8 | 0.87 | 8.7 | 0.0032 | 179 | 70 | 4.5 | 70.2 | 0.95 | 3.2 | 0.07 |
| | | | 200µM Resv | 202 | 66 | 0.0 | 63.9 | 0.99 | 0.99 | 0.32 | 174 | 70 | 4.5 | 69.1 | 1.2 | 5.4 | 0.02 |
| 2 | yw | 3% CSY | control | 80 | 29 | | 30.5 | 1.2 | | | 113 | 38 | | 40.1 | 1.1 | | |
| | | | 10µM Resv | 93 | 32 | 10.3 | 34.6 | 1.1 | 5.5 | 0.019 | 98 | 40 | 5.3 | 44 | 1.2 | 3.8 | 0.053 |
| | | | 100µM Resv | 100 | 36 | 24.1 | 38 | 1.3 | 19.7 | <0.0001 | 118 | 49 | 28.9 | 47.5 | 1.2 | 16.4 | <0.0001 |
| | | 2% CSY | control | 106 | 36 | | 37.9 | 1.3 | | | 118 | 41 | | 42.7 | 1.2 | | |
| | | | 10µM Resv | 103 | 36 | 0.0 | 38.6 | 1.1 | 0.65 | 0.42 | 102 | 43 | 4.9 | 43.6 | 1.3 | 1.3 | 0.26 |
| | | | 100µM Resv | 127 | 37 | 2.8 | 38.4 | 1.2 | 0.003 | 0.95 | 100 | 51 | 24.4 | 48.4 | 1.6 | 21.7 | <0.0001 |
| 3 | yw | 3% CSY | control | 237 | 43 | | 45.3 | 0.8 | | | 210 | 55 | | 53.5 | 1.2 | | |
| | | | 10µM Resv | 223 | 47 | 9.3 | 46.5 | 0.78 | 0.16 | 0.69 | 218 | 65 | 18.2 | 57.9 | 1.3 | 14.0 | 0.0002 |
| | | | 100µM Resv | 274 | 51 | 18.6 | 50.7 | 0.81 | 28.7 | <0.0001 | 308 | 64 | 16.4 | 62 | 0.97 | 38.7 | <0.0001 |
| | | | 10µM Fisetin | 305 | 43 | 0.0 | 42.9 | 0.81 | 1.85 | 0.17 | 284 | 50 | -9.1 | 52.2 | 1 | 0.0 | 0.958 |
| | | | 100µM Fisetin | 288 | 53 | 23.3 | 48.6 | 0.76 | 10.3 | 0.0013 | 285 | 67 | 21.8 | 60.4 | 0.94 | 17.2 | <0.0001 |
| | | 2% CSY | control | 311 | 47 | | 47.4 | 0.82 | | | 281 | 58 | | 57.6 | 0.98 | | |
| | | | 10µM Resv | 456 | 53 | 12.8 | 49.7 | 0.66 | 2.45 | 0.118 | 284 | 55 | -5.2 | 55.2 | 1 | 1.6 | 0.21 |
| | | | 100µM Resv | 300 | 43 | -8.5 | 43.2 | 0.74 | 21.5 | <0.0001 | 290 | 48 | -17.2 | 50.1 | 0.88 | 42.8 | <0.0001 |
| | | | 10µM Fisetin | 307 | 45 | -4.3 | 47 | 0.82 | 0.11 | 0.737 | 274 | 54 | -6.9 | 54.1 | 0.99 | 7.8 | 0.0052 |
| | | | 100µM Fisetin | 300 | 46 | -2.1 | 45.9 | 0.8 | 3.98 | 0.046 | 290 | 52 | -10.3 | 51.6 | 1 | 17.1 | <0.0001 |
| 4 | SIR2 loss of function dSir2 [4.5]/dSir2 [5.26] | 15% SY | control | 175 | 58 | | 53.5 | 1.2 | | | 168 | 64 | | 61.7 | 1.1 | | |
| | | | 100µM Resv | 196 | 54 | -6.9 | 51.5 | 1 | 16.9 | <0.0001 | 166 | 61 | -4.7 | 57.3 | 0.94 | 24.5 | <0.0001 |
| 5 | SIR2 hypomorphism dSir2 [17]/KG00871 | 15% SY | control | 185 | 55 | | 51.7 | 0.84 | | | 168 | 38 | | 39.4 | 0.72 | | |
| | | | 100µM Resv | 183 | 54 | -1.8 | 51.7 | 0.86 | 0.29 | 0.59 | 177 | 40 | 5.3 | 40.6 | 0.78 | 1.6 | 0.21 |
| 6 | SIR2 hypomorphism KG00871/KG00871 | 15% SY | control | 184 | 50 | | 47 | 1.1 | | | 167 | 53 | | 50.1 | 1.2 | | |
| | | | 10µM Resv | 184 | 52 | 4.0 | 49.1 | 1.2 | 10.9 | 0.0009 | 152 | 59 | 11.3 | 55.9 | 1.1 | 8.4 | 0.0037 |
| | | | 100µM Resv | 173 | 52 | 4.0 | 50.2 | 1 | 6.98 | 0.0083 | 163 | 59 | 11.3 | 56.4 | 1 | 10.8 | 0.001 |
| | | | 200µM Resv | 141 | 48 | -4.0 | 43.3 | 1.6 | 7.23 | 0.027 | 139 | 54 | 1.9 | 50.8 | 1.5 | 2.4 | 0.125 |
| 7 | SIR2 hypomorphism KG00871/Canton-S | 15% SY | control | 194 | 62 | | 59.2 | 1.3 | | | 172 | 68 | | 67.2 | 0.85 | | |
| | | | 10µM Resv | 199 | 72 | 16.1 | 67.7 | 1.1 | 26.1 | <0.0001 | 185 | 74 | 8.8 | 69 | 1.2 | 7.9 | 0.005 |
| | | | 100µM Resv | 195 | 63 | 1.6 | 59.3 | 1.5 | 1.62 | 0.202 | 171 | 69 | 1.5 | 64.8 | 1.3 | 0.4 | 0.507 |
| | | | 200µM Resv | 186 | 73 | 17.7 | 67 | 1.2 | 22.1 | <0.0001 | 176 | 73 | 7.4 | 71.1 | 0.94 | 14.3 | 0.0002 |

† percent change is relative to control
Bold: increase in lifespan at significance criterion: $p < 0.01$
*Italics*: decrease in lifespan at significance criterion: $p < 0.01$
SY: sugar-yeast diet    CSY: cornmeal-sugar-yeast diet

Figure 35A

Table 21. Sirtuin activators.

| Compound | Fold Activation | Structure | Included in formula number |
|---|---|---|---|
| 2-[1-(2-hydroxyphenyl) ethylidene] hydrazine-1-carbothioamide | 1.1 | 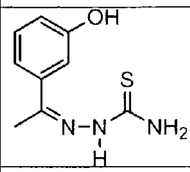 | 32 |
| prop-2-ynyl 3-(2,6-dichlorophenyl)-5-methylisoxazole-4-carboxylate | 1.1 | 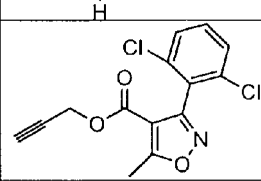 | 33 |
| 4-{3-[(3,5-dichloro-2-hydroxybenzylidene)amino]propyl}-4,5-dihydro-1H-pyrazol-5-one | 1.2 | 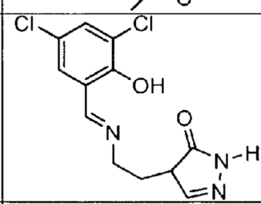 | 34 |
| 6-(phenylthio)-2-[2-(2-pyridyl)ethyl]-2,3-dihydro-1H-benzo[de]isoquinoline-1,3-dione | 1.15 | 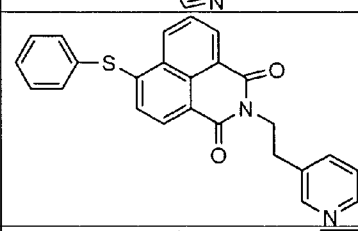 | 35 |
| 5-[(4-chloroanilino)methylene]-3-(4-chlorophenyl)-1lambda~6~,3-thiazolane-1,1,4-trione | 1.15 | 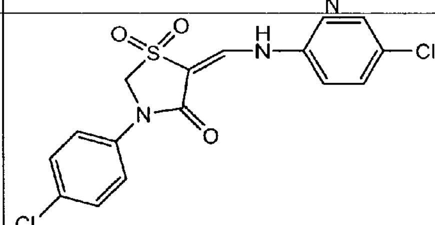 | 36 |
| 2-(4-chlorophenyl)-7-methylimidazo[1,2-a]pyridine-3-carbaldehyde O-(3-fluorobenzyl)oxime | 1.1 | 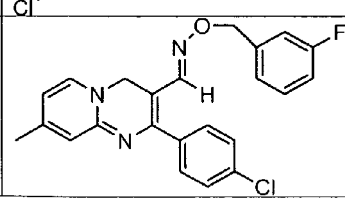 | 37 |

Figure 35B

| | | | |
|---|---|---|---|
| 2-(4-tert-butylphenoxy)-N-(3-methoxyphenyl)acetamide | 1.12 | | 38 |
| 3,4,5-trimethoxy-N-(4-methyl-1,3-benzothiazol-2-yl)benzamide | 1.12 | | 39 |
| 3-(1,3-benzodioxol-5-yl)-N-(pentafluorophenyl)acrylamide | 1.09 | | 40 |
| 'ethyl [(4-cyano-1-morpholin-4-yl-5,6,7,8-tetrahydroisoquinolin-3-yl)thio]acetate | 1.11 | | 41 |
| 'ethyl 2-({[5-(4-methylphenyl)-7-(trifluoromethyl)-4,5,6,7-tetrahydropyrazolo[1,5-a]pyrimidin-3-yl]carbonyl}amino)-4,5,6,7-tetrahydro-1-benzothiophene-3-carboxylate | 1.1 | | 42 |
| '6-amino-3-(4-bromophenyl)-4-(3-hydroxy-4-methoxyphenyl)-1,4-dihydropyrano[2,3-c]pyrazole-5-carbonitrile | 1.1 | | 43 |

Figure 35c

| | | | |
|---|---|---|---|
| 'dimethyl 5-{[({4-oxo-5-[3-(trifluoromethyl)phenyl]-4,5-dihydro-1H-pyrazolo[3,4-d]pyrimidin-6-yl}thio)acetyl]amino}isophthalate | 1.08 | | 44 |
| 'N-{2-[4-(aminosulfonyl)phenyl]ethyl}-2-{[4-oxo-3-(tetrahydrofuran-2-ylmethyl)-3,4-dihydroquinazolin-2-yl]thio}acetamide | 1.05 | | 45 |
| 'N-{3-chloro-4-[(4-chloro-1-naphthyl)oxy]phenyl}-2-hydroxy-3,5-diiodobenzamide | 1.24 | | 46 |
| | 1.2 | | 47 |

Figure 35 D

| | | | |
|---|---|---|---|
| 'tetramethyl 5',5',9'-trimethyl-6'-(trifluoroacetyl)-5',6'-dihydrospiro[1,3-dithiole-2,1'-thiopyrano[2,3-c]quinoline]-2',3',4,5-tetracarboxylate | 1.14 | | 48 |
| 'dimethyl 2-[2,2,6-trimethyl-1-(3-methylbutanoyl)-3-thioxo-2,3-dihydroquinolin-4(1H)-ylidene]-1,3-dithiole-4,5-dicarboxylate | 1.17 | | 49 |
| 'ethyl 4-[5-[(cyanomethyl)thio]-2-thioxo[1,3]thiazolo[4',5':4,5]pyrimido[1,6-a]benzimidazol-3(2H)-yl]benzoate | 1.47 | | 50 |
| '6-chloro-2,3-diphenyl-7-(trifluoromethyl)quinoxaline | 1.12 | | 51 |
| '6-fluoro-2,3-bis(4-methylphenyl)quinoxaline | 1.27 | | 51 |
| | 1.1 | | 52 |

Figure 35 E
| | | | |
|---|---|---|---|
| | 1.28 | 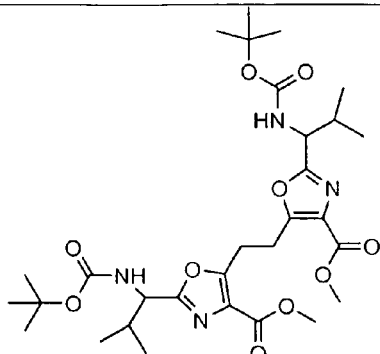 | 53 |
| Pyridine, 2-(p-chlorostyryl)-4-[[4-(diethylamino)-1-methylbutyl]amino]-, (E)- | 1.06 | 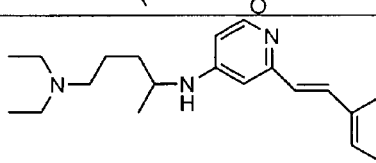 | 54 |
| Gloxazone | 1.16 | 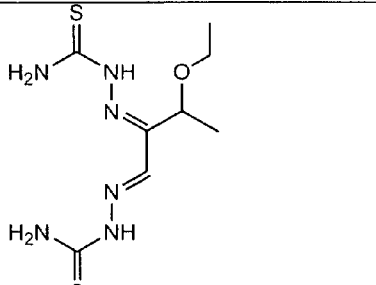 | 55 |
| | 1.25 | 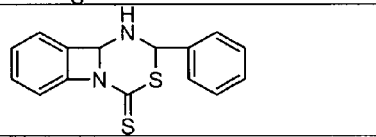 | 56 |
| | 1.1 | 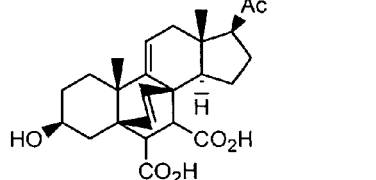 | 57 |

Figure 35 F
| | | | |
|---|---|---|---|
| Ouabaine | 1.07 | 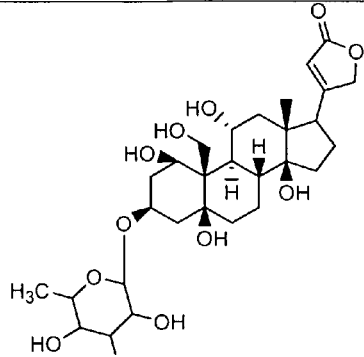 | 58 |
| | 1.16 | H₂N⌒Se⌒NH₂ | 59 |
| | 1.06 | 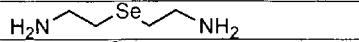 | 60 |
| Pinosylvin | 3.28 | 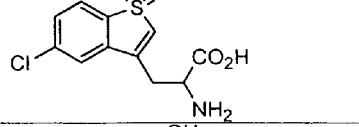 | 61 |
| Resveratrol 4"-Methyl Ether | 2.1 | 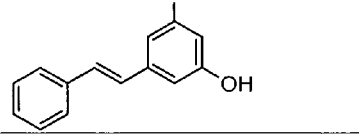 | 1 |
| Resveratrol | 2.2 | 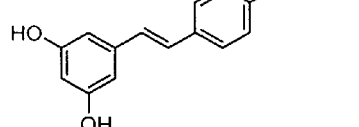 | 1 |
| Aloin | 1.2 | 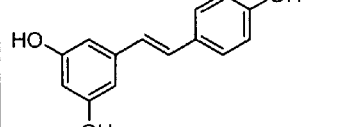 | 62 |

Figure 35G
| | | | |
|---|---|---|---|
| Piromidic Acid | 1.47 | 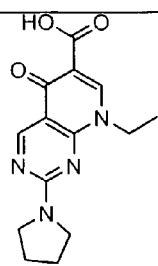 | 63 |
| Meclocycline Sulfosalicylate | 1.12 | 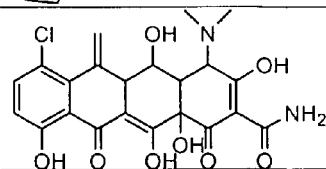 | 64 |
| Methacycline Hydrochloride | 1.14 | 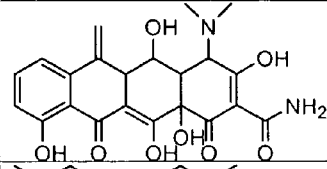 | 64 |
| Ofloxacin | 1.5 | 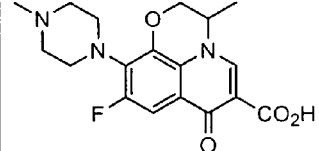 | 65 |

Figure 36
Table 22. Sirtuin inhibitors
| Compound | Fold Activation | Structure | Included in formula number |
|---|---|---|---|
| Chlortetracycline | <1 | 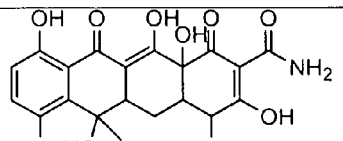 | 66 |
|  | 0.27 | 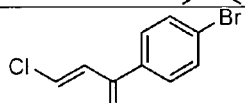 | 67 |
| Methotrexane | 0.53 | 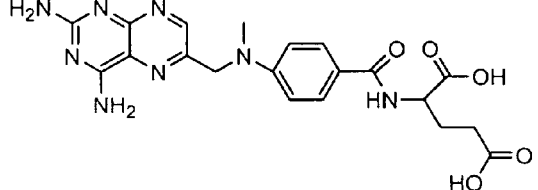 | 68 |

COMPOSITIONS FOR MANIPULATING THE LIFESPAN AND STRESS RESPONSE OF CELLS AND ORGANISMS

CROSS-REFERENCE TO RELATED APPLICATIONS

This application claims the benefit of U.S. Provisional Application No. 60/483,949, filed Jul. 1, 2003 and U.S. Provisional Application No. 60/532,158, filed Dec. 23, 2003, the content of both of which is specifically incorporated by reference herein.

GOVERNMENTAL SUPPORT

This invention was made with government support under Grant number AG019972 awarded by the National Institutes of Health. The government has certain rights in this invention.

BACKGROUND

There is now good evidence from model organisms that the pace of aging can be regulated[1]. Longevity regulatory genes have been identified in many eukaryotes, including rodents, flies, nematode worms and even single-celled organisms such as baker's yeast (reviewed in[2,3]). These genes appear to be part of an evolutionarily conserved longevity pathway that evolved to promote survival in response to deteriorating environmental conditions[1,4]. The yeast *S. cerevisiae* has proven a particularly useful model in which to study cell autonomous pathways of longevity regulation[2]. In this organism, replicative lifespan is defined as the number of daughter cells an individual mother cell produces before dying. Yeast lifespan extension is governed by PNC1, a calorie restriction (CR)— and stress-responsive gene that depletes nicotinamide, a potent inhibitor of the longevity protein Sir2. Both PNC1 and SIR2 are required for lifespan extension by CR or mild stress[5,6] and additional copies of these genes extend lifespan 30-70%[5-7]. Based on these results we proposed that CR may confer health benefits in a variety of species because it is a mild stress that induces a sirtuin-mediated organismal defense response[6].

Sir2, a histone deacetylase (HDAC), is the founding member of the sirtuin deacetylase family, which is characterized by a requirement for NAD$^+$ as a co-substrate[8-13]. SIR2 was originally identified as a gene required for the formation of transcriptionally silent heterochromatin at yeast mating-type loci[14]. Subsequent studies have shown that Sir2 suppresses recombination between repetitive DNA sequences at ribosomal RNA genes (rDNA)[15-17]. Sir2 has also been implicated in the partitioning of carbonylated proteins to yeast mother cells during budding[18]. Studies in *C. elegans*, mammalian cells, and the single-celled parasite *Leishmania*, indicate that the survival and longevity functions of sirtuins are conserved[19-22]. In *C. elegans* additional copies of sir-2.1 extend lifespan by 50% via the insulin/IGF-1 signalling pathway, the same pathway recently shown to regulate lifespan in rodents[23-25].

SUMMARY

Provided herein are methods for activating a sirtuin deacetylase protein family member. The method may comprise contacting a sirtuin deacetylase protein family member with a compound having a structure selected from the group consisting of formulas 1-25, 30 and 32-65. Compounds falling within formulas 1-25, 30 and 32-65 and activating a sirtuin protein are referred to herein as "activating compounds." The activating compound may be a polyphenol compound, such as a plant polyphenol or an analog or derivative thereof. Exemplary compounds are selected from the group consisting of flavones, stilbenes, flavanones, isoflavones, catechins, chalcones, tannins and anthocyanidins or analog or derivative thereof. In illustrative embodiments, compounds are selected from the group consisting of resveratrol, butein, piceatannol, isoliquiritgenin, fisetin, luteolin, 3,6,3',4'-tetrahydroxyflavone, quercetin, and analogs and derivatives thereof. In certain embodiments, if the activating compound is a naturally occurring compound, it may not in a form in which it is naturally occurring.

The sirtuin deacetylase protein family member may be the human SIRT1 protein or the yeast Sir2 protein.

The sirtuin deacetylase protein family member may be in a cell, in which case the method may comprise contacting the cell with an activating compound or introducing a compound into the cell. The cell may be in vitro. The cell may be a cell of a subject. The cell may be in a subject and the method may comprise administering the activating compound to the subject. Methods may further comprise determining the activity of the sirtuin deacetylase protein family member.

A cell may be contacted with an activating compound at a concentration of about 0.1-100 µM. In certain embodiments, a cell is further contacted with an additional activating compound. In other embodiments, a cell is contacted with a least three different activating compounds.

Other methods encompassed herein include methods for inhibiting the activity of p53 in a cell and optionally protecting the cell against apoptosis, e.g., comprising contacting the cell with an activating compound at a concentration of less than about 0.5 µM. Another method comprises stimulating the activity of p53 in a cell and optionally inducing apoptosis in the cell, comprising contacting the cell with an activating compound at a concentration of at least about 50 µM.

Also provided herein is a method for extending the lifespan of a eukaryotic cell, such as by increasing its resistance to stress, comprising contacting the cell with a compound selected from the group consisting of stilbene, flavone and chalcone family members. Such compounds are referred to as "lifespan extending compounds." The compound may have the structure set forth in formula 7. Other compounds may be activating compounds having a structure set forth in any of formulas 1-25, 30 and 32-65, provided they extend lifespan or increase resistance to stress. The compound may be selected from the group consisting of resveratrol, butein and fisetin and analogs and derivatives thereof. In certain embodiments, if the lifespan extending compound is a naturally occurring compound, it is not in a form in which it is naturally occurring. The method may further comprise determining the lifespan of the cell. The method may also further comprise contacting the cell with an additional compound or with at least three compounds selected from the group consisting of stilbene, flavone and chalcone family members or other lifespan extending compound. The cell may be contacted with a compound at a concentration of less than about 10 µM or at a concentration of about 10-100 µM. The cell may be in vitro or in vivo, it may be a yeast cell or a mammalian cell. If the cell is in a subject, the method may comprise administering the compound to the subject.

Methods for inhibiting sirtuins; inhibiting deacetylation of p53; stimulating apoptosis; shorting lifespan and rendering cells and organisms sensitive to stress are also encompassed. One method comprises contacting a sirtuin or cell or organism comprising such with an inhibitory compound having a formula selected from the group of formulas 26-29, 31 and 66-68.

Also provided herein are compositions comprising, e.g., at least one or at least two compounds each having a formula selected from the group consisting of formulas 1-68. Further provided herein are screening methods for identifying compounds, e.g., small molecules, that modulate sirtuins and/or modulate the life span or resistance to stress of cells. Methods may comprise (i) contacting a cell comprising a SIRT1 protein with a peptide of p53 comprising an acetylated residue 382 in the presence of an inhibitor of class I and class II HDAC under conditions appropriate for SIRT1 to deacetylate the peptide and (ii) determining the level of acetylation of the peptide, wherein a different level of acetylation of the peptide in the presence of the test compound relative to the absence of the test compound indicates that the test compound modulates SIRT1 in vivo.

BRIEF DESCRIPTION OF THE DRAWINGS

FIG. 1 shows the effects of resveratrol on the kinetics of recombinant human SIRT1. a, Resveratrol dose-response of SIRT1 catalytic rate at 25 μM NAD$^+$, 25 μM p53-382 acetylated peptide. Relative initial rates are the mean of two determinations, each derived from the slopes of fluorescence (arbitrary fluorescence units, AFU) vs. time plots with data obtained at 0, 5, 10 and 20 min. of deacetylation. b, SIRT1 initial rate at 3 mM NAD$^+$, as a function of p53-382 acetylated peptide concentration in the presence (Δ) or absence (v) of 100 μM resveratrol. Lines represent non-linear least-squares fits to the Michaelis-Menten equation. Kinetic constants: $K_m$(control, v)=64 μM, $K_m$ (+resveratrol, Δ)=1.8 μM; $V_{max}$(control, v)=1107 AFU/min., $V_{max}$(+resveratrol, Δ)=926 AFU/min. c, SIRT1 initial rate at 1 mM p53-382 acetylated peptide, as a function of NAD$^+$ concentration, in the presence (Δ) or absence (v) of 100 μM resveratrol. Lines represent non-linear least-squares fits to the Michaelis-Menten equation. Kinetic constants: $K_m$(control, v)=558 μM, $K_m$(+resveratrol, Δ)=101 μM; $V_{max}$(control, v)=1863 AFU/min., $V_{max}$(+resveratrol, Δ)=1749 AFU/min. d, Effects of resveratrol on nicotinamide inhibition of SIRT1. Kinetic constants are shown relative to those of the control (no nicotinamide, no resveratrol) and represent the mean of two determinations. Error bars are standard errors of the mean. The variable substrate in each experiment (N=NAD$^+$, P=p53 acetylated peptide), the presence/absence of nicotinamide (+/−) and the resveratrol concentration (μM) are indicated beneath each pair of $K_m$-$V_{max}$ bars.

FIG. 4 shows that resveratrol and other polyphenols stimulate SIRT1 activity in human cells. a, Method for assaying intracellular deacetylase activity with a fluorogenic, cell-permeable substrate, FdL ('Fluor de Lys', BIOMOL). FdL (200 μM) is added to growth media and cells incubated for 1-3 hours to allow FdL to enter the cells and the lysine-deacetylated product (deAc-FdL) to accumulate intracellularly. Cells are lysed with detergent in the presence of 1 μM TSA, 1 mM nicotinamide. Addition of the non-cell-permeable Developer (BIOMOL) releases a fluorophor, specifically from deAc-FdL. b, SIRT1 activating polyphenols can stimulate TSA-insensitive, FdL deacetylation by HeLa S3 cells. Cells were grown adherently in DMEM/10% FCS and treated for 1 hour with 200 μM FdL, 1 μM TSA and either vehicle (0.5% final DMSO, Control) or 500 μM of the indicated compound. Intracellular accumulation of deAc-FdL was then determined as described briefly in a. The intracellular deAc-FdL level for each compound (mean of six replicates) are plotted against the ratios to the control rate obtained in the in vitro SIRT1 polyphenol screen (see Table 1, Supplementary Tables 1 and 3). c, U2OS osteosarcoma cells grown to ≧90% confluence in DMEM/10% FCS were exposed to 0 or 10 grays of gamma irradiation (IR). Whole cell lysates were prepared 4 hours post-irradiation and were probed by Western blotting with indicated antibodies. d, U2OS cells cultured as above were pre-treated with the indicated amounts of resveratrol or a 0.5% DMSO blank for 4 hours after which cells were exposed to 0 or 50 J/cm$^2$ of UV radiation. Lysates were prepared and analyzed by Western blot as in c. e, Human embryonic kidney cells (HEK 293) expressing wild type SIRT1 or dominant negative SIRT1-H363Y (SIRT1-HY) protein were cultured as above, pre-treated with the indicated amounts of resveratrol or a 0.5% DMSO blank for 4 hours and exposed to 50 J/cm$^2$ of UV radiation as above. Lysates were prepared and analyzed as above.

FIG. 8 shows an alignment of the amino acid sequences of hSIRT2 (SEQ ID NO: 3), hSIRT1 (SEQ ID NO: 2) and *S. cerevisiae* Sir2 (SEQ ID NO: 4).

FIG. 9A shows resveratrol and BML-230 dose responses of SIRT1 catalytic rate. Points represent the mean of three determinations and error bars are standard errors of the mean.

FIG. 9B shows the ratio of BML-230-activated to resveratrol-activated SIRT1 rates as a function of activator concentration (the ratios were calculated from data of FIG. 9A).

FIG. 15 shows the stimulation of SIRT 1 catalytic rate by 100 µM plant polyphenols (Table 1).

FIG. 16 shows the effect of 100 µM stilbenes and chalcones on SIRT 1 catalytic rate (Supplementary Table 1).

FIG. 17 shows the effect of 100 µM flavones on SIRT 1 catalytic rate (Supplementary Table 2).

FIG. 18 shows the effect of 100 µM flavones on SIRT 1 catalytic rate (Supplementary Table 3).

FIG. 19 shows the effect of 100 µM isoflavones, flavanones and anthocyanidins on SIRT 1 catalytic rate (Supplementary Table 4).

FIG. 20 shows the effect of 100 µM catechins (Flavan-3-ols) on SIRT 1 catalytic rate (Supplementary Table 5).

FIG. 21 shows the effect of 100 µM free radical protective compounds on SIRT 1 catalytic rate (Supplementary Table 6).

FIG. 22 shows the effect of 100 µM miscellaneous compounds on SIRT 1 catalytic rate (Supplementary Table 7).

FIG. 23 shows the effect of 100 µM of various modulators on SIRT 1 catalytic rate (Supplementary Table 8).

FIG. 24 shows the effect of 100 µM of new resveratrol analogs on SIRT 1 catalytic rate (Table 9).

FIG. 25 shows the effect of 100 µM of new resveratrol analogs on SIRT 1 catalytic rate (Table 10).

FIG. 26 shows the effect of 100 µM of new resveratrol analogs on SIRT 1 catalytic rate (Table 11).

FIG. 27 shows the effect of 100 µM of new resveratrol analogs on SIRT 1 catalytic rate (Table 12).

FIG. 28 shows the effect of 100 µM of new resveratrol analogs on SIRT 1 catalytic rate (Table 13).

FIG. 29 shows synthetic intermediates of resveratrol analog synthesis (Table 14).

FIG. 30 shows synthetic intermediates of resveratrol analog synthesis (Table 15).

FIG. 31 shows synthetic intermediates of resveratrol analog synthesis (Table 16).

FIG. 32 shows synthetic intermediates of resveratrol analog synthesis (Table 17).

FIG. 33 shows synthetic intermediates of resveratrol analog synthesis (Table 18).

FIG. 34 shows the effect of resveratrol on *Drosophila melanogaster* (Table 20).

FIGS. 35A-G shows sirtuin activators and the fold activation of SIRT1 (Table 21).

FIG. 36 shows sirtuin inhibitors and the fold inhibition of SIRT1 (Table 22).

DETAILED DESCRIPTION

Definitions

Figure 2:
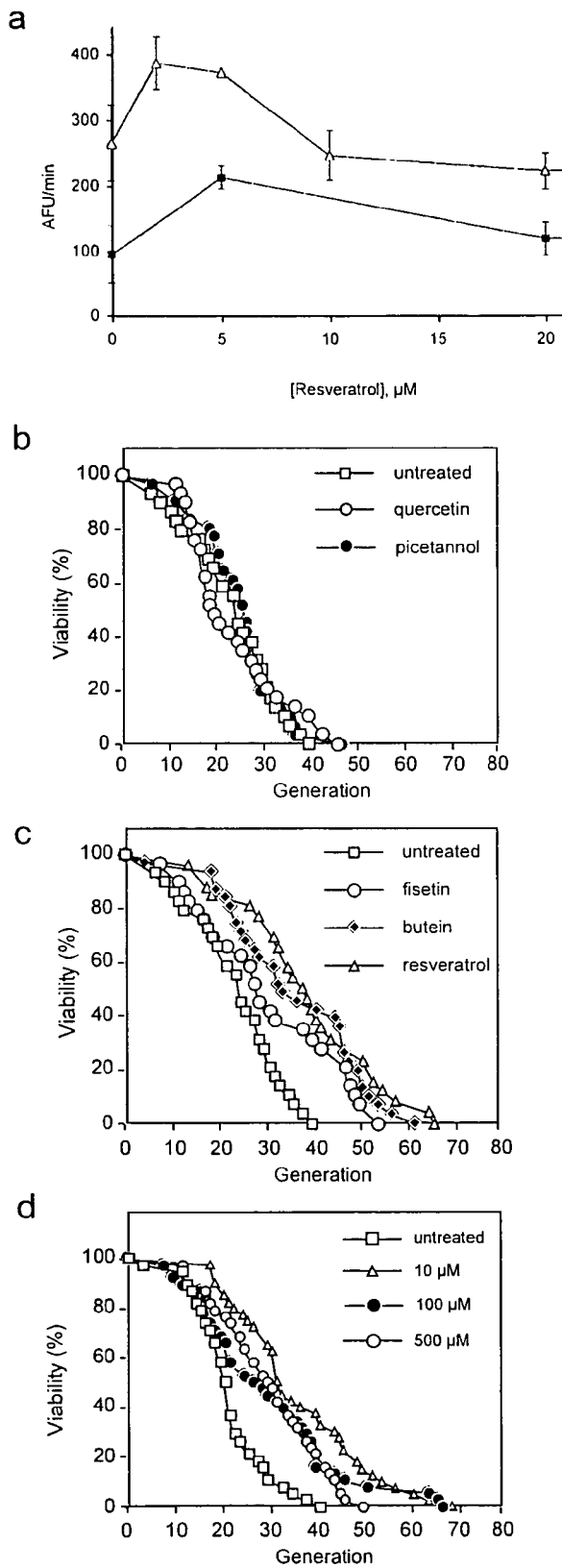
FIG. 2 shows the effects of polyphenols on Sir2 and *S. cerevisiae* lifespan. a, Initial deacetylation rate of recombinant GST-Sir2 as a function of resveratrol concentration. Rates were determined at the indicated resveratrol concentrations, either with 100 μM 'Fluor de Lys' acetylated lysine substrate (FdL) plus 3 mM NAD$^+$ (Δ) or with 200 μM p53-382 acetylated peptide substrate plus 200 μM NAD$^+$ (v). b, Lifespan analyses were determined by micro-manipulating individual yeast cells as described[37] on complete 2% glucose medium with 10 μM of each compound, unless otherwise stated. Average lifespan for wild type, 22.9 generations, quercetin, 23.4; piceatannol. 24.0. c, Average lifespan for wild type, 22.9 generations; fisetin, 30.0; butein, 35.5; resveratrol, 36.8. d, Average lifespan for wild type untreated, 21.0 generations; growth on resveratrol, 10 μM, 35.7; 100 μM, 29.4; 500 μM, 29.3.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

"Activating a sirtuin protein" refers to the action of producing an activated sirtuin protein, i.e., a sirtuin protein that is capable of performing at least one of its biological activities to at least some extent, e.g., with an increase of activity of at least about 10%, 50%, 2 fold or more. Biological activities of sirtuin proteins include deacetylation, e.g., of histones and p53; extending lifespan; increasing genomic stability; silencing transcription; and controlling the segregation of oxidized proteins between mother and daughter cells.

An "activating compound" or a "sirtuin activating compound" refers to a compound that activates a sirtuin protein or stimulates or increases at least one of its activities. Activating compounds may have a formula selected from the group of formulas 1-25, 30 and 32-65.

A "form that is naturally occurring" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature.

"Inhibiting a sirtuin protein" refers to the action of reducing at least one of the biological activities of a sirtuin protein to at least some extent, e.g., at least about 10%, 50%, 2 fold or more.

An "inhibitory compound" or "inhibiting compound" or "sirtuin inhibitory compound" refers to a compound that inhibits a sirtuin protein. Inhibitory compounds may have a formula selected from the group of formulas 26-29, 31 and 66-68.

A "naturally occurring compound" refers to a compound that can be found in nature, i.e., a compound that has not been designed by man. A naturally occurring compound may have been made by man or by nature. For example, resveratrol is a naturally-occurring compound. A "non-naturally occurring compound" is a compound that is not known to exist in nature or that does not occur in nature.

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress. Lifespan can be increased by at least about 20%, 30%, 40%, 50%, 60% or between 20% and 70%, 30% and 60%, 40% and 60% or more using methods described herein.

"Sirtuin deacetylase protein family members;" "Sir2 family members;" "Sir2 protein family members;" or "sirtuin proteins" includes yeast Sir2, Sir-2.1, and human SIRT1 and SIRT2 proteins. The nucleotide and amino acid sequences of the human sirtuin, SIRT1 (silent mating type information regulation 2 homolog), are set forth as SEQ ID NOs: 1 and 2, respectively (corresponding to GenBank Accession numbers NM_012238 and NP_036370, respectively). Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"Biologically active portion of a sirtuin" refers to a portion of a sirtuin protein having a biological activity, such as the ability to deacetylate. Biologically active portions of sirtuins may comprise the core domain of sirtuins. For example, amino acids 62-293 of SIRT1 having SEQ ID NO: 2, which are encoded by nucleotides 237 to 932 of SEQ ID NO: 1, encompass the $NAD^+$ binding domain and the substrate binding domain. Therefore, this region is sometimes referred to as the core domain. Other biologically active portions of SIRT1, also sometimes referred to as core domains, include about amino acids 261 to 447 of SEQ ID NO: 2, which are encoded by nucleotides 834 to 1394 of SEQ ID NO: 1; about amino acids 242 to 493 of SEQ ID NO: 2, which are encoded by nucleotides 777 to 1532 of SEQ ID NO: 1; or about amino acids 254 to 495 of SEQ ID NO: 2, which are encoded by nucleotides 813 to 1538 of SEQ ID NO: 1.

The terms "comprise" and "comprising" are used in the inclusive, open sense, meaning that additional elements may be included.

The term "including" is used to mean "including but not limited to". "Including" and "including but not limited to" are used interchangeably.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. The term thus means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a at a reasonable benefit/risk ratio applicable to such treatment.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "structure-activity relationship" or "(SAR)" is art-recognized and refers to the way in which altering the molecular structure of a drug or other compound alters its biological activity, e.g., its interaction with a receptor, enzyme, nucleic acid or other target and the like.

The term "aliphatic" is art-recognized and refers to a linear, branched, cyclic alkane, alkene, or alkyne. In certain embodiments, aliphatic groups in the present compounds are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, naphtalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

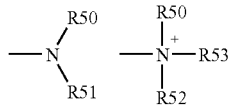

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

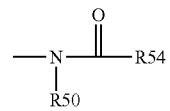

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

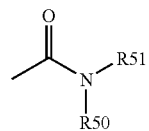

wherein R50 and R51 are as defined above. Certain embodiments of amides may not include imides which may be unstable.

The term "alkylthio" refers to an alkyl group, as defined above, having a sulfur radical attached thereto. In certain embodiments, the "alkylthio" moiety is represented by one of -S-alkyl, -S-alkenyl, -S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

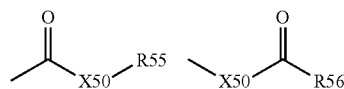

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of -O-alkyl, -O-alkenyl, -O-alkynyl, —O—(CH$_2$)$_m$—R61, where m and R61 are described above.

The term "sulfonate" is art recognized and refers to a moiety that may be represented by the general formula:

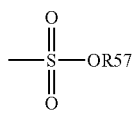

in which R57 is an electron pair, hydrogen, alkyl, cycloalkyl, or aryl.

The term "sulfate" is art recognized and includes a moiety that may be represented by the general formula:

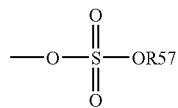

in which R57 is as defined above.

The term "sulfonamido" is art recognized and includes a moiety that may be represented by the general formula:

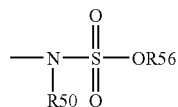

in which R50 and R56 are as defined above.

The term "sulfamoyl" is art-recognized and refers to a moiety that may be represented by the general formula:

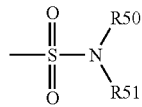

in which R50 and R51 are as defined above.

The term "sulfonyl" is art-recognized and refers to a moiety that may be represented by the general formula:

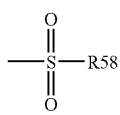

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

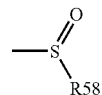

in which R58 is defined above.

The term "phosphoryl" is art-recognized and may in general be represented by the formula:

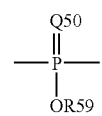

wherein Q50 represents S or O, and R59 represents hydrogen, a lower alkyl or an aryl. When used to substitute, e.g., an alkyl, the phosphoryl group of the phosphorylalkyl may be represented by the general formulas:

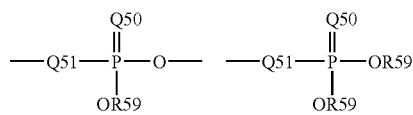

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

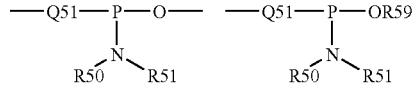

wherein Q51, R50, R51 and R59 are as defined above.

The term "phosphonamidite" is art-recognized and may be represented in the general formulas:

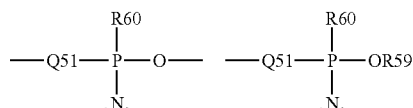

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of -Se-alkyl, -Se-alkenyl, -Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. In addition, compounds may also be optically active. Contemplated herein are all such compounds, including cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are encompassed herein.

If, for instance, a particular enantiomer of a compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. Heteroatoms such as nitrogen may have hydrogen substituents and/or any permissible substituents of organic compounds described herein which satisfy the valences of the heteroatoms. Compounds are not intended to be limited in any manner by the permissible substituents of organic compounds.

The chemical elements are identified in accordance with the Periodic Table of the Elements, CAS version, *Handbook of Chemistry and Physics*, 67th Ed., 1986-87, inside cover.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2nd ed., Wiley: New York, 1991).

The term "hydroxyl-protecting group" is art-recognized and refers to those groups intended to protect a hydroxyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, March, *Advanced Organic Chemistry* 251-59 (McGraw Hill Book Company: New York, 1977). The Hammett constant values are generally negative for electron donating groups (σ(P)=−0.66 for NH₂) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays described herein. The term "small organic molecule" refers to a small molecule that is often identified as being an organic or medicinal compound, and does not include molecules that are exclusively nucleic acids, peptides or polypeptides.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease or preventing a condition or disease from worsening.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Exemplary Methods and Compositions

Provided herein are methods and compounds for activating a sirtuin deacetylase protein family member (referred to as a "sirtuin protein"). The methods may comprise contacting the sirtuin deacetylase protein family member with a compound, such as a polyphenol, e.g. a plant polyphenol, and referred to herein as "activation compound" or "activating compound." Exemplary sirtuin deacetylase proteins include the yeast silent information regulator 2 (Sir2) and human SIRT1. Other family members include proteins having a significant amino acid sequence homology and biological activity, e.g., the ability to deacetylate target proteins, such as histones and p53, to those of Sir2 and SIRT1.

Exemplary activating compounds are those selected from the group consisting of flavones, stilbenes, flavanones, isoflavanones, catechins, chalcones, tannins and anthocyanidins. Exemplary stilbenes include hydroxystilbenes, such as trihydroxystilbenes, e.g., 3,5,4'-trihydroxystilbene ("resveratrol"). Resveratrol is also known as 3,4',5-stilbenetriol. Tetrahydroxystilbenes, e.g., piceatannol, are also encompassed. Hydroxychalones including trihydroxychalones, such as isoliquiritigenin, and tetrahydroxychalones, such as butein, can also be used. Hydroxyflavones including tetrahydroxyflavones, such as fisetin, and pentahydroxyflavones, such as quercetin, can also be used. Exemplary compounds are set forth in Tables 1-13 and 21 (compounds for which the ratio to control rate is >1). The compounds of Tables 1-8 may be obtained from Biomol, Sigma/Aldrich or Indofine.

In one embodiment, methods for activating a sirtuin protein comprise using an activating compound that is a stilbene or chalcone compound of formula 1:

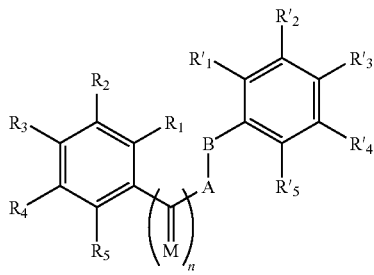

wherein, independently for each occurrence, $R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents O, NR, or S;

A-B represents a bivalent alkyl, alkenyl, alkynyl, amido, sulfonamido, diazo, ether, alkylamino, alkylsulfide, hydroxylamine, or hydrazine group; and n is 0 or 1.

In a further embodiment, the methods comprise a compound of formula 1 and the attendant definitions, wherein n is 0. In a further embodiment, the methods comprise a compound of formula 1 and the attendant definitions, wherein n is 1. In a further embodiment, the methods comprise a compound of formula 1 and the attendant definitions, wherein A-B is ethenyl. In a further embodiment, the methods comprise a compound of formula 1 and the attendant definitions, wherein A-B is —$CH_2CH(Me)CH(Me)CH_2$—. In a further embodiment, the methods comprise a compound of formula 1 and the attendant definitions, wherein M is O. In a further embodiment, the methods comprises a compound of formula 1 and the attendant definitions, wherein $R_1$, $R_2$, $R_3$, $R_4$, $R_5$, $R'_1$, $R'_2$, $R'_3$, $R'_4$, and $R'_5$ are H. In a further embodiment, the methods comprise a compound of formula 1 and the attendant definitions, wherein $R_2$, $R_4$, and $R'_3$ are OH. In a further embodiment, the methods comprise a compound of formula 1 and the attendant definitions, wherein $R_2$, $R_4$, $R'_2$ and $R'_3$ are OH. In a further embodiment, the methods comprise a compound of formula 1 and the attendant definitions, wherein $R_3$, $R_5$, $R'_2$ and $R'_3$ are OH. In a further embodiment, the methods comprise a compound of formula 1 and the attendant definitions, wherein $R_1$, $R_3$, $R_5$, $R'_2$ and $R'_3$ are OH. In a further embodiment, the methods comprise a compound of formula 1 and the attendant definitions, wherein $R_2$ and $R'_2$ are OH; $R_4$ is O-β-D-glucoside; and $R'_3$ is $OCH_3$. In a further embodiment, the methods comprise a compound of formula 1 and the attendant definitions, wherein $R_2$ is OH; $R_4$ is O-β-D-glucoside; and $R'_3$ is $OCH_3$.

In a further embodiment, the methods comprise a compound of formula 1 and the attendant definitions, wherein n is 0; A-B is ethenyl; and $R_1$, $R_2$, $R_3$, $R_4$, $R_5$, $R'_1$, $R'_2$, $R'_3$, $R'_4$, and $R'_5$ are H (trans stilbene). In a further embodiment, the methods comprise a compound of formula 1 and the attendant definitions, wherein n is 1; A-B is ethenyl; M is O; and $R_1$, $R_2$, $R_3$, $R_4$, $R_5$, $R'_1$, $R'_2$, $R'_3$, $R'_4$, and $R'_5$ are H (chalcone). In a further embodiment, the methods comprise a compound of formula 1 and the attendant definitions, wherein n is 0; A-B is ethenyl; $R_2$, $R_4$, and $R'_3$ are OH; and $R_1$, $R_3$, $R_5$, $R'_1$, $R'_2$, $R'_4$, and $R'_5$ are H (resveratrol). In a further embodiment, the methods comprise a compound of formula 1 and the attendant definitions, wherein n is 0; A-B is ethenyl; $R_2$, $R_4$, $R'_2$ and $R'_3$ are OH; and $R_1$, $R_3$, $R_5$, $R'_1$, $R'_4$ and $R'_5$ are H (piceatannol). In a further embodiment, the methods comprise a compound of formula 1 and the attendant definitions, wherein n is 1; A-B is ethenyl; M is O; $R_3$, $R_5$, $R'_2$ and $R'_3$ are OH; and $R_1$, $R_2$, $R_4$, $R'_1$, $R'_4$, and $R'_5$ are H (butein). In a further embodiment, the methods comprise a compound of formula 1 and the attendant definitions, wherein n is 1; A-B is ethenyl; M is O; $R_1$, $R_3$, $R_5$, $R'_2$ and $R'_3$ are OH; and $R_2$, $R_4$, $R'_1$, $R'_4$, and $R'_5$ are H (3,4,2',4',6'-pentahydroxychalcone). In a further embodiment, the methods comprise a compound of formula 1 and the attendant definitions, wherein n is 0; A-B is ethenyl; $R_2$ and $R'_2$ are OH, $R_4$ is O-β-D-glucoside, $R'_3$ is $OCH_3$; and $R_1$, $R_3$, $R_5$, $R'_1$, $R'_4$, and $R'_5$ are H (rhapontin). In a further embodiment, the methods comprise a compound of formula 1 and the attendant definitions, wherein n is 0; A-B is ethenyl; $R_2$ is OH, $R_4$ is O-β-D-glucoside, $R'_3$ is $OCH_3$; and $R_1$, $R_3$, $R_5$, $R'_1$, $R'_2$, $R'_4$, and $R'_5$ are H (deoxyrhapontin). In a further embodiment, the methods comprise a compound of formula 1 and the attendant definitions, wherein n is 0; A-B is —$CH_2CH(Me)CH(Me)CH_2$—; $R_2$, $R_3$, $R'_2$, and $R'_3$ are OH; and $R_1$, $R_4$, $R_5$, $R'_1$, $R'_4$, and $R'_5$ are H (NDGA).

In another embodiment, methods for activating a sirtuin protein comprise using an activating compound that is a flavanone compound of formula 2:

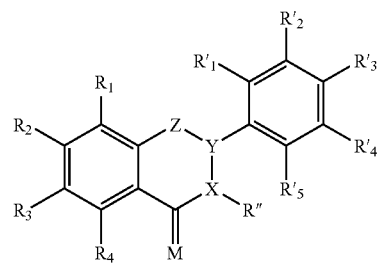

wherein, independently for each occurrence, $R_1$, $R_2$, $R_3$, $R_4$, $R'_1$, $R'_2$, $R'_3$, $R'_4$, $R'_5$, and R" represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents CR, O, NR, or S;

X represents CR or N; and

Y represents CR or N.

In a further embodiment, the methods comprise a compound of formula 2 and the attendant definitions, wherein X and Y are both CH. In a further embodiment, the methods comprise a compound of formula 2 and the attendant definitions, wherein M is O. In a further embodiment, the methods comprise a compound of formula 2 and the attendant definitions, wherein M is $H_2$. In a further embodiment, the methods comprise a compound of formula 2 and the attendant definitions, wherein Z is O. In a further embodiment, the methods comprise a compound of formula 2 and the attendant definitions, wherein R" is H. In a further embodiment, the methods comprise a compound of formula 2 and the attendant definitions, wherein R" is OH. In a further embodiment, the methods comprise a compound of formula 2 and the attendant definitions, wherein R" is an alkoxycarbonyl. In a further embodiment, the methods comprise a compound of formula 2 and the attendant definitions, wherein $R_1$ is

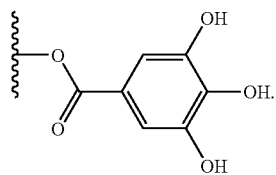

In a further embodiment, the methods comprise a compound of formula 2 and the attendant definitions, wherein $R_1$, $R_2$, $R_3$, $R_4$, $R'_1$, $R'_2$, $R'_3$, $R'_4$, $R'_5$ and R" are H. In a further embodiment, the methods comprise a compound of formula 2 and the attendant definitions, wherein $R_2$, $R_4$, and $R'_3$ are OH. In a further embodiment, the methods comprise a compound of formula 2 and the attendant definitions, wherein $R_4$, $R'_2$, $R'_3$, and R" are OH. In a further embodiment, the methods comprise a compound of formula 2 and the attendant definitions, wherein $R_2$, $R_4$, $R'_2$, $R'_3$, and R" are OH. In a further embodiment, the methods comprise a compound of formula 2 and the attendant definitions, wherein $R_2$, $R_4$, $R'_2$, $R'_3$, $R'_4$, and R" are OH.

In a further embodiment, the methods comprise a compound of formula 2 and the attendant definitions, wherein X and Y are CH; M is O; Z and O; R" is H; and $R_1$, $R_2$, $R_3$, $R_4$, $R'_1$, $R'_2$, $R'_3$, $R'_4$, $R'_5$ and R" are H (flavanone). In a further embodiment, the methods comprise a compound of formula 2 and the attendant definitions, wherein X and Y are CH; M is O; Z and O; R" is H; $R_2$, $R_4$, and $R'_3$ are OH; and $R_1$, $R_3$, $R'_1$, $R'_2$, $R'_4$, and $R'_5$ are H (naringenin). In a further embodiment, the methods comprise a compound of formula 2 and the attendant definitions, wherein X and Y are CH; M is O; Z and O; R" is OH; $R_2$, $R_4$, $R'_2$, and $R'_3$ are OH; and $R_1$, $R_3$, $R'_1$, $R'_4$, and $R'_5$ are H (3,5,7,3',4'-pentahydroxyflavanone). In a further embodiment, the methods comprise a compound of formula 2 and the attendant definitions, wherein X and Y are CH; M is $H_2$; Z and O; R" is OH; $R_2$, $R_4$, $R'_2$, and $R'_3$, are OH; and $R_1$, $R_3$, $R'_1$, $R'_4$ and $R'_5$ are H (epicatechin). In a further embodiment, the methods comprise a compound of formula 2 and the attendant definitions, wherein X and Y are CH; M is $H_2$; Z and O; R" is OH; $R_2$, $R_4$, $R'_2$, $R'_3$, and $R'_4$ are OH; and $R_1$, $R_3$, $R'_1$, and $R'_5$ are H (gallocatechin). In a further embodiment, the methods comprise a compound of formula 2 and the attendant definitions, wherein X and Y are CH; M is $H_2$; Z and O; R" is

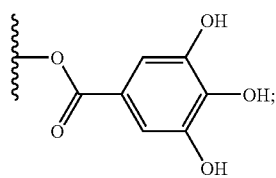

$R_2$, $R_4$, $R'_2$, $R'_3$, $R'_4$, and R" are OH; and $R_1$, $R_3$, $R'_1$, and $R'_5$ are H (epigallocatechin gallate).

In another embodiment, methods for activating a sirtuin protein comprise using an activating compound that is an isoflavanone compound of formula 3:

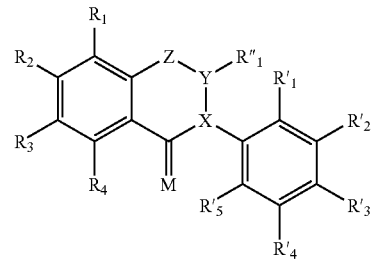

wherein, independently for each occurrence, $R_1$, $R_2$, $R_3$, $R_4$, $R'_1$, $R'_2$, $R'_3$, $R'_4$, $R'_5$, and $R''_1$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents $C(R)_2$, O, NR, or S;

X represents CR or N; and

Y represents CR or N.

In another embodiment, methods for activating a sirtuin protein comprise using an activating compound that is a flavone compound of formula 4:

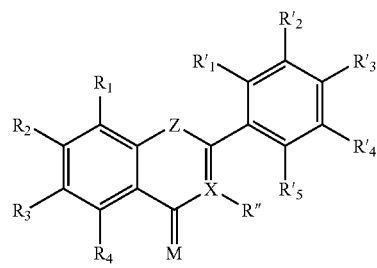

wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents CR, O, NR, or S; and

X represents CR" or N, wherein

R" is H, alkyl, aryl, heteroaryl, alkaryl, heteroaralkyl, halide, $NO_2$, SR, OR, $N(R)_2$, or carboxyl.

In a further embodiment, the methods comprise a compound of formula 4 and the attendant definitions, wherein X is C. In a further embodiment, the methods comprise a compound of formula 4 and the attendant definitions, wherein X is CR. In a further embodiment, the methods comprise a compound of formula 4 and the attendant definitions, wherein Z is O. In a further embodiment, the methods comprise a compound of formula 4 and the attendant definitions, wherein M is O. In a further embodiment, the methods comprise a compound of formula 4 and the attendant definitions, wherein R" is H. In a further embodiment, the methods comprise a compound of formula 4 and the attendant definitions, wherein R" is OH. In a further embodiment, the methods comprise a compound of formula 4 and the attendant definitions, wherein $R_1$, $R_2$, $R_3$, $R_4$, $R'_1$, $R'_2$, $R'_3$, $R'_4$, and $R'_5$ are H. In a further embodiment, the methods comprise a compound of formula 4 and the attendant definitions, wherein $R_2$, $R'_2$, and $R'_3$ are OH. In a further embodiment, the methods comprise a compound of formula 4 and the attendant definitions, wherein $R_2$, $R_4$, $R'_2$, $R'_3$, and $R'_4$ are OH. In a further embodiment, the methods comprise a compound of formula 4 and the attendant definitions, wherein $R_2$, $R_4$, $R'_2$, and $R'_3$ are OH. In a further embodiment, the methods comprise a compound of formula 4 and the attendant definitions, wherein $R_3$, $R'_2$, and $R'_3$ are OH. In a further embodiment, the methods comprise a compound of formula 4 and the attendant definitions, wherein $R_2$, $R_4$, $R'_2$, and $R'_3$ are OH. In a further embodiment, the methods comprise a compound of formula 4 and the attendant definitions, wherein $R_2$, $R'_2$, $R'_3$, and $R'_4$ are OH. In a further embodiment, the methods comprise a compound of formula 4 and the attendant definitions, wherein $R_2$, $R_4$, and $R'_3$ are OH. In a further embodiment, the methods comprise a compound of formula 4 and the attendant definitions, wherein $R_2$, $R_3$, $R_4$, and $R'_3$ are OH. In a further embodiment, the methods comprise a compound of formula 4 and the attendant definitions, wherein $R_2$, $R_4$, and $R'_3$ are OH. In a further embodiment, the methods comprise a compound of formula 4 and the attendant definitions, wherein $R_3$, $R'_1$, and $R'_3$ are OH. In a further embodiment, the methods comprise a compound of formula 4 and the attendant definitions, wherein $R_2$ and $R'_3$ are OH. In a further embodiment, the methods comprise a compound of formula 4 and the attendant definitions, wherein $R_1$, $R_2$, $R'_2$, and $R'_3$ are OH. In a further embodiment, the methods comprise a compound of formula 4 and the attendant definitions, wherein $R_3$, $R'_1$, and $R'_2$ are OH. In a further embodiment, the methods comprise a compound of formula 4 and the attendant definitions, wherein $R'_3$ is OH. In a further embodiment, the methods comprise a compound of formula 4 and the attendant definitions, wherein $R_4$ and $R'_3$ are OH. In a further embodiment, the methods comprise a compound of formula 4 and the attendant definitions, wherein $R_2$ and $R_4$ are OH. In a further embodiment, the methods comprise a compound of formula 4 and the attendant definitions, wherein $R_2$, $R_4$, $R'_1$, and $R'_3$ are OH. In a further embodiment, the methods comprise a compound of formula 4 and the attendant definitions, wherein $R_4$ is OH. In a further embodiment, the methods comprise a compound of formula 4 and the attendant definitions, wherein $R_2$, $R_4$, $R'_2$, $R'_3$, and $R'_4$ are OH. In a further embodiment, the methods comprise a compound of formula 4 and the attendant definitions, wherein $R_2$, $R'_2$, $R'_3$, and $R'_4$ are OH. In a further embodiment, the methods comprise a compound of formula 4 and the attendant definitions, wherein $R_1$, $R_2$, $R_4$, $R'_2$, and $R'_3$ are OH.

In a further embodiment, the methods comprise a compound of formula 4 and the attendant definitions, wherein X is CH; Z is O; M is O; and $R_1$, $R_2$, $R_3$, $R_4$, $R'_1$, $R'_2$, $R'_3$, $R'_4$, and $R'_5$ are H (flavone). In a further embodiment, the methods comprise a compound of formula 4 and the attendant definitions, wherein X is COH; Z is O; M is O; $R_2$, $R'_2$, and $R'_3$ are OH; and $R_1$, $R_3$, $R_4$, $R'_1$, $R'_4$, and $R'_5$ are H (fisetin). In a further embodiment, the methods comprise a compound of formula 4 and the attendant definitions, wherein X is CH; Z is O; M is O; $R_2$, $R_4$, $R'_2$, $R'_3$, and $R'_4$ are OH; and $R_1$, $R_3$, $R'_1$, and $R'_5$ are H (5,7,3',4',5'-pentahydroxyflavone). In a further embodiment, the methods comprise a compound of formula 4 and the attendant definitions, wherein X is CH; Z is O; M is O; $R_2$, $R_4$, $R'_2$, and $R'_3$ are OH; and $R_1$, $R_3$, $R'_1$, $R'_4$, and $R'_5$ are H (luteolin). In a further embodiment, the methods comprise a compound of formula 4 and the attendant definitions, wherein X is COH; Z is O; M is O; $R_3$, $R'_2$, and $R'_3$ are OH; and $R_1$, $R_2$, $R_4$, $R'_1$, $R'_4$, and $R'_5$ are H (3,6,3',4'-tetrahydroxyflavone). In a further embodiment, the methods comprise a compound of formula 4 and the attendant definitions, wherein X is COH; Z is O; M is O; $R_2$, $R_4$, $R'_2$, and $R'_3$ are OH; and $R_1$, $R_3$, $R'_1$, $R'_4$, and $R'_5$ are H (quercetin). In a further embodiment, the methods comprise a compound of formula 4 and the attendant definitions, wherein X is CH; Z is O; M is O; $R_2$, $R'_2$, $R'_3$, and $R'_4$ are OH; and $R_1$, $R_3$, $R_4$, $R'_1$, and $R'_5$ are H. In a further embodiment, the methods comprise a compound of formula 4 and the attendant definitions, wherein X is COH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 4 and the attendant definitions, wherein X is CH; Z is O; M is O; $R_2$, $R_3$, $R_4$, and $R'_3$ are OH; and $R_1$, $R'_1$, $R'_2$, $R'_4$, and $R'_5$ are H. In a further embodiment, the methods comprise a compound of formula 4 and the attendant definitions, wherein X is CH; Z is O; M is O; $R_2$, $R_4$, and $R'_3$ are OH; and $R_1$, $R_3$, $R'_1$, $R'_2$, $R'_4$, and $R'_5$ are H. In a further embodiment, the methods comprise a compound of formula 4 and the attendant definitions, wherein X is COH; Z is O; M is O; $R_3$, $R'_1$, and $R'_3$ are OH; and $R_1$, $R_2$, $R_4$, $R'_2$, $R'_4$, and $R'_5$ are H. In a further embodiment, the methods comprise a compound of formula 4 and the attendant definitions, wherein X is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, the methods comprise a compound of formula 4 and the attendant definitions, wherein X is COH; Z is O; M is O; $R_1$, $R_2$, $R'_2$, and $R'_3$ are OH; and $R_1$, $R_2$, $R_4$, $R'_3$, $R'_4$, and $R'_5$ are H. In a further embodiment, the methods comprise a compound of formula 4 and the attendant definitions, wherein X is COH; Z is O; M is O; $R_3$, $R'_1$, and $R'_2$ are OH; and $R_1$, $R_2$, $R_4$; $R'_3$, $R'_4$, and $R'_5$ are H. In a further embodiment, the methods comprise a compound of formula 4 and the attendant definitions, wherein X is CH; Z is O; M is O; $R'_3$ is OH; and $R_1$, $R_2$, $R_3$, $R_4$, $R'_1$, $R'_2$, $R'_4$, and $R'_5$ are H. In a further embodiment, the methods comprise a compound of formula 4 and the attendant definitions, wherein X is CH; Z is O; M is O; $R_4$ and $R'_3$ are OH; and $R_1$, $R_2$, $R_3$, $R'_1$, $R'_2$, $R'_4$, and $R'_5$ are H. In a further embodiment, the methods comprise a compound of formula 4 and the attendant definitions, wherein X is CH; Z is O; M is O; $R_2$ and $R_4$ are OH; and $R_1$, $R_3$, $R'_1$, $R'_2$, $R'_3$, $R'_4$, and $R'_5$ are H. In a further embodiment, the methods comprise a compound of formula 4 and the attendant definitions, wherein X is COH; Z is O; M is O; $R_2$, $R_4$, $R'_1$, and $R'_3$ are OH; and $R_1$, $R_3$, $R'_2$, $R'_4$, and $R'_5$ are H. In a further embodiment, the methods comprise a compound of formula 4 and the attendant definitions, wherein X is CH; Z is O; M is O; $R_4$ is OH; and $R_1$, $R_2$, $R_3$, $R'_1$, $R'_2$, $R'_3$, $R'_4$, and $R'_5$ are H. In a further embodiment, the methods comprise a compound of formula 4 and the attendant definitions, wherein X is COH; Z is O; M is O; $R_2$, $R_4$, $R'_2$, $R'_3$, and $R'_4$ are OH; and $R_1$, $R_3$, $R'_1$, and $R'_5$ are H. In a further embodiment, the methods comprise a compound of formula 4 and the attendant definitions, wherein X is COH; Z is O; M is O; $R_2$, $R'_2$, $R'_3$, and $R'_4$ are OH; and $R_1$, $R_3$, $R_4$, $R'_1$, and $R'_5$ are H. In a further embodiment, the methods comprise a compound of formula 4 and the attendant definitions, wherein X is COH; Z is O; M is O; $R_1$, $R_2$, $R_4$, $R'_2$, and $R'_3$ are OH; and $R_3$, $R'_1$, $R'_4$, and $R'_5$ are H.

In another embodiment, methods for activating a sirtuin protein comprise using an activating compound that is an isoflavone compound of formula 5:

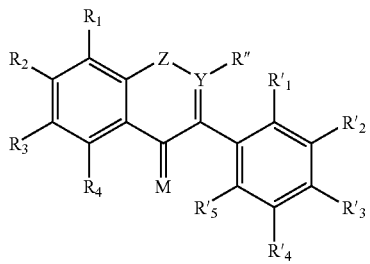

wherein, independently for each occurrence, $R_1$, $R_2$, $R_3$, $R_4$, $R'_1$, $R'_2$, $R'_3$, $R'_4$, and $R'_5$, represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl;

M represents $H_2$, O, NR, or S;

Z represents $C(R)_2$, O, NR, or S; and

Y represents CR" or N, wherein

R" represents H, alkyl, aryl, heteroaryl, alkaryl, heteroaralkyl, halide, $NO_2$, SR, OR, $N(R)_2$, or carboxyl.

In a further embodiment, the methods comprise a compound of formula 5 and the attendant definitions, wherein Y is CR". In a further embodiment, the methods comprise a compound of formula 5 and the attendant definitions, wherein Y is CH. In a further embodiment, the methods comprise a compound of formula 5 and the attendant definitions, wherein Z is O. In a further embodiment, the methods comprise a compound of formula 5 and the attendant definitions, wherein M is O. In a further embodiment, the methods comprise a compound of formula 5 and the attendant definitions, wherein $R_2$ and $R'_3$ are OH. In a further embodiment, the methods comprise a compound of formula 5 and the attendant definitions, wherein $R_2$, $R_4$, and $R'_3$ are OH.

In a further embodiment, the methods comprise a compound of formula 5 and the attendant definitions, wherein Y is CH; Z is O; M is O; $R_2$ and $R'_3$ are OH; and $R_1$, $R_3$, $R_4$, $R'_1$, $R'_2$, $R'_4$, and $R'_5$ are H. In a further embodiment, the methods comprise a compound of formula 5 and the attendant definitions, wherein Y is CH; Z is O; M is O; $R_2$, $R_4$, and $R'_3$ are OH; and $R_1$, $R_3$, $R'_1$, $R'_2$, $R'_4$, and $R'_5$ are H.

In another embodiment, methods for activating a sirtuin protein comprise using an activating compound that is an anthocyanidin compound of formula 6:

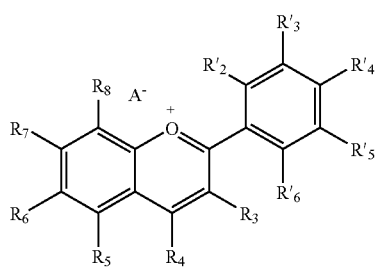

wherein, independently for each occurrence, $R_3$, $R_4$, $R_5$, $R_6$, $R_7$, $R_8$, $R'_2$, $R'_3$, $R'_4$, $R'_5$, and $R'_6$ represent H, alkyl, aryl, heteroaryl, aralkyl, alkaryl, heteroaralkyl, halide, $NO_2$, SR, OR, $N(R)_2$, or carboxyl;

R represents H, alkyl, aryl, heteroaryl, or aralkyl; and $A^-$ represents an anion selected from the following: $Cl^-$, $Br^-$, or $I^-$.

In a further embodiment, the methods comprise a compound of formula 6 and the attendant definitions, wherein $A^-$ is $Cl^-$. In a further embodiment, the methods comprise a compound of formula 6 and the attendant definitions, wherein $R_3$, $R_5$, $R_7$, and $R'_4$ are OH. In a further embodiment, the methods comprise a compound of formula 6 and the attendant definitions, wherein $R_3$, $R_5$, $R_7$, $R'_3$, and $R'_4$ are OH. In a further embodiment, the methods comprise a compound of formula 6 and the attendant definitions, wherein $R_3$, $R_5$, $R_7$, $R'_3$, $R'_4$, and $R'_5$ are OH.

In a further embodiment, the methods comprise a compound of formula 6 and the attendant definitions, wherein $A^-$ is $Cl^-$; $R_3$, $R_5$, $R_7$, and $R'_4$ are OH; and $R_4$, $R_6$, $R_8$, $R'_2$, $R'_3$, $R'_5$, and $R'_6$ are H. In a further embodiment, the methods comprise a compound of formula 6 and the attendant definitions, wherein $A^-$ is $Cl^-$; $R_3$, $R_5$, $R_7$, $R'_3$, and $R'_4$ are OH; and $R_4$, $R_6$, $R_8$, $R'_2$, $R'_5$, and $R'_6$ are H. In a further embodiment, the methods comprise a compound of formula 6 and the attendant definitions, wherein $A^-$ is $Cl^-$; $R_3$, $R_5$, $R_7$, $R'_3$, $R'_4$, and $R'_5$ are OH; and $R_4$, $R_6$, $R_8$, $R'_2$, and $R'_6$ are H.

Methods for activating a sirtuin protein may also comprise using a stilbene, chalcone, or flavone compound represented by formula 7:

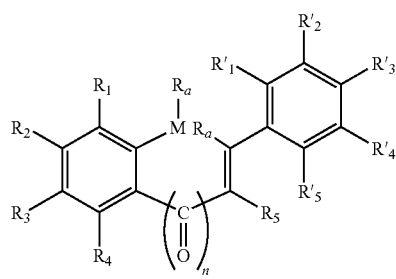

wherein, independently for each occurrence,

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

$R_a$ represents H or the two instances of $R_a$ form a bond;

R represents H, alkyl, aryl, heteroaryl, aralkyl; and n is 0 or 1.

In a further embodiment, the methods comprise an activating compound represented by formula 7 and the attendant definitions, wherein n is 0. In a further embodiment, the methods comprise an activating compound represented by formula 7 and the attendant definitions, wherein n is 1. In a further embodiment, the methods comprise an activating compound represented by formula 7 and the attendant definitions, wherein M is absent. In a further embodiment, the methods comprise an activating compound represented by formula 7 and the attendant definitions, wherein M is O. In a further embodiment, the methods comprise an activating compound represented by formula 7 and the attendant definitions, wherein $R_a$ is H. In a further embodiment, the methods comprise an activating compound represented by formula 7 and the attendant definitions, wherein M is O and the two $R_a$ form a bond.

In a further embodiment, the methods comprise an activating compound represented by formula 7 and the attendant definitions, wherein $R_5$ is H. In a further embodiment, the methods comprise an activating compound represented by formula 7 and the attendant definitions, wherein $R_5$ is OH. In a further embodiment, the methods comprise an activating compound represented by formula 7 and the attendant definitions, wherein $R_1$, $R_3$, and $R'_3$ are OH. In a further embodiment, the methods comprise an activating compound represented by formula 7 and the attendant definitions, wherein $R_2$, $R_4$, $R'_2$, and $R'_3$ are OH. In a further embodiment, the methods comprise an activating compound represented by formula 7 and the attendant definitions, wherein $R_2$, $R'_2$, and $R'_3$ are OH. In a further embodiment, the methods comprise an activating compound represented by formula 7 and the attendant definitions, wherein $R_2$ and $R_4$ are OH.

In a further embodiment, the methods include contacting a cell with an activating compound represented by formula 7 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the methods comprise an activating compound represented by formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the methods comprise an activating compound represented by formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

Other compounds for activating sirtuin deacetylase protein family members include compounds having a formula selected from the group consisting of formulas 8-25 and 30 set forth below.

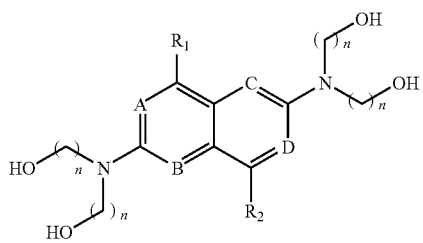

8

$R_1$, $R_2$ = H, aryl, heterocycle, small alkyl
A, B, C, D = $CR_1$, N
n = 0, 1, 2, 3

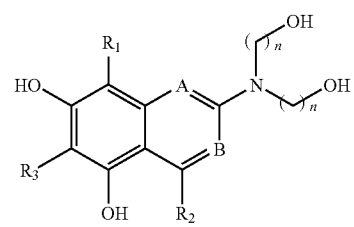

9

$R_1$, $R_2$ = H, aryl, heterocycle, small alkyl
$R_3$ = H, small alkyl
A, B = $CR_1$, N
n = 0, 1, 2, 3

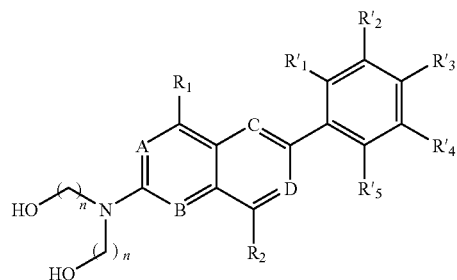

10

$R_1$, $R_2$ = H, aryl, heterocycle, small alkyl
$R'_1$-$R'_5$ = H, OH
A, B, C, D = $CR_1$, N
n = 0, 1, 2, 3

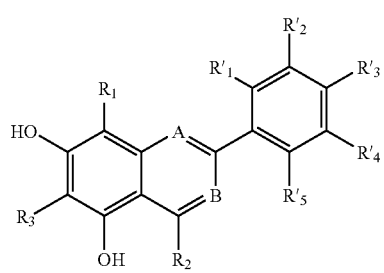

11

$R_1$, $R_2$ = H, aryl, heterocycle, small alkyl
$R_3$ = H, small alkyl
$R'_1$-$R'_5$ = H, OH
A, B = $CR_1$, N
n = 0, 1, 2, 3

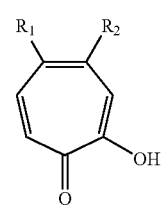

12

$R_1$, $R_2$ = H, alkyl, alkenyl

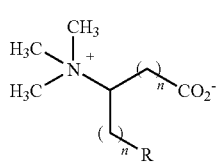

13

R = Heterocycle, aryl
n = 0-10

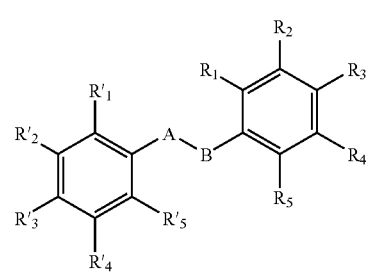

14

-continued

15
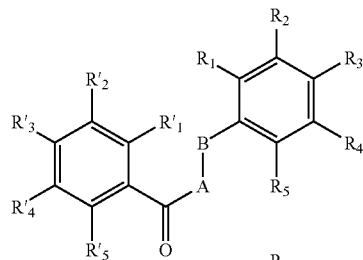

16
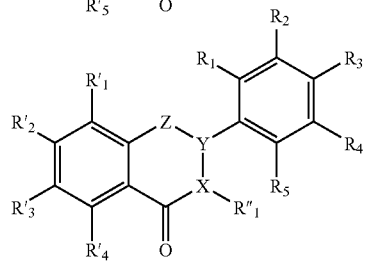

17
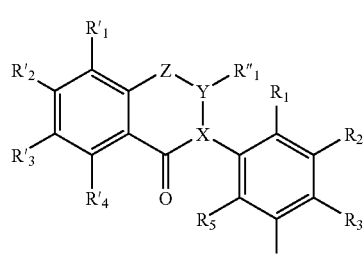

18
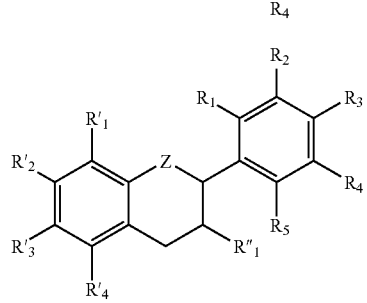

$R_1$ = H, halogen, $NO_2$, SR(R = H, alkyl, aryl), OR(R = H, alkyl, aryl), NRR'(R, R' = alkyl, aryl), alkyl, aryl, carboxy
$R_2$ = H, halogen, $NO_2$, SR(R = H, alkyl, aryl), OR(R = H, alkyl, aryl), NRR'(R, R' = alkyl, aryl), alkyl, aryl, carboxy
$R_3$ = H, halogen, $NO_2$, SR(R = H, alkyl, aryl), OR(R = H, alkyl, aryl), NRR'(R, R' = alkyl, aryl), alkyl, aryl, carboxy
$R_4$ = H, halogen, $NO_2$, SR(R = H, alkyl, aryl), OR(R = H, alkyl, aryl), NRR'(R, R' = alkyl, aryl), alkyl, aryl, carboxy
$R_5$ = H, halogen, $NO_2$, SR(R = H, alkyl, aryl), OR(R = H, alkyl, aryl), NRR'(R, R' = alkyl, aryl), alkyl, aryl, carboxy
$R'_1$ = H, halogen, $NO_2$, SR(R = H, alkyl, aryl), OR(R = H, alkyl, aryl), NRR'(R, R' = alkyl, aryl), alkyl, aryl, carboxy
$R'_2$ = H, halogen, $NO_2$, SR(R = H, alkyl, aryl), OR(R = H, alkyl, aryl), NRR'(R, R' = alkyl, aryl), alkyl, aryl, carboxy
$R'_3$ = H, halogen, $NO_2$, SR(R = H, alkyl, aryl), OR(R = H, alkyl, aryl), NRR'(R, R' = alkyl, aryl), alkyl, aryl, carboxy
$R'_4$ = H, halogen, $NO_2$, SR(R = H, alkyl, aryl), OR(R = H, alkyl, aryl), NRR'(R, R' = alkyl, aryl), alkyl, aryl, carboxy
$R'_5$ = H, halogen, $NO_2$, SR(R = H, alkyl, aryl), OR(R = H, alkyl, aryl), NRR'(R, R' = alkyl, aryl), alkyl, aryl, carboxy
$R''_1$ = H, halogen, $NO_2$, SR(R = H, alkyl, aryl), OR(R = H, alkyl, aryl), NRR'(R, R' = alkyl, aryl), alkyl, aryl, carboxy
A-B = ethene, ethyne, amide, sulfonamide, diazo, alkyl, ether, alkyl amine, alkyl sulfide, hydroxyamine, hydrazine
X = CR, N
Y = CR, N
Z = O, S, $C(R)_2$, NR
R = H, alkyl, aryl, aralkyl 19
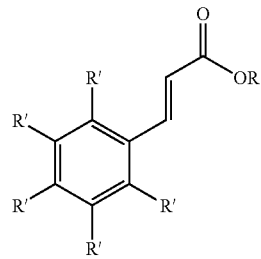

wherein, independently for each occurrence,
R=H, alkyl, aryl, heterocyclyl, heteroaryl, or aralkyl; and
R'=H, halogen, $NO_2$, SR, OR, $NR_2$, alkyl, aryl, or carboxy.

20
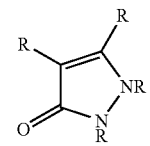

wherein, independently for each occurrence,
R=H, alkyl, aryl, heterocyclyl, heteroaryl, or aralkyl.

21
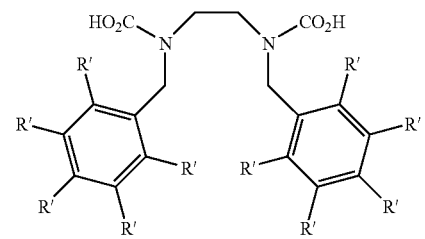

wherein, independently for each occurrence,
R'=H, halogen, $NO_2$, SR, OR, $NR_2$, alkyl, aryl, aralkyl, or carboxy; and
R=H, alkyl, aryl, heterocyclyl, heteroaryl, or aralkyl.

22
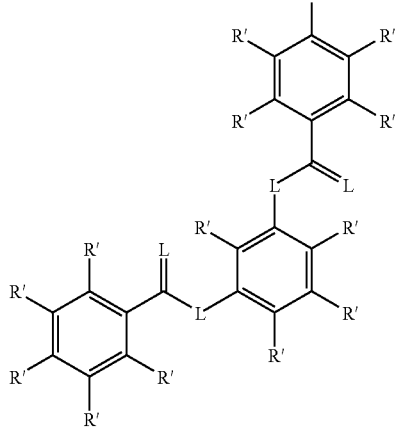

wherein, independently for each occurrence,

L represents $CR_2$, O, NR, or S;

R represents H, alkyl, aryl, aralkyl, or heteroaralkyl; and

R' represents H, halogen, $NO_2$, SR, OR, $NR_2$, alkyl, aryl, aralkyl, or carboxy.

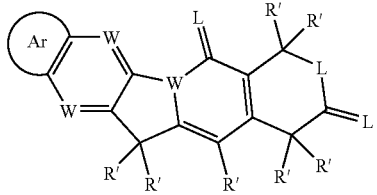

wherein, independently for each occurrence,

L represents $CR_2$, O, NR, or S;

W represents CR or N;

R represents H, alkyl, aryl, aralkyl, or heteroaralkyl;

Ar represents a fused aryl or heteroaryl ring; and

R' represents H, halogen, $NO_2$, SR, OR, $NR_2$, alkyl, aryl, aralkyl, or carboxy.

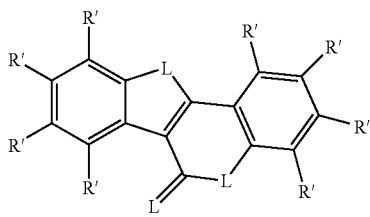

wherein, independently for each occurrence,

L represents $CR_2$, O, NR, or S;

R represents H, alkyl, aryl, aralkyl, or heteroaralkyl; and

R' represents H, halogen, $NO_2$, SR, OR, $NR_2$, alkyl, aryl, aralkyl, or carboxy.

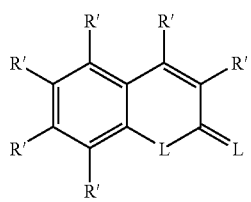

wherein, independently for each occurrence,

L represents $CR_2$, O, NR, or S;

R represents H, alkyl, aryl, aralkyl, or heteroaralkyl; and

R' represents H, halogen, $NO_2$, SR, OR, $NR_2$, alkyl, aryl, aralkyl, or carboxy.

Methods for activating a sirtuin protein may also comprise using a stilbene, chalcone, or flavone compound represented by formula 30:

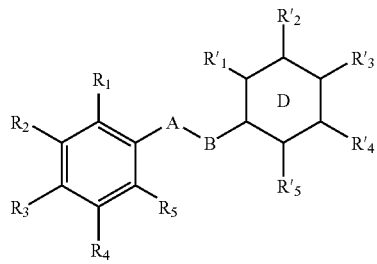

wherein, independently for each occurrence,

D is a phenyl or cyclohexyl group;

$R_1$, $R_2$, $R_3$, $R_4$, $R_5$, $R'_1$, $R'_2$, $R'_3$, $R'_4$, and $R'_5$ represent H, alkyl, aryl, heteroaryl, alkaryl, heteroaralkyl, halide, $NO_2$, SR, OR, $N(R)_2$, carboxyl, azide, ether; or any two adjacent R or R' groups taken together form a fused benzene or cyclohexyl group;

R represents H, alkyl, aryl, or aralkyl; and

A-B represents an ethylene, ethenylene, or imine group;

provided that when A-B is ethenylene, D is phenyl, and $R'_3$ is H: $R_3$ is not OH when $R_1$, $R_2$, $R_4$, and $R_5$ are H; and $R_2$ and $R_4$ are not OMe when $R_1$, $R_3$, and $R_5$ are H; and $R_3$ is not OMe when $R_1$, $R_2$, $R_4$, and $R_5$ are H.

In a further embodiment, the methods include contacting a cell with an activating compound represented by formula 30 and the attendant definitions, wherein D is a phenyl group.

In a further embodiment, the methods include contacting a cell with an activating compound represented by formula 30 and the attendant definitions, wherein A-B is an ethenylene or imine group.

In a further embodiment, the methods include contacting a cell with an activating compound represented by formula 30 and the attendant definitions, wherein A-B is an ethenylene group.

In a further embodiment, the methods include contacting a cell with an activating compound represented by formula 30 and the attendant definitions, wherein $R_2$ is OH.

In a further embodiment, the methods include contacting a cell with an activating compound represented by formula 30 and the attendant definitions, wherein $R_4$ is OH.

In a further embodiment, the methods include contacting a cell with an activating compound represented by formula 30 and the attendant definitions, wherein $R_2$ and $R_4$ are OH.

In a further embodiment, the methods include contacting a cell with an activating compound represented by formula 30 and the attendant definitions, wherein D is a phenyl group; and A-B is an ethenylene group.

In a further embodiment, the methods include contacting a cell with an activating compound represented by formula 30 and the attendant definitions, wherein D is a phenyl group; A-B is an ethenylene group; and $R_2$ and $R_4$ are OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is Cl.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is H.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $CH_2CH_3$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is F.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is Me.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is an azide.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is SMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $NO_2$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is $CH(CH_3)_2$.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OMe.

In a further embodiment, the methods include contacting a cell with an activating compound represented by formula 30 and the attendant definitions, wherein A-B is ethenylene; D is a phenyl ring; $R_2$ and $R_4$ are OH; $R'_2$ is OH; and $R'_3$ is OMe.

In a further embodiment, the methods include contacting a cell with an activating compound represented by formula 30 and the attendant definitions, wherein A-B is ethenylene; D is a phenyl ring; $R_2$ is OH; $R_4$ is carboxyl; and $R'_3$ is OH.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ and $R'_4$ taken together form a fused benzene ring.

In a further embodiment, the methods include contacting a cell with an activating compound represented by formula 30 and the attendant definitions, wherein A-B is ethenylene; D is a phenyl ring; and $R_4$ is OH.

In a further embodiment, the methods include contacting a cell with an activating compound represented by formula 30 and the attendant definitions, wherein A-B is ethenylene; D is a phenyl ring; $R_2$ and $R_4$ are $OCH_2OCH_3$; and $R'_3$ is SMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is carboxyl.

In a further embodiment, the methods include contacting a cell with an activating compound represented by formula 30 and the attendant definitions, wherein A-B is ethenylene; D is a cyclohexyl ring; and $R_2$ and $R_4$ are OH.

In a further embodiment, the methods include contacting a cell with an activating compound represented by formula 30 and the attendant definitions, wherein A-B is ethenylene; D is a phenyl ring; and $R_3$ and $R_4$ are OMe.

In a further embodiment, the methods include contacting a cell with an activating compound represented by formula 30 and the attendant definitions, wherein A-B is ethenylene; D is a phenyl ring; $R_2$ and $R_4$ are OH; and $R'_3$ is OH.

In another embodiment, methods for activating a sirtuin protein comprise using an activating compound of formula 32:

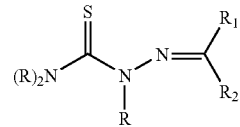

wherein, independently for each occurrence:

R is H, or a substituted or unsubstituted alkyl, aryl, aralkyl, heterocyclyl, heterocyclylalkyl, heteroaryl, or heteroaralkyl; and $R_1$ and $R_2$ are a substituted or unsubstituted alkyl, aryl, aralkyl, heterocyclyl, heterocyclylalkyl, heteroaryl, or heteroaralkyl.

In a further embodiment, the methods comprise a compound of formula 32 and the attendant definitions wherein R is H.

In a further embodiment, the methods comprise a compound of formula 32 and the attendant definitions wherein $R_1$ is 3-hydroxyphenyl.

In a further embodiment, the methods comprise a compound of formula 32 and the attendant definitions wherein $R_2$ is methyl.

In a further embodiment, the methods comprise a compound of formula 32 and the attendant definitions wherein R is H and $R_1$ is 3-hydroxyphenyl.

In a further embodiment, the methods comprise a compound of formula 32 and the attendant definitions wherein R is H, $R_1$ is 3-hydroxyphenyl, and $R_2$ is methyl.

In another embodiment, methods for activating a sirtuin protein comprise using an activating compound of formula 33:

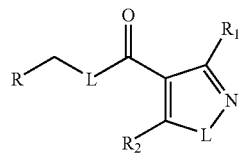

wherein, independently for each occurrence:

R is H, or a substituted or unsubstituted alkyl, alkenyl, or alkynyl;

$R_1$ and $R_2$ are a substituted or unsubstituted alkyl, aryl, aralkyl, heterocyclyl, heterocyclylalkyl, heteroaryl, or heteroaralkyl; and L is O, S, or NR.

In a further embodiment, the methods comprise a compound of formula 33 and the attendant definitions wherein R is alkynyl.

In a further embodiment, the methods comprise a compound of formula 33 and the attendant definitions wherein $R_1$ is 2,6-dichlorophenyl.

In a further embodiment, the methods comprise a compound of formula 33 and the attendant definitions wherein $R_2$ is methyl.

In a further embodiment, the methods comprise a compound of formula 33 and the attendant definitions wherein L is O.

In a further embodiment, the methods comprise a compound of formula 33 and the attendant definitions wherein R is alkynyl and $R_1$ is 2,6-dichlorophenyl.

In a further embodiment, the methods comprise a compound of formula 33 and the attendant definitions wherein R is alkynyl, $R_1$ is 2,6-dichlorophenyl, and $R_2$ is methyl.

In a further embodiment, the methods comprise a compound of formula 33 and the attendant definitions wherein R is alkynyl, $R_1$ is 2,6-dichlorophenyl, $R_2$ is methyl, and L is O.

In another embodiment, methods for activating a sirtuin protein comprise using an activating compound of formula 34:

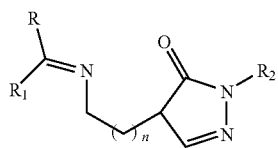

34 wherein, independently for each occurrence:

R, $R_1$, and $R_2$ are H, or a substituted or unsubstituted alkyl, aryl, aralkyl, heterocyclyl, heterocyclylalkyl, heteroaryl, or heteroaralkyl; and n is an integer from 0 to 5 inclusive.

In a further embodiment, the methods comprise a compound of formula 34 and the attendant definitions wherein R is 3,5-dichloro-2-hydroxyphenyl.

In a further embodiment, the methods comprise a compound of formula 34 and the attendant definitions wherein $R_1$ is H.

In a further embodiment, the methods comprise a compound of formula 34 and the attendant definitions wherein $R_2$ is H.

In a further embodiment, the methods comprise a compound of formula 34 and the attendant definitions wherein n is 1.

In a further embodiment, the methods comprise a compound of formula 34 and the attendant definitions wherein R is 3,5-dichloro-2-hydroxyphenyl and $R_1$ is H.

In a further embodiment, the methods comprise a compound of formula 34 and the attendant definitions wherein R is 3,5-dichloro-2-hydroxyphenyl, $R_1$ is H, and $R_2$ is H.

In a further embodiment, the methods comprise a compound of formula 34 and the attendant definitions wherein R is 3,5-dichloro-2-hydroxyphenyl, $R_1$ is H, $R_2$ is H, and n is 1.

In another embodiment, methods for activating a sirtuin protein comprise using an activating compound of formula 35:

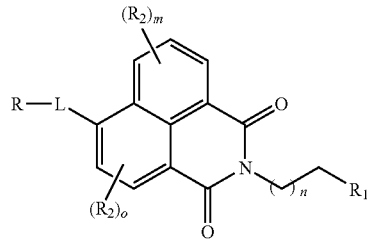

35 wherein, independently for each occurrence:

R is H or a substituted or unsubstituted alkyl, aryl, aralkyl, heterocyclyl, heterocyclylalkyl, heteroaryl, or heteroaralkyl;

$R_1$ is a substituted or unsubstituted alkyl, aryl, aralkyl, heterocyclyl, heterocyclylalkyl, heteroaryl, or heteroaralkyl;

$R_2$ is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, heteroaralkyl;

L is O, NR, or S;

m is an integer from 0 to 3 inclusive;

n is an integer from 0 to 5 inclusive; and o is an integer from 0 to 2 inclusive.

In a further embodiment, the methods comprise a compound of formula 35 and the attendant definitions wherein R is phenyl.

In a further embodiment, the methods comprise a compound of formula 35 and the attendant definitions wherein $R_1$ is pyridine.

In a further embodiment, the methods comprise a compound of formula 35 and the attendant definitions wherein L is S.

In a further embodiment, the methods comprise a compound of formula 35 and the attendant definitions wherein m is 0.

In a further embodiment, the methods comprise a compound of formula 35 and the attendant definitions wherein n is 1.

In a further embodiment, the methods comprise a compound of formula 35 and the attendant definitions wherein o is 0.

In a further embodiment, the methods comprise a compound of formula 35 and the attendant definitions wherein R is phenyl and $R_1$ is pyridine.

In a further embodiment, the methods comprise a compound of formula 35 and the attendant definitions wherein R is phenyl, $R_1$ is pyridine, and L is S.

In a further embodiment, the methods comprise a compound of formula 35 and the attendant definitions wherein R is phenyl, $R_1$ is pyridine, L is S, and m is 0.

In a further embodiment, the methods comprise a compound of formula 35 and the attendant definitions wherein R is phenyl, $R_1$ is pyridine, L is S, m is 0, and n is 1.

In a further embodiment, the methods comprise a compound of formula 35 and the attendant definitions wherein R is phenyl, $R_1$ is pyridine, L is S, m is 0, n is 1, and o is 0.

In another embodiment, methods for activating a sirtuin protein comprise using an activating compound of formula 36:

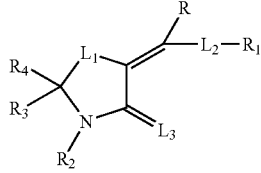

36 wherein, independently for each occurrence:

R, $R_3$, and $R_4$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_1$ and $R_2$ are H or a substituted or unsubstituted alkyl, aryl, aralkyl, heterocyclyl, heterocyclylalkyl, heteroaryl, heteroaralkyl;

$L_1$ is O, $NR_1$, S, $C(R)_2$, or $SO_2$; and $L_2$ and $L_3$ are O, $NR_1$, S, or $C(R)_2$.

In a further embodiment, the methods comprise a compound of formula 36 and the attendant definitions wherein R is H.

In a further embodiment, the methods comprise a compound of formula 36 and the attendant definitions wherein $R_1$ is 4-chlorophenyl.

In a further embodiment, the methods comprise a compound of formula 36 and the attendant definitions wherein $R_2$ is 4-chlorophenyl.

In a further embodiment, the methods comprise a compound of formula 36 and the attendant definitions wherein $R_3$ is H.

In a further embodiment, the methods comprise a compound of formula 36 and the attendant definitions wherein $R_4$ is H.

In a further embodiment, the methods comprise a compound of formula 36 and the attendant definitions wherein $L_1$ is $SO_2$.

In a further embodiment, the methods comprise a compound of formula 36 and the attendant definitions wherein $L_2$ is NH.

In a further embodiment, the methods comprise a compound of formula 36 and the attendant definitions wherein $L_3$ is 0.

In a further embodiment, the methods comprise a compound of formula 36 and the attendant definitions wherein R is H and $R_1$ is 4-chlorophenyl.

In a further embodiment, the methods comprise a compound of formula 36 and the attendant definitions wherein R is H, $R_1$ is 4-chlorophenyl, and $R_2$ is 4-chlorophenyl.

In a further embodiment, the methods comprise a compound of formula 36 and the attendant definitions wherein R is H, $R_1$ is 4-chlorophenyl, $R_2$ is 4-chlorophenyl, and $R_3$ is H.

In a further embodiment, the methods comprise a compound of formula 36 and the attendant definitions wherein R is H, $R_1$ is 4-chlorophenyl, $R_2$ is 4-chlorophenyl, $R_3$ is H, and $R_4$ is H.

In a further embodiment, the methods comprise a compound of formula 36 and the attendant definitions wherein R is H, $R_1$ is 4-chlorophenyl, $R_2$ is 4-chlorophenyl, $R_3$ is H, $R_4$ is H, and $L_1$ is $SO_2$.

In a further embodiment, the methods comprise a compound of formula 36 and the attendant definitions wherein R is H, $R_1$ is 4-chlorophenyl, $R_2$ is 4-chlorophenyl, $R_3$ is H, $R_4$ is H, $L_1$ is $SO_2$, and $L_2$ is NH.

In a further embodiment, the methods comprise a compound of formula 36 and the attendant definitions wherein R is H, $R_1$ is 4-chlorophenyl, $R_2$ is 4-chlorophenyl, $R_3$ is H, $R_4$ is H, $L_1$ is $SO_2$, $L_2$ is NH, and $L_3$ is O.

In another embodiment, methods for activating a sirtuin protein comprise using an activating compound of formula 37:

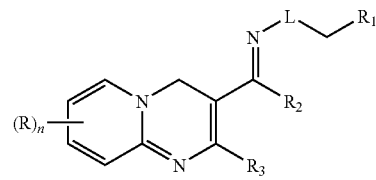

37 wherein, independently for each occurrence:

R is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, heteroaralkyl;

$R_1$ is H or a substituted or unsubstituted alkyl, aryl, aralkyl, heterocyclyl, heterocyclylalkyl, heteroaryl, heteroaralkyl;

$R_2$ and $R_3$ are H or a substituted or unsubstituted alkyl, aryl, aralkyl, heterocyclyl, heterocyclylalkyl, heteroaryl, heteroaralkyl;

L is O, $NR_1$, or S; and n is an integer from 0 to 4 inclusive.

In a further embodiment, the methods comprise a compound of formula 37 and the attendant definitions wherein R is methyl.

In a further embodiment, the methods comprise a compound of formula 37 and the attendant definitions wherein n is 1.

In a further embodiment, the methods comprise a compound of formula 37 and the attendant definitions wherein $R_1$ is 3-fluorophenyl.

In a further embodiment, the methods comprise a compound of formula 37 and the attendant definitions wherein $R_2$ is H.

In a further embodiment, the methods comprise a compound of formula 37 and the attendant definitions wherein $R_3$ is 4-chlorophenyl.

In a further embodiment, the methods comprise a compound of formula 37 and the attendant definitions wherein L is O.

In a further embodiment, the methods comprise a compound of formula 37 and the attendant definitions wherein R is methyl and n is 1.

In a further embodiment, the methods comprise a compound of formula 37 and the attendant definitions wherein R is methyl, n is 1, and $R_1$ is 3-fluorophenyl.

In a further embodiment, the methods comprise a compound of formula 37 and the attendant definitions wherein R is methyl, n is 1, $R_1$ is 3-fluorophenyl, and $R_2$ is H.

In a further embodiment, the methods comprise a compound of formula 37 and the attendant definitions wherein R is methyl, n is 1, $R_1$ is 3-fluorophenyl, $R_2$ is H, and $R_3$ is 4-chlorophenyl.

In another embodiment, methods for activating a sirtuin protein comprise using an activating compound of formula 38:

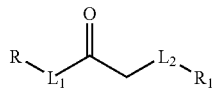

wherein, independently for each occurrence:
R and $R_1$ are H or a substituted or unsubstituted alkyl, aryl, aralkyl, heterocyclyl, heterocyclylalkyl, heteroaryl, or heteroaralkyl; and
$L_1$ and $L_2$ are O, NR, or S.

In a further embodiment, the methods comprise a compound of formula 38 and the attendant definitions wherein R is 3-methoxyphenyl.

In a further embodiment, the methods comprise a compound of formula 38 and the attendant definitions wherein $R_1$ is 4-t-butylphenyl.

In a further embodiment, the methods comprise a compound of formula 38 and the attendant definitions wherein $L_1$ is NH.

In a further embodiment, the methods comprise a compound of formula 38 and the attendant definitions wherein $L_2$ is O.

In a further embodiment, the methods comprise a compound of formula 38 and the attendant definitions wherein R is 3-methoxyphenyl and $R_1$ is 4-t-butylphenyl.

In a further embodiment, the methods comprise a compound of formula 38 and the attendant definitions wherein R is 3-methoxyphenyl, $R_1$ is 4-t-butylphenyl, and $L_1$ is NH.

In a further embodiment, the methods comprise a compound of formula 38 and the attendant definitions wherein R is 3-methoxyphenyl, $R_1$ is 4-t-butylphenyl, $L_1$ is NH, and $L_2$ is O.

In another embodiment, methods for activating a sirtuin protein comprise using an activating compound of formula 39:

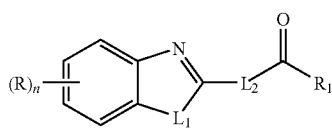

wherein, independently for each occurrence:
R is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_1$ is H or a substituted or unsubstituted alkyl, aryl, alkaryl, heterocyclyl, heterocyclylalkyl, heteroaryl, or heteroaralkyl;
$L_1$ and $L_2$ are O, NR, or S; and
n is an integer from 0 to 4 inclusive.

In a further embodiment, the methods comprise a compound of formula 39 and the attendant definitions wherein R is methyl.

In a further embodiment, the methods comprise a compound of formula 39 and the attendant definitions wherein n is 1.

In a further embodiment, the methods comprise a compound of formula 39 and the attendant definitions wherein $R_1$ is 3,4,5-trimethoxyphenyl.

In a further embodiment, the methods comprise a compound of formula 39 and the attendant definitions wherein $L_1$ is S.

In a further embodiment, the methods comprise a compound of formula 39 and the attendant definitions wherein $L_2$ is NH.

In a further embodiment, the methods comprise a compound of formula 39 and the attendant definitions wherein R is methyl and n is 1.

In a further embodiment, the methods comprise a compound of formula 39 and the attendant definitions wherein R is methyl, n is 1, and $R_1$ is 3,4,5-trimethoxyphenyl.

In a further embodiment, the methods comprise a compound of formula 39 and the attendant definitions wherein R is methyl, n is 1, $R_1$ is 3,4,5-trimethoxyphenyl, and $L_1$ is S.

In a further embodiment, the methods comprise a compound of formula 39 and the attendant definitions wherein R is methyl, n is 1, $R_1$ is 3,4,5-trimethoxyphenyl, $L_1$ is S, and $L_2$ is NH.

In another embodiment, methods for activating a sirtuin protein comprise using an activating compound of formula 40:

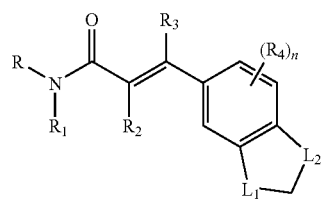

wherein, independently for each occurrence:
R, $R_1$, $R_2$, $R_3$ are H or a substituted or unsubstituted alkyl, aryl, alkaryl, heterocyclyl, heterocyclylalkyl, heteroaryl, or heteroaralkyl;
$R_4$ is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$L_1$ and $L_2$ are O, NR, or S; and
n is an integer from 0 to 3 inclusive.

In a further embodiment, the methods comprise a compound of formula 40 and the attendant definitions wherein R is H.

In a further embodiment, the methods comprise a compound of formula 40 and the attendant definitions wherein $R_1$ is perfluorophenyl.

In a further embodiment, the methods comprise a compound of formula 40 and the attendant definitions wherein $R_2$ is H.

In a further embodiment, the methods comprise a compound of formula 40 and the attendant definitions wherein $R_3$ is H.

In a further embodiment, the methods comprise a compound of formula 40 and the attendant definitions wherein $L_1$ is O.

In a further embodiment, the methods comprise a compound of formula 40 and the attendant definitions wherein $L_2$ is O.

In a further embodiment, the methods comprise a compound of formula 40 and the attendant definitions wherein n is O.

In a further embodiment, the methods comprise a compound of formula 40 and the attendant definitions wherein R is H and $R_1$ is perfluorophenyl.

In a further embodiment, the methods comprise a compound of formula 40 and the attendant definitions wherein R is H, $R_1$ is perfluorophenyl, and $R_2$ is H.

In a further embodiment, the methods comprise a compound of formula 40 and the attendant definitions R is H, $R_1$ is perfluorophenyl, $R_2$ is H, and $R_3$ is H.

In a further embodiment, the methods comprise a compound of formula 40 and the attendant definitions wherein R is H, $R_1$ is perfluorophenyl, $R_2$ is H, $R_3$ is H, and $L_1$ is O.

In a further embodiment, the methods comprise a compound of formula 40 and the attendant definitions wherein R is H, $R_1$ is perfluorophenyl, $R_2$ is H, $R_3$ is H, $L_1$ is O, and $L_2$ is O.

In a further embodiment, the methods comprise a compound of formula 40 and the attendant definitions wherein R is H, $R_1$ is perfluorophenyl, $R_2$ is H, $R_3$ is H, $L_1$ is O, $L_2$ is O, and n is 0.

In another embodiment, methods for activating a sirtuin protein comprise using an activating compound of formula 41:

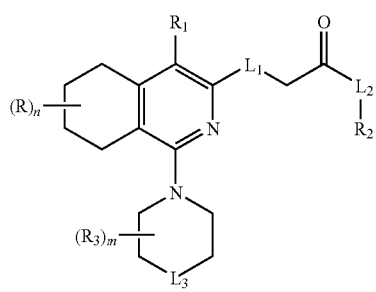

41 wherein, independently for each occurrence:
R, $R_1$, and $R_3$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_2$ is H or a substituted or unsubstituted alkyl, aryl, aralkyl, heterocyclyl, heterocyclylalkyl, heteroaryl, or heteroaralkyl;
$L_1$, $L_2$, and $L_3$ are O, $NR_2$, or S; and
m and n are integers from 0 to 8 inclusive.

In a further embodiment, the methods comprise a compound of formula 41 and the attendant definitions wherein n is 0.

In a further embodiment, the methods comprise a compound of formula 41 and the attendant definitions wherein $R_1$ is cyano.

In a further embodiment, the methods comprise a compound of formula 41 and the attendant definitions wherein $R_2$ is ethyl.

In a further embodiment, the methods comprise a compound of formula 41 and the attendant definitions wherein m is 0.

In a further embodiment, the methods comprise a compound of formula 41 and the attendant definitions wherein $L_1$ is S.

In a further embodiment, the methods comprise a compound of formula 41 and the attendant definitions wherein $L_2$ is O.

In a further embodiment, the methods comprise a compound of formula 41 and the attendant definitions wherein $L_3$ is O.

In a further embodiment, the methods comprise a compound of formula 41 and the attendant definitions wherein n is 0 and $R_1$ is cyano.

In a further embodiment, the methods comprise a compound of formula 41 and the attendant definitions wherein n is 0, $R_1$ is cyano, and $R_2$ is ethyl.

In a further embodiment, the methods comprise a compound of formula 41 and the attendant definitions wherein n is 0, $R_1$ is cyano, $R_2$ is ethyl, and m is 0.

In a further embodiment, the methods comprise a compound of formula 41 and the attendant definitions wherein n is 0, $R_1$ is cyano, $R_2$ is ethyl, m is 0, and $L_1$ is S.

In a further embodiment, the methods comprise a compound of formula 41 and the attendant definitions wherein n is 0, $R_1$ is cyano, $R_2$ is ethyl, m is 0, $L_1$ is S, and $L_2$ is O.

In a further embodiment, the methods comprise a compound of formula 41 and the attendant definitions wherein n is 0, $R_1$ is cyano, $R_2$ is ethyl, m is 0, $L_1$ is S, $L_2$ is O, and $L_3$ is O.

In another embodiment, methods for activating a sirtuin protein comprise using an activating compound of formula 42:

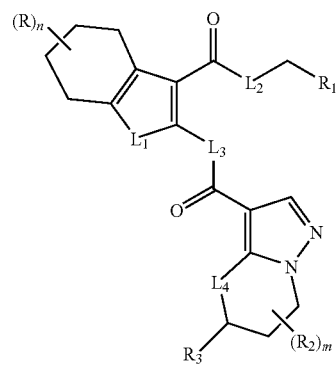

42 wherein, independently for each occurrence:
R and $R_2$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_1$ and $R_3$ are H or a substituted or unsubstituted alkyl, aryl, aralkyl, heterocyclyl, heterocyclylalkyl, heteroaryl, or heteroaralkyl;
$L_1$, $L_2$, $L_3$, and $L_4$ are O, $NR_1$, or S;
m is an integer from 0 to 6 inclusive; and
n is an integer from 0 to 8 inclusive.

In a further embodiment, the methods comprise a compound of formula 42 and the attendant definitions wherein n is 0.

In a further embodiment, the methods comprise a compound of formula 42 and the attendant definitions wherein $R_1$ is methyl.

In a further embodiment, the methods comprise a compound of formula 42 and the attendant definitions wherein $R_2$ is $CF_3$ and m is 1.

In a further embodiment, the methods comprise a compound of formula 42 and the attendant definitions wherein $R_3$ is 4-methylphenyl.

In a further embodiment, the methods comprise a compound of formula 42 and the attendant definitions wherein $L_1$ is S.

In a further embodiment, the methods comprise a compound of formula 42 and the attendant definitions wherein $L_2$ is O.

In a further embodiment, the methods comprise a compound of formula 42 and the attendant definitions wherein $L_3$ is $NR_1$.

In a further embodiment, the methods comprise a compound of formula 42 and the attendant definitions wherein $L_4$ is $NR_1$.

In a further embodiment, the methods comprise a compound of formula 42 and the attendant definitions wherein n is 0 and $R_1$ is methyl.

In a further embodiment, the methods comprise a compound of formula 42 and the attendant definitions wherein n is 0, $R_1$ is methyl, $R_2$ is $CF_3$, and m is 1.

In a further embodiment, the methods comprise a compound of formula 42 and the attendant definitions wherein n is 0, $R_1$ is methyl, $R_2$ is $CF_3$, m is 1; and $R_3$ is 4-methylphenyl.

In a further embodiment, the methods comprise a compound of formula 42 and the attendant definitions wherein n is 0, $R_1$ is methyl, $R_2$ is $CF_3$, m is 1; $R_3$ is 4-methylphenyl; and $L_1$ is S.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, and $L_2$ is O.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, $L_2$ is O; and $L_3$ is $NR_1$.

In a further embodiment, the methods comprise a compound of formula 42 and the attendant definitions wherein n is 0, $R_1$ is methyl, $R_2$ is $CF_3$, m is 1; $R_3$ is 4-methylphenyl; $L_1$ is S, $L_2$ is O; $L_3$ is $NR_1$, and $L_4$ is $NR_1$.

In another embodiment, methods for activating a sirtuin protein comprise using an activating compound of formula 43:

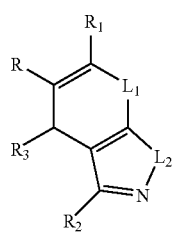

wherein, independently for each occurrence:

R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ and $R_3$ are H or a substituted or unsubstituted alkyl, aryl, aralkyl, heterocyclyl, heterocyclylalkyl, heteroaryl, or heteroaralkyl; and $L_1$ and $L_2$ are O, $NR_2$, or S.

In a further embodiment, the methods comprise a compound of formula 43 and the attendant definitions wherein R is cyano.

In a further embodiment, the methods comprise a compound of formula 43 and the attendant definitions wherein $R_1$ is $NH_2$.

In a further embodiment, the methods comprise a compound of formula 43 and the attendant definitions wherein $R_2$ is 4-bromophenyl.

In a further embodiment, the methods comprise a compound of formula 43 and the attendant definitions wherein $R_3$ is 3-hydroxy-4-methoxyphenyl.

In a further embodiment, the methods comprise a compound of formula 43 and the attendant definitions wherein $L_1$ is O.

In a further embodiment, the methods comprise a compound of formula 43 and the attendant definitions wherein $L_2$ is $NR_2$.

In a further embodiment, the methods comprise a compound of formula 43 and the attendant definitions wherein R is cyano and $R_1$ is $NH_2$.

In a further embodiment, the methods comprise a compound of formula 43 and the attendant definitions wherein R is cyano, $R_1$ is $NH_2$, and $R_2$ is 4-bromophenyl.

In a further embodiment, the methods comprise a compound of formula 43 and the attendant definitions wherein R is cyano, $R_1$ is $NH_2$, $R_2$ is 4-bromophenyl, and $R_3$ is 3-hydroxy-4-methoxyphenyl.

In a further embodiment, the methods comprise a compound of formula 43 and the attendant definitions wherein R is cyano, $R_1$ is $NH_2$, $R_2$ is 4-bromophenyl, $R_3$ is 3-hydroxy-4-methoxyphenyl, and $L_1$ is O.

In a further embodiment, the methods comprise a compound of formula 43 and the attendant definitions wherein R is cyano, $R_1$ is $NH_2$, $R_2$ is 4-bromophenyl, $R_3$ is 3-hydroxy-4-methoxyphenyl, $L_1$ is O, and $L_2$ is $NR_2$.

In another embodiment, methods for activating a sirtuin protein comprise using an activating compound of formula 44:

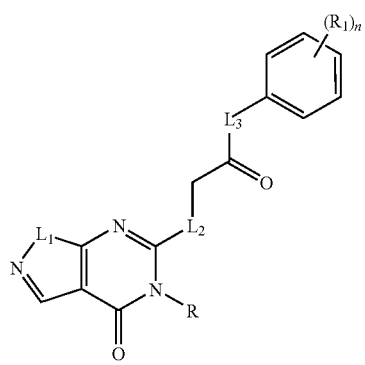

wherein, independently for each occurrence:

R is H or a substituted or unsubstituted alkyl, aryl, aralkyl, heterocyclyl, heterocyclylalkyl, heteroaryl, or heteroaralkyl;

$R_1$ is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, NR, or S; and n is an integer from 0 to 5 inclusive.

In a further embodiment, the methods comprise a compound of formula 44 and the attendant definitions wherein R is 3-trifluoromethylphenyl.

In a further embodiment, the methods comprise a compound of formula 44 and the attendant definitions wherein $R_1$ is $C(O)OCH_3$.

In a further embodiment, the methods comprise a compound of formula 44 and the attendant definitions wherein $L_1$ is NR.

In a further embodiment, the methods comprise a compound of formula 44 and the attendant definitions wherein $L_2$ is S.

In a further embodiment, the methods comprise a compound of formula 44 and the attendant definitions wherein $L_3$ is NR.

In a further embodiment, the methods comprise a compound of formula 44 and the attendant definitions wherein n is 2.

In a further embodiment, the methods comprise a compound of formula 44 and the attendant definitions wherein R is 3-trifluoromethylphenyl and $R_1$ is $C(O)OCH_3$.

In a further embodiment, the methods comprise a compound of formula 44 and the attendant definitions wherein R is 3-trifluoromethylphenyl, $R_1$ is $C(O)OCH_3$, and $L_1$ is NR.

In a further embodiment, the methods comprise a compound of formula 44 and the attendant definitions wherein R is 3-trifluoromethylphenyl, $R_1$ is $C(O)OCH_3$, $L_1$ is NR, and $L_2$ is S.

In a further embodiment, the methods comprise a compound of formula 44 and the attendant definitions wherein R is 3-trifluoromethylphenyl, $R_1$ is $C(O)OCH_3$, $L_1$ is NR, $L_2$ is S, and $L_3$ is NR.

In a further embodiment, the methods comprise a compound of formula 44 and the attendant definitions wherein R is 3-trifluoromethylphenyl, $R_1$ is $C(O)OCH_3$, $L_1$ is NR, $L_2$ is S, $L_3$ is NR, and n is 2.

In another embodiment, methods for activating a sirtuin protein comprise using an activating compound of formula 45:

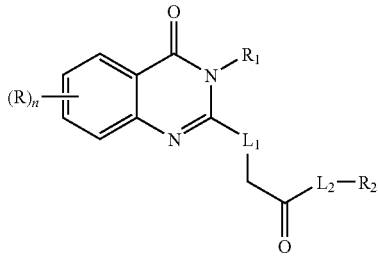

wherein, independently for each occurrence:

R is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H or a substituted or unsubstituted alkyl, aryl, aralkyl, heterocyclyl, heterocyclylalkyl, heteroaryl, or heteroaralkyl;

$L_1$ and $L_2$ are O, $NR_1$, or S; and n is an integer from 0 to 4 inclusive.

In a further embodiment, the methods comprise a compound of formula 45 and the attendant definitions wherein n is 0.

In a further embodiment, the methods comprise a compound of formula 45 and the attendant definitions wherein $R_1$ is 2-tetrahydrofuranylmethyl.

In a further embodiment, the methods comprise a compound of formula 45 and the attendant definitions wherein $R_2$ is $-CH_2CH_2C_6H_4SO_2NH_2$.

In a further embodiment, the methods comprise a compound of formula 45 and the attendant definitions wherein $L_1$ is S.

In a further embodiment, the methods comprise a compound of formula 45 and the attendant definitions wherein $L_2$ is $NR_1$.

In a further embodiment, the methods comprise a compound of formula 45 and the attendant definitions wherein n is 0 and $R_1$ is 2-tetrahydrofuranylmethyl.

In a further embodiment, the methods comprise a compound of formula 45 and the attendant definitions wherein n is 0, $R_1$ is 2-tetrahydrofuranylmethyl, and $R_2$ is $-CH_2CH_2C_6H_4SO_2NH_2$.

In a further embodiment, the methods comprise a compound of formula 45 and the attendant definitions wherein n is 0, $R_1$ is 2-tetrahydrofuranylmethyl, $R_2$ is $-CH_2CH_2C_6H_4SO_2NH_2$, and $L_1$ is S.

In a further embodiment, the methods comprise a compound of formula 45 and the attendant definitions wherein n is 0, $R_1$ is 2-tetrahydrofuranylmethyl, $R_2$ is $-CH_2CH_2C_6H_4SO_2NH_2$, $L_1$ is S, and $L_2$ is $NR_1$.

In another embodiment, methods for activating a sirtuin protein comprise using an activating compound of formula 46:

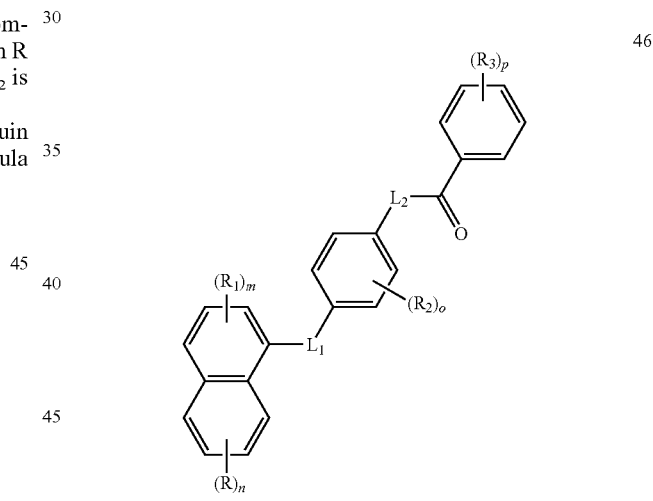

wherein, independently for each occurrence:

R, $R_1$, $R_2$, and $R_3$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$ and $L_2$ are O, $NR_4$, or S;

$R_4$ is H or a substituted or unsubstituted alkyl, aryl, aralkyl, heterocyclyl, heterocyclylalkyl, heteroaryl, or heteroaralkyl;

n is an integer from 0 to 4 inclusive;

m is an integer from 0 to 3 inclusive;

o is an integer from 0 to 4 inclusive; and p is an integer from 0 to 5 inclusive.

In a further embodiment, the methods comprise a compound of formula 46 and the attendant definitions wherein n is 0.

In a further embodiment, the methods comprise a compound of formula 46 and the attendant definitions wherein m is 1.

In a further embodiment, the methods comprise a compound of formula 46 and the attendant definitions wherein $R_1$ is Cl.

In a further embodiment, the methods comprise a compound of formula 46 and the attendant definitions wherein o is 1.

In a further embodiment, the methods comprise a compound of formula 46 and the attendant definitions wherein $R_2$ is Cl.

In a further embodiment, the methods comprise a compound of formula 46 and the attendant definitions wherein p is 3.

In a further embodiment, the methods comprise a compound of formula 46 and the attendant definitions wherein $R_3$ is OH or I.

In a further embodiment, the methods comprise a compound of formula 46 and the attendant definitions wherein n is 0 and m is 1.

In a further embodiment, the methods comprise a compound of formula 46 and the attendant definitions wherein n is 0, m is 1, and o is 1.

In a further embodiment, the methods comprise a compound of formula 46 and the attendant definitions wherein n is 0, m is 1, o is 1, and $R_1$ is Cl.

In a further embodiment, the methods comprise a compound of formula 46 and the attendant definitions wherein n is 0, m is 1, o is 1, $R_1$ is Cl, and p is 3.

In a further embodiment, the methods comprise a compound of formula 46 and the attendant definitions wherein n is 0, m is 1, o is 1, $R_1$ is Cl, p is 3, and $R_2$ is OH or I.

In another embodiment, methods for activating a sirtuin protein comprise using an activating compound of formula 47:

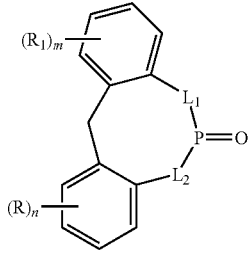

wherein, independently for each occurrence:
R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$L_1$ and $L_2$ are O, $NR_4$, or S;
$R_4$ is H or a substituted or unsubstituted alkyl, aryl, aralkyl, heterocyclyl, heterocyclylalkyl, heteroaryl, or heteroaralkyl; and
m and n are integers from 0 to 4 inclusive.

In a further embodiment, the methods comprise a compound of formula 47 and the attendant definitions wherein n is 2.

In a further embodiment, the methods comprise a compound of formula 47 and the attendant definitions wherein R is methyl or t-butyl.

In a further embodiment, the methods comprise a compound of formula 47 and the attendant definitions wherein m is 2.

In a further embodiment, the methods comprise a compound of formula 47 and the attendant definitions wherein $R_1$ is methyl or t-butyl.

In a further embodiment, the methods comprise a compound of formula 47 and the attendant definitions wherein $L_1$ is O.

In a further embodiment, the methods comprise a compound of formula 47 and the attendant definitions wherein $L_2$ is O.

In a further embodiment, the methods comprise a compound of formula 47 and the attendant definitions wherein n is 2 and R is methyl or t-butyl.

In a further embodiment, the methods comprise a compound of formula 47 and the attendant definitions wherein n is 2, R is methyl or t-butyl, and m is 2.

In a further embodiment, the methods comprise a compound of formula 47 and the attendant definitions wherein n is 2, R is methyl or t-butyl, m is 2, and $R_1$ is methyl or t-butyl.

In a further embodiment, the methods comprise a compound of formula 47 and the attendant definitions wherein n is 2, R is methyl or t-butyl, m is 2, $R_1$ is methyl or t-butyl, and $L_1$ is O.

In a further embodiment, the methods comprise a compound of formula 47 and the attendant definitions wherein n is 2, R is methyl or t-butyl, m is 2, $R_1$ is methyl or t-butyl, $L_1$ is O, and $L_2$ is O.

In another embodiment, methods for activating a sirtuin protein comprise using an activating compound of formula 48:

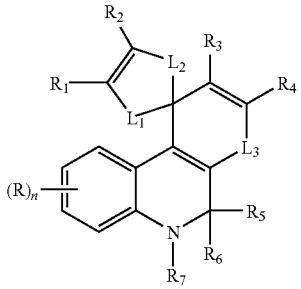

wherein, independently for each occurrence:
R, $R_1$, $R_2$, $R_3$, $R_4$, $R_5$, and $R_6$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_7$ is H or a substituted or unsubstituted alkyl, acyl, aryl, aralkyl, heterocyclyl, heterocyclylalkyl, heteroaryl, or heteroaralkyl;
$L_1$, $L_2$, and $L_3$ are O, $NR_7$, or S and n is an integer from 0 to 4 inclusive.

In a further embodiment, the methods comprise a compound of formula 48 and the attendant definitions wherein n is 1.

In a further embodiment, the methods comprise a compound of formula 48 and the attendant definitions wherein R is methyl.

In a further embodiment, the methods comprise a compound of formula 48 and the attendant definitions wherein $R_1$ is $C(O)OCH_3$.

In a further embodiment, the methods comprise a compound of formula 48 and the attendant definitions wherein $R_2$ is $C(O)OCH_3$.

In a further embodiment, the methods comprise a compound of formula 48 and the attendant definitions wherein $R_3$ is $C(O)OCH_3$.

In a further embodiment, the methods comprise a compound of formula 48 and the attendant definitions wherein $R_4$ is $C(O)OCH_3$.

In a further embodiment, the methods comprise a compound of formula 48 and the attendant definitions wherein $R_5$ is methyl.

In a further embodiment, the methods comprise a compound of formula 48 and the attendant definitions wherein $R_6$ is methyl.

In a further embodiment, the methods comprise a compound of formula 48 and the attendant definitions wherein $R_7$ is $C(O)CF_3$.

In a further embodiment, the methods comprise a compound of formula 48 and the attendant definitions wherein $L_1$ is S.

In a further embodiment, the methods comprise a compound of formula 48 and the attendant definitions wherein $L_2$ is S.

In a further embodiment, the methods comprise a compound of formula 48 and the attendant definitions wherein $L_3$ is S.

In a further embodiment, the methods comprise a compound of formula 48 and the attendant definitions wherein n is 1 and R is methyl.

In a further embodiment, the methods comprise a compound of formula 48 and the attendant definitions wherein n is 1, R is methyl, and $R_1$ is $C(O)OCH_3$.

In a further embodiment, the methods comprise a compound of formula 48 and the attendant definitions wherein n is 1, R is methyl, $R_1$ is $C(O)OCH_3$, and $R_2$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, and $R_3$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, and $R_4$ is $C(O)OCH_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, and $R_5$ is methyl.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, and $R_6$ is methyl.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, and $R_7$ is $C(O)CF_3$.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, and $L_1$ is S.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, and $L_2$ is S.

In a further embodiment, the methods comprise a compound of formula 48 and the attendant definitions wherein n is 1, R is methyl, $R_1$ is $C(O)OCH_3$, $R_2$ is $C(O)OCH_3$, $R_3$ is $C(O)OCH_3$, $R_4$ is $C(O)OCH_3$, $R_5$ is methyl, $R_6$ is methyl, $R_7$ is $C(O)CF_3$, $L_1$ is S, $L_2$ is S, and $L_3$ is S.

In another embodiment, methods for activating a sirtuin protein comprise using an activating compound of formula 49:

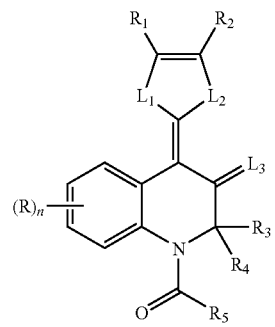

49 wherein, independently for each occurrence:

R, $R_1$, $R_2$, $R_3$, $R_4$, and $R_5$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, $NR_6$, or S;

$R_6$ is H or a substituted or unsubstituted alkyl, aryl, aralkyl, heterocyclyl, heterocyclylalkyl, heteroaryl, or heteroaralkyl; and n is an integer from 0 to 4 inclusive.

In a further embodiment, the methods comprise a compound of formula 49 and the attendant definitions wherein n is 1.

In a further embodiment, the methods comprise a compound of formula 49 and the attendant definitions wherein R is methyl.

In a further embodiment, the methods comprise a compound of formula 49 and the attendant definitions wherein $R_1$ is $C(O)OCH_3$.

In a further embodiment, the methods comprise a compound of formula 49 and the attendant definitions wherein $R_2$ is $C(O)OCH_3$.

In a further embodiment, the methods comprise a compound of formula 49 and the attendant definitions wherein $R_3$ is methyl.

In a further embodiment, the methods comprise a compound of formula 49 and the attendant definitions wherein $R_4$ is methyl.

In a further embodiment, the methods comprise a compound of formula 49 and the attendant definitions wherein $R_5$ is $CH_2CH(CH_3)_2$.

In a further embodiment, the methods comprise a compound of formula 49 and the attendant definitions wherein $L_1$ is S.

In a further embodiment, the methods comprise a compound of formula 49 and the attendant definitions wherein $L_2$ is S.

In a further embodiment, the methods comprise a compound of formula 49 and the attendant definitions wherein $L_3$ is S.

In a further embodiment, the methods comprise a compound of formula 49 and the attendant definitions wherein n is 1 and R is methyl.

In a further embodiment, the methods comprise a compound of formula 49 and the attendant definitions wherein n is 1, R is methyl, and $R_1$ is $C(O)OCH_3$.

In a further embodiment, the methods comprise a compound of formula 49 and the attendant definitions wherein n is 1, R is methyl, $R_1$ is $C(O)OCH_3$, and $R_2$ is $C(O)OCH_3$.

In a further embodiment, the methods comprise a compound of formula 49 and the attendant definitions wherein n is 1, R is methyl, $R_1$ is $C(O)OCH_3$, $R_2$ is $C(O)OCH_3$, and $R_3$ is methyl.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, and $R_4$ is methyl.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, and $R_5$ is $CH_2CH(CH_3)_2$.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, and $L_1$ is S.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, and $L_1$ is S.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, and $L_2$ is S.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, and $L_2$ is S.

In a further embodiment, the methods comprise a compound of formula 49 and the attendant definitions wherein n is 1, R is methyl, $R_1$ is $C(O)OCH_3$, $R_2$ is $C(O)OCH_3$, $R_3$ is methyl, $R_4$ is methyl, $R_5$ is $CH_2CH(CH_3)_2$, $L_1$ is S, $L_2$ is S, and $L_3$ is S.

In another embodiment, methods for activating a sirtuin protein comprise using an activating compound of formula 50:

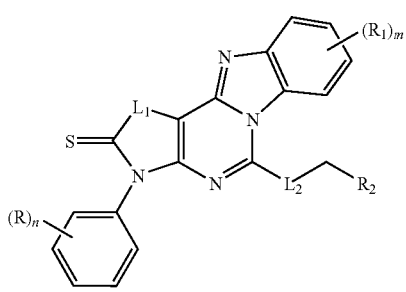

wherein, independently for each occurrence:
R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$R_2$ is H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
$L_1$ and $L_2$ are O, $NR_3$, or S;
$R_3$ is H or a substituted or unsubstituted alkyl, aryl, aralkyl, heterocyclyl, heterocyclylalkyl, heteroaryl, or heteroaralkyl;
n is an integer from 0 to 5 inclusive; and
m is an integer from 0 to 4 inclusive.

In a further embodiment, the methods comprise a compound of formula 50 and the attendant definitions wherein n is 1.

In a further embodiment, the methods comprise a compound of formula 50 and the attendant definitions wherein R is $CO_2Et$.

In a further embodiment, the methods comprise a compound of formula 50 and the attendant definitions wherein m is 0.

In a further embodiment, the methods comprise a compound of formula 50 and the attendant definitions wherein $R_2$ is cyano.

In a further embodiment, the methods comprise a compound of formula 50 and the attendant definitions wherein $L_1$ is S.

In a further embodiment, the methods comprise a compound of formula 50 and the attendant definitions wherein $L_2$ is S.

In a further embodiment, the methods comprise a compound of formula 50 and the attendant definitions wherein n is 1 and R is $CO_2Et$.

In a further embodiment, the methods comprise a compound of formula 50 and the attendant definitions wherein n is 1, R is $CO_2Et$, and m is 0.

In a further embodiment, the methods comprise a compound of formula 50 and the attendant definitions wherein n is 1, R is $CO_2Et$, m is 0, and $R_2$ is cyano.

In a further embodiment, the methods comprise a compound of formula 50 and the attendant definitions wherein n is 1, R is $CO_2Et$, m is 0, $R_2$ is cyano, and $L_1$ is S.

In a further embodiment, the methods comprise a compound of formula 50 and the attendant definitions wherein n is 1, R is $CO_2Et$, m is 0, $R_2$ is cyano, $L_1$ is S, and $L_2$ is S.

In another embodiment, methods for activating a sirtuin protein comprise using an activating compound of formula 51:

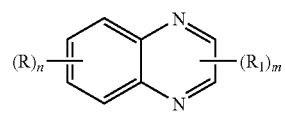

wherein, independently for each occurrence:
R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;
n is an integer from 0 to 4 inclusive; and
m is an integer from 0 to 2 inclusive.

In a further embodiment, the methods comprise a compound of formula 51 and the attendant definitions wherein n is 2.

In a further embodiment, the methods comprise a compound of formula 51 and the attendant definitions wherein R is Cl or trifluoromethyl.

In a further embodiment, the methods comprise a compound of formula 51 and the attendant definitions wherein m is 2.

In a further embodiment, the methods comprise a compound of formula 51 and the attendant definitions wherein $R_1$ is phenyl.

In a further embodiment, the methods comprise a compound of formula 51 and the attendant definitions wherein n is 2 and R is Cl or trifluoromethyl.

In a further embodiment, the methods comprise a compound of formula 51 and the attendant definitions wherein n is 2, R is Cl or trifluoromethyl, and m is 2.

In a further embodiment, the methods comprise a compound of formula 51 and the attendant definitions wherein n is 2, R is Cl or trifluoromethyl, m is 2, and $R_1$ is phenyl.

In a further embodiment, the methods comprise a compound of formula 51 and the attendant definitions wherein n is 1.

In a further embodiment, the methods comprise a compound of formula 51 and the attendant definitions wherein R is F.

In a further embodiment, the methods comprise a compound of formula 51 and the attendant definitions wherein $R_1$ is 4-methylphenyl.

In a further embodiment, the methods comprise a compound of formula 51 and the attendant definitions wherein n is 1 and R is F.

In a further embodiment, the methods comprise a compound of formula 51 and the attendant definitions wherein n is 1, R is F, and m is 2.

In a further embodiment, the methods comprise a compound of formula 51 and the attendant definitions wherein n is 1, R is F, m is 2, and $R_1$ is 4-methylphenyl.

In another embodiment, methods for activating a sirtuin protein comprise using an activating compound of formula 52:

52 wherein, independently for each occurrence:

R is H or a substituted or unsubstituted alkyl, aryl, aralkyl, heterocyclyl, heterocyclylalkyl, heteroaryl, or heteroaralkyl;

$R_1$ and $R_6$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_2$ is alkylene, alkenylene, or alkynylene; $R_3$, $R_4$, and $R_5$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, NR, or S;

n and p are integers from 0 to 3 inclusive; and m and o are integers from 0 to 2 inclusive.

In a further embodiment, the methods comprise a compound of formula 52 and the attendant definitions wherein R is $CH_2CH_2OH$.

In a further embodiment, the methods comprise a compound of formula 52 and the attendant definitions wherein n is 1.

In a further embodiment, the methods comprise a compound of formula 52 and the attendant definitions wherein $R_1$ is 1.

In a further embodiment, the methods comprise a compound of formula 52 and the attendant definitions wherein $R_2$ is alkynylene.

In a further embodiment, the methods comprise a compound of formula 52 and the attendant definitions wherein m is 1.

In a further embodiment, the methods comprise a compound of formula 52 and the attendant definitions wherein $R_3$ is OH.

In a further embodiment, the methods comprise a compound of formula 52 and the attendant definitions wherein $R_4$ is C(O)OEt.

In a further embodiment, the methods comprise a compound of formula 52 and the attendant definitions wherein o is 1.

In a further embodiment, the methods comprise a compound of formula 52 and the attendant definitions wherein $R_5$ is OH.

In a further embodiment, the methods comprise a compound of formula 52 and the attendant definitions wherein p is 0.

In a further embodiment, the methods comprise a compound of formula 52 and the attendant definitions wherein $L_1$ is NH.

In a further embodiment, the methods comprise a compound of formula 52 and the attendant definitions wherein $L_2$ is O.

In a further embodiment, the methods comprise a compound of formula 52 and the attendant definitions wherein $L_3$ is O.

In a further embodiment, the methods comprise a compound of formula 52 and the attendant definitions wherein R is $CH_2CH_2OH$ and n is 1.

In a further embodiment, the methods comprise a compound of formula 52 and the attendant definitions wherein R is $CH_2CH_2OH$, n is 1, and $R_1$ is I.

In a further embodiment, the methods comprise a compound of formula 52 and the attendant definitions wherein R is $CH_2CH_2OH$, n is 1, $R_1$ is I, and $R_2$ is alkynylene.

In a further embodiment, the methods comprise a compound of formula 52 and the attendant definitions wherein R is $CH_2CH_2OH$, n is 1, $R_1$ is I, $R_2$ is alkynylene, and m is 1.

In a further embodiment, the methods comprise a compound of formula 52 and the attendant definitions wherein R is $CH_2CH_2OH$, n is 1, $R_1$ is I, $R_2$ is alkynylene, m is 1, and $R_3$ is OH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, and $R_4$ is C(O)OEt.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, and o is 1.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, and $R_5$ is OH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, and p is 0.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, and $L_1$ is NH.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, $L_1$ is NH, and $L_2$ is O.

In a further embodiment, the methods comprise a compound of formula 52 and the attendant definitions wherein R is $CH_2CH_2OH$, n is 1, $R_1$ is I, $R_2$ is alkynylene, m is 1, $R_3$ is OH, $R_4$ is C(O)OEt, o is 1, $R_5$ is OH, p is 0, $L_1$ is NH, $L_2$ is O, and $L_3$ is O.

In another embodiment, methods for activating a sirtuin protein comprise using an activating compound of formula 53:

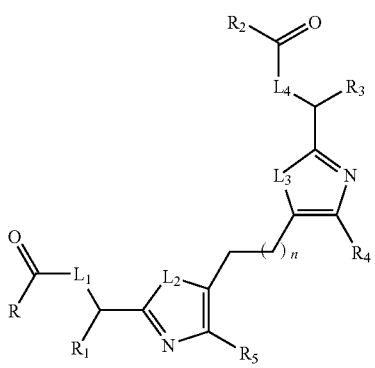

wherein, independently for each occurrence:

R, $R_1$, $R_2$, $R_3$, $R_4$, and $R_5$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, $L_3$, and $L_4$ are O, $NR_6$, or S;

$R_6$ is and H, or a substituted or unsubstituted alkyl, aryl, aralkyl, heterocyclyl, heterocyclylalkyl, heteroaryl, or heteroaralkyl; and n is an integer from 0 to 5 inclusive.

In a further embodiment, the methods comprise a compound of formula 53 and the attendant definitions wherein R is O-t-butyl.

In a further embodiment, the methods comprise a compound of formula 53 and the attendant definitions wherein $R_1$ is O-t-butyl.

In a further embodiment, the methods comprise a compound of formula 53 and the attendant definitions wherein $R_2$ is O-t-butyl.

In a further embodiment, the methods comprise a compound of formula 53 and the attendant definitions wherein $R_3$ is t-butyl.

In a further embodiment, the methods comprise a compound of formula 53 and the attendant definitions wherein $R_4$ is C(O)OMe.

In a further embodiment, the methods comprise a compound of formula 53 and the attendant definitions wherein $R_5$ is C(O)OMe.

In a further embodiment, the methods comprise a compound of formula 53 and the attendant definitions wherein $L_1$ is NH.

In a further embodiment, the methods comprise a compound of formula 53 and the attendant definitions wherein $L_2$ is O.

In a further embodiment, the methods comprise a compound of formula 53 and the attendant definitions wherein $L_3$ is O.

In a further embodiment, the methods comprise a compound of formula 53 and the attendant definitions wherein $L_4$ is NH.

In a further embodiment, the methods comprise a compound of formula 53 and the attendant definitions wherein n is 1.

In a further embodiment, the methods comprise a compound of formula 53 and the attendant definitions wherein R is O-t-butyl and $R_1$ is t-butyl.

In a further embodiment, the methods comprise a compound of formula 53 and the attendant definitions wherein R is O-t-butyl, $R_1$ is t-butyl, and $R_2$ is O-t-butyl.

In a further embodiment, the methods comprise a compound of formula 53 and the attendant definitions wherein R is O-t-butyl, $R_1$ is t-butyl, $R_2$ is O-t-butyl, and $R_3$ is t-butyl.

In a further embodiment, the methods comprise a compound of formula 53 and the attendant definitions wherein R is O-t-butyl, R is t-butyl, $R_2$ is O-t-butyl, $R_3$ is t-butyl, and $R_4$ is C(O)OMe.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, and $R_5$ is C(O)OMe.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, and $L_1$ is NH.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, and $L_2$ is O.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, and $L_3$ is O.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, $L_3$ is O, and $L_4$ is NH.

In a further embodiment, the methods comprise a compound of formula 53 and the attendant definitions wherein R is O-t-butyl, $R_1$ is t-butyl, $R_2$ is O-t-butyl, $R_3$ is t-butyl, $R_4$ is C(O)OMe, $R_5$ is C(O)OMe, $L_1$ is NH, $L_2$ is O, $L_3$ is O, $L_4$ is NH, and n is 1.

In another embodiment, methods for activating a sirtuin protein comprise using an activating compound of formula 54:

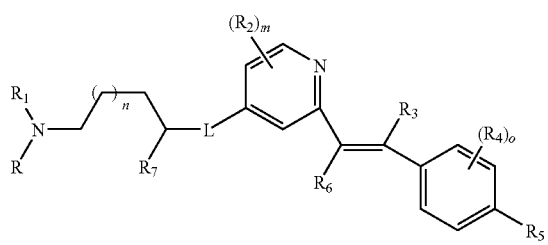

54 wherein, independently for each occurrence:

R and $R_1$ are H or a substituted or unsubstituted alkyl, aryl, aralkyl, heterocyclyl, heterocyclylalkyl, heteroaryl, or heteroaralkyl;

$R_2$, $R_4$, and $R_5$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_3$, $R_6$, and $R_7$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L is O, NR, or S;

n and o are integers from 0 to 4 inclusive; and m is an integer from 0 to 3 inclusive.

In a further embodiment, the methods comprise a compound of formula 54 and the attendant definitions wherein R is ethyl.

In a further embodiment, the methods comprise a compound of formula 54 and the attendant definitions wherein $R_1$ is ethyl.

In a further embodiment, the methods comprise a compound of formula 54 and the attendant definitions wherein m is 0.

In a further embodiment, the methods comprise a compound of formula 54 and the attendant definitions wherein $R_3$ is H.

In a further embodiment, the methods comprise a compound of formula 54 and the attendant definitions wherein o is 0.

In a further embodiment, the methods comprise a compound of formula 54 and the attendant definitions wherein $R_5$ is Cl.

In a further embodiment, the methods comprise a compound of formula 54 and the attendant definitions wherein $R_6$ is H.

In a further embodiment, the methods comprise a compound of formula 54 and the attendant definitions wherein $R_7$ is methyl.

In a further embodiment, the methods comprise a compound of formula 54 and the attendant definitions wherein L is NH.

In a further embodiment, the methods comprise a compound of formula 54 and the attendant definitions wherein n is 1.

In a further embodiment, the methods comprise a compound of formula 54 and the attendant definitions wherein R is ethyl and $R_1$ is ethyl.

In a further embodiment, the methods comprise a compound of formula 54 and the attendant definitions wherein R is ethyl, $R_1$ is ethyl, and m is 0.

In a further embodiment, the methods comprise a compound of formula 54 and the attendant definitions wherein R is ethyl, $R_1$ is ethyl, m is 0, and $R_3$ is H.

In a further embodiment, the methods comprise a compound of formula 54 and the attendant definitions wherein R is ethyl, $R_1$ is ethyl, m is 0, $R_3$ is H, and o is 0.

In a further embodiment, the methods comprise a compound of formula 54 and the attendant definitions wherein R is ethyl, $R_1$ is ethyl, m is 0, $R_3$ is H, o is 0, and $R_5$ is Cl.

In a further embodiment, the methods comprise a compound of formula 54 and the attendant definitions wherein R is ethyl, $R_1$ is ethyl, m is 0, $R_3$ is H, o is 0, $R_5$ is Cl, and $R_6$ is H.

In a further embodiment, the methods comprise a compound of formula 54 and the attendant definitions wherein R is ethyl, $R_1$ is ethyl, m is 0, $R_3$ is H, o is 0, $R_5$ is Cl, $R_6$ is H, and $R_7$ is methyl.

In a further embodiment, the methods comprise a compound of formula 54 and the attendant definitions wherein R is ethyl, $R_1$ is ethyl, m is 0, $R_3$ is H, o is 0, $R_5$ is CL, $R_6$ is H, $R_7$ is methyl, and L is NH.

In a further embodiment, the methods comprise a compound of formula 54 and the attendant definitions wherein R is ethyl, $R_1$ is ethyl, m is 0, $R_3$ is H, o is 0, $R_5$ is CL, $R_6$ is H, $R_7$ is methyl, L is NH, and n is 1.

In another embodiment, methods for activating a sirtuin protein comprise using an activating compound of formula 55:

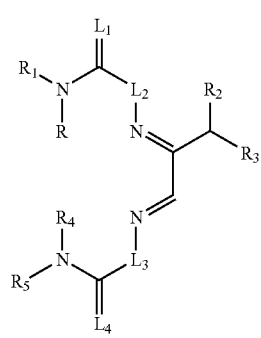

55 wherein, independently for each occurrence:

R, $R_1$, $R_4$, and $R_5$ are H or a substituted or unsubstituted alkyl, aryl, aralkyl, heterocyclyl, heterocyclylalkyl, heteroaryl, or heteroaralkyl;

$R_2$ and $R_3$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and $L_1$, $L_2$, $L_3$, and $L_4$ are O, NR, or S.

In a further embodiment, the methods comprise a compound of formula 55 and the attendant definitions wherein R is H.

In a further embodiment, the methods comprise a compound of formula 55 and the attendant definitions wherein $R_1$ is H.

In a further embodiment, the methods comprise a compound of formula 55 and the attendant definitions wherein $R_2$ is OEt.

In a further embodiment, the methods comprise a compound of formula 55 and the attendant definitions wherein $R_3$ is methyl.

In a further embodiment, the methods comprise a compound of formula 55 and the attendant definitions wherein $R_4$ is H. In a further embodiment, the methods comprise a compound of formula 55 and the attendant definitions wherein $R_5$ is H.

In a further embodiment, the methods comprise a compound of formula 55 and the attendant definitions wherein $L_1$ is S.

In a further embodiment, the methods comprise a compound of formula 55 and the attendant definitions wherein $L_2$ is NH.

In a further embodiment, the methods comprise a compound of formula 55 and the attendant definitions wherein $L_3$ is NH.

In a further embodiment, the methods comprise a compound of formula 55 and the attendant definitions wherein $L_4$ is S.

In a further embodiment, the methods comprise a compound of formula 55 and the attendant definitions wherein R is H and $R_1$ is H.

In a further embodiment, the methods comprise a compound of formula 55 and the attendant definitions wherein R is H, $R_1$ is H, and $R_2$ is OEt.

In a further embodiment, the methods comprise a compound of formula 55 and the attendant definitions wherein R is H, $R_1$ is H, $R_2$ is OEt, and $R_3$ is methyl.

In a further embodiment, the methods comprise a compound of formula 55 and the attendant definitions wherein R is H, $R_1$ is H, $R_2$ is OEt, $R_3$ is methyl, and $R_4$ is H.

In a further embodiment, the methods comprise a compound of formula 55 and the attendant definitions wherein R is H, $R_1$ is H, $R_2$ is OEt, $R_3$ is methyl, $R_4$ is H, and $R_5$ is H.

In a further embodiment, the methods comprise a compound of formula 55 and the attendant definitions wherein R is H, $R_1$ is H, $R_2$ is OEt, $R_3$ is methyl, $R_4$ is H, $R_5$ is H, and $L_1$ is S.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, and $L_2$ is NH.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, $L_2$ is NH, and $L_3$ is NH.

In a further embodiment, the methods comprise a compound of formula 55 and the attendant definitions wherein R is H, $R_1$ is H, $R_2$ is OEt, $R_3$ is methyl, $R_4$ is H, $R_5$ is H, $L_1$ is S, $L_2$ is NH, $L_3$ is NH, and $L_4$ is S.

In another embodiment, methods for activating a sirtuin protein comprise using an activating compound of formula 56:

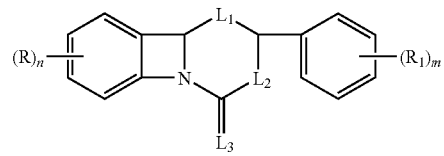

wherein, independently for each occurrence:

R and $R_1$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, $NR_2$, or S;

$R_2$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 0 to 5 inclusive.

In a further embodiment, the methods comprise a compound of formula 56 and the attendant definitions wherein n is 0.

In a further embodiment, the methods comprise a compound of formula 56 and the attendant definitions wherein m is 0.

In a further embodiment, the methods comprise a compound of formula 56 and the attendant definitions wherein $L_1$ is NH.

In a further embodiment, the methods comprise a compound of formula 56 and the attendant definitions wherein $L_2$ is S.

In a further embodiment, the methods comprise a compound of formula 56 and the attendant definitions wherein $L_3$ is S.

In a further embodiment, the methods comprise a compound of formula 56 and the attendant definitions wherein m is 0 and n is 0.

In a further embodiment, the methods comprise a compound of formula 56 and the attendant definitions wherein m is 0, n is 0, and $L_1$ is NH.

In a further embodiment, the methods comprise a compound of formula 56 and the attendant definitions wherein m is 0, n is 0, $L_1$ is NH, and $L_2$ is S.

In a further embodiment, the methods comprise a compound of formula 56 and the attendant definitions wherein m is 0, n is 0, $L_1$ is NH, $L_2$ is S, and $L_3$ is S.

In another embodiment, methods for activating a sirtuin protein comprise using an activating compound of formula 57:

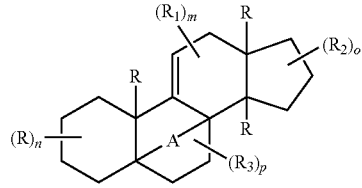

wherein, independently for each occurrence:

R, $R_1$, $R_2$, and $R_3$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

A is alkylene, alkenylene, or alkynylene;

n is an integer from 0 to 8 inclusive;

m is an integer from 0 to 3 inclusive;

o is an integer from 0 to 6 inclusive; and p is an integer from 0 to 4 inclusive.

In a further embodiment, the methods comprise a compound of formula 57 and the attendant definitions wherein n is 2.

In a further embodiment, the methods comprise a compound of formula 57 and the attendant definitions wherein R is OH or methyl.

In a further embodiment, the methods comprise a compound of formula 57 and the attendant definitions wherein m is 1.

In a further embodiment, the methods comprise a compound of formula 57 and the attendant definitions wherein $R_1$ is methyl.

In a further embodiment, the methods comprise a compound of formula 57 and the attendant definitions wherein o is 1.

In a further embodiment, the methods comprise a compound of formula 57 and the attendant definitions wherein $R_2$ is $C(O)CH_3$.

In a further embodiment, the methods comprise a compound of formula 57 and the attendant definitions wherein p is 2.

In a further embodiment, the methods comprise a compound of formula 57 and the attendant definitions wherein $R_3$ is $CO_2H$.

In a further embodiment, the methods comprise a compound of formula 57 and the attendant definitions wherein A is alkenylene.

In a further embodiment, the methods comprise a compound of formula 57 and the attendant definitions wherein n is 2 and R is OH or methyl.

In a further embodiment, the methods comprise a compound of formula 57 and the attendant definitions wherein n is 2, R is OH or methyl, and m is 1.

In a further embodiment, the methods comprise a compound of formula 57 and the attendant definitions wherein n is 2, R is OH or methyl, m is 1, and $R_1$ is methyl.

In a further embodiment, the methods comprise a compound of formula 57 and the attendant definitions wherein n is 2, R is OH or methyl, m is 1, $R_1$ is methyl, and o is 1.

In a further embodiment, the methods comprise a compound of formula 57 and the attendant definitions wherein n is 2, R is OH or methyl, m is 1, $R_1$ is methyl, o is 1, and $R_2$ is $C(O)CH_3$.

In a further embodiment, the methods comprise a compound of formula 57 and the attendant definitions wherein n is 2, R is OH or methyl, m is 1, $R_1$ is methyl, o is 1, $R_2$ is $C(O)CH_3$, and p is 2.

In a further embodiment, the methods comprise a compound of formula 57 and the attendant definitions wherein n is 2, R is OH or methyl, m is 1, $R_1$ is methyl, o is 1, $R_2$ is $C(O)CH_3$, p is 2, and $R_3$ is $CO_2H$.

In a further embodiment, the methods comprise a compound of formula 57 and the attendant definitions wherein n is 2, R is OH or methyl, m is 1, $R_1$ is methyl, o is 1, $R_2$ is $C(O)CH_3$, p is 2, $R_3$ is $CO_2H$, and A is alkenylene.

In another embodiment, methods for activating a sirtuin protein comprise using an activating compound of formula 58:

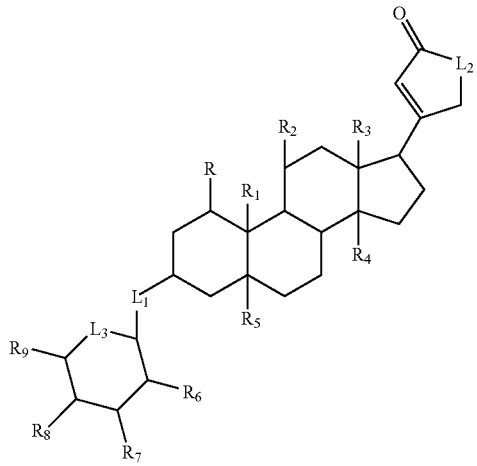

wherein, independently for each occurrence:

R, $R_1$, $R_2$, $R_3$, $R_4$, $R_5$, $R_6$, $R_7$, $R_8$, and $R_9$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$L_1$, $L_2$, and $L_3$ are O, $NR_{10}$, or S; and $R_{10}$ is H or a substituted or unsubstituted alkyl, aryl, aralkyl, heterocyclyl, heterocyclylalkyl, heteroaryl, or heteroaralkyl.

In a further embodiment, the methods comprise a compound of formula 58 and the attendant definitions wherein R is OH.

In a further embodiment, the methods comprise a compound of formula 58 and the attendant definitions wherein $R_1$ is $CH_2OH$.

In a further embodiment, the methods comprise a compound of formula 58 and the attendant definitions wherein $R_2$ is OH.

In a further embodiment, the methods comprise a compound of formula 58 and the attendant definitions wherein $R_3$ is methyl.

In a further embodiment, the methods comprise a compound of formula 58 and the attendant definitions wherein $R_4$ is OH.

In a further embodiment, the methods comprise a compound of formula 58 and the attendant definitions wherein $R_5$ is OH.

In a further embodiment, the methods comprise a compound of formula 58 and the attendant definitions wherein $R_6$ is OH.

In a further embodiment, the methods comprise a compound of formula 58 and the attendant definitions wherein $R_7$ is OH.

In a further embodiment, the methods comprise a compound of formula 58 and the attendant definitions wherein $R_8$ is OH.

In a further embodiment, the methods comprise a compound of formula 58 and the attendant definitions wherein $R_9$ is methyl.

In a further embodiment, the methods comprise a compound of formula 58 and the attendant definitions wherein $L_1$ is O.

In a further embodiment, the methods comprise a compound of formula 58 and the attendant definitions wherein $L_2$ is O.

In a further embodiment, the methods comprise a compound of formula 58 and the attendant definitions wherein $L_3$ is O.

In a further embodiment, the methods comprise a compound of formula 58 and the attendant definitions wherein R is OH and $R_1$ is $CH_2OH$.

In a further embodiment, the methods comprise a compound of formula 58 and the attendant definitions wherein R is OH, $R_1$ is $CH_2OH$, and $R_2$ is OH.

In a further embodiment, the methods comprise a compound of formula 58 and the attendant definitions wherein R is OH, $R_1$ is $CH_2OH$, $R_2$ is OH, and $R_3$ is methyl.

In a further embodiment, the methods comprise a compound of formula 58 and the attendant definitions wherein R is OH, $R_1$ is $CH_2OH$, $R_2$ is OH, $R_3$ is methyl, and $R_4$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, and $R_5$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, and $R_6$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, and $R_7$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, and $R_8$ is OH.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, and $R_9$ is methyl.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, and $L_1$ is O.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, $L_1$ is O, and $L_2$ is O.

In a further embodiment, the methods comprise a compound of formula 58 and the attendant definitions wherein R is OH, $R_1$ is $CH_2OH$, $R_2$ is OH, $R_3$ is methyl, $R_4$ is OH, $R_5$ is OH, $R_6$ is OH, $R_7$ is OH, $R_8$ is OH, $R_9$ is methyl, $L_1$ is O, $L_2$ is O, and $L_3$ is O.

In another embodiment, methods for activating a sirtuin protein comprise using an activating compound of formula 59:

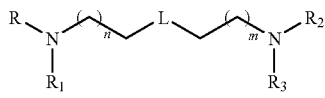

wherein, independently for each occurrence:

R, $R_1$, $R_2$, and $R_3$ are H or a substituted or unsubstituted alkyl, aryl, aralkyl, heterocyclyl, heterocyclylalkyl, heteroaryl, or heteroaralkyl;

L is O, NR, S, or Se; and n and m are integers from 0 to 5 inclusive.

In a further embodiment, the methods comprise a compound of formula 59 and the attendant definitions wherein R is H.

In a further embodiment, the methods comprise a compound of formula 59 and the attendant definitions wherein $R_1$ is H.

In a further embodiment, the methods comprise a compound of formula 59 and the attendant definitions wherein $R_2$ is H.

In a further embodiment, the methods comprise a compound of formula 59 and the attendant definitions wherein $R_3$ is H.

In a further embodiment, the methods comprise a compound of formula 59 and the attendant definitions wherein L is Se.

In a further embodiment, the methods comprise a compound of formula 59 and the attendant definitions wherein n is 1.

In a further embodiment, the methods comprise a compound of formula 59 and the attendant definitions wherein m is 1.

In a further embodiment, the methods comprise a compound of formula 59 and the attendant definitions wherein R is H and $R_1$ is H.

In a further embodiment, the methods comprise a compound of formula 59 and the attendant definitions wherein R is H, $R_1$ is H, and $R_2$ is H.

In a further embodiment, the methods comprise a compound of formula 59 and the attendant definitions wherein R is H, $R_1$ is H, $R_2$ is H, and $R_3$ is H.

In a further embodiment, the methods comprise a compound of formula 59 and the attendant definitions wherein R is H, $R_1$ is H, $R_2$ is H, $R_3$ is H, and L is Se.

In a further embodiment, the methods comprise a compound of formula 59 and the attendant definitions wherein R is H, $R_1$ is H, $R_2$ is H, $R_3$ is H, L is Se, and n is 1.

In a further embodiment, the methods comprise a compound of formula 59 and the attendant definitions wherein R is H, $R_1$ is H, $R_2$ is H, $R_3$ is H, L is Se, n is 1, and m is 1.

In another embodiment, methods for activating a sirtuin protein comprise using an activating compound of formula 60:

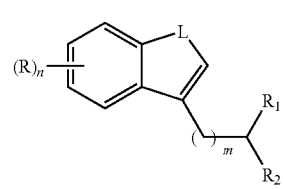

wherein, independently for each occurrence:

R is hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

$R_1$ and $R_2$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L is O, $NR_3$, S, or $SO_2$;

$R_3$ is H or a substituted or unsubstituted alkyl, aryl, aralkyl, heterocyclyl, heterocyclylalkyl, heteroaryl, or heteroaralkyl;

n is an integer from 0 to 4 inclusive; and m is an integer from 1 to 5 inclusive.

In a further embodiment, the methods comprise a compound of formula 60 and the attendant definitions wherein n is 1.

In a further embodiment, the methods comprise a compound of formula 60 and the attendant definitions wherein R is Cl.

In a further embodiment, the methods comprise a compound of formula 60 and the attendant definitions wherein $R_1$ is $NH_2$.

In a further embodiment, the methods comprise a compound of formula 60 and the attendant definitions wherein $R_2$ is $CO_2H$.

In a further embodiment, the methods comprise a compound of formula 60 and the attendant definitions wherein L is $SO_2$.

In a further embodiment, the methods comprise a compound of formula 60 and the attendant definitions wherein m is 1.

In a further embodiment, the methods comprise a compound of formula 60 and the attendant definitions wherein n is 1 and R is Cl.

In a further embodiment, the methods comprise a compound of formula 60 and the attendant definitions wherein n is 1, R is Cl, and $R_1$ is $NH_2$.

In a further embodiment, the methods comprise a compound of formula 60 and the attendant definitions wherein n is 1, R is Cl, $R_1$ is $NH_2$, and $R_2$ is $CO_2H$.

In a further embodiment, the methods comprise a compound of formula 60 and the attendant definitions wherein n is 1, R is Cl, $R_1$ is $NH_2$, $R_2$ is $CO_2H$, and L is $SO_2$.

In a further embodiment, the methods comprise a compound of formula 60 and the attendant definitions wherein n is 1, R is Cl, $R_1$ is $NH_2$, $R_2$ is $CO_2H$, L is $SO_2$, and m is 1.

In another embodiment, methods for activating a sirtuin protein comprise using an activating compound of formula 61:

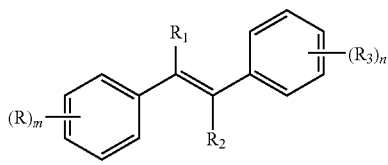

61 wherein, independently for each occurrence:

R, $R_1$, $R_2$, and $R_3$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

n and m are integers from 0 to 5 inclusive.

In a further embodiment, the methods comprise a compound of formula 61 and the attendant definitions wherein n is 2.

In a further embodiment, the methods comprise a compound of formula 61 and the attendant definitions wherein R is 3-hydroxy and 5-hydroxy.

In a further embodiment, the methods comprise a compound of formula 61 and the attendant definitions wherein $R_1$ is H.

In a further embodiment, the methods comprise a compound of formula 61 and the attendant definitions wherein $R_2$ is H.

In a further embodiment, the methods comprise a compound of formula 61 and the attendant definitions wherein m is 0.

In a further embodiment, the methods comprise a compound of formula 61 and the attendant definitions wherein m is 1.

In a further embodiment, the methods comprise a compound of formula 61 and the attendant definitions wherein $R_3$ is 4-hydroxy.

In a further embodiment, the methods comprise a compound of formula 61 and the attendant definitions wherein $R_3$ is 4-methoxy.

In a further embodiment, the methods comprise a compound of formula 61 and the attendant definitions wherein n is 2 and R is 3-hydroxy and 5-hydroxy.

In a further embodiment, the methods comprise a compound of formula 61 and the attendant definitions wherein n is 2, R is 3-hydroxy and 5-hydroxy, and $R_1$ is H.

In a further embodiment, the methods comprise a compound of formula 61 and the attendant definitions wherein n is 2, R is 3-hydroxy and 5-hydroxy, $R_1$ is H, and $R_2$ is H.

In a further embodiment, the methods comprise a compound of formula 61 and the attendant definitions wherein n is 2, R is 3-hydroxy and 5-hydroxy, $R_1$ is H, $R_2$ is H, and m is 0.

In a further embodiment, the methods comprise a compound of formula 61 and the attendant definitions wherein n is 2, R is 3-hydroxy and 5-hydroxy, $R_1$ is H, $R_2$ is H, and m is 1.

In a further embodiment, the methods comprise a compound of formula 61 and the attendant definitions wherein n is 2, R is 3-hydroxy and 5-hydroxy, $R_1$ is H, $R_2$ is H, m is 1, and $R_3$ is 4-hydroxy.

In a further embodiment, the methods comprise a compound of formula 61 and the attendant definitions wherein n is 2, R is 3-hydroxy and 5-hydroxy, $R_1$ is H, $R_2$ is H, m is 1, and $R_3$ is 4-methoxy.

In another embodiment, methods for activating a sirtuin protein comprise using an activating compound of formula 62:

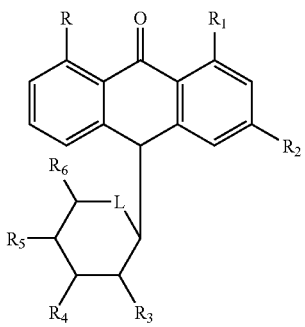

62 wherein, independently for each occurrence:

R, $R_1$, $R_2$, $R_3$, $R_4$, $R_5$, and $R_6$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L is O, NR$_7$, or S; and

R$_7$ is H or a substituted or unsubstituted alkyl, aryl, aralkyl, heterocyclyl, heterocyclylalkyl, heteroaryl, or heteroaralkyl.

In a further embodiment, the methods comprise a compound of formula 62 and the attendant definitions wherein R is OH.

In a further embodiment, the methods comprise a compound of formula 62 and the attendant definitions wherein R$_1$ is OH.

In a further embodiment, the methods comprise a compound of formula 62 and the attendant definitions wherein R$_2$ is CH$_2$OH.

In a further embodiment, the methods comprise a compound of formula 62 and the attendant definitions wherein R$_3$ is OH.

In a further embodiment, the methods comprise a compound of formula 62 and the attendant definitions wherein R$_4$ is OH.

In a further embodiment, the methods comprise a compound of formula 62 and the attendant definitions wherein R$_5$ is OH.

In a further embodiment, the methods comprise a compound of formula 62 and the attendant definitions wherein R$_6$ is CH$_2$OH.

In a further embodiment, the methods comprise a compound of formula 62 and the attendant definitions wherein L is O.

In a further embodiment, the methods comprise a compound of formula 62 and the attendant definitions wherein R is OH and R$_1$ is OH.

In a further embodiment, the methods comprise a compound of formula 62 and the attendant definitions wherein R is OH, R$_1$ is OH, and R$_2$ is CH$_2$OH.

In a further embodiment, the methods comprise a compound of formula 62 and the attendant definitions wherein R is OH, R$_1$ is OH, R$_2$ is CH$_2$OH, and R$_3$ is OH.

In a further embodiment, the methods comprise a compound of formula 62 and the attendant definitions wherein R is OH, R$_1$ is OH, R$_2$ is CH$_2$OH, R$_3$ is OH, and R$_4$ is OH.

In a further embodiment, the methods comprise a compound of formula 62 and the attendant definitions wherein R is OH, R$_1$ is OH, R$_2$ is CH$_2$OH, R$_3$ is OH, R$_4$ is OH, and R$_5$ is OH.

In a further embodiment, the methods comprise a compound of formula 62 and the attendant definitions wherein R is OH, R$_1$ is OH, R$_2$ is CH$_2$OH, R$_3$ is OH, R$_4$ is OH, R$_5$ is OH, and R$_6$ is CH$_2$OH.

In a further embodiment, the methods comprise a compound of formula 62 and the attendant definitions wherein R is OH, R$_1$ is OH, R$_2$ is CH$_2$OH, R$_3$ is OH, R$_4$ is OH, R$_5$ is OH, R$_6$ is CH$_2$OH, and L is O.

In another embodiment, methods for activating a sirtuin protein comprise using an activating compound of formula 63:

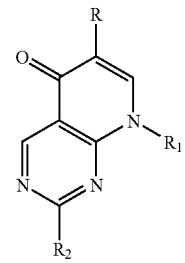

wherein, independently for each occurrence:

R, R$_1$, and R$_2$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl.

In a further embodiment, the methods comprise a compound of formula 63 and the attendant definitions wherein R is CO$_2$H.

In a further embodiment, the methods comprise a compound of formula 63 and the attendant definitions wherein R$_1$ is ethyl.

In a further embodiment, the methods comprise a compound of formula 63 and the attendant definitions wherein R$_2$ is N-1-pyrrolidine.

In a further embodiment, the methods comprise a compound of formula 63 and the attendant definitions wherein R is CO$_2$H and R$_1$ is ethyl.

In a further embodiment, the methods comprise a compound of formula 63 and the attendant definitions wherein R is CO$_2$H and R$_2$ is N-1-pyrrolidine.

In a further embodiment, the methods comprise a compound of formula 63 and the attendant definitions wherein R$_1$ is ethyl and R$_2$ is N-1-pyrrolidine.

In a further embodiment, the methods comprise a compound of formula 63 and the attendant definitions wherein R is CO$_2$H, R$_1$ is ethyl, and R$_2$ is N-1-pyrrolidine.

In another embodiment, methods for activating a sirtuin protein comprise using an activating compound of formula 64:

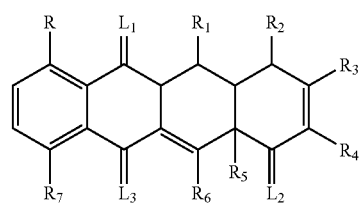

wherein, independently for each occurrence:

R, R$_1$, R$_2$, R$_3$, R$_4$, R$_5$, R$_6$, and R$_7$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L$_1$, L$_2$, and L$_3$ are CH$_2$, O, NR$_8$, or S; and

R$_8$ is H or a substituted or unsubstituted alkyl, aryl, aralkyl, heterocyclyl, heterocyclylalkyl, heteroaryl, or heteroaralkyl.

In a further embodiment, the methods comprise a compound of formula 64 and the attendant definitions wherein R is Cl.

In a further embodiment, the methods comprise a compound of formula 64 and the attendant definitions wherein R is H.

In a further embodiment, the methods comprise a compound of formula 64 and the attendant definitions wherein $R_1$ is OH.

In a further embodiment, the methods comprise a compound of formula 64 and the attendant definitions wherein $R_2$ is $N(Me)_2$.

In a further embodiment, the methods comprise a compound of formula 64 and the attendant definitions wherein $R_3$ is OH.

In a further embodiment, the methods comprise a compound of formula 64 and the attendant definitions wherein $R_4$ is $C(O)NH_2$.

In a further embodiment, the methods comprise a compound of formula 64 and the attendant definitions wherein $R_5$ is OH.

In a further embodiment, the methods comprise a compound of formula 64 and the attendant definitions wherein $R_6$ is OH.

In a further embodiment, the methods comprise a compound of formula 64 and the attendant definitions wherein $R_7$ is OH.

In a further embodiment, the methods comprise a compound of formula 64 and the attendant definitions wherein $L_1$ is $CH_2$.

In a further embodiment, the methods comprise a compound of formula 64 and the attendant definitions wherein $L_2$ is O.

In a further embodiment, the methods comprise a compound of formula 64 and the attendant definitions wherein $L_3$ is O.

In a further embodiment, the methods comprise a compound of formula 64 and the attendant definitions wherein R is Cl and $R_1$ is OH.

In a further embodiment, the methods comprise a compound of formula 64 and the attendant definitions wherein R is Cl, $R_1$ is OH, and $R_2$ is $N(Me)_2$.

In a further embodiment, the methods comprise a compound of formula 64 and the attendant definitions wherein R is Cl, $R_1$ is OH, $R_2$ is $N(Me)_2$, and $R_3$ is OH.

In a further embodiment, the methods comprise a compound of formula 64 and the attendant definitions wherein R is Cl, $R_1$ is OH, $R_2$ is $N(Me)_2$, $R_3$ is OH, and $R_4$ is $C(O)NH_2$.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, and $R_5$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, and $L_2$ is O.

In a further embodiment, the methods comprise a compound of formula 64 and the attendant definitions wherein R is Cl, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In a further embodiment, the methods comprise a compound of formula 64 and the attendant definitions wherein R is H and $R_1$ is OH.

In a further embodiment, the methods comprise a compound of formula 64 and the attendant definitions wherein R is H, $R_1$ is OH, and $R_2$ is $N(Me)_2$.

In a further embodiment, the methods comprise a compound of formula 64 and the attendant definitions wherein R is H, $R_1$ is OH, $R_2$ is $N(Me)_2$, and $R_3$ is OH.

In a further embodiment, the methods comprise a compound of formula 64 and the attendant definitions wherein R is H, $R_1$ is OH, $R_2$ is $N(Me)_2$, $R_3$ is OH, and $R_4$ is $C(O)NH_2$.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, and $R_5$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, and $R_6$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, and $R_7$ is OH.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, and $L_1$ is $CH_2$.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, L is $CH_2$, and $L_2$ is O.

In a further embodiment, the methods comprise a compound of formula 64 and the attendant definitions wherein R is H, $R_1$ is OH, $R_2$ is $N(Me)_2$, $R_3$ is OH, $R_4$ is $C(O)NH_2$, $R_5$ is OH, $R_6$ is OH, $R_7$ is OH, $L_1$ is $CH_2$, $L_2$ is O, and $L_3$ is O.

In another embodiment, methods for activating a sirtuin protein comprise using an activating compound of formula 65:

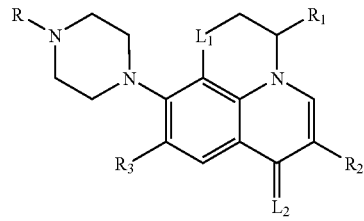

wherein, independently for each occurrence:

R is H or a substituted or unsubstituted alkyl, aryl, aralkyl, heterocyclyl, heterocyclylalkyl, heteroaryl, or heteroaralkyl;

$R_1$, $R_2$, and $R_3$ are hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl; and $L_1$ and $L_2$ are O, NR, or S.

In a further embodiment, the methods comprise a compound of formula 65 and the attendant definitions wherein R is methyl.

In a further embodiment, the methods comprise a compound of formula 65 and the attendant definitions wherein $R_1$ is methyl.

In a further embodiment, the methods comprise a compound of formula 65 and the attendant definitions wherein $R_2$ is $CO_2H$.

In a further embodiment, the methods comprise a compound of formula 65 and the attendant definitions wherein $R_3$ is F.

In a further embodiment, the methods comprise a compound of formula 65 and the attendant definitions wherein $L_1$ is O.

In a further embodiment, the methods comprise a compound of formula 65 and the attendant definitions wherein $L_2$ is O.

In a further embodiment, the methods comprise a compound of formula 65 and the attendant definitions wherein R is methyl and $R_1$ is methyl.

In a further embodiment, the methods comprise a compound of formula 65 and the attendant definitions wherein R is methyl, $R_1$ is methyl, and $R_2$ is $CO_2H$.

In a further embodiment, the methods comprise a compound of formula 65 and the attendant definitions wherein R is methyl, $R_1$ is methyl, $R_2$ is $CO_2H$, and $R_3$ is F.

In a further embodiment, the methods comprise a compound of formula 65 and the attendant definitions wherein R is methyl, $R_1$ is methyl, $R_2$ is $CO_2H$, $R_3$ is F, and $L_1$ is O.

In a further embodiment, the methods comprise a compound of formula 65 and the attendant definitions wherein R is methyl, $R_1$ is methyl, $R_2$ is $CO_2H$, $R_3$ is F, $L_1$ is O, and $L_2$ is O.

Exemplary activating compounds are those listed in the appended Tables having a ratio to control rate of more than one. A preferred compound of formula 8 is Dipyridamole; a preferred compound of formula 12 is Hinokitiol; a preferred compound of formula 13 is L-(+)-Ergothioneine; a preferred compound of formula 19 is Caffeic Acid Phenol Ester; a preferred compound of formula 20 is MCI-186 and a preferred compound of formula 21 is HBED (Supplementary Table 6). Activating compounds may also be oxidized forms of the compounds of Table 21.

Also included are pharmaceutically acceptable addition salts and complexes of the compounds of formulas 1-25, 30, and 32-65. In cases wherein the compounds may have one or more chiral centers, unless specified, the compounds contemplated herein may be a single stereoisomer or racemic mixtures of stereoisomers.

In cases in which the compounds have unsaturated carbon-carbon double bonds, both the cis (Z) and trans (E) isomers are contemplated herein. In cases wherein the compounds may exist in tautomeric forms, such as keto-enol tautomers, such as

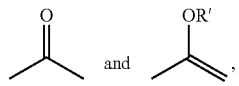

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the compounds of formulas 1-25, 30, and 32-65. Prodrugs are considered to be any covalently bonded carriers that release the active parent drug in vivo.

Analogs and derivatives of the above-described compounds can also be used for activating a member of the sirtuin protein family. For example, derivatives or analogs may make the compounds more stable or improve their ability to traverse cell membranes or being phagocytosed or pinocytosed. Exemplary derivatives include glycosylated derivatives, as described, e.g., in U.S. Pat. No. 6,361,815 for resveratrol. Other derivatives of resveratrol include cis- and trans-resveratrol and conjugates thereof with a saccharide, such as to form a glucoside (see, e.g., U.S. Pat. No. 6,414,037). Glucoside polydatin, referred to as piceid or resveratrol 3-O-beta-D-glucopyranoside, can also be used. Saccharides to which compounds may be conjugated include glucose, galactose, maltose, lactose and sucrose. Glycosylated stilbenes are further described in Regev-Shoshani et al. Biochemical J. (published on Apr. 16, 2003 as BJ20030141). Other derivatives of compounds described herein are esters, amides and prodrugs. Esters of resveratrol are described, e.g., in U.S. Pat. No. 6,572,882. Resveratrol and derivatives thereof can be prepared as described in the art, e.g., in U.S. Pat. Nos. 6,414,037; 6,361,815; 6,270,780; 6,572,882; and Brandolini et al. (2002) J. Agric. Food. Chem. 50:7407. Derivatives of hydroxyflavones are described, e.g., in U.S. Pat. No. 4,591,600. Resveratrol and other activating compounds can also be obtained commercially, e.g., from Sigma.

In certain embodiments, if an activating compound occurs naturally, it may be at least partially isolated from its natural environment prior to use. For example, a plant polyphenol may be isolated from a plant and partially or significantly purified prior to use in the methods described herein. An activating compound may also be prepared synthetically, in which case it would be free of other compounds with which it is naturally associated. In an illustrative embodiment, an activating composition comprises, or an activating compound is associated with, less than about 50%, 10%, 1%, 0.1%, $10^{-2}$% or $10^{-3}$% of a compound with which it is naturally associated.

Sirtuin proteins may be activated in vitro, e.g., in a solution or in a cell. In one embodiment, a sirtuin protein is contacted with an activating compound in a solution. A sirtuin is activated by a compound when at least one of its biological activities, e.g., deacetylation activity, is higher in the presence of the compound than in its absence. Activation may be by a factor of at least about 10%, 30%, 50%, 100% (i.e., a factor of two), 3, 10, 30, or 100. The extent of activation can be determined, e.g., by contacting the activated sirtuin with a deacetylation substrate and determining the extent of deacetylation of the substrate, as further described herein. The observation of a lower level of acetylation of the substrate in the presence of a test sirtuin relative to the presence of a non activated control sirtuin indicates that the test sirtuin is activated. The solution may be a reaction mixture. The solution may be in a dish, e.g., a multiwell dish. Sirtuin proteins may be prepared recombinantly or isolated from cells according to methods known in the art.

In another embodiment, a cell comprising a sirtuin deacetylase protein is contacted with an activating compound. The cell may be a eukaryotic cell, e.g., a mammalian cell, such as a human cell, a yeast cell, a non-human primate cell, a bovine cell, an ovine cell, an equine cell, a porcine cell, a sheep cell, a bird (e.g., chicken or fowl) cell, a canine cell, a feline cell or a rodent (mouse or rat) cell. It can also be a non-mammalian cell, e.g., a fish cell. Yeast cells include *S. cerevesiae* and *C. albicans*. The cell may also be a prokaryotic cell, e.g., a bacterial cell. The cell may also be a single-cell microorganism, e.g., a protozoan. The cell may also be a metazoan cell, a plant cell or an insect cell. The application of the methods decribed herein to a large number of cell types is based at least on the high convervation of sirtuins from humans to fungi, protozoans, metazoans and plants.

In one embodiment, the cells are in vitro. A cell may be contacted with a solution having a concentration of an activating compound of less than about 0.1 µM; 0.5 µM; less than about 1 µM; less than about 10 µM or less than about 100 µM.

The concentration of the activating compound may also be in the range of about 0.1 to 1 µM, about 1 to 10 µM or about 10 to 100 µM. The appropriate concentration may depend on the particular compound and the particular cell used as well as the desired effect. For example, a cell may be contacted with a "sirtuin activating" concentration of an activating compound, e.g., a concentration sufficient for activating the sirtuin by a factor of at least 10%, 30%, 50%, 100%, 3, 10, 30, or 100.

In certain embodiments, a cell is contacted with an activating compound in vivo, such as in a subject. The subject can be a human, a non-human primate, a bovine, an ovine, an equine, a porcine, a sheep, a canine, a feline or a rodent (mouse or rat). For example, an activating compound may be administered to a subject. Administration may be local, e.g., topical, parenteral, oral, or other depending on the desired result of the administration (as further described herein). Administration may be followed by measuring a factor in the subject or the cell, such as the activity of the sirtuin, lifespan or stress resistance. In an illustrative embodiment, a cell is obtained from a subject following administration of an activating compound to the subject, such as by obtaining a biopsy, and the activity of the sirtuin is determined in the biopsy. The cell may be any cell of the subject, but in cases in which an activating compound is administered locally, the cell is preferably a cell that is located in the vicinity of the site of administration.

Also provided are methods for modulating the acetylation level of p53 proteins. As shown herein (see, e.g., the Examples), lysine 382 of p53 proteins in cells is deacetylated following incubation of cells in the presence of low concentrations of resveratrol. Accordingly, "p53 deacetylating concentrations" of compounds include, e.g., concentrations of less than about 0.1 µM, 0.5 µM, 1 µM, 3 µM, 50 µM, 100 µM or 300 µM. It has also been shown herein that p53 proteins in cells are acetylated in the presence of higher concentrations of resveratrol. Accordingly, "p53 acetylating concentrations" of compounds include, e.g., concentrations of at least about 10 µM, 30 µM, 100 µM or 300 µM. The level of acetylation of p53 can be determined by methods known in the art, e.g., as further described in the Examples.

Other methods contemplated are methods for protecting a cell against apoptosis. Without wanting to be limited to a particular mechanism of action, but based at least in part on the fact that acetylation of p53 proteins activates p53 proteins and that activated p53 proteins induce apoptosis, incubating cells comprising p53 proteins in the presence of a p53 deacetylating concentration of an activating compound prevents the induction of apoptosis of the cells. Accordingly, a cell can be protected from apoptosis by activating sirtuins by contacting the cell with an amount of an activating compound sufficient or adequate for protecting against apoptosis, e.g., less than about 0.1 µM, 0.5 µM, 1 µM, 3 µM or 10 µM. An amount sufficient or adequate for protection against apoptosis can also be determined experimentally, such as by incubating a cell with different amounts of an activating compound, subjecting the cell to an agent or condition that induces apoptosis, and comparing the extent of apoptosis in the presence of different concentrations or the absence of an enhancing compound and determining the concentration that provides the desired protection. Determining the level of apoptosis in a population of cells can be performed according to methods known in the art.

Yet other methods contemplated herein are methods for inducing apoptosis in a cell. Without wanting to be limited to a particular mechanism of action, as shown in the Examples, at certain concentrations of compounds, p53 proteins are acetylated rather than deacetylated, thereby activating the p53 proteins, and inducing apoptosis. Apoptosis inducing concentrations of compounds may be, e.g., at least about 10 µM, 30 µM, 100 µM or 300 µM.

Appropriate concentrations for modulating p53 deacetylation and apoptosis can be determined according to methods, e.g., those described herein. Concentrations may vary slightly from one cell to another, from one activating compound to another and whether the cell is isolated or in an organism.

Cells in which p53 acetylation and apoptosis may be modulated can be in vitro, e.g., in cell culture, or in vivo, e.g., in a subject. Administration of an activating compound to a subject can be conducted as further described herein. The level of p53 acetylation and/or apoptosis in cells of the subject can be determined, e.g., by obtaining a sample of cells from the subject and conducting an in vitro analysis of the level of p53 acetylation and/or apoptosis.

Also provided herein are methods for extending the lifespan of a eukaryotic cell and/or increasing its resistance to stress comprising, e.g., contacting the eukaryotic cell with a compound, e.g., a polyphenol compound. Exemplary compounds include the activating compounds described herein, such as compounds of the stilbene, flavone and chalcone families. Although the Examples show that quercetin and piceatannol, which activate sirtuins, were not found to significantly affect the lifespan of eukaryotic cells, it is believed that this may be the result of a lack of entry of the compounds into the cell or potentially the existence of another pathway overriding activation of sirtuins. Derivatives and analogs of these compounds or administration of these compounds to other cells or by other methods are expected to activate sirtuins.

In one embodiment, methods for extending the lifespan of a eukaryotic cell and/or increasing its resistance to stress comprise contacting the cell with a stilbene, chalcone, or flavone compound represented by formula 7:

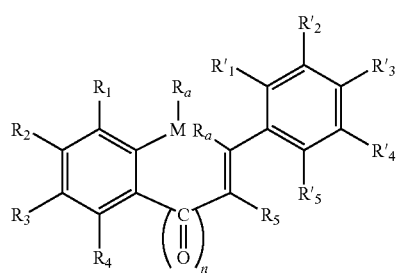

7 wherein, independently for each occurrence,

M is absent or O;

$R_1$, $R_2$, $R_3$, $R_4$, $R_5$, $R'_1$, $R'_2$, $R'_3$, $R'_4$, and $R'_5$ represent H, alkyl, aryl, heteroaryl, aralkyl, alkaryl, heteroaralkyl, halide, $NO_2$, SR, OR, $N(R)_2$, or carboxyl;

$R_a$ represents H or the two instances of $R_a$ form a bond;

R represents H, alkyl, or aryl; and n is 0 or 1.

In a further embodiment, the methods comprise a compound represented by formula 7 and the attendant definitions, wherein n is 0. In a further embodiment, the methods comprise a compound represented by formula 7 and the attendant definitions, wherein n is 1. In a further embodiment, the methods comprise a compound represented by formula 7 and the attendant definitions, wherein M is absent. In a further embodiment, the methods comprise a compound represented by formula 7 and the attendant definitions, wherein M is O. In a further embodiment, the methods comprise a compound represented by formula 7 and the attendant definitions, wherein $R_a$ is H. In a further embodiment, the methods comprise a compound represented by formula 7 and the attendant definitions, wherein M is O and the two $R_a$ form a bond. In a further embodiment, the methods comprise a compound represented by formula 7 and the attendant definitions, wherein $R_5$ is H. In a further embodiment, the methods comprise a compound represented by formula 7 and the attendant definitions, wherein $R_5$ is OH. In a further embodiment, the methods comprise a compound represented by formula 7 and the attendant definitions, wherein $R_1$, $R_3$, and $R'_3$ are OH. In a further embodiment, the methods comprise a compound represented by formula 7 and the attendant definitions, wherein $R_2$, $R_4$, $R'_2$, and $R'_3$ are OH. In a further embodiment, the methods comprise a compound represented by formula 7 and the attendant definitions, wherein $R_2$, $R'_2$, and $R'_3$ are OH.

In a further embodiment, methods for extending the lifespan of a eukaryotic cell comprise contacting the cell with a compound represented by formula 7 and the attendant definitions, wherein n is 0; M is absent; $R_a$ is H; $R_5$ is H; $R_1$, $R_3$, and $R'_3$ are OH; and $R_2$, $R_4$, $R'_1$, $R'_2$, $R'_4$, and $R'_5$ are H. In a further embodiment, the methods comprise a compound represented by formula 7 and the attendant definitions, wherein n is 1; M is absent; $R_a$ is H; $R_5$ is H; $R_2$, $R_4$, $R'_2$, and $R'_3$ are OH; and $R_1$, $R_3$, $R'_1$, $R'_4$, and $R'_5$ are H. In a further embodiment, the methods comprise a compound represented by formula 7 and the attendant definitions, wherein n is 1; M is O; the two $R_a$ form a bond; $R_5$ is OH; $R_2$, $R'_2$, and $R'_3$ are OH; and $R_1$, $R_3$, $R_4$, $R'_1$, $R'_4$, and $R'_5$ are H.

The eukaryotic cell whose lifespan may be extended can be a human, a non-human primate, a bovine, an ovine, an equine, a porcine, a sheep, a canine, a feline, a rodent (mouse or rat) or a yeast cell. A yeast cell may be *Saccharomyces cerevisiae* or *Candida albicans*. Concentrations of compounds for this purpose may be about 0.1 µM, 0.3 µM, 0.5 µM, 1 µM, 3 µM, 10 µM, 30 µM, 100 µM or 300 µM. Based at least on the high conservation of Sir2 proteins in various organisms, lifespan can also be prolonged in prokaryotes, protozoans, metazoans, insects and plants.

The cell may be in vitro or in vivo. In some embodiments, a life extending compound is administered to an organism (e.g., a subject) such as to induce hormesis, i.e., an increasing resistance to mild stress that results in increasing the lifespan of the organism. In fact, it has been shown that SIR2 is essential for the increased longevity provided by calorie restriction, a mild stress, that extends the lifespan of every organism it has been tested on (Lin et al. (2000) Science 249:2126). For example, overexpression of a *Caenorhabditis elegans* SIR2 homologue, sir-2.1, increases lifespan via a forkhead transcription factor, DAF-16, and a SIR2 gene has recently been implicated in lifespan regulation in *Drosophila melanogaster* (Rogina et al. Science (2002) 298:1745). Furthermore, the closest human Sir2 homologue, SIRT1, promotes survival in human cells by down-regulating the activity of the tumor suppressor p53 (Tissenbaum et al. Nature 410, 227-30 (2001); Rogina et al. Science 298:1745 (2002); and Vaziri, H. et al. Cell 107, 149-59. (2001)). The role of SIR2 in stress resistance and cell longevity is further supported by the identification of PNC1 as a calorie restriction- and stress-responsive gene that increases lifespan and stress resistance of cells by depleting intracellular nicotinamide (Anderson et al. (2003) Nature 423:181 and Bitterman et al. (2002) J. Biol. Chem. 277: 45099). Accordingly, compounds may be administered to a subject for protecting the cells of the subject from stresses and thereby extending the lifespan of the cells of the subject.

Also encompassed are methods for inhibiting sirtuins; inhibiting deacetylation of p53, e.g., for stimulating acetylation of p53; stimulating apoptosis; reducing lifespan and/or rendering cells or organisms more sensitive to stresses. Methods may include contacting a cell or a molecule, such as a sirtuin or a p53 protein, with a compound that inhibits sirtuins, i.e., an "inhibiting compound" or "sirtuin inhibitory compound." Exemplary inhibiting compounds are set forth in Tables 1-13 and 22 (compounds for which the ratio to control rate is <1). Another compound is Mercury, (2-hydroxy-5-nitrophenyl)(6-thioguanosinato-N7,S6). The compounds of Tables 1-8 may be obtained from Biomol, Sigma/Aldrich or Indofine.

A sirtuin inhibitory compound may have a formula selected from the group of formulas 26-29, 31, and 67-68:

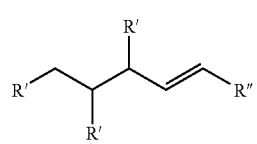

26 wherein, independently for each occurrence,
R' represents H, halogen, $NO_2$, SR, OR, $NR_2$, alkyl, aryl, aralkyl, or carboxy;
R represents H, alkyl, aryl, aralkyl, or heteroaralkyl; and
R" represents alkyl, alkenyl, or alkynyl;

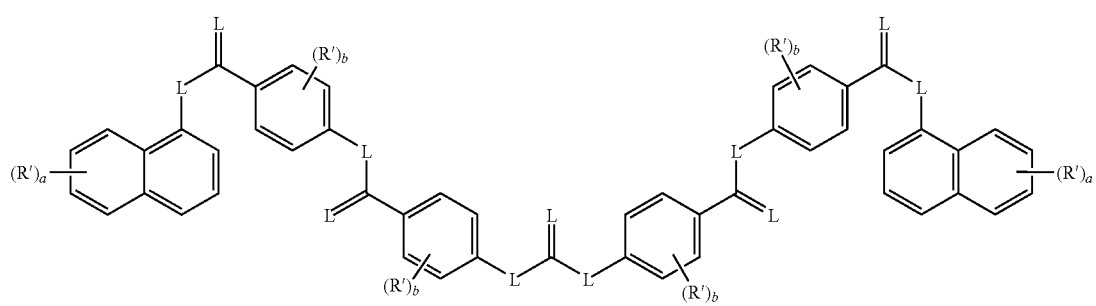

27 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, aralkyl, or carboxy;
a represents an integer from 1 to 7 inclusive; and
b represents an integer from 1 to 4 inclusive;

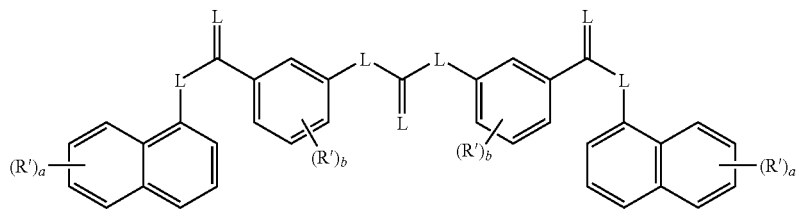

28 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, or carboxy;
a represents an integer from 1 to 7 inclusive; and
b represents an integer from 1 to 4 inclusive;

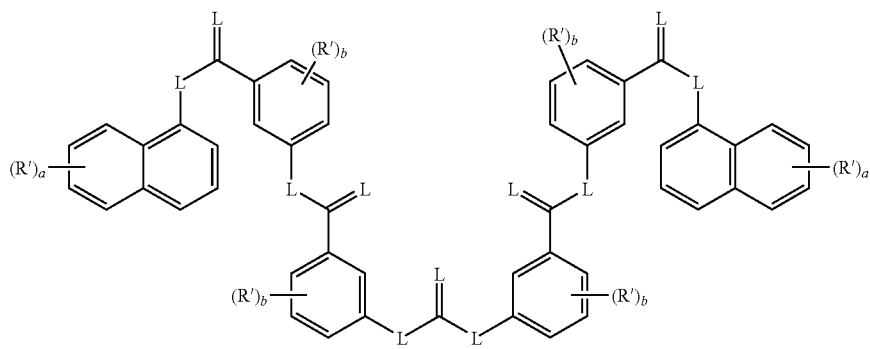

29 wherein, independently for each occurrence,
L represents O, NR, or S;
R represents H, alkyl, aryl, aralkyl, or heteroaralkyl;
R' represents H, halogen, $NO_2$, SR, $SO_3$, OR, $NR_2$, alkyl, aryl, aralkyl, or carboxy;
a represents an integer from 1 to 7 inclusive; and
b represents an integer from 1 to 4 inclusive;

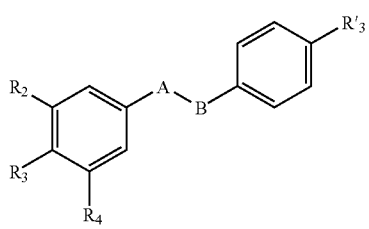

31 wherein, independently for each occurrence,
$R_2$, $R_3$, and $R_4$ are H, OH, or O-alkyl;
$R'_3$ is H or $NO_2$; and
A-B is an ethenylene or amido group.

In a further embodiment, the inhibiting compound is represented by formula 31 and the attendant definitions, wherein $R_3$ is OH, A-B is ethenylene, and $R'_3$ is H.

In a further embodiment, the inhibiting compound is represented by formula 31 and the attendant definitions, wherein $R_2$ and $R_4$ are OH, A-B is an amido group, and $R'_3$ is H.

In a further embodiment, the inhibiting compound is represented by formula 31 and the attendant definitions, wherein $R_2$ and $R_4$ are OMe, A-B is ethenylene, and $R'_3$ is $NO_2$.

In a further embodiment, the inhibiting compound is represented by formula 31 and the attendant definitions, wherein $R_3$ is OMe, A-B is ethenylene, and $R'_3$ is H.

In another embodiment, methods for activating a sirtuin protein comprise using an activating compound of formula 66:

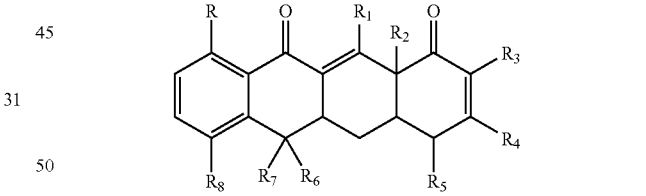

66 wherein, independently for each occurrence:
R, $R_1$, $R_2$, $R_3$, $R_4$, $R_5$, $R_6$, $R_7$, and $R_8$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl.

In a further embodiment, the methods comprise a compound of formula 66 and the attendant definitions wherein R is OH.

In a further embodiment, the methods comprise a compound of formula 66 and the attendant definitions wherein $R_1$ is OH.

In a further embodiment, the methods comprise a compound of formula 66 and the attendant definitions wherein $R_2$ is OH.

In a further embodiment, the methods comprise a compound of formula 66 and the attendant definitions wherein $R_3$ is $C(O)NH_2$.

In a further embodiment, the methods comprise a compound of formula 66 and the attendant definitions wherein $R_4$ is OH.

In a further embodiment, the methods comprise a compound of formula 66 and the attendant definitions wherein $R_5$ is $NMe_2$.

In a further embodiment, the methods comprise a compound of formula 66 and the attendant definitions wherein $R_6$ is methyl.

In a further embodiment, the methods comprise a compound of formula 66 and the attendant definitions wherein $R_7$ is OH.

In a further embodiment, the methods comprise a compound of formula 66 and the attendant definitions wherein $R_8$ is Cl.

In a further embodiment, the methods comprise a compound of formula 66 and the attendant definitions wherein R is OH and $R_1$ is OH.

In a further embodiment, the methods comprise a compound of formula 66 and the attendant definitions wherein R is OH, $R_1$ is OH, and $R_2$ is OH.

In a further embodiment, the methods comprise a compound of formula 66 and the attendant definitions wherein R is OH, $R_1$ is OH, $R_2$ is OH, and $R_3$ is $C(O)NH_2$.

In a further embodiment, the methods comprise a compound of formula 66 and the attendant definitions wherein R is OH, $R_1$ is OH, $R_2$ is OH, $R_3$ is $C(O)NH_2$, and $R_4$ is OH.

In a further embodiment, the methods comprise a compound of formula 66 and the attendant definitions wherein R is OH, $R_1$ is OH, $R_2$ is OH, $R_3$ is $C(O)NH_2$, $R_4$ is OH, and $R_5$ is $NMe_2$.

In a further embodiment, the methods comprise a compound of formula 66 and the attendant definitions wherein R is OH, $R_1$ is OH, $R_2$ is OH, $R_3$ is $C(O)NH_2$, $R_4$ is OH, $R_5$ is $NMe_2$, and $R_6$ is methyl.

In a further embodiment, the methods comprise a compound of formula 66 and the attendant definitions wherein R is OH, $R_1$ is OH, $R_2$ is OH, $R_3$ is $C(O)NH_2$, $R_4$ is OH, $R_5$ is $NMe_2$, $R_6$ is methyl, and $R_7$ is OH.

In a further embodiment, the methods comprise a compound of formula 66 and the attendant definitions wherein R is OH, $R_1$ is OH, $R_2$ is OH, $R_3$ is $C(O)NH_2$, $R_4$ is OH, $R_5$ is $NMe_2$, $R_6$ is methyl, $R_7$ is OH, and $R_8$ is Cl.

In another embodiment, methods for inhibiting a sirtuin protein comprise using an inhibiting compound of formula 67:

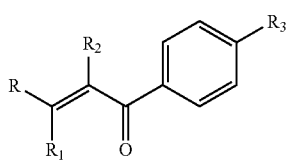

67 wherein, independently for each occurrence:

R, $R_1$, $R_2$, and $R_3$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl.

In a further embodiment, the methods comprise a compound of formula 67 and the attendant definitions wherein R is Cl.

In a further embodiment, the methods comprise a compound of formula 67 and the attendant definitions wherein $R_1$ is H.

In a further embodiment, the methods comprise a compound of formula 67 and the attendant definitions wherein $R_2$ is H.

In a further embodiment, the methods comprise a compound of formula 67 and the attendant definitions wherein $R_3$ is Br.

In a further embodiment, the methods comprise a compound of formula 67 and the attendant definitions wherein R is Cl and $R_1$ is H.

In a further embodiment, the methods comprise a compound of formula 67 and the attendant definitions wherein R is Cl, $R_1$ is H, and $R_2$ is H.

In a further embodiment, the methods comprise a compound of formula 67 and the attendant definitions wherein R is Cl, $R_1$ is H, $R_2$ is H, and $R_3$ is Br.

In another embodiment, methods for inhibiting a sirtuin protein comprise using an inhibiting compound of formula 68:

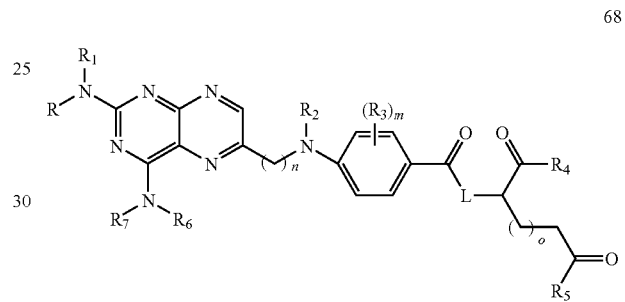

68 wherein, independently for each occurrence:

R, $R_1$, $R_2$, $R_6$, and $R_7$ are H or a substituted or unsubstituted alkyl, aryl, aralkyl, heterocyclyl, heterocyclylalkyl, heteroaryl, or heteroaralkyl;

$R_3$, $R_4$, and $R_5$ are H, hydroxy, amino, cyano, halide, alkoxy, ether, ester, amido, ketone, carboxylic acid, nitro, or a substituted or unsubstituted alkyl, aryl, aralkyl, heterocyclyl, heterocyclylalkyl, heteroaryl, or heteroaralkyl;

L is O, NR, or S;

m is an integer from 0 to 4 inclusive; and n and o are integers from 0 to 6 inclusive.

In a further embodiment, the methods comprise a compound of formula 68 and the attendant definitions wherein R is H.

In a further embodiment, the methods comprise a compound of formula 68 and the attendant definitions wherein $R_1$ is H.

In a further embodiment, the methods comprise a compound of formula 68 and the attendant definitions wherein $R_2$ is methyl.

In a further embodiment, the methods comprise a compound of formula 68 and the attendant definitions wherein m is 0.

In a further embodiment, the methods comprise a compound of formula 68 and the attendant definitions wherein $R_4$ is OH.

In a further embodiment, the methods comprise a compound of formula 68 and the attendant definitions wherein $R_5$ is OH.

In a further embodiment, the methods comprise a compound of formula 68 and the attendant definitions wherein $R_6$ is H.

In a further embodiment, the methods comprise a compound of formula 68 and the attendant definitions wherein $R_7$ is H.

In a further embodiment, the methods comprise a compound of formula 68 and the attendant definitions wherein L is NH.

In a further embodiment, the methods comprise a compound of formula 68 and the attendant definitions wherein n is 1.

In a further embodiment, the methods comprise a compound of formula 68 and the attendant definitions wherein o is 1.

In a further embodiment, the methods comprise a compound of formula 68 and the attendant definitions wherein R is H and $R_1$ is H.

In a further embodiment, the methods comprise a compound of formula 68 and the attendant definitions wherein R is H, $R_1$ is H, and $R_2$ is methyl.

In a further embodiment, the methods comprise a compound of formula 68 and the attendant definitions wherein R is H, $R_1$ is H, $R_2$ is methyl, and m is 0.

In a further embodiment, the methods comprise a compound of formula 68 and the attendant definitions wherein R is H, $R_1$ is H, $R_2$ is methyl, m is 0, and $R_4$ is OH.

In a further embodiment, the methods comprise a compound of formula 68 and the attendant definitions wherein R is H, $R_1$ is H, $R_2$ is methyl, m is 0, $R_4$ is OH, and $R_5$ is OH.

In a further embodiment, the methods comprise a compound of formula 68 and the attendant definitions wherein R is H, $R_1$ is H, $R_2$ is methyl, m is 0, $R_4$ is OH, $R_5$ is OH, and $R_6$ is H.

In a further embodiment, the methods comprise a compound of formula 68 and the attendant definitions wherein R is H, $R_1$ is H, $R_2$ is methyl, m is 0, $R_4$ is OH, $R_5$ is OH, $R_6$ is H, and $R_7$ is H.

In a further embodiment, the methods comprise a compound of formula 68 and the attendant definitions wherein R is H, $R_1$ is H, $R_2$ is methyl, m is 0, $R_4$ is OH, $R_5$ is OH, $R_6$ is H, $R_7$ is H, and L is NH.

In a further embodiment, the methods comprise a compound of formula 68 and the attendant definitions wherein R is H, $R_1$ is H, $R_2$ is methyl, m is 0, $R_4$ is OH, $R_5$ is OH, $R_6$ is H, $R_7$ is H, L is NH, and n is 1.

In a further embodiment, the methods comprise a compound of formula 68 and the attendant definitions wherein R is H, $R_1$ is H, $R_2$ is methyl, m is 0, $R_4$ is OH, $R_5$ is OH, $R_6$ is H, $R_7$ is H, L is NH, n is 1, and o is 1.

Inhibitory compounds may also be oxidized forms of the compounds of Table 22. An oxidized form of chlortetracyclin may be an activator.

Also included are pharmaceutically acceptable addition salts and complexes of the compounds of formulas 26-29, 31 and 66-68. In cases wherein the compounds may have one or more chiral centers, unless specified, the compounds contemplated herein may be a single stereoisomer or racemic mixtures of stereoisomers.

Exemplary inhibitory compounds are those set forth in the appended Tables for which the "ratio to control rate" is lower than one.

In cases in which the compounds have unsaturated carbon-carbon double bonds, both the cis (Z) and trans (E) isomers are contemplated herein. In cases wherein the compounds may exist in tautomeric forms, such as keto-enol tautomers, such as

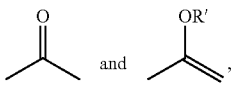

each tautomeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Also included in the methods presented herein are prodrugs of the compounds of formulas 26-29, 31 and 66-68. Prodrugs are considered to be any covalently bonded carriers that release the active parent drug in vivo.

Inhibitory compounds may be contacted with a cell, administered to a subject, or contacted with one or more molecules, such as a sirtuin protein and a p53 protein. Doses of inhibitory compounds may be similar to those of activating compounds.

Whether in vitro or in vivo, a cell may also be contacted with more than one compound (whether an activating compound or an inhibiting compound). A cell may be contacted with at least 2, 3, 5, or 10 different compounds. A cell may be contacted simultaneously or sequentially with different compounds.

Also encompassed are compositions comprising one or more activating or inhibiting compounds having a formula selected from the group of formulas 1-68. Compounds may be in a pharmaceutical composition, such as a pill or other formulation for oral administration, further described herein. Compositions may also comprise or consist of extracts of plants, red wine or other source of the compounds.

In certain embodiments, a certain biological function, e.g., extending lifespan, is modulated by any one of a compound of a genus of compounds (e.g., having formula I), with the proviso that the genus does not include one or more specific compounds. For example, in certain embodiments, a sirtuin activator compound may be a compound of any one of formulas 1-25, 30 and 32-65 with the proviso that the compound is not resveratrol, flavone or any of the other compounds specifically cited herein.

Yet other methods contemplated herein include sceening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be activated by an agent known to activate the sirtuin, and monitoring or determining the level of activation of the sirtuin in the presence of the test agent relative to the absence of the test agent. The level of activation of a sirtuin can be determined by determining its ability to deacetylate a substrate. Exemplary substrates are acetylated peptides, e.g., those set forth in FIG. 5, which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid (see FIG. 5). Substrates may be fluorogenic. The sirtuin may be SIRT1 or Sir2 or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of activation of the sirtuin in an assay may be compared to the level of activation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In one embodiment, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

Methods for identifying an agent that modulates, e.g., stimulate or inhibit, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also prefeably fluorogenic, as further described herein (Examples). The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo. An exemplary assay is further described in the Examples and shown in FIG. 4a.

Also provided herein are assays for identifying agents that are capable of extending or reducing the lifespan of cells and/or increasing or decreasing their resistance to stress. A method may comprise incubating cells with a test agent and determining the effect of the test agent on rDNA silencing and rDNA recombination, wherein an increase in the frequency of rDNA recombination and an absence of effect on rDNA silencing in the presence of the test agent relative to the absence of the test agent indicates that the test agent extends lifespan. This assay is based at least on the observation that resveratrol reduced the frequency of rDNA recombination by about 60% in a SIR2 dependent manner, but did not increase rDNA silencing.

Also provided herein are methods for identifying the binding site of activating or inhibitory compounds in sirtuin proteins. In one embodiment, BML-232 (Table 10) is used. BML-232, has very similar SIRT1 activating properties to resveratrol and contains a phenylazide function. Phenylazide groups may be activated by the absorption of ultraviolet light to form reactive nitrenes. When a protein-bound phenylazide is light-activated it can react to form covalent adducts with various protein functional groups in the site to which it is bound. The photo cross-linked protein may then be analyzed by proteolysis/mass spectrometry to identify amino acid residues which may form part of the binding site for the compound. This information, in combination with published three dimensional structural information on SIRT1 homologs could be used to aid the design of new, possibly higher affinity, SIRT1 activating ligands.

Exemplary Uses

In one embodiment, cells are treated in vitro as described herein to mimic caloric restriction, such as to extend their lifespan, e.g., to keep them proliferating longer and/or increasing their resistance to stress or prevent apoptosis. That compounds described herein may increase resistance to stress is based at least on the observation that Sir2 provides stress resistance and that PNC1 modulates Sir2 activity in response to cell stress (Anderson et al. (2003) Nature 423:181). This is particularly useful for primary cell cultures (i.e., cells obtained from an organism, e.g., a human), which are known to have only a limited lifespan in culture. Treating such cells according to methods described herein, e.g., by contacting them with an activating or lifespan extending compound, will result in increasing the amount of time that the cells are kept alive in culture. Embryonic stem (ES) cells and pluripotent cells, and cells differentiated therefrom, can also be treated according to the methods described herein such as to keep the cells or progeny thereof in culture for longer periods of time. Primary cultures of cells, ES cells, pluripotent cells and progeny thereof can be used, e.g., to identify compounds having particular biological effects on the cells or for testing the toxicity of compounds on the cells (i.e., cytotoxicity assays). Such cells can also be used for transplantation into a subject, e.g., after ex vivo modification.

In other embodiments, cells that are intended to be preserved for long periods of time are treated as described herein. The cells can be cells in suspension, e.g., blood cells, serum, biological growth media, or tissues or organs. For example, blood collected from an individual for administering to an individual can be treated as described herein, such as to preserve the blood cells for longer periods of time, such as for forensic purposes. Other cells that one may treat for extending their lifespan or protect against apoptosis include cells for consumption, e.g., cells from non-human mammals (such as meat), or plant cells (such as vegetables).

Generally, sirtuin-activating compounds may be used for extending the lifespan of a cell; extending the proliferative capacity of a cell; slowing ageing of a cell; promoting the survival of a cell; delaying cellular senescence in a cell; or mimicking the effects of calorie restriction. In certain embodiments, a sirtuin-activating compound does not significantly increase the resistance of a cell to oxidative stress, although it may increase its resistance to other types of stresses. For example, a compound may increase the resistance of a cell to oxidative stress less than about 2, 5, 10, 30, or 100 fold relative to another compound, e.g., reseveratrol.

Compounds may also be applied during developmental and growth phases in mammals, plants, insects or microorganisms, in order to, e.g., alter, retard or accelerate the developmental and/or growth process.

In another embodiment, cells obtained from a subject, e.g., a human or other mammal, are treated according to methods described herein and then administered to the same or a different subject. Accordingly, cells or tissues obtained from a donor for use as a graft can be treated as described herein prior to administering to the recipient of the graft. For example, bone marrow cells can be obtained from a subject, treated ex vivo, e.g., to extend their lifespan, and then administered to a recipient. The graft can be an organ, a tissue or loose cells.

In yet other embodiments, cells are treated in vivo, e.g., to increase their lifespan or prevent apoptosis. For example, skin can be protected from aging, e.g., developing wrinkles, by treating skin, e.g., epithelial cells, as described herein. In an exemplary embodiment, skin is contacted with a pharmaceutical or cosmetic composition comprising a compound described herein. Exemplary skin afflictions or skin conditions include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging. The formulations may be administered topically, to the skin or mucosal tissue, as an ointment, lotion, cream, microemulsion, gel, solution or the like, as further described herein, within the context of a dosing regimen effective to bring about the desired result. A dose of active agent may be in the range of about 0.005 to about 1 micromoles per kg per day, preferably about 0.05 to about 0.75 micromoles per kg per day, more typically about 0.075 to about 0.5 micromoles per kg per day. It will be recognized by those skilled in the art that the optimal quantity and spacing of individual dosages will be determined by the nature and extent of the condition being treated, the site of administration, and the particular individual undergoing treatment, and that such optimums can be determined by conventional techniques. That is, an optimal dosing regimen for any particular patient, i.e., the number and frequency of doses, can be ascertained using conventional course of treatment determination tests. Generally, a dosing regimen involves administration of the topical formulation at least once daily, and preferably one to four times daily, until symptoms have subsided.

Topical formulations may also be used as preventive, e.g., chemopreventive, compositions. When used in a chemopreventive method, susceptible skin is treated prior to any visible condition in a particular individual.

Compounds can also be delivered locally, e.g., to a tissue or organ within a subject, such as by injection, e.g., to extend the lifespan of the cells; protect against apoptosis or induce apoptosis.

Generally, sirtuin-activating compounds may be used in methods for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the disease or condition does not result from oxidative stress. In certain embodiments, a method does not significantly increase the resistance of the subject to oxidative stress. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin activating compound is administered to a subject, such as to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan. For example, a compound can be taken by subjects as a food or dietary supplement. In one embodiment, such a compound is a component of a multi-vitamin complex. Compounds can also be added to existing formulations that are taken on a daily basis, e.g., statins and aspirin. Compounds may also be used as food additives.

Compounds described herein could also be taken as one component of a multi-drug complex or as a supplement in addition to a multi-drug regimen. In one embodiment, this multi-drug complex or regimen would include drugs or compounds for the treatment or prevention of aging-related diseases, e.g., stroke, heart disease, arthritis, high blood pressure, Alzheimer's. In another embodiment, this multi-drug regimen would include chemotherapeutic drugs for the treatment of cancer. In a specific embodiment, a compound could be used to protect non-cancerous cells from the effects of chemotherapy.

Sirtuin-activating compounds may be administered to a subject to prevent aging and aging-related consequences or diseases, such as stroke, heart disease, such as heart failure, arthritis, high blood pressure, and Alzheimer's disease. Other conditions that can be treated include ocular disorders, e.g., associated with the aging of the eye, such as cataracts, glaucoma, and macular degeneration. Sirtuin-activating compounds described herein can also be administered to subjects for treatment of diseases, e.g., chronic diseases, associated with cell death, such as to protect the cells from cell death. Exemplary diseases include those associated with neural cell death or muscular cell death, such as Parkinson's disease, Alzheimer's disease, multiple sclerosis, amniotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections.

Cardiovascular diseases that can be treated or prevented include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to the retinal arterioles, the glomerular arterioles, the vasa nervorum, cardiac arterioles, and associated capillary beds of the eye, the kidney, the heart, and the central and peripheral nervous systems. The compounds may also be used for increasing HDL levels in plasma of an individual.

Yet other disorders that may be treated with sirtuin activators include restenosis, e.g., following coronary intervention, and disorders relating to an abnormal level of high density and low density cholesterol. Sirtuin activators may also be used for treating or preventing viral infections, such as infections by influenza, herpes or papilloma virus. They may also be used as antifungal agents, anti-inflammatory agents and neuroprotective agents.

Sirtuin-activating compounds described herein can also be administered to a subject suffering from an acute disease, e.g., damage to an organ or tissue, e.g., a subject suffering from stroke or myocardial infarction or a subject suffering from a spinal cord injury. Compounds can also be used to repair an alcoholic's liver.

Sirtuin-activating compounds can also be administered to subjects who have recently received or are likely to receive a dose of radiation. In one embodiment, the dose of radiation is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation exposure is received unintentionally, e.g., as a result of an industrial accident, terrorist act, or act of war involving radioactive material. In such a case, the compound is preferably administered as soon as possible after the exposure to inhibit apoptosis and the subsequent development of acute radiation syndrome.

Based at least on the discovery that certain concentrations of activating compounds prevent deacetylation of p53 in cells and thereby may induce apoptosis in cells, the activating compounds can also be administered to a subject in conditions in which apoptosis of certain cells is desired. For example, cancer may be treated or prevented. Exemplary cancers are those of the brain and kidney; hormone-dependent cancers including breast, prostate, testicular, and ovarian cancers; lymphomas, and leukemias. In cancers associated with solid tumors, a activating compound may be administered directly into the tumor. Cancer of blood cells, e.g., leukemia can be treated by administering a activating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of compounds. Alternatively, cells can be obtained from a subject, treated ex vivo to remove certain undesirable cells, e.g., cancer cells, and administered back to the same or a different subject.

Chemotherapeutic agents that may be coadministered with compounds described herein as having anti-cancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

These chemotherapeutic agents may be used by themselves with a compound described herein as inducing cell death or reducing lifespan or increasing sensitivity to stress and/or in combination with other chemotherapeutics agents. Many combinatorial therapies have been developed, including but not limited to those listed in Table 23.

TABLE 23

Exemplary conventional combination cancer chemotherapy

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |

TABLE 23-continued

Exemplary conventional combination cancer chemotherapy

| Name | Therapeutic agents |
|---|---|
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |

TABLE 23-continued

Exemplary conventional combination cancer chemotherapy

| Name | Therapeutic agents |
|---|---|
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the compounds described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

The methods may be advantageous over combination therapies known in the art because it allows conventional chemotherapeutic agent to exert greater effect at lower dosage. In a preferred embodiment, the effective dose ($ED_{50}$) for a chemotherapeutic agent or combination of conventional chemotherapeutic agents when used in combination with a compound described herein is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a compound described herein can be at least 2 fold greater than the TI for conventional chemotherapeutic regimen alone, and even more preferably at 5 fold, 10 fold or even 25 fold greater.

Other combination therapies include conjoint administration with nicotinamide, NAD$^+$ or salts thereof, or other Vitamin B3 analogs. Carnitines, such as L-carnitine, may also be co-administered, particularly for treating cerebral stroke, loss of memory, pre-senile dementia, Alzheimer's disease or preventing or treating disorders elicted by the use of neurotoxic drugs. Cyclooxygenase inhibitors, e.g., a COX-2 inhibitor, may also be co-administered for treating certain conditions described herein, such as an inflammatory condition or a neurologic disease.

Compositions or coformulations comprising a sirtuin activator or inhibitor and another agent, e.g., a chemotherapeutic agent, an antiviral agent, nicotinamide, NAD$^+$ or salts thereof, Vitamin B3 analogs, retinoids, alpha-hydroxy acid, ascorbic acid, are also encompassed herein.

In certain embodiments, the subject sirtuin activators, such as SIRT1 activators, do not have any substantial ability to inhibit PI3-kinase, inhibit aldoreductase and/or inhibit tyrosine protein kinases at concentrations (e.g., in vivo) effective for activating the deacetylase activity of the sirtuin, e.g., SIRT1. For instance, in preferred embodiments the sirtuin activator is chosen to have an $EC_{50}$ for activating sirtuin deacetylase activity that is at least 5 fold less than the $EC_{50}$ for inhibition of one or more of aldoreductase and/or tyrosine protein kinases, and even more preferably at least 10 fold, 100 fold or even 1000 fold less.

In certain embodiments, the subject sirtuin activators do not have any substantial ability to transactivate EGFR tyrosine kinase activity at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for transactivating EGFR tyrosine kinase activity, and even more preferably at least 10 fold, 100 fold or even 1000 fold less.

In certain embodiments, the subject sirtuin activators do not have any substantial ability to cause coronary dilation at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for coronary dilation, and even more preferably at least 10 fold, 100 fold or even 1000 fold less.

In certain embodiments, the subject sirtuin activators do not have any substantial spasmolytic activity at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for spasmolytic effects (such as on gastrointestinal muscle), and even more preferably at least 10 fold, 100 fold or even 1000 fold less.

In certain embodiments, the subject sirtuin activators do not have any substantial ability to inhibit hepatic cytochrome P450 1B1 (CYP) at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for inhibition of P450 1B1, and even more preferably at least 10 fold, 100 fold or even 1000 fold less.

In certain embodiments, the subject sirtuin activators do not have any substantial ability to inhibit nuclear factor-kappaB (NF-κB) at concentrations (e.g., in vivo) effective for activating the deacetylase activity of the sirtuin. For instance, in preferred embodiments the sirtuin activator is chosen to have an $EC_{50}$ for activating sirtuin deacetylase activity that is at least 5 fold less than the $EC_{50}$ for inhibition of NF-κB, and even more preferably at least 10 fold, 100 fold or even 1000 fold less.

In certain embodiments, the subject SIRT1 activators do not have any substantial ability to activate SIRT1 orthologs in lower eukaryotes, particularly yeast or human pathogens, at concentrations (e.g., in vivo) effective for activating the deacetylase activity of human SIRT1. For instance, in preferred embodiments the SIRT1 activator is chosen to have an EC50 for activating human SIRT1 deacetylase activity that is at least 5 fold less than the EC50 for activating yeast Sir2 (such as *Candida, S. cerevisiae*, etc), and even more preferably at least 10 fold, 100 fold or even 1000 fold less.

In other embodiments, the subject sirtuin activators do not have any substantial ability to inhibit protein kinases; to phosphorylate mitogen activated protein (MAP) kinases; to inhibit the catalytic or transcriptional activity of cyclo-oxygenases, such as COX-2; to inhibit nitric oxide synthase (iNOS); or to inhibit platelet adhesion to type I collagen at concentrations (e.g., in vivo) effective for activating the deacetylase activity of the sirtuin. For instance, in preferred embodiments, the sirtuin activator is chosen to have an $EC_{50}$ for activating sirtuin deacetylase activity that is at least 5 fold less than the $EC_{50}$ for performing any of these activities, and even more preferably at least 10 fold, 100 fold or even 1000 fold less.

In other embodiments, a compound described herein, e.g., a sirtuin activator or inhibitor, does not have significant or detectable anti-oxidant activities, as determined by any of the standard assays known in the art. For example, a compound does not significantly scavenge free-radicals, such as $O_2$ radicals. A compound may have less than about 2, 3, 5, 10, 30 or 100 fold anti-oxidant activity relative to another compound, e.g., resveratrol.

A compound may also have a binding affinity for a sirtuin of about $10^{-9}$ M, $10^{-10}$ M, $10^{-11}$ M, $10^{-12}$ M or less. A compound may reduce the $K_m$ of a sirtuin for its substrate or $NAD^+$ by a factor of at least about 2, 3, 4, 5, 10, 20, 30, 50 or 100. A compound may have an $EC_{50}$ for activating the deacetylase activity of a sirtuin of less than about 1 nM, less than about 10 nM, less than about 100 nM, less than about 1 μM, less than about 10 μM, less than about 100 μM, or from about 1-10 nM, from about 10-100 nM, from about 0.1-1 μM, from about 1-10 μM or from a bout 10-100 μM. A compound may activate the deacetylase activity of a sirtuin by a factor of at least about 5, 10, 20, 30, 50, or 100, as measured in an a cellular assay or in a cell based assay as described in the Examples. A compound may cause at least a 10%, 30%, 50%, 80%, 2 fold, 5 fold, 10 fold, 50 fold or 100 fold greater induction of the deacetylase activity of SIRT1 relative to the same concentration of resveratrol or other compound described herein. A compound may also have an $EC_{50}$ for activating SIRT5 that is at least about 10 fold, 20 fold, 30 fold, 50 fold greater than that for activating SIRT1.

A compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells TNF-induced apoptosis.

In other embodiments, methods described herein are applied to yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin activators may also be used for treating or preventing viral infections, such as infections by influenz, herpes or papillomavirus. They may also be used as antifungal agents, anti-inflammatory agents and neuroprotective agents.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, activating compounds may be administered to farm animals to improve their ability to withstand farming conditions longer.

Compounds may also be used to increase lifespan, stress resistance, and resistance to apoptosis in plants. In one embodiment, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preverse them.

Compounds may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, that may have commercial importance. For example, they can be applied to fish (aquaculture) and birds (e.g., chicken and fowl).

Higher doses of compounds may also be used as a pesticide by interfering with the regulation of silenced genes and the regulation of apoptosis during development. In this embodiment, a compound may be applied to plants using a method known in the art that ensures the compound is bio-available to insect larvae, and not to plants.

Activated sirtuin proteins that are in vitro outside of a cell may be used, e.g., for deacetylating target proteins, thereby, e.g., activating the target proteins. Activated sirtuins may be used, e.g., for the identification, in vitro, of previously unknown targets of sirtuin deacetylation, for example using 2D electrophoresis of acetyl labeled proteins.

At least in view of the link between reproduction and longevity (Longo and Finch, Science, 2002), the compounds can be applied to affect the reproduction of organisms such as insects, animals and microorganisms.

Inhibitory compounds may be used for similar purposes as those described herein for high concentrations of activating compounds. For example, inhibitory compounds may be used to stimulate acetylation of substrates such as p53 and thereby increase apoptosis, as well as to reduce the lifespan of cells and organisms and/or rendering them more sensitive to stress. Thus, inhibitory compounds may be used, e.g., for treating cancer.

Pharmaceutical Compositions and Methods

Pharmaceutical compositions for use in accordance with the present methods may be formulated in conventional manner using one or more physiologically acceptable carriers or excipients. Thus, activating compounds and their physiologically acceptable salts and solvates may be formulated for administration by, for example, injection, inhalation or insufflation (either through the mouth or the nose) or oral, buccal, parenteral or rectal administration. In one embodiment, the compound is administered locally, at the site where the target cells, e.g., diseased cells, are present, i.e., in the blood or in a joint.

Compounds can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions (including cosmetic preparations) may comprise from about 0.00001 to 100% such as from 0.001 to 10% or from 0.1% to 5% by weight of one or more compounds described herein.

In one embodiment, a compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington 's, cited in the preceding section, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor$^{RTM}$ from Beiersdorf, Inc. (Norwalk, Conn.).

Compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington 's, supra, is generally a nonionic, anionic, cationic or amphoteric surfactant.

Compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Compounds may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide (C.sub.10 MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; C.sub.2-C.sub.6 alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone$^{RTM}$ from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol$^{RTM}$) and diethylene glycol monoethyl ether oleate (available commercially as Soficutol$^{RTM}$); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol$^{RTM}$); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition as herein defined.

In an alternative embodiment, a pharmaceutical formulation is provided for oral or parenteral administration, in which case the formulation may comprises an activating compound-containing microemulsion as described above, but may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Phospholipids complexes, e.g., resveratrol-phospholipid complexes, and their preparation are described in U.S. 2004116386. Methods for stabilizing active components using polyol/polymer microcapsules, and their preparation are described in U.S. 20040108608. Processes for dissolving lipophilic compounds in aqueous solution with amphiphilic block copolymers are described in WO 04/035013.

Conditions of the eye can be treated or prevented by, e.g., systemic, topical, intraocular injection of a compound described herein, or by insertion of a sustained release device that releases a compound described herein.

Compounds described herein may be stored in oxygen free environment according to methods in the art. For example, resveratrol or analog thereof can be prepared in an airtight capusule for oral administration, such as Capsugel from Pfizer, Inc.

Cells, e.g., treated ex vivo with a compound described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population). The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Kits

Also provided herein are kits, e.g., kits for therapeutic purposes or kits for modulating the lifespan of cells or modulating apoptosis. A kit may comprise one or more activating or inhibitory compounds described herein, e.g., in premeasured doses. A kit may optionally comprise devices for contacting cells with the compounds and instructions for use. Devices include syringes, stents and other devices for introducing a compound into a subject or applying it to the skin of a subject.

The present description is further illustrated by the following examples, which should not be construed as limiting in any way. The contents of all cited references (including literature references, issued patents, published patent applications as cited throughout this application) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Small Molecule Activators of SIRT1

Figure 5:
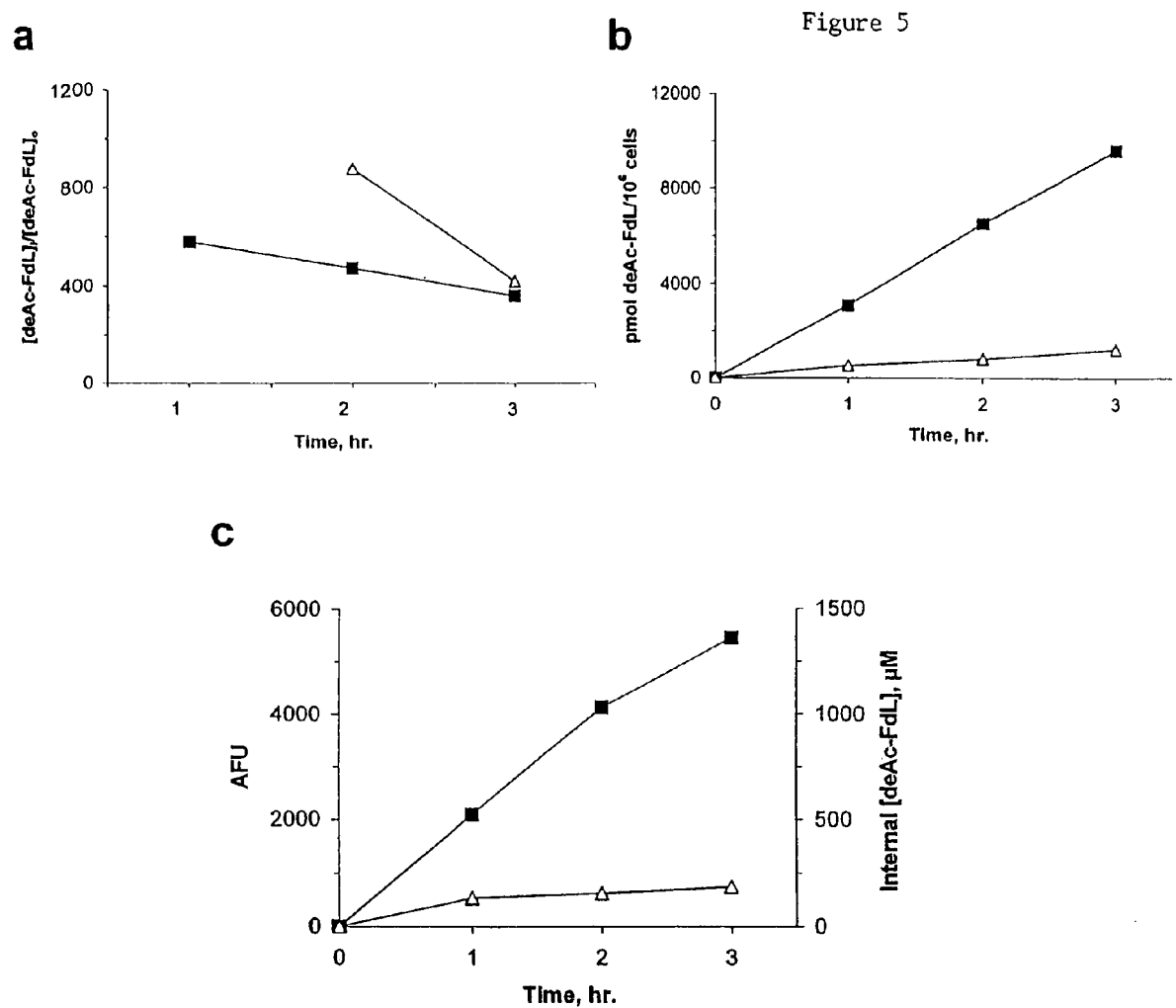
FIG. 5 shows that intracellular deacetylation activity may be measured with a cell-permeable, fluorogenic HDAC and sirtuin substrate. HeLa S3 cells were grown to confluence in DMEM/10% FCS and then incubated with fresh medium containing 200 μM FdL for the indicated times, 37° C. Intracellular and medium levels of deacetylated substrate (deAc-FdL) were determined according to the manufacturer's instructions (HDAC assay kit, BIOMOL). All data points represent the mean of two determinations. a, Concentration ratio of intracellular ([deAc-FdL]$_i$) to medium ([deAc-FdL]$_o$) concentrations in the presence (Δ) or absence (v) of 1 μM trichostatin A (TSA). b, Total accumulation of deacetylated substrate (deAc-FdL) in the presence (Δ) or absence (v) of 1 μM TSA. c, Intracellular accumulation of deacetylated substrate (deAc-FdL) in the presence (Δ) or absence (v) of 1 μM TSA.

To identify compounds that modulate SIRT1 activity, we screened a number of small molecule libraries using a fluorescent deacetylation assay in 96-well plates[26]. The substrate used in the assay was a fluorogenic peptide based on the sequence encompassing the p53-K382 acetylation site, a known target of SIRT1 in vivo[20,21,27]. This substrate was preferred over a variety of other fluorogenic peptide substrates that were based on other known HDAC targets (FIG. 5). The small molecule libraries included analogues of nicotinamide, ε-acetyl lysine, NAD$^+$, nucleotides, nucleotide analogues and purinergic ligands. From the initial screen, several sirtuin inhibitors were found (Supplementary Table 7). However, the most striking outcome was the identification of two compounds, quercetin and piceatannol, that stimulated SIRT1 activity five and eight-fold, respectively (Table 1). Both quercetin and piceatannol have been previously identified as protein kinase inhibitors[28,29].

Comparison of the structures of the two activating compounds suggested a possible structure-activity relationship. Piceatannol comprises two phenyl groups trans to one another across a linking ethylene moiety. The trans-stilbene ring structures of piceatannol are superimposable on the flavonoid A and B rings of quercetin, with the ether oxygen and carbon-2 of the C ring aligning with the ethylene carbons in piceatannol (see structures, Table 1). Further, the 5, 7, 3' and 4' hydroxyl group positions in quercetin can be aligned, respectively, with the 3, 5, 3' and 4' hydroxyls of piceatannol.

Given the demonstrated longevity-enhancing effects of sirtuin activity in S. cerevisiae[7] and C. elegans[19], it was naturally of interest to further explore the structure-activity relationship among compounds that stimulate SIRT1. Both quercetin and piceatannol are polyphenols, members of a large and diverse group of plant secondary metabolites that includes flavones, stilbenes, flavanones, isoflavones, catechins (flavan-3-ols), chalcones, tannins and anthocyanidins[30,31]. Polyphenols noteworthy with respect to potential longevity-enhancing effects include resveratrol, a stilbene found in red wine and epigallocatechin gallate (EGCG) from green tea. Both have been suggested on the basis of epidemiological and mechanistic investigations to exert cancer chemopreventive and cardioprotective effects[30-32]. We therefore performed a secondary screen encompassing resveratrol, EGCG and additional representatives from a number of the polyphenol classes listed above. The screen emphasized flavones due to the great number of hydroxyl position variants available in this group[31]. The results of this screen are summarized in Supplementary Tables 1-6. In the tables, a "ratio to control rate" above 1 indicates that a compound with such a rate is an activator of the sirtuin tested and a number under 1 indicates that a compound is an inhibitor.

Additional potent SIRT1 activators were found among the stilbenes, chalcones and flavones (Table 1, Supplementary Tables 1 and 2). The six most active flavones had 3' and 4' hydroxyls (Supplementary Table 2), although it should be noted that the most active compound overall, resveratrol (3,5, 4'-trihydroxystilbene), was more active than piceatannol, which differs only by its additional 3'-hydroxyl (Table 1). The importance of the 4'-hydroxyl to activity is underscored by the fact that each of the 12 most stimulatory flavones share this feature (Supplementary Tables 1 and 2).

Many, but not all of the most active compounds include hydroxyls in the two meta positions (e.g. 5,7-dihydroxylated flavones) of the ring (A ring), trans to that with the 4' or 3',4' pattern (B ring, see Table 1, Supplementary Tables 1 and 2). A potentially coplanar orientation of the trans phenyl rings may be important for activity since catechins and flavanones, which lack the 2,3 double-bond, have weak activity despite having equivalent hydroxylation patterns to various stimulatory flavones (compare Supplementary Tables 2 and 3 with 4 and 5). The absence of activity in the isoflavone genistein, although hydroxylated in an equivalent way to the stimulatory compounds apigenin and resveratrol (see Supplementary Tables 1, 2 and 4), is consistent with the idea that the trans positioning and spacing of the hydroxylated rings contributes strongly to activity.

The biological effects of polyphenols are frequently attributed to antioxidant, metal ion chelating and/or free-radical scavenging activity[30,32]. We considered the possibility that the apparent polyphenol stimulation of SIRT1 might simply represent the repair of oxidative and/or metal-ion induced damage incurred during preparation of the recombinant protein. Two features of our results argue against this being the case. First, a variety of free-radical protective compounds, including antioxidants, chelators and radical scavengers, failed to stimulate SIRT1 (see Supplementary Table 6.). Second, among various polyphenols of equivalent antioxidant capacity we observed diverse SIRT1 stimulating activity (e.g. compare resveratrol, quercetin and the epicatechins in Supplementary Tables 1, 2 and 5 and see[33]).

Example 2

Resveratrol's Effects on SIRT1 Kinetics

Detailed enzyme kinetic investigations were performed using the most potent activator, resveratrol. Dose-response experiments performed under the conditions of the polyphenol screening assays (25 μM NAD$^+$, 25 μM p53-382 acetylated peptide), showed that the activating effect doubled the rate at ~11 μM and was essentially saturated at 100 μM resveratrol (FIG. 1a). Initial enzyme rates, in the presence or absence of 100 μM resveratrol, were determined either as a function of acetyl-peptide concentration with high NAD$^+$ (3 mM NAD$^+$, FIG. 1b) or as a function of NAD$^+$ concentration with high acetyl-peptide (1 mM p53-382 acetylated peptide, FIG. 1c). Although resveratrol had no significant effect on the two $V_{max}$ determinations (FIGS. 1b, 1c), it had pronounced effects on the two apparent $K_m$s. Its effect on the acetylated peptide $K_m$ was particularly striking, amounting to a 35-fold decrease (FIG. 1b). Resveratrol also lowered the $K_m$ for NAD$^+$ over 5-fold (FIG. 1c). Since resveratrol acts only on $K_m$, it could be classified as an allosteric effector of 'K system' type[34]. This can imply that only the substrate binding affinity of the enzyme has been altered, rather than a rate-limiting catalytic step.

Our previous kinetic analysis of SIRT1 and Sir2[26] and our genetic analysis of Sir2's role in yeast lifespan extension[6,35] have implicated nicotinamide (a product of the sirtuin reaction) as a physiologically important inhibitor of sirtuin activity. Therefore the effects of resveratrol on nicotinamide inhibition were tested. In experiments similar to those of FIGS. 1b and 1c, kinetic constants in the presence of 50 μM nicotinamide were determined either by varying the concentration of NAD$^+$ or that of the p53-382 acetylated peptide (FIG. 1d). Nicotinamide, in contrast to resveratrol, affects the SIRT1 $V_{max}$ (note 30% and 36% $V_{max}$ decreases in absence of resveratrol, FIG. 1d and see ref.[26]). In the presence of 50 μM nicotinamide, resveratrol appears to have complex, concentration-dependent effects on the kinetics of SIRT1 (FIG. 1d).

Apparent $K_m$ for NAD$^+$ and acetylated substrate appear to actually be raised by 5 µM resveratrol when nicotinamide is present. At 20 and 100 µM, in the presence of 50 µM nicotinamide, resveratrol lowers the $K_m$ for both NAD$^+$ and acetylated peptide, without reversing the nicotinamide-induced $V_{max}$ decrease. It has been proposed that sirtuins may bind nicotinamide at a second site, known as "the C pocket", distinct from the "B" site that interacts with the nicotinamide moiety of NAD$^{+26}$. In light of this potential complexity, further kinetic studies, supplemented by structural/crystallographic information, will likely be necessary to fully elucidate the interplay between the effects of nicotinamide and polyphenols.

Example 3

Activating Compounds Extend Yeast Lifespan

To investigate whether these compounds could stimulate sirtuins in vivo, we utilized *S. cerevisiae*, an organism in which the upstream regulators and downstream targets of Sir2 are relatively well understood. A resveratrol dose-response study of Sir2 deacetylation rates (FIG. 2a) indeed reveals that resveratrol stimulates Sir2 in vitro, with the optimum concentration of activator being 2-5 µM. Levels of activation were somewhat lower than those for SIRT1, and unlike SIRT1, inhibition was seen at concentrations greater than 100 µM.

Resveratrol and four other potent sirtuin activators, representatives of the stilbene, flavone, and chalcone families, were tested for their effect on yeast lifespan. Due to the potential impediment by the yeast cell wall or plasma membrane and suspected slow oxidation of the compound in the medium, we chose to use a concentration (10 µM) slightly higher than the optimal resveratrol concentration in vitro. As shown in FIG. 2b, quercetin and piceatannol had no significant effect on lifespan. In contrast, butein, fisetin and resveratrol increased average lifespan by 31, 55 and 70%, respectively, and all three significantly increased maximum lifespan (FIG. 2c). Concentrations of resveratrol higher than 10 µM provided no added lifespan benefit and there was no lasting effect of the compound on the lifespan of pre-treated young cells (FIG. 2d and data not shown).

Figure 3:
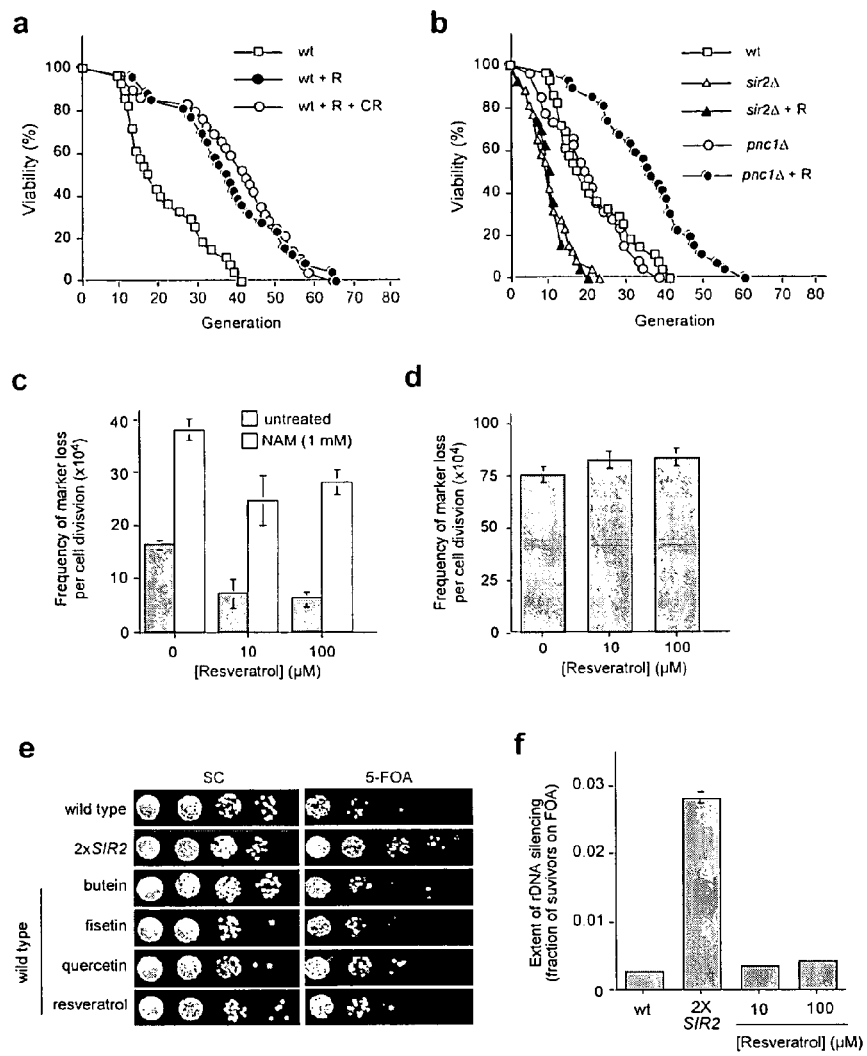
FIG. 3 shows that resveratrol extends lifespan by mimicking CR and suppressing rDNA recombination. Yeast lifespans were determined as in FIG. 2. a, Average lifespan for wild type (wt) untreated, 19.0 generations; wild type+resveratrol (wt+R) 37.8; glucose-restricted+resveratrol (CR+R), 39.9. b, Average lifespans for wild type sir2Δ, 9.9; sir2Δ+resveratrol, 10.0; pnc1Δ, 19.2; pnc1Δ+resveratrol, 33.1. c, Resveratrol suppresses the frequency of ribosomal DNA recombination in the presence and absence of nicotinamide (NAM). Frequencies were determined by loss of the ADE2 marker gene from the rDNA locus (RDN1). d, Resveratrol does not suppress rDNA recombination in a sir2 strain. e, Resveratrol and other sirtuin activators do not significantly increase rDNA silencing compared to a 2xSIR2 strain. Pre-treated cells (RDNI::URA3) were harvested and spotted as 10-fold serial dilutions on either SC or SC with 5-fluororotic acid (5-FOA). In this assay, increased rDNA silencing results in increased survival on 5-FOA medium. f, Quantitation of the effect of resveratrol on rDNA silencing by counting numbers of surviving cells on FOA/total plated.

For subsequent yeast genetic experiments we focused on resveratrol because it was the most potent SIRT1 activator and provided the greatest lifespan extension. Glucose restriction, a form of CR in yeast, resulted in no significant extension of the long-lived resveratrol-treated cells (FIG. 3a), indicating that resveratrol likely acts via the same pathway as CR. Consistent with this, resveratrol had no effect on the lifespan of a sir2 null mutant (FIG. 3b). Given that resveratrol is reported to have fungicidal properties at high concentrations[36], and that mild stress can extend yeast lifespan by activating PNC1[6], it was plausible that resveratrol was extending lifespan by inducing PNC1, rather than acting on Sir2 directly. However, resveratrol extended the lifespan of a pnc1 null mutant nearly as well as it did wild type cells (FIG. 3b). Together these data show that resveratrol acts downstream of PNC1 and requires SIR2 for its effect. Thus, the simplest explanation for our observations is that resveratrol increases lifespan by directly stimulating Sir2 activity.

A major cause of yeast aging is thought to stem from the inherent instability of the repetitive rDNA locus[2,5,37-39]. Homologous recombination between rDNA repeats can generate an extrachromosomal circular form of rDNA (ERC) that is replicated until it reaches toxic levels in old cells. Sir2 is thought to extend lifespan by suppressing recombination at the replication fork barrier of rDNA[40]. Consistent with the lifespan extension we observed for resveratrol, this compound reduced the frequency of rDNA recombination by ~60% (FIG. 3c), in a SIR2-dependent manner (FIG. 3d). In the presence of the Sir2 inhibitor nicotinamide, recombination was also decreased by resveratrol (FIG. 3c), in agreement with the kinetic data (see FIG. 1d). Interestingly, we found that resveratrol and other sirtuin activators had only minor effects on rDNA silencing (FIGS. 3e and f). Work is underway to elucidate how these various compounds can differentially affect rDNA stability and silencing.

Another measure of lifespan in *S. cerevisiae* is the length of time cells can survive in a metabolically active but nutrient deprived state. Aging under these conditions (i.e. chronological aging) is primarily due to oxidative damage[41]. Resveratrol (10 µM or 100 µM) failed to extend chronological lifespan (not shown), indicating that the sirtuin-stimulatory effect of resveratrol may be more relevant in vivo than its antioxidant activity[30,31].

Example 4

Effects of Activators in Human Cells

Figure 6:
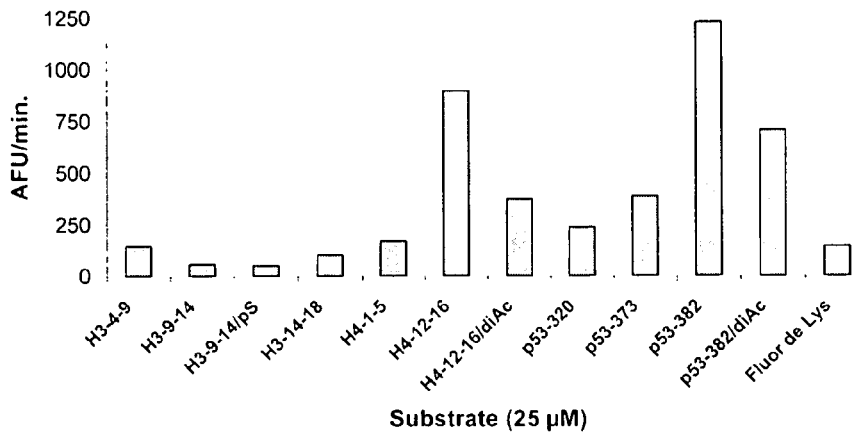
FIG. 6 shows that deacetylation site preferences of recombinant SIRT1. Initial rates of deacetylation were determined for a series of fluorogenic acetylated peptide substrates (see SEQ ID NOS: 5-15, respectively) based on short stretches of human histone H3, H4 and p53 sequence (see key to substrate name and single letter peptide sequence below the bar graph). Recombinant human SIRT1 (1 µg, BIOMOL), was incubated 10 min, 37° C., with 25 µM of the indicated fluorogenic acetylated peptide substrate and 500 µM $NAD^+$. Reactions were stopped by the addition of 1 mM nicotinamide and the deacetylation-dependent fluorescent signal was determined.

To test whether these compounds could stimulate human SIRT1 in vivo, we first employed a cellular deacetylase assay that we had developed. A schematic of the assay procedure is depicted in FIG. 4a. Cells are incubated with media containing the fluorogenic ε-acetyl-lysine substrate, 'Fluor de Lys' (FdL). This substrate, neutral when acetylated, becomes positively charged upon deacetylation and accumulates within cells (see FIG. 6a). Lysis of the cells and addition of the non-cell-permeable 'Developer' reagent releases a fluorophor specifically from those substrate molecules that have been deacetylated (FIG. 4a and see Methods). With HeLa cells growing adherently, 5-10% of the signal produced in this assay is insensitive to 1 µM trichostatin A (TSA), a potent inhibitor of class I and II HDACs but not sirtuins (class III)[42] (FIGS. 6b and 6c).

A selection of SIRT1-stimulatory and non-stimulatory polyphenols were tested for their effects on this TSA-insensitive signal (FIG. 4b). Cellular deacetylation signals in the presence of each compound (y-axis, FIG. 4b) were plotted against their fold-stimulations of SIRT1 in vitro (x-axis, FIG. 4b, data from Supplementary Tables 1-3). For most of the compounds, the in vitro activity roughly corresponded to the cellular signal. Compounds with little or no in vitro activity clustered around the negative control (Group A, FIG. 4b). Another grouping, of strong in vitro activators is clearly distanced from the low activity cluster in both dimensions (Group B, FIG. 4b). A notable outlier was butein, a potent activator of SIRT1 in vitro which had no effect on the cellular signal. With allowances for possible variation among these compounds in properties unrelated to direct sirtuin stimulation, such as cell-permeability and rates of metabolism, these data are consistent with the idea that certain polyphenols can activate native sirtuins in vivo.

One known target of SIRT1 in vivo is lysine 382 of p53. Deacetylation of this residue by SIRT1 decreases the activity and half-life of p53[20,21,27]. To follow the acetylation status of K382 we generated a rabbit polyclonal antibody that recognizes the acetylated form of K382 (Ac-K382) on Western blots of whole cell lysates. As a control we showed that the signal was specifically detected in extracts from cells exposed to ionizing radiation (FIG. 4c), but not in extracts from cells lacking p53 or where arginine had been substituted for lysine 382 (data not shown). U2OS osteosarcoma cells were pretreated for 4 hours with resveratrol (0.5 and 50 µM) and exposed to UV radiation. We consistently observed a marked decrease in the level of Ac-K382 in the presence of 0.5 µM resveratrol, compared to untreated cells (FIG. 4d). At higher concentrations of resveratrol (>50 µM) the effect was reversed (FIG. 4d and data not shown), consistent with previous reports of increased p53 activity at such concentrations[43]. The ability of low concentrations of resveratrol to promote deacetylation of p53 was diminished in cells expressing a dominant-negative SIRT1 allele (H363Y) (FIG. 4e), demonstrating that SIRT1 is necessary for this effect. This biphasic dose-response of resveratrol could explain the dichotomy in the literature regarding the effects of resveratrol on cell survival[30,43,44].

Thus, we have discovered the first known class of small molecule sirtuin activators, all of which are plant polyphenols. These compounds can dramatically stimulate sirtuin activity in vitro and promote effects consistent with increased sirtuin activity in vivo. In human cells, resveratrol promotes SIRT1-mediated p53 deacetylation of K382. In yeast, the effect of resveratrol on lifespan is as great as any longevity-promoting genetic manipulation[6] and has been linked convincingly to the direct activation of Sir2. The correlation between lifespan and rDNA recombination, but not silencing, adds to the body of evidence that yeast aging is due to DNA instability[2,5,37-39] not gene dysregulation[45].

How can we explain the activation of the yeast and human sirtuins by so many plant metabolites? Sirtuins have been found in diverse eukaryotes, including fungi, protozoans, metazoans and plants[46,47], and likely evolved early in life's history[1]. Plants are known to produce a variety of polyphenols, including resveratrol, in response to stresses such as dehydration, nutrient deprivation, UV radiation and pathogens[48,49]. Therefore it is plausible that these compounds may be synthesized to regulate a sirtuin-mediated plant stress response. This would be consistent with the recently discovered relationship between environmental stress and Sir2 activity in yeast[6]. Perhaps these compounds have stimulatory activity on sirtuins from fungi and animals because they mimic an endogenous activator, as is the case for the opiates/endorphins, cannabinols/endocannabinoids and various polyphenols with estrogen-like activity[30,31]. Alternatively, animal and fungal sirtuins may have retained or developed an ability to respond to these plant metabolites because they are a useful indicator of a deteriorating environment and/or food supply.

Example 5

Materials and Methods for Examples 1-4

Compound Libraries and Deacetylation Assays

His$_6$-tagged recombinant SIRT1 and GST-tagged recombinant Sir2 were prepared as previously described[26]. From 0.1 to 1 μg of SIRT1 and 1.5 μg of Sir2 were used per deacetylation assay (in 50 μl total reaction) as previously described[26]. SIRT1 assays and certain of those for Sir2 employed the p53-382 acetylated substrate ('Fluor de Lys-SIRT1', BIOMOL) rather than FdL.

Themed compound libraries (BIOMOL) were used for primary and secondary screening. Most polyphenol compounds were dissolved at 10 mM in dimethylsulfoxide (DMSO) on the day of the assay. For water soluble compounds and negative controls, 1% v/v DMSO was added to the assay. In vitro fluorescence assay results were read in white ½-volume 96-well microplates (Corning Costar 3693) with a CytoFluor™.II fluorescence plate reader (PerSeptive Biosystems, Ex. 360 nm, Em. 460 nm, gain=85). HeLa cells were grown and the cellular deacetylation assays were performed and read, as above, but in full-volume 96-well microplates (Corning Costar 3595). Unless otherwise indicated all initial rate measurements were means of three or more replicates, obtained with single incubation times, at which point 5% or less of the substrate initially present had been deacetylated. Calculation of net fluorescence increases included subtraction of a blank value, which in the case of Sir2 was obtained by omitting the enzyme from the reaction and in the case of SIRT1 by adding an inhibitor (200 μM suramin or 1 mM nicotinamide) to the reaction prior to the acetylated substrate. A number of the polyphenols partially quenched the fluorescence produced in the assay and correction factors were obtained by determining the fluorescence increase due to a 3 μM spike of an FdL deacetylated standard (BIOMOL, catalog number KI-142). All error bars represent the standard error of the mean.

Media and Strains

All yeast strains were grown at 30° C. in complete yeast extract/bactopeptone, 2.0% (w/v) glucose (YPD) medium except where stated otherwise. Calorie restriction was induced in 0.5% glucose. Synthetic complete (SC) medium consisted of 1.67% yeast nitrogen base, 2% glucose, 40 mg/litre each of auxotrophic markers. SIR2 was integrated in extra copy and disrupted as described[5]. Other strains are described elsewhere. For cellular deacetylation assays, HeLa S3 cells were used. U2OS osteosarcoma and human embryonic kidney (HEK 293) cells were cultured adherently in Dulbecco's Modified Eagle's Medium (DMEM) containing 10% fetal calf serum (FCS) with 1.0% glutamine and 1.0% penecillin/streptomycin. HEK 293 overexpressing dominant negative SIRT1 H363Y was a gift of R. Frye (U. Pittsburgh).

Lifespan Determinations

Lifespan measurements were performed using PSY316AT MATα as previously described[35]. All compounds for lifespan analyses were dissolved in 95% ethanol and plates were dried and used within 24 hours. Prior to lifespan analysis, cells were pre-incubated on their respective media for at least 15 hours. Following transfer to a new plate, cells were equilibrated on the medium for a minimum of 4 hours prior to micro-manipulating them. At least 30 cells were examined per experiment and each experiment was performed at least twice. Statistical significance of lifespan differences was determined using the Wilcoxon rank sum test. Differences are stated to be significant when the confidence is higher than 95%.

Silencing and Recombination Assays

Ribosomal DNA silencing assays using the URA3 reporters were performed as previously described[26]. Ribosomal DNA recombination frequencies were determined by plating W303AR cells[37] on YPD medium with low adenine/histidine and counting the fraction of half-red sectored colonies using Bio-Rad Quantity One software as previously described[35]. At least 6000 cells were analyzed per experiment and all experiments were performed in triplicate. All strains were pre-grown for 15 hours with the relevant compound prior to plating.

Proteins and Western Analyses

Recombinant Sir2-GST was expressed and purified from E. coli as previously described except that lysates were prepared using sonication[26]. Recombinant SIRT1 from E. coli was prepared as previously described[26]. Polyclonal antiserum against p53-AcK382 was generated using an acetylated peptide antigen as previously described[20], with the following modifications. Anti-Ac-K382 antibody was affinity purified using non-acetylated p53-K382 peptides and stored in PBS at −70° C. and recognized an acetylated but not a non-acetylated p53 peptide. Western hybridizations using anti-acetylated K382 or anti-actin (Chemicon) antibody were performed at 1:1000 dilution of antibody. Hybridizations with polyclonal p53 antibody (Santa Cruz Biotech.) used 1:500 dilution of antibody. Whole cell extracts were prepared by lysing cells in buffer containing 150 mM NaCl, 1 mM MgCl$_2$, 10% glycerol, 1% NP40, 1 mM DTT and anti-protease cocktail (Roche).

REFERENCES FOR EXAMPLES 1-4 AND BACKGROUND

1. Kenyon, C. *Cell* 105, 165-168 (2001).
2. Sinclair, D. A. *Mech Ageing Dev* 123, 857-67 (2002).
3. Hekimi, S. & Guarente *Science* 299, 1351-4 (2003).
4. Guarente, L. & Kenyon, C. *Nature* 408, 255-62. (2000).
5. Lin et al. *Science* 289, 2126-8. (2000).
6. Anderson et al. *Nature* 423, 181-5 (2003).
7. Kaeberlein et al. *Genes Dev* 13, 2570-80. (1999).
8. Landry et al. *Proc Natl Acad Sci USA* 97, 5807-11. (2000).
9. Imai et al. *Nature* 403, 795-800 (2000).
10. Smith et al. *Proc Natl Acad Sci USA* 97, 6658-63. (2000).
11. Tanner et al. *Proc Natl Acad Sci USA* 97, 14178-82. (2000).
12. Tanny et al. *Cell* 99, 735-45. (1999).
13. Tanny et al. *Proc Natl Acad Sci USA* 98, 415-20. (2001).
14. Laurenson et al. *Microbiol Rev* 56, 543-60. (1992).
15. Smith et al. *Genes Dev* 11, 241-54. (1997).
16. Bryk, M. et al. *Genes Dev* 11, 255-69. (1997).
17. Gottlieb et al. *Cell* 56, 771-6. (1989).
18. Aguilaniu et al. *Science* (2003).
19. Tissenbaum et al. *Nature* 410, 227-30. (2001).
20. Vaziri et al. *Cell* 107, 149-59. (2001).
21. Luo et al. *Cell* 107, 137-48. (2001).
22. Vergnes et al. *Gene* 296, 139-50 (2002).
23. Holzenberger et al. *Nature* 421, 182-7 (2003).
24. Shimokawa et al. *Faseb J* 17, 1108-9 (2003).
25. Tatar et al. *Science* 299, 1346-51 (2003).
26. Bitterman et al. *J Biol Chem* 277, 45099-107. (2002).
27. Langley et al. *EMBO J* 21, 2383-2396 (2002).
28. Glossmann et al. *Naunyn Schmiedebergs Arch Pharmacol* 317, 100-2 (1981).
29. Oliver et al. *J Biol Chem* 269, 29697-703 (1994).
30. Ferguson et al. *Mutat Res* 475, 89-111 (2001).
31. Middleton et al. *Pharmacol Rev* 52, 673-751 (2000).
32. Jang et al. *Science* 275, 218-20 (1997).
33. Stojanovic et al. *Arch Biochem Biophys* 391, 79-89 (2001).
34. Monod et al. *J. Mol. Biol.* 12, 88-118 (1965).
35. Anderson et al. *J Biol Chem* 277, 18881-90. (2002).
36. Pont et al. *J Phytopathol* 130, 1-8 (1990).
37. Sinclair et al. *Cell* 91, 1033-42. (1997).
38. Defossez et al. *Mol Cell* 3, 447-55 (1999).
39. Park et al. *Mol Cell Biol* 19, 3848-56 (1999).
40. Benguria et al. *Nucleic Acids Res* 31, 893-8 (2003).
41. Longo et al. *Science* 299, 1342-6 (2003).
42. Denu et al. *Trends Biochem Sci* 28, 41-8 (2003).
43. Dong et al. *Mutat Res* 523-524, 145-50 (2003).
44. Nicolini et al. *Neurosci Lett* 302, 41-4 (2001).
45. Jazwinski, S. M. et al. *Ann NY Acad Sci* 908, 21-30 (2000).
46. Pandey et al. *Nucleic Acids Res* 30, 5036-55 (2002).
47. Frye, R. A. *Biochem Biophys Res Commun* 273, 793-8. (2000).
48. Soleas et al. *Clin Biochem* 30, 91-113 (1997).
49. Coronado et al. *Plant Physiol* 108, 533-542 (1995).
50. Masoro, E. *J. Exp Gerontol* 35, 299-305. (2000).

Example 6

Localization of the Activation Domain of Sirtuins to their N-Terminus

Figure 7:
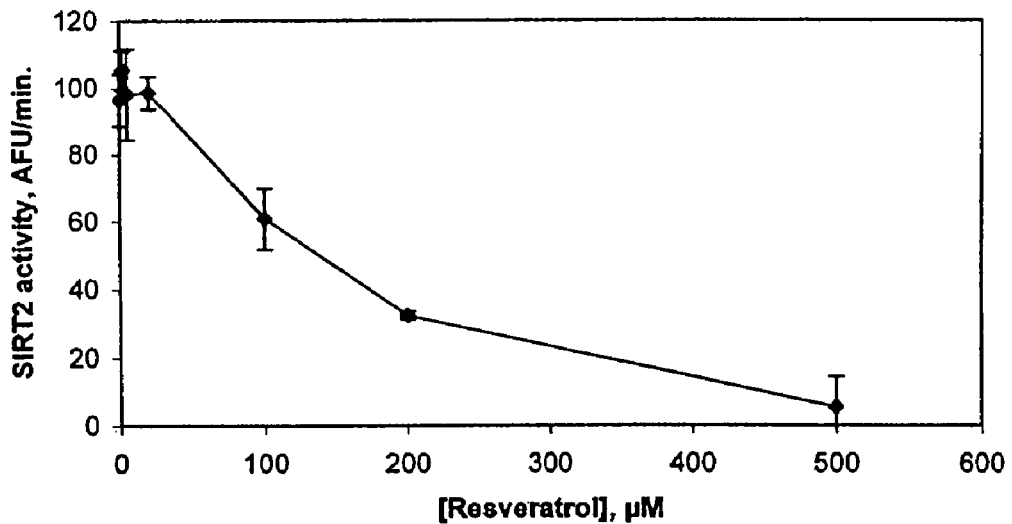
FIG. 7 is a graph representing SIRT2 activity as a function of resveratrol concentration.
Figure 8:
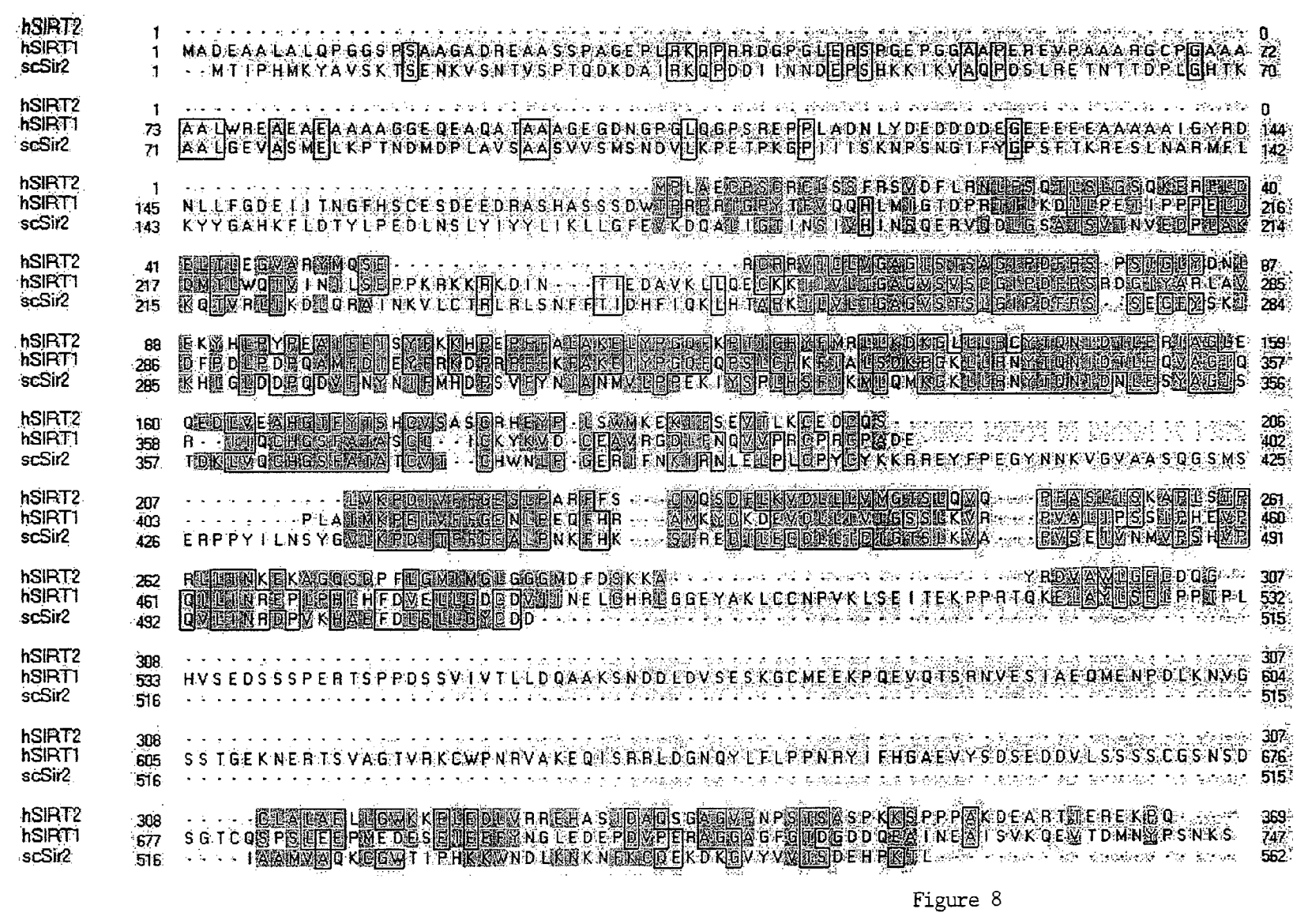

Yeast Sir2 and human SIRT1 are very homologous and differ from human SIRT2 by the addition of an N-terminal domain that is absent in SIRT2. The effect of resveratrol was assayed on human recombinant SIRT2 as follows. Human recombinant SIRT2 was incubated at a concentration of 1.25 µg/well with 25 µM of Fluor de Lys-SIRT2 (BIOMOL cat. # KI-179) and 25 µM NAD+ for 20 minutes at 37° C., as described above. The results, which are shown in FIG. 7, indicate that, in contrast to SIRT1, increasing concentrations of resveratrol decrease SIRT2 activity. Thus, based on the difference in structure of SIRT1 and SIRT2, i.e., the absence of an N-terminal domain (see FIG. 8), it is believed that the N-terminal domain of SIRT1 and Sir2 is necessary for activation by the compounds described herein. In particular, it is likely that the activator compounds described herein interact with the N-terminal portion of sirtuins. The N-terminal portion of SIRT1 that is necessary for the action of the compounds is from about amino acid 1 to about amino acid 176, and that of Sir2 is from about amino acid 1 to about amino acid 175.

Example 7

Resveratrol Extends the Lifespan of *C. elegans*

50 *C. elegans* worms (strain N2) were grown in the presence or absence of 100 µM resveratrol for 17 days. On day 17, only 5 worms in the control group without resveratrol were alive, whereas 17 worms were alive in the group that was treated with resveratrol. Thus, the presence of resveratrol in the growth media of *C. elegans* extends their lifespan.

Example 8

Identification of Additional Activators of Sirtuins

Using the screening assay described in Example 1, five more sirtuin activators have been identified. These are set forth in supplementary Table 8.

Example 9

Identification of Inhibitors of Sirtuins

Using the screening assay described in Example 1, more inhibitors were identified. These are set forth in the appended supplementary Table 8, and correspond to the compounds having a ratio to control rate of less than 1.

Example 10

Identification of Further Activators and Inhibitors of Sirtuins

Additional activators and inhibitors of sirtuins were identified, and are listed in Tables 9-13. In these Tables, "SE" stands for Standard error of the mean and N is the number of replicates used to calculate mean ratio to the control rate and standard error.

All SIRT1 rate measurements used in the calculation of "Ratio to Control Rate" were obtained with 25 µM NAD+ and 25 µM p53-382 acetylated peptide substrate as described above and in K. T. Howitz et al. *Nature* (2003) 425: 191. All ratio data were calculated from experiments in which the total deacetylation in the control reaction was 0.25-1.25 µM peptide or 1-5% of the initial concentration of acetylated peptide.

Stability determinations ($t_{1/2}$) derived from SIRT1 rate measurements performed in a similar way to those described above, except that 5 µM p53-382 acetylated peptide substrate was used rather than 25 µM. The fold-stimulation (ratio to control) obtained with a compound diluted from an aged stock solution was compared to an identical dilution from a stock solution freshly prepared from the solid compound. "$t_{1/2}$" is defined as the time required for the SIRT1 fold-stimulation of the compound from the aged solution to decay to one-half of that obtained from a freshly prepared solution. Ethanol stocks of resveratrol, BML-212 and BML-221 were prepared at 2.5 mM and the compounds were assayed at a final concentration of 50 µM. The water stock of resveratrol was 100 µM and the assay performed at 10 µM. Stocks were aged by storage at room temperature, in glass vials, under a nitrogen atmosphere.

The effect of some of these compounds on lifespan was determined in yeast and *C. elegans*, as described above. The results are set forth below in Table 19:

| Compound | % change in yeast replicative lifespan relative to untreated organisms (10 µM)[a] | % change in *C. elegans* lifespan relative to untreated organisms (100/500 µM)[b] |
|---|---|---|
| untreated | 100% | 100% |
| Resveratrol 3,5,4'-Trihydroxy-trans-stilbene | 170-180% | 110% |
| Pinosylvin 3,5-Dihydroxy-trans-stilbene | 114% | ND |
| BML-212 3,5-Dihydroxy-4'-fluoro-trans-stilbene | 98% | ND |
| BML-217 3,5-Dihydroxy-4'-chloro-trans-stilbene | 90% | ND |
| BML-221 3,4'-Dihydroxy-5-acetoxy-trans-stilbene | 165% | >100% (ongoing) |
| BML-233 3,5-Dihydroxy-4'-methoxy-trans-stilbene | ND | 70% (10) 50% (500) |

[a]Replicative lifespans performed using 2% (w/v) glucose standard yeast compete medium (YPD) under standard conditions.
[b]Lifespan assays performed on N2 worms using *E. coli* as food under standard conditions.
ND. Not determined.

The results indicate that resveratrol significantly extends lifespan in yeast and in *C. elegans*. Since BML-233 was shown to be a strong activator of sirtuins (see above), the results obtained in *C. elegans* may indicate that the compound is toxic to the cells.

Without wanting to be limited to particular structures, it appears that the following structure/activity relationships exist. SIRT1 activation results from several of these new analogs confirmed the importance of planarity, or at least the potential for planarity, between and within the two rings of the active compounds. Reduction of the double bond of the ethylene function, between, the two rings essentially abolishes activity (compare Resveratrol, Table A and Dihydroresveratrol, Table E). Replacement of a phenyl moiety with a cyclohexyl group is nearly as detrimental to SIRT1 stimulating activity (compare Pinosylvin, Table 9 and BML-224, Table 12). Amide bonds are thought to have a partially double bond character. However, replacement of the ethylene function with a carboxamide abolished activity (compare Pinosylvin, Table 9, with BML-219, Table 13). It is possible that this effect could be due in part to the position that carbonyl oxygen must assume in the conformation that places the two rings trans to one another. If so, a compound in which the positions of the amide nitrogen and carbonyl are reversed might be expected to have greater activity.

In twelve of the analogs resveratrol's 4'-hydroxy was replaced with various functionalities (see Tables 9 and 10, BML-221 in Table 11, BML-222 in Table 12). Although none of the replacements tried led to substantial increases in SIRT1 stimulating activity, this parameter was, in general, remarkably tolerant of substitutions at this position. Small groups (H— in Pinosylvin, Cl— in BML-217, —CH$_3$ in BML-228) did the least to decrease activity. There is some evidence of a preference in the enzyme's stilbene binding/activation site for unbranched (ethyl in BML-225, azido in BML-232, —SCH$_3$ in BML-230) and hydrophobic functions (compare isopropyl in BML-231 to acetoxy in BML-221, acetamide in BML-222). Solution stability relative to resveratrol was strongly increased by one of the two 4'-substitutions (acetoxy, BML-221) tested for this so far.

Resveratrol is currently one of the most potent known activator of SIRT1. The collection of analogs described above, particularly the group entailing substitutions at the 4' position, may be instrumental in informing the design of new SIRT1 ligands with improved pharmacological properties. One parameter that may be of interest in this regard is stability. One 4'-substituted analog, BML-221, displays a vast improvement in solution stability relative to resveratrol and although diminished in in vitro SIRT1 activating ability, retains much of resveratrol's biological activity (see lifespan data). The 4'-hydroxyl of resveratrol is thought to be of primary importance to resveratrol's free-radical scavenging reactivity (S. Stojanovic et al. *Arch. Biochem. Biophys.* 2001 391 79). Most of the 4'-substituted analogs have yet to be tested for solution stability, but if resveratrol's instability in solution is due to redox reactivity, many of the other analogs would be expected to also exhibit improved stability.

The results obtained with 4'-substituted analogs may indicate promising routes to explore while seeking to increase SIRT1 binding affinity. For example, the efficacy of the 4'-ethyl compound (BML-225) might indicate the presence of a narrow, hydrophobic binding pocket at the SIRT1 site corresponding to the 4' end of resveratrol. Several new series of 4'-substituted analogs are planned, the simplest comprising straight-chain aliphatic groups of various lengths.

Example 11

Methods of Synthesis of the Compounds in Tables 9-13

Most of the resveratrol analogs were synthesized by the same general procedure, from a pair of intermediates, a benzylphosphonate and an aldehyde. The synthesis or sources of these intermediates are described in section II. Section III. describes the procedures for synthesizing the final compounds from any of the benzylphosphonate/aldehyde pairs. The coupling reaction (Section III. A.) is followed by one of two deprotection reactions depending on whether the intermediates contained methoxymethyl (Section III. B.) or methoxy (Section III. C.) protecting groups. Section IV corresponds to Tables 14-18, which list the particular benzylphosphonate and aldehyde used in the synthesis of particular final compounds. Seven of the compounds-Resveratrol, 3,5-Dihydroxy-4'-methoxy-trans-stilbene, Rhapontin aglycone, BML-227, BML-221, Dihydroresveratrol, BML-219-were not synthesized by the general procedure and "N/A" appears next to their entries in the table. Resveratrol was from BIOMOL and the syntheses of the remaining compounds are described in Section V.

II. Synthetic Intermediates

A. Benzylphosphonates (Synthesized)

Synthesis of Diethyl 4-Acetamidobenzylphosphonate: To diethyl 4-aminobenzylphosphonate in 1:1 methylene chloride/pyridine was added catalytic DMAP and acetic anhydride (1.1 eq.). After 3 hours, the reaction was evaporated to dryness and purified via flash chromatography (silica gel).

Synthesis of Diethyl 4-Methylthiobenzylphosphonate: 4-Methylthiobenzyl chloride was heated with triethylphosphite (as solvent) at 120° C. overnight. Excess triethyl phosphite was distilled off under high vacuum and heat. Flash chromatography (silica gel) yielded the desired product.

Synthesis of Diethyl 3,5-Dimethoxybenzylphosphonate: From 3-5-Dimethoxybenzyl bromide. See synthesis of Diethyl 4-Methylthiobenzylphosphonate.

Synthesis of Diethyl 4-Fluorobenzylphosphonate: From 4-Fluorobenzylphosphonate. See synthesis of Diethyl 4-Methylthiobenzylphosphonate.

Synthesis of Diethyl 4-azidobenzylphosphonate: To diethyl 4-aminobenzylphosphonate in acetonitrile (2.5 mL) at 0° C. was added 6M HCl (1 mL). Sodium nitrite (1.12 eq.) in water (1 mL) was added drop wise and the resulting solution stirred at 0° C. for 30 mins. Sodium azide (8 eq.) in water (1 mL) added drop wise (bubbling) and the solution stirred at 0° C. for 30 mins., then at room temperature for 1 hour. The reaction was diluted with ethyl acetate and washed with water and brine and dried over sodium sulfate. Flash chromatography (silica gel) yielded the desired product.

B. Aldehydes (Synthesized)

Synthesis of 3,5-Dimethoxymethoxybenzaldehyde: To 3,5-dihydroxybenzaldehyde in DMF at 0° C. was added sodium hydride (2.2 eq.). The reaction was stirred for 30 min. at 0° C. Chloromethylmethyl ether (2.2 eq.) was added neat, drop wise and the reaction allowed to warm to room temperature over 1.5 hrs. The reaction mixture was diluted with diethyl ether and washed with water (2×) and brine (1×) and dried over sodium sulfate. Flash chromatography (silica gel) yielded the desired product.

C. Purchased Intermediates: Unless listed above, all synthetic intermediates were purchase from Sigma-Aldrich.

III. General Procedure for the Synthesis of Resveratrol Analogues

A. Benzylphosphonate/Aldehyde Coupling Procedure

To the appropriate benzylphosphonate (1.2 eq.) in dimethylformamide (DMF) at room temperature was added sodium methoxide (1.2 eq.). This solution was allowed to stir at room temperature for approximately 45 minutes. The appropriate aldehyde (1 eq.) was then added (neat or in a solution of dimethylformamide). The resulting solution was then allowed to stir overnight at room temperature. Thin layer chromatography (TLC) was used to determine completeness of the reaction. If the reaction was not complete, the solution was heated at 45-50° C. until complete. The reaction mixture was poured into water and extracted with ethyl acetate (2×). The combined organic layers were washed with brine and dried over sodium sulfate. Flash chromatography (silica gel) yielded the desired products.

B. General Procedure for the Deprotection of Methoxymethylresveratrol Analogues

To the appropriate methoxymethylstilbene derivative in methanol was added two drops of concentrated HCl. The resulting solution was heated overnight at 50° C. The solution was evaporated to dryness upon completion of the reaction. Flash chromatography (silica gel) yielded the desired product.

C. General Procedure for the Deprotection of Methoxyresveratrol Analogues

To the appropriate methoxystilbene derivative in methylene chloride was added tetrabutylammonium iodide (1.95 eq. per methoxy group). The reaction was cooled to 0° C. and boron trichloride (1 M in methylene chloride; 2 eq. per methoxy group) was added dropwise. Following the addition of boron trichloride, the cooling bath was removed and the reaction allowed to stir at room temperature until complete (as indicated by TLC). Saturated sodium bicarbonate solution was added and the reaction vigorously stirred for 1 hour. The reaction was poured into cold 1M HCl and extracted with ethyl acetate (3×). The combined organic layers were washed with water (1×) and brine (1×) and dried over sodium sulfate. Flash chromatography (silica gel) yielded the desired products.

V. Special Syntheses

Synthesis of BML-219 (N-(3,5-Dihydroxyphenyl)benzamide): To benzoyl chloride (1 eq.) in dry methylene chloride at room temperature was added triethylamine (1.5 eq.) and a catalytic amount of DMAP followed by 3,5-dimethoxyaniline (1 eq.). The reaction was allowed to stir overnight at room temperature. Upon completion, the reaction was diluted with ethyl acetate and washed with 1M HCl, water and brine and dried over sodium sulfate. Flash chromatography (silica gel) yielded the methoxystilbene derivative. To the methoxystilbene in dry methylene chloride at 0° C. was added tetrabutylammonium iodide (3.95 eq.) followed by boron trichloride (4 eq.; 1M in methylene chloride). Upon completion of the reaction (TLC), saturated sodium bicarbonate was added and the mixture was vigorously stirred for 1 hour. The reaction was diluted with ethyl acetate and washed with 1M HCl and brine and dried over sodium sulfate. Flash chromatography (silica gel) yielded the desired product.

Synthesis of BML-220 (3,3',5-trihydroxy-4'-methoxystilbene): To Rhapontin in methanol was added catalytic p-toluenesulfonic acid. The reaction was refluxed overnight. Upon completion of the reaction (TLC), the reaction mixture was evaporated to dryness and taken up in ethyl acetate. The organics were washed with water and brine and dried over sodium sulfate. Flash chromatography (silica gel) yielded the desired product.

Synthesis of BML-233 (3,5-Dihydroxy-4'-methoxystilbene): To deoxyrhapontin in methanol was added catalytic p-toluenesulfonic acid. The reaction was refluxed overnight. Upon completion of the reaction (TLC), the reaction mixture was evaporated to dryness and taken up in ethyl acetate. The organics were washed with water and brine and dried over sodium sulfate. Flash chromatography (silica gel) yielded the desired product.

Synthesis of BML-221 and 227 (4' and 3 monoacetylresveratrols): To resveratrol in tetrahydrofuran at room temperature was added pyridine (1 eq.) followed by acetic anhydride (1 eq.). After stirring for 48 hrs., another 0.25 eq.

acetic anhydride added followed by 24 hrs. of stirring. The reaction was diluted with methylene chloride (reaction was not complete) and washed with cold 0.5M HCl, water and brine. Organics were dried over sodium sulfate. Flash chromatography yielded a mixture of 4'- and 3-acetyl resveratrols. Preparative HPLC yielded both monoacetyl resveratrols.

Synthesis of Dihydroresveratrol: To resveratrol in argon-purged ethyl acetate in a Parr shaker was added 10% palladium on carbon (10 wt %). The mixture was shaken under an atmosphere of hydrogen (30 psi) for 5 hours. Filtration through a pad of celite yielded the desired material.

Example 12

Dose-Response Analysis of SIRT1 Deacetylation by Resveratrol and BML-230

SIRT1 initial rates as a function of activator concentration were determined at 25 µM each of NAD$^+$ and p53-382 acetylated peptide, with 20 minutes incubations. Plots of the dose responses of SIRT1 to BML-230 and resveratrol show that the BML-230-stimulated activity exceeds that stimulated by resveratrol at all concentrations tested (FIG. 9a). This could be due to a greater binding affinity of SIRT1 for BML-230, greater activity of the SIRT1/BML-230 complex or some combination of the two. A plot of the ratio of the rates of BML-230-stimulated enzyme to that of resveratrol-stimulated enzyme suggests that increased binding affinity does contribute to the improvement in activity of BML-230 (FIG. 9b). A simple two state model of the binding and activation process assumes that the observed rate (v) is the sum of the fractional contributions of the unliganded and liganded enzymes, where $v_0$ is the unstimulated rate, $v_1$ is the rate of the enzyme with bound ligand-1 (L1) and $K_{L1}$ is the dissociation constant of the enzyme/ligand-1 complex:

$$v = v_0(1-[L1]/(K_{L1}+[L1])) + v_1(-[L1]/(K_{L1}+[L1]))$$

A similar equation can be prepared for ligand-2 and the ratio (R) of the two rates calculated, an equation which will include, given the conditions of FIG. 9, the substitution [L]=[L1]=[L2]. It can be shown that if the two ligand dissociation constants were equal ($K_{L1}=K_{L2}=K_L$), this ratio would be:

$$R = (v_0 K_L + v_1[L])/(v_0 K_L + v_2[L])$$

If $K_{L1} \neq K_{L2}$, this ratio would instead be:

$$R = (v_1[L]^2 + (v_0 K_{L1} + v_1 K_{L2})[L] + v_0 K_{L1} K_{L2})/(v_2[L]^2 + (v_0 K_{L2} + v_2 K_{L1})[L] + v_0 K_{L1} K_{L2})$$

In the first case the plot of R vs. [L] would be a simple hyperbola that monotonically approaches $v_1/v_2$ as [L] increases. In the second case, as in FIG. 9b, the plot would pass through a maximum before approaching $v_1/v_2$ at higher [L] values. The data of FIG. 9b would imply that $v_1/v_2$ (rate for pure SIRT1/BML-230 divided by that for pure SIRT1/resveratrol) is no more than ~1.4 (R at 500 µM) and that the SIRT1/BML-230 complex indeed has a lower dissociation constant than SIRT1/resveratrol ($K_{L1} < K_{L2}$).

One of the difficulties in the use of resveratrol as a pharmacologic agent is the relatively low serum concentrations of the aglycone form that can be achieved and maintained when it is administered orally (<<1 µM; see for example D. M Goldberg et al. *Clin. Biochem.* 2003 36 79). Increasing the SIRT1 binding affinity of synthetic derivatives will improve this aspect of the drug. As sest forth above, various replacements of the resveratrol 4'-hydroxyl, e.g. the H— of pinosylvin or Cl— of BML-217, did not significantly diminish the SIRT1 activating effect. The results obtained with BML-230 indicate that it will be possible to actually increase SIRT1/activator binding affinity by modifications at that site. The 4'-thiomethyl of BML-230 therefore represents a new starting point in seeking further improvements in SIRT1 binding affinity by the synthesis of related derivatives (e.g. 4'-thioethyl etc.).

Example 13

Survival Rates

Human 293 were grown to exponential phase under standard conditions and subjected to a dose of compound (50 micromolar) for 96 hours. The number of live cells each time point was counted using a Coulter counter.

TABLE 24

Survival statistics of 293 cells:

| Time (h) | Resveratrol | Thio-Methyl BML-230 | Ethyl BML-225 | Methyl BML-228 | Isopropyl BML-231 |
|---|---|---|---|---|---|
| 0 | 100% | 100% | 100% | 100% | 100% |
| 48 | 5% | 55% | 5% | 46% | 0% |
| 96 | 0% | 57% | 8% | 32% | 0% |

The results indicate that thiomethyl (BML-230) was the least toxic on 293 cells.

Example 14

Sirtuin Activators Mimic Calorie Restriction and Delay Aging in Metazoans

Caloric restriction (CR) extends lifespan in numerous species. In the budding yeast *S. cerevisiae*, this effect requires Sir2[1], a member of the sirtuin family of NAD$^+$-dependent deacetylases[2,3]. Sirtuin activating compounds (STACs) can promote the survival of human cells and extend the replicative lifespan of yeast[4]. Here we show that resveratrol and other STACs activate sirtuins from *Caenorhabditis elegans* and *Drosophila melanogaster* and extend the lifespan of these animals up to 29% without reducing fecundity. Lifespan extension is dependent on functional Sir2 and is not observed when nutrients are restricted. Together these data indicate that STACs slow metazoan ageing by mechanisms related to CR.

Sir2-like proteins (sirtuins) are a family of NAD$^+$-dependent deacetylases conserved from *E. coli* to humans[5-9] (FIG. 10a) that play important roles in gene silencing, DNA repair, rDNA recombination and ageing in model organisms[2,10-12]. When diet is restricted (calorie restriction, CR), lifespan is extended in diverse species, suggesting there is a conserved mechanism for nutrient regulation of ageing[13-17]. In budding yeast, extra copies this gene extend lifespan by 30% apparently by mimicking CR[1,18]. We recently described a group of compounds (STACs) that stimulate the catalytic activity of yeast and human sirtuins, and extend the replicative lifespan of yeast cells up to 60%[4].

Figure 10:
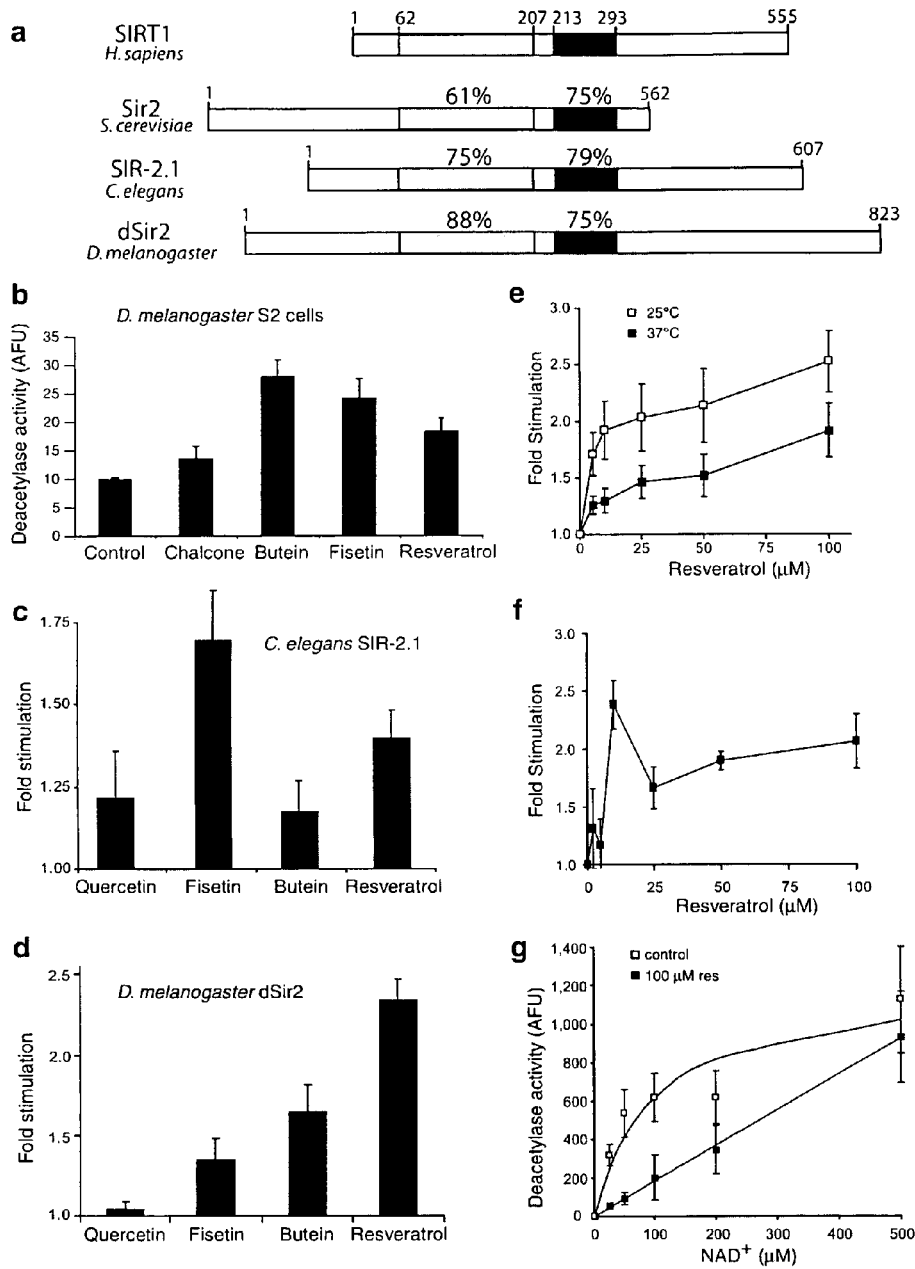
FIG. 10 shows the effect of polyphenolic STACs on metazoan sirtuins. a, Schematic of Sir2 polypeptides from human, yeast, *C. elegans* and *D. melanogaster* aligned to show conserved regions. Amino acids forming the $NAD^+$-binding pocket (grey) and substrate binding groove (black) are indicated. Percentages refer to the homology to SIRT1. b, Effect of polyphenolic STACs (500 µM) on $NAD^+$-dependent, trichostatin A (TSA)-insensitive deacetylase activity in *Drosophila* S2 cells. c, Fold stimulation of recombinant SIR-2.1 by STACs (10 µM). d, Fold stimulation of recombinant dSir2 by STACs (10 µM). Values are the mean of at least three determinations (+/-standard error). e, Dose-dependent activation of *C. elegans* SIR-2.1 by resveratrol. Rates were determined using a fluorigenic acetylated lysine substrate (Fluor de Lys). f, Dose-dependent activation of *Drosophila* dSir2 by resveratrol. g, SIR-2.1 initial rate at 10 µM Fluor de Lys as a function of $NAD^+$ concentration, in the presence or absence of 100 µM resveratrol. AFU, arbitrary fluorescence units.

To establish whether STACs could activate sirtuins from multicellular animals, we developed a cell-based deacetylation assay for *D. melanogaster* S2 cells. Several classes of polyphenolic STACs, including chalcones, flavones and stilbenes, increased the rate of deacetylation in an NAD$^+$-dependent manner (FIG. 10b). To determine whether this activity was due to direct stimulation of a Sir2 homolog, we purified recombinant SIR-2.1 of *C. elegans* and dSir2 of *D. melanogaster* and determined the effect of various STACs on enzymatic activity in vitro (FIG. 10c, d). In a dose-dependent manner, resveratrol stimulated deacetylation up to 2.5-fold for SIR-2.1 (FIG. 10e) and 2.4-fold for dSir2 (FIG. 10f). As previously observed with the yeast and human Sir2 enzymes, resveratrol lowered the $K_m$ of SIR-2.1 for the co-substrate NAD$^+$ (FIG. 10g).

Figure 11:
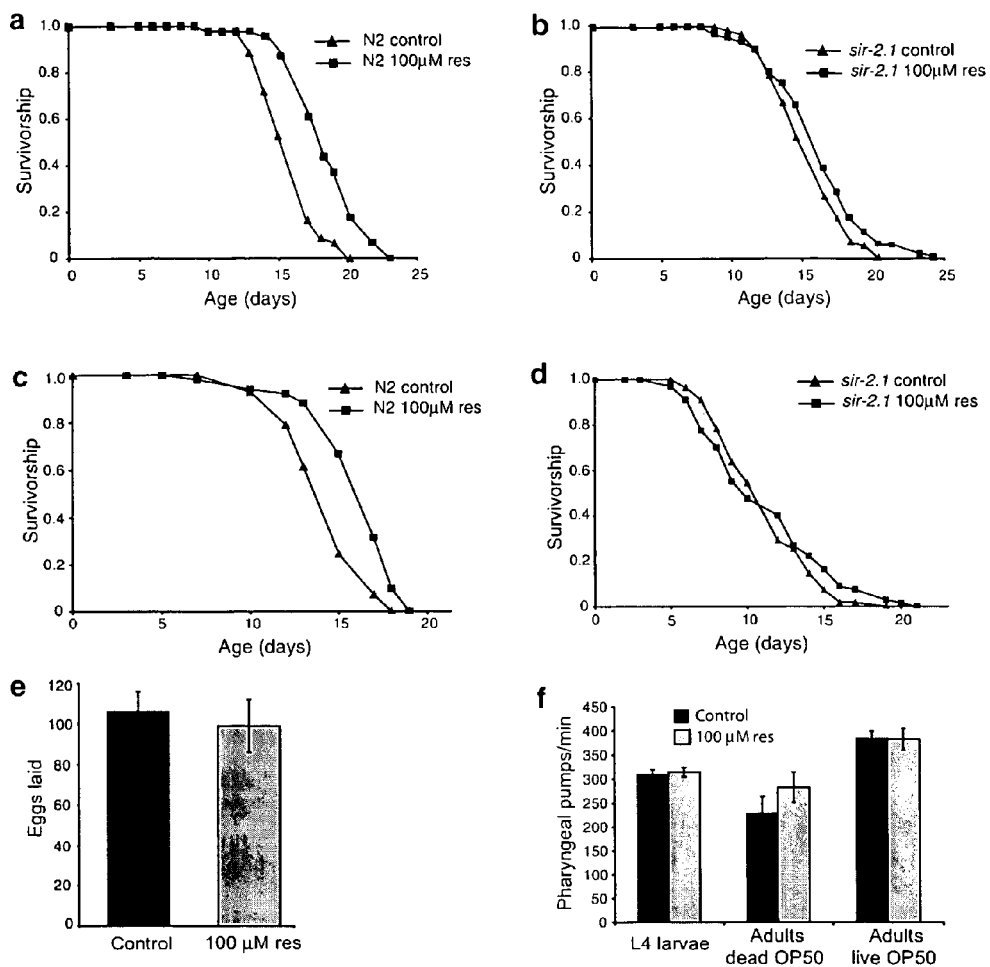
FIG. 11 shows the *C. elegans* survival on resveratrol. a, Survivorship of adult wild-type N2 *C. elegans* treated with 100 µM resveratrol fed with heat-killed OP50 *E. coli*. Mean lifespan relative to control (triangles, n=47) was increased by 14.5% (Log-Rank test, P<0.0001) by 100 µM resveratrol (squares, n=46). b, Survivorship of sir-2.1 mutants treated with resveratrol fed with heat-killed OP50. Adult lifespan of sir-2.1 animals does not differ significantly from N2 controls (Log-Rank, P=0.68) and the effect on lifespan of 100 □M resveratrol on sir-2.1 mutant animals was not statistically significant (5.2% extension, Log-Rank P=0.058; n=60 control, 58 treated). c, Survivorship of wild-type N2 *C. elegans* on 100 µM resveratrol fed with live OP50 (12.6% extension, P<0.0001; n=47 control, 67 treated). d, Survivorship of sir-2.1 mutants on 100 µM resveratrol fed with live OP50 (3.3% extension, P=0.81; n=57 control, 51 treated) e, Fecundity of adult hermaphrodites treated with 100 □M resveratrol. Controls: 106 eggs/5 worms/5 hours (s.d. 10.0); resveratrol-treated: 99 eggs/5 worms/5 hours (s.d. 13.0). f, Feeding rates of L4 larval and adult hermaphrodites treated with 100 µM resveratrol. L4 on live OP50: control 310±10.2 pumps/min, resveratrol 315±9.8; Adult on dead OP50: control 228±26.2, resveratrol 283±31.9; Adult on live OP50: control 383±16.0, resveratrol 383±22.7.
Figure 14:
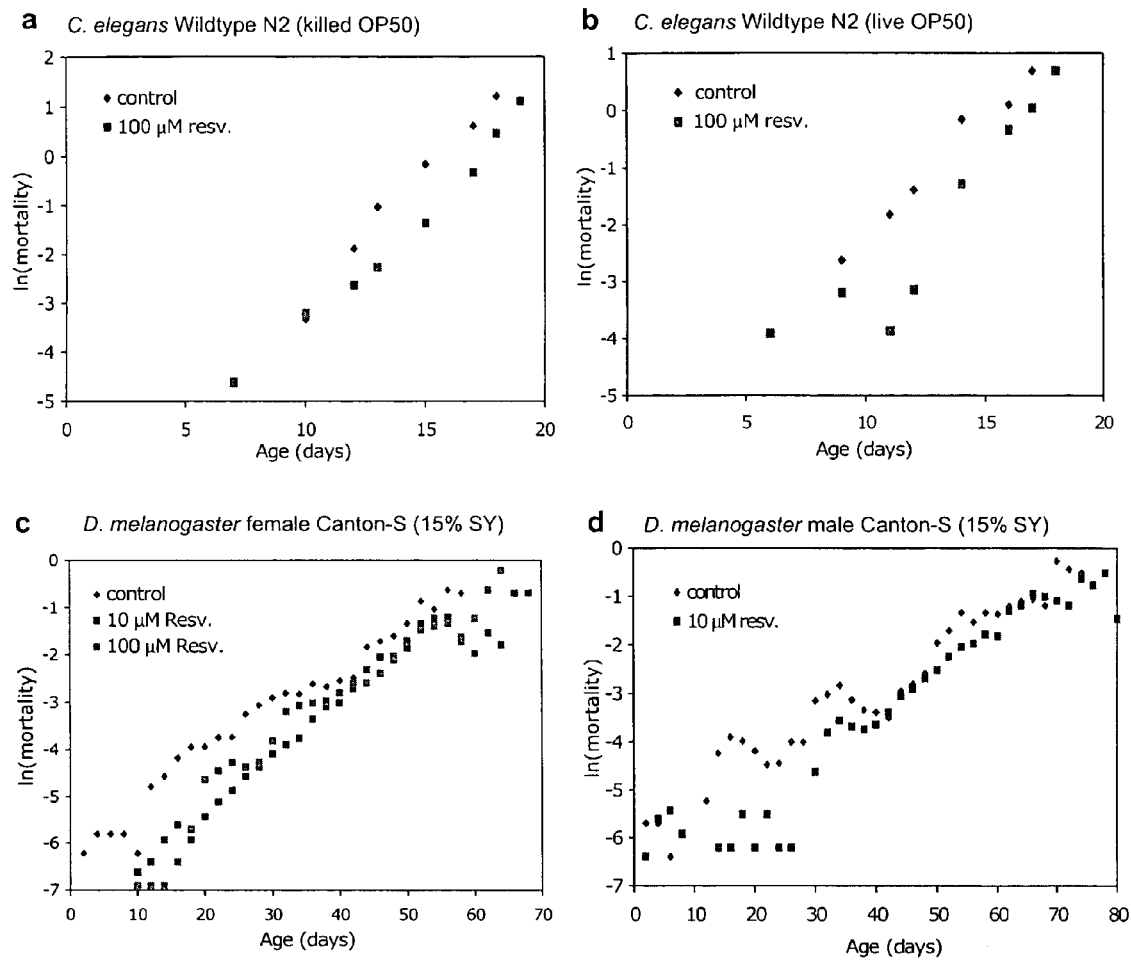
FIG. 14 shows the mortality rates of control and resveratrol treated adults. Mortality was estimated as $\ln(-\ln(p_x))$ where $p_x$ is the survival probability at day x to x+1. a, *C. elegans* wild-type N2 on heat-killed OP50 *E. coli*. b, *C. elegans* wild-type N2 on live OP50 *E. coli*. In a and b mortality is plotted only at days with observed mortality. c, *D. melanogaster* wildtype females of Trial 1 at effective doses of resveratrol on 15% SY diet. d, *D. melanogaster* wildtype males of Trial 1 at effective doses of resveratrol on 15% SY diet. In c and d mortality is smoothed from 3-day running average of $p_x$.

Because resveratrol can significantly extend replicative lifespan in yeast[4], we asked whether STACs could also extend lifespan in the metazoans C. elegans and D. melanogaster. Wild-type worms were transferred to plates containing 0 or 100 µM of resveratrol shortly after reaching adulthood. Lifespan was reproducibly extended up to 15%, using either heat-killed or live E. coli as food supply (FIG. 11a, c respectively) and mortality was decreased across all adult ages (FIG. 14). To test whether the lifespan extension depends on functional SIR-2.1, we constructed a sir-2.1 null mutant. The lifespan of this strain was not appreciably shorter than the wildtype N2 control and adults treated with resveratrol did not exhibit a significant lifespan extension relative to untreated worms (FIG. 11b, d). There was no decrease in fecundity associated with resveratrol treatment (FIG. 11e). To rule out the possibility that resveratrol was causing the animals to eat less, thereby inducing a CR effect indirectly, we measured feeding rates of both L4 larval and adult worms with or without resveratrol and found no differences (FIG. 11f).

Figure 12:
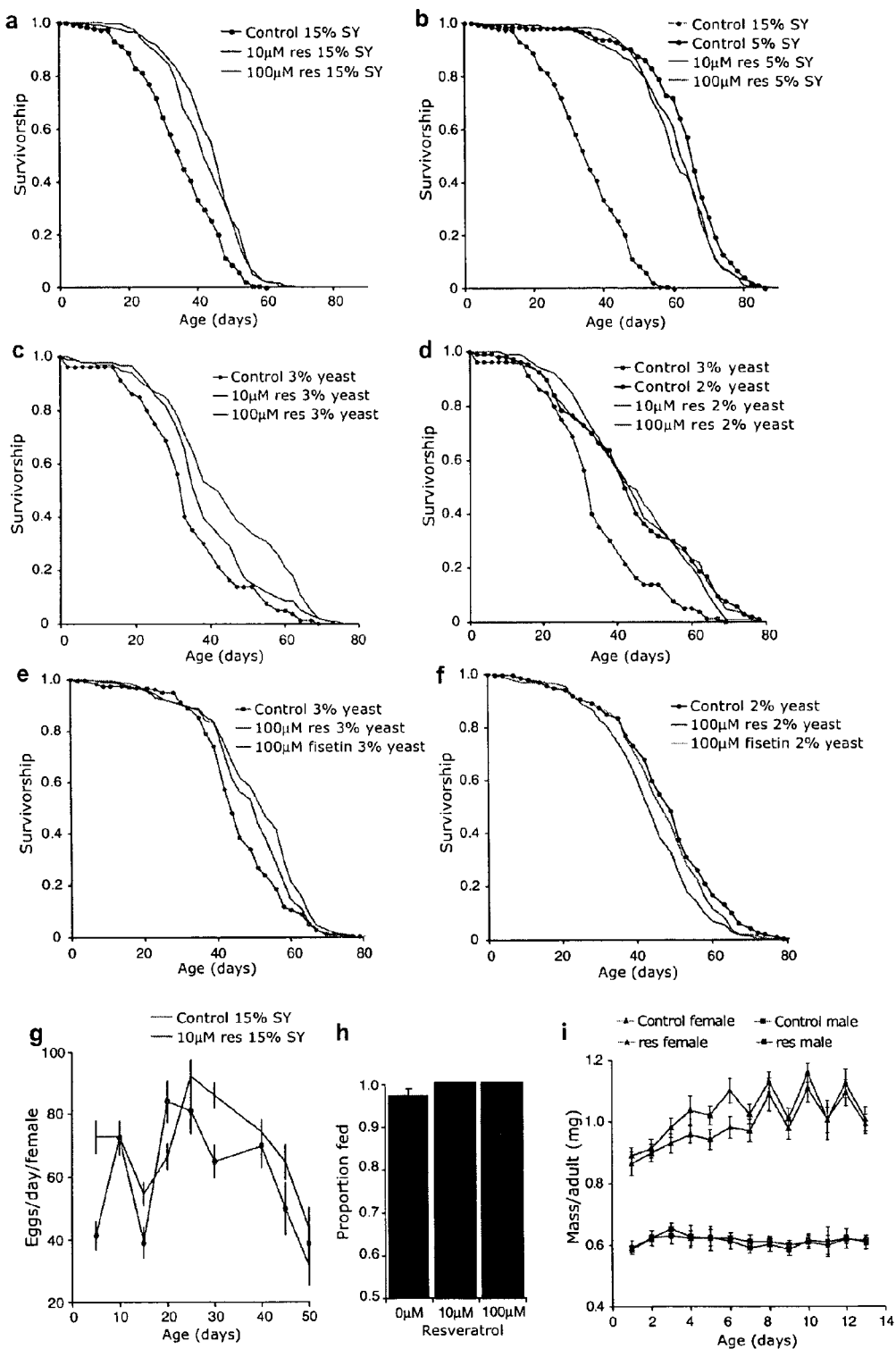
FIG. 12 shows wild-type female *D. melanogaster* survival with adults fed resveratrol or fisetin. a, Canton-S on 15% SY media. b, Canton-S on 5% SY media with resveratrol at two concentrations. c, Strain yw on 3% CSY media. d, Strain yw on 2% CSY media with resveratol at two concentrations. e, Strain yw on 3% CSY media with 100 µM resveratrol or fisetin. f, Strain yw on 2% CSY media with 100 µM resveratrol or fisetin. Life table statistics for this figure, for males and for additional trials are in Table 20. g, Mean daily fecundity per female (s.e.) estimated over 5-day intervals of Canton-S on 15% SY media with 0 or 10 µM resveratrol. h, Proportion (s.e.) of yw females feeding on diet with and without resveratrol in crop-filling assay. i, Mean (s.e.) body mass of Canton-S males and females feeding on diet without and with resveratrol (10 µM).

We also tested whether STACs could extend lifespan in D. melanogaster using the standard laboratory wild type strain Canton-S and normal fly culturing conditions (vials), and a yw marked wild type strain and demographic culturing conditions (cages) (Table 20). Across independent tests in males and females, lifespan was extended up to 23% with fisetin and up to 29% with resveratrol (FIG. 12a, c, e). Increased longevity was associated with reduced mortality prior to day 40 (FIG. 14). A restricted diet increased lifespan by 40% in females and by 14% in males (averaged across trials), and under these conditions neither resveratrol nor fisetin further increased longevity (FIG. 12b, d, f), suggesting that resveratrol extends lifespan through a mechanism related to CR.

Surprisingly, while diet manipulations that extend D. melanogaster longevity typically reduce fecundity[19,20], longevity-extending doses of resveratrol modestly increased egg production (10 µM resveratrol: 69.8 eggs/5 days, s.e.=2.2; control: 59.9 eggs/5 days, s.e.=2.2; t=3.17, P=0.0017), particularly in the earliest days of adult life (FIG. 12g). The increase in egg production suggests that the lifespan extending effect of resveratrol in D. melanogaster was not due to CR induced by food aversion or lack of appetite. Consistent with this, no decrease in food uptake was seen with resveratrol-fed flies (FIG. 12h). Furthermore, resveratrol-fed flies maintained normal weight (FIG. 12i), except during days 3 through when resveratrol fed females were laying significantly more eggs than control fed females.

Figure 13:
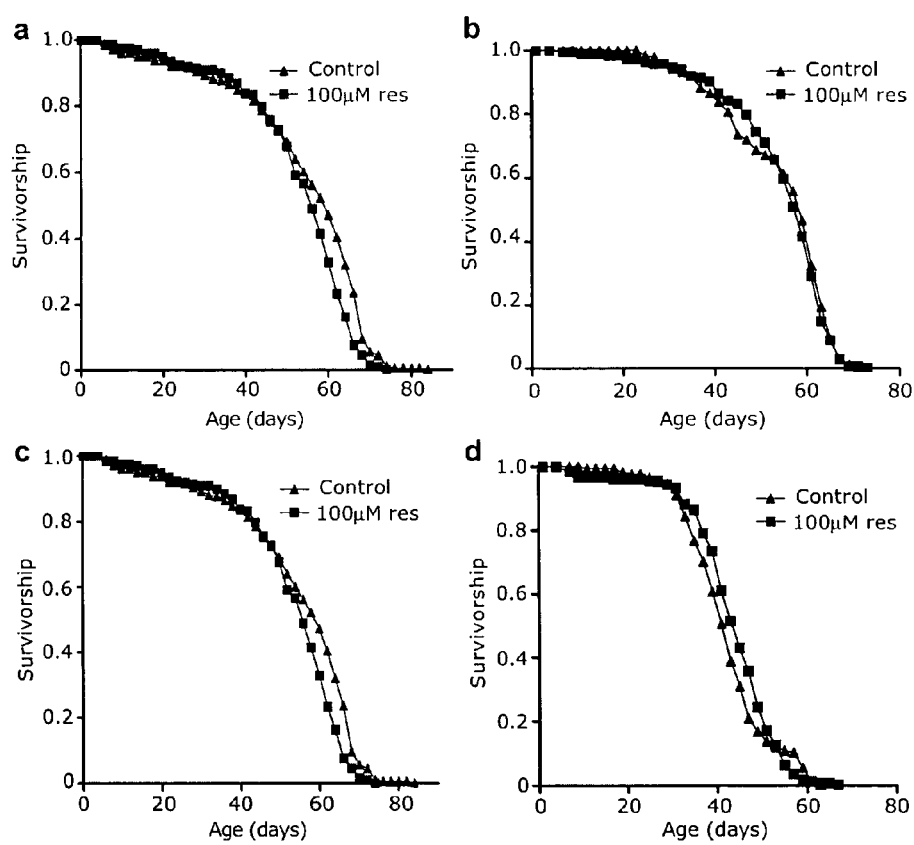
FIG. 13 shows the survivorship of *D. melanogaster* adults with mutant alleles of dSir2 when fed resveratrol (100 µM). Females (a) and males (b) with loss-of-function genotype $dSir2^{4-5}/dSir2^{5.26}$. Females (c) and males (d) with strong hypomorphic genotype $dSir2^{17}/dSir2^{KG00871}$.

To determine whether resveratrol extends fly lifespan in a Sir2-dependent manner, we analyzed a dSir2 allelic series with increasing amounts of dSir2. Adult offspring from crosses between independently derived alleles of dSir2 were tested. Resveratrol failed to extend lifespan in flies completely lacking functional dSir2 (dSir2$^{4.5}$/dSir2$^{5.26}$) (FIG. 13a, b) or in flies in which dSir2 is severely decreased (dSir2$^{17}$/dSir2$^{KG00871}$) (FIG. 13c, d). Resveratrol increased longevity a small but statistically significant amount in flies homozygous for a hypomorphic dSir2 allele (dSir2$^{KG0087}$/dSir2$^{KG0087}$) (Table 20, Trial 6) and increased lifespan up to 17% in flies with one copy of the hypomorphic allele and one copy of a wild-type dSir2 (Canton-S/dSir2$^{KG0087}$) (Table 20, Trial 7). These data demonstrate that the ability of resveratrol to extend fly lifespan requires functional Sir2.

We previously reported that STACs extend the lifespan of replicating yeast cells by mimicking CR[4]. In yeast, chronological and reproductive aging are inseparable in the measure of replicative lifespan. Here we show that STACs can extend lifespan in C. elegans and D. melanogaster, both of which are comprised of primarily non-dividing (post-mitotic) cells as adults, and whose somatic and reproductive aging are independent measures of senescence. In both species, resveratrol increases lifespan in a Sir2-dependent manner and, at least for the fly, this action appears to function through a pathway common to CR.

Our observation that resveratrol can increase longevity without an apparent cost of reproduction is counter to prevalent concepts of senescence evolution. However, STACs may still entail trade-offs under some environmental conditions[21,22] or in the context of selection acting upon the network of traits that determine fitness[23,24]. Plants synthesize STACs such as resveratrol in response to stress and nutrient limitation[25], possibly to activate their own sirtuin pathways[4]. These molecules may activate animal sirtuins because they serve as plant defense mechanisms against consumers or because they are ancestrally orthologous to endogenous activators within metazoans. Alternatively, animals may use plant stress molecules as a cue to prepare for a decline in their environment or food supply[4]. Understanding the adaptive significance, endogenous function, and evolutionary origin of sirtuin activators will lead to further insights into the underlying mechanisms of longevity regulation and aid in the development of interventions that provide the health benefits of CR.

Example 15

Materials and Methods for Example 14

Sirtuin Purification

His$_6$-tagged recombinant SIR-2.1 and dSir2 were purified from E. coli BL21(DE3) plysS cells harboring either pET28a-sir-2.1 or pRSETc-dSir2 plasmids. Cells were grown in LB medium containing kanamycin (50 µg/mL) for pET28a-sir-2.1 or ampicillin (100 µg/ml) and chloramphenicol (25 µg/ml) for pRSETc-dSir2 at 30° C. (dSir2) or 37° C. (SIR-2.1) to an OD$_{600}$ of 0.6-0.8. After addition of IPTG (1 mM), flasks were shifted to 16° C. for 20 h. Cell pellets were resuspended in cold PBS buffer containing 300 mM NaCl, 0.5 mM DTT, 0.5 mM PMSF and EDTA-free protease inhibitor tablets and lysed by sonication. Ni$^{2+}$-NTA beads were added to the clarified extract and after 1-3 hours they were loaded on a column, washed with buffer (50 mM Tris. Cl pH 7.4, 200 mM NaCl, 30 mM imidazole) then eluted with the same buffer containing 600 mM imidazole.

Deacetylation Assays

From 0.1 to 1 µg of SIR-2.1 and 1 µg of dSir2 were used per deacetylation assay as previously described with modifications (SIR-2.1: 200 µM NAD$^+$, 10 µM Fluor de Lys, FdL; dSir2: 25 µM NAD$^+$, 10 µM FdL)[26]. STACs were dissolved at 10 mM in dimethylsulfoxide (DMSO) the day of the assay. In vitro fluorescence assay results were read in 96-well microplates (Corning Costar 3693) with a Wallac Victor Multilabel counter (Perkin Elmer, excitation at 360 nm, emission at 450 nm). Drosophila S2 cells were grown in Schneider media with fetal calf serum at 23-28° C., seeded at 9×10$^4$ cells/well, grown overnight and then exposed to 1 µM TSA, 500 µM polyphenols, and 200 µM FdL for 2 hr. Deacetylation of FdL with lysate from whole cells was determined as described[4]. Unless otherwise indicated all initial rate measurements were means of three or more replicates obtained with single incubation times, at which point 5% or less of the substrate initially present was deacetylated.

C. elegans Media, Strains, Lifespan, and Feeding Assays

Bristol N2 (Caenorhabditis Genetics Center) was used as the wild-type strain. The sir-2.1 mutant strain was generated by backcrossing VC199 (sir-2.1 (ok434)) to N2 four times.

Cultures were grown on standard NGM media and maintained on *E. coli* strain OP50. For the lifespan assays, synchronized animals were transferred to treatment plates as young adults (2 d after hatching, day 0 of assay), and were transferred to fresh treatment plates every 2 days for the first 6 to 8 days of the assay. Treatment plates were standard NGM media with the reproductive suppressant FUdR (Sigma; 100 mg/L) containing resveratrol or solvent (DMSO, which does not affect lifespan) added either directly into the agar before pouring (for live OP50 trials) or diluted into PBS and added to the surface of a dry plate to the indicated final concentration (for dead OP50 trials). For some lifespan trials, heat-killed OP50 were used as a food source. OP50 cultures were heated to 65° C. for 30 minutes, then pelleted and resuspended in 1/10 volume in S Basal supplemented with 10 mM $MgSO_4$. In all assays, worms were monitored daily for mortality by gently probing with a platinum pick. Assays were performed at 24° C.

To assay worm feeding rates, worms at the indicated stages were placed on treatment plates (no FUdR) for 4-5 hours, then videoed for 1 minute using a Pixelink PL-662 camera. The frame rate was slowed and the pumping rate of the pharynx was counted. To assay fecundity, gravid hermaphrodites (5 per plate, raised from synchronized L1s on normal or treatment plates) were allowed to lay eggs on their respective media for 5 hours, and the total number of eggs was counted.

*D. melanogaster* Media, Strains, Feeding Assay and Lifespan Assays

Survival assays were conducted independently with adult *D. melanogaster* in two laboratories. In the first laboratory, all trials used an yw marked wild-type strain. Larvae were reared on standard cornmeal-sugar-yeast (CSY) agar diet (cornmeal 5%, sucrose 10.5%, SAF yeast 2%, and agar 0.7%). Newly eclosed adults were placed in 1L demography cages with approximately 75 males and 75 females. Three to four replicate 1L demography cages were used for each treatment group in each trial. Every two days, dead flies were removed and scored, and food vials were replenished. Food vials contained cornmeal-sugar-yeast diet with SAF yeast as either 2% or 3% by weight. Test compounds in 100 µl of EtOH (or blank EtOH in controls) were mixed into melted aliquots of the adult food media to make a final concentration of 0, 10 or 100 µM. Fresh stock solutions and adult media were prepared weekly. In the second laboratory, lifespan trials were conducted with the wild type strain Canton-S, $dSir2^{4.5}$ and $dSir2^{5.26}$ (S. Smolik, University of Oregon), $dSir2^{17}$ (S. Astrom, Stockholm University, Sweden), and $dSir2^{KG00871}$ (*Drosophila* Stock Center, Bloomington, Ind.). Larvae for all tests were reared on standard cornmeal-sugar-yeast diet. Newly eclosed adults were incubated in plastic shell vials containing 5 ml of 15% sugar-yeast diet (15% SY) or 5% sugar-yeast (5% SY) diet (15% SY: 15% yeast, 15% sucrose, 2% agar; 5% SY: 5% yeast, 5% sucrose, 2% agar as per Ref.[26]). In all trials, ~20 males with ~20 females were placed into each of 10 vials/treatment group. Every two days, flies were passed into new vials and dead flies were counted. Resveratrol in EtOH (or EtOH alone in controls) was added to the media during its preparation after it had cooled to 65° C. and mixed vigorously. Final compound concentrations were 0, 10, 100 or 200 µM. Fresh stock solution and adult media was prepared weekly.

Feeding rate was measured in yw females with the crop-filling assay[27]. Females were held overnight with water and placed on 2% CSY diet containing food colour (FDA Blue 1) and 0, 10 or 100 µM resveratrol with EtOH. The presence of dye-marked food in the crop was scored in sets of 20 females across five 5-minute intervals. For body mass measurements, 10 vials with 20 males and 20 females each of wild type CS-5 flies were kept on 15% SY diet with EtOH or with resveratrol in EtOH (10 µM). Males and females were weighed daily.

REFERENCES FOR EXAMPLES 14 AND 15

1. Lin, S. J., Defossez, P. A. & Guarente, L. Requirement of NAD and SIR2 for life-span extension by calorie restriction in *Saccharomyces cerevisiae*. *Science* 289, 2126-8. (2000).
2. Gasser, S. C. M. The molecular biology of the SIR proteins. *Gene* 279, 1-16 (2001).
3. Hekimi, S. & Guarente, L. Genetics and the specificity of the aging process. *Science* 299, 1351-4 (2003).
4. Howitz, K. T. et al. Small molecule activators of sirtuins extend *Saccharomyces cerevisiae* lifespan. *Nature* 425, 191-6 (2003).
5. Landry, J. et al. The silencing protein SIR2 and its homologs are NAD-dependent protein deacetylases. *Proc Natl Acad Sci USA* 97, 5807-11. (2000).
6. Imai, S., Armstrong, C. M., Kaeberlein, M. & Guarente, L. Transcriptional silencing and longevity protein Sir2 is an NAD-dependent histone deacetylase. *Nature* 403, 795-800 (2000).
7. Smith, J. S. et al. A phylogenetically conserved NAD+-dependent protein deacetylase activity in the Sir2 protein family. *Proc Natl Acad Sci USA* 97, 6658-63. (2000).
8. Tanner, K. G., Landry, J., Sternglanz, R. & Denu, J. M. Silent information regulator 2 family of NAD-dependent histone/protein deacetylases generates a unique product, 1-O-acetyl-ADP-ribose. *Proc Natl Acad Sci USA* 97, 14178-82. (2000).
9. Tanny, J. C., Dowd, G. J., Huang, J., Hilz, H. & Moazed, D. An enzymatic activity in the yeast Sir2 protein that is essential for gene silencing. *Cell* 99, 735-45. (1999).
10. Guarente, L. Sir2 links chromatin silencing, metabolism, and aging. *Genes Dev* 14, 1021-6. (2000).
11. Tissenbaum, H. A. & Guarente, L. Increased dosage of a sir-2 gene extends lifespan in *Caenorhabditis elegans*. *Nature* 410, 227-30. (2001).
12. Rogina, B., Helfand, S. L. & Frankel, S. Longevity regulation by *Drosophila* Rpd3 deacetylase and caloric restriction. *Science* 298, 1745. (2002).
13. Jiang, J. C., Jaruga, E., Repnevskaya, M. V. & Jazwinski, S. M. An intervention resembling caloric restriction prolongs life span and retards aging in yeast. *Faseb J* 14, 2135-7. (2000).
14. Kenyon, C. A conserved regulatory mechanism for aging. *Cell* 105, 165-168 (2001).
15. Masoro, E. J. Caloric restriction and aging: an update. *Exp Gerontol* 35, 299-305. (2000).
16. Koubova, J. & Guarente, L. How does calorie restriction work? *Genes Dev* 17, 313-21 (2003).
17. Sinclair, D. A. Paradigms and pitfalls of yeast longevity research. *Mech Ageing Dev* 123, 857-67 (2002).
18. Kaeberlein, M., McVey, M. & Guarente, L. The SIR2/3/4 complex and SIR2 alone promote longevity in *Saccharomyces cerevisiae* by two different mechanisms. Genes Dev 13, 2570-80. (1999).
19. Chippindale, A. K., Leroi, Armand M., Kim, Sung B., and Rose, Michael R. Phenotypic plasticity and selection in *Drosophila* life-history evolution. *Journal of Evolutionary Biology* 6, 171-193 (1993).
20. Chapman, T. & Partridge, L. Female fitness in *Drosophila melanogaster*: an interaction between the effect of nutrition and of encounter rate with males. *Proc R Soc Lond B Biol Sci* 263, 755-9 (1996).

21. Walker, D. W., McColl, G., Jenkins, N. L., Harris, J. & Lithgow, G. J. Evolution of lifespan in *C. elegans. Nature* 405, 296-7 (2000).
22. Marden, J. H., Rogina, B., Montooth, K. L. & Helfand, S. L. Conditional tradeoffs between aging and organismal performance of Indy long-lived mutant flies. *Proc Natl Acad Sci USA* 100, 3369-73 (2003).
23. Schmid-Hempel, P. On the evolutionary ecology of host-parasite interactions: addressing the question with regard to bumblebees and their parasites. *Naturwissenschaften* 88, 147-58 (2001).
24. Ebert, D. & Bull, J. J. Challenging the trade-off model for the evolution of virulence: is virulence management feasible? *Trends Microbiol* 11, 15-20 (2003).
25. Soleas, G. J., Diamandis, E. P. & Goldberg, D. M. Resveratrol: a molecule whose time has come? And gone? *Clin Biochem* 30, 91-113 (1997).
26. Bitterman, K. J., Anderson, R. M., Cohen, H. Y., Latorre-Esteves, M. & Sinclair, D. A. Inhibition of silencing and accelerated aging by nicotinamide, a putative negative regulator of yeast sir2 and human SIRT1. *J Biol Chem* 277, 45099-107. (2002).
27. Edgecomb, R. S., Harth, C. E. & Schneiderman, A. M. Regulation of feeding behavior in adult *Drosophila melanogaster* varies with feeding regime and nutritional state. *J Exp Biol* 197, 215-35 (1994).

Example 16

Identification of Additional Activators and Inhibitors or Sirtuins

The following high-throughput screening protocol was used to identify additional small molecule sirtuin activators and inhibitors from an ICCB library.

The following wells were designated for control reactions: a) with enzyme; DMSO blank, b) with enzyme; with resveratrol (50 μM) positive control. The reaction mixture contains (final): 0.5 units/reaction SIRT1 deacetylase (BIOMOL); 200 μM NAD$^+$; 5 μM Fluor de Lys-SIRT1 substrate (BIOMOL); buffer (25 mM Tris/Cl, pH 8.0, 137 mM NaCl, 2.7 mM KCl, 1 mM MgCl$_2$, and 1 mg/ml BSA). In addition, a reaction mixture containing no enzyme was made so that each well receiving compound has a corresponding "no enzyme control" well. Reactions were performed in black 384 well plates (NUNC) in a final volume of 25 μl/well.

The reactions were started by combining enzyme and substrate in a reaction mixture immediately prior to aliquoting in plates (or substrate only for "no enzyme control" plates). Mixture were aliquoted to plates using Biotek μFill (Biotek Instruments). Control mixtures were manually added to designated wells. A library compound was added at a desired concentration by pin transfer to both "with enzyme" and "no enzyme" plates. Compounds were added in at least triplicate (with enzyme reaction in duplicate and no enzyme controls) at a final concentration of roughly 50 μM. The plates were incubated at 37° C. for 30-60 minutes. Then 25 μl of 1× Developer II (BIOMOL) plus 2 mM nicotinamide were added to all wells to stop the reactions. The reactions were left for at least 30 minutes at 37° C. for the signal to develop. The plates were read in a microplate-reading fluorometer capable of excitation at a wavelength in the range of 350-380 nm and detection of emitted light in the range of 440-460 nm. A read time of 0.1 sec per well was used.

The following positive controls were used: resveratrol, resveratrol 4"-methyl ether (3,5-dihydroxy-4'-methoxy-trans-stilbene, also referred to herein as BML-233, and set forth in Table 10), and pinosylvin, which activated SIRT1 2.2 fold, 2.1 fold and 3.28 fold, respectively. The activators are listed in Table 21 and the inhibitors are listed in Table 22.

Equivalents

Those skilled in the art will recognize, or be able to ascertain using no more than routine experimentation, many equivalents of the specific embodiments described herein. Such equivalents are intended to be encompassed by the following claims.

The invention claimed is:

1. A method for increasing the deacetylase activity of SIRT1 in a eukaryotic cell, comprising contacting a eukaryotic cell with a non-naturally occurring agent that binds SIRT1, reduces the $K_m$ of SIRT1 for substrate and thereby increases the deacetylase activity of SIRT1.

2. The method of claim 1, wherein the agent is an organic molecule.

3. The method of claim 1, wherein the agent is an isolated agent.

4. The method of claim 1, wherein the agent does not have significant anti-oxidant activities.

5. The method of claim 1, wherein the agent reduces the $K_m$ of SIRT1 for substrate by a factor of at least about 30.

6. The method of claim 1, wherein the agent reduces the $K_m$ of SIRT1 for NAD$^+$ by a factor of at least about 3.

7. The method of claim 1, wherein the agent activates the deacetylase activity of SIRT1 by a factor of at least about 10.

8. The method of claim 1, wherein the agent causes at least a 10% greater induction of the deacetylase activity of SIRT1 relative to that caused by the same concentration of resveratrol.

9. The method of claim 1, wherein the eukaryotic cell is a mammalian cell.

10. The method of claim 9, wherein the mammalian cell is a human cell.

11. The method of claim 1 further comprising contacting the eukaryotic cell with a second agent that binds SIRT1, reduces the $K_m$ of SIRT1 for substrate and thereby increases the deacetylase activity of SIRT1.

12. The method of claim 1, further comprising contacting the eukaryotic cell with another agent that binds another sirtuin, reduces the $K_m$ of the other sirtuin for substrate and thereby increases the deacetylase activity of the other sirtuin.

* * * * *

SEQUENCE LISTING

```
<160> NUMBER OF SEQ ID NOS: 15

<210> SEQ ID NO 1
<211> LENGTH: 4107
<212> TYPE: DNA
<213> ORGANISM: Homo sapiens
<220> FEATURE:
<221> NAME/KEY: CDS
<222> LOCATION: (54)..(2297)

<400> SEQUENCE: 1
gtcgagcggg agcagaggag gcgagggagg agggccagag aggcagttgg aag atg        56
                                                              Met
                                                              1 gcg gac gag gcg gcc ctc gcc ctt cag ccc ggc ggc tcc ccc tcg gcg      104
Ala Asp Glu Ala Ala Leu Ala Leu Gln Pro Gly Gly Ser Pro Ser Ala
            5                  10                  15 gcg ggg gcc gac agg gag gcc gcg tcg tcc ccc gcc ggg gag ccg ctc      152
Ala Gly Ala Asp Arg Glu Ala Ala Ser Ser Pro Ala Gly Glu Pro Leu
        20                  25                  30 cgc aag agg ccg cgg aga gat ggt ccc ggc ctc gag cgg agc ccg ggc      200
Arg Lys Arg Pro Arg Arg Asp Gly Pro Gly Leu Glu Arg Ser Pro Gly
    35                  40                  45
```

```
gag ccc ggt ggg gcg gcc cca gag cgt gag gtg ccg gcg gcg gcc agg      248
Glu Pro Gly Gly Ala Ala Pro Glu Arg Glu Val Pro Ala Ala Ala Arg
 50              55                  60                  65 ggc tgc ccg ggt gcg gcg gcg gcg gcg ctg tgg cgg gag gcg gag gca      296
Gly Cys Pro Gly Ala Ala Ala Ala Ala Leu Trp Arg Glu Ala Glu Ala
                 70                  75                  80 gag gcg gcg gcg gca ggc ggg gag caa gag gcc cag gcg act gcg gcg      344
Glu Ala Ala Ala Ala Gly Gly Glu Gln Glu Ala Gln Ala Thr Ala Ala
                 85                  90                  95 gct ggg gaa gga gac aat ggg ccg ggc ctg cag ggc cca tct cgg gag      392
Ala Gly Glu Gly Asp Asn Gly Pro Gly Leu Gln Gly Pro Ser Arg Glu
            100                 105                 110 cca ccg ctg gcc gac aac ttg tac gac gaa gac gac gac gag ggc          440
Pro Pro Leu Ala Asp Asn Leu Tyr Asp Glu Asp Asp Asp Glu Gly
        115                 120                 125 gag gag gag gaa gag gcg gcg gcg gcg gcg att ggg tac cga gat aac      488
Glu Glu Glu Glu Glu Ala Ala Ala Ala Ala Ile Gly Tyr Arg Asp Asn
130                 135                 140                 145 ctt ctg ttc ggt gat gaa att atc act aat ggt ttt cat tcc tgt gaa      536
Leu Leu Phe Gly Asp Glu Ile Ile Thr Asn Gly Phe His Ser Cys Glu
                150                 155                 160 agt gat gag gag gat aga gcc tca cat gca agc tct agt gac tgg act      584
Ser Asp Glu Glu Asp Arg Ala Ser His Ala Ser Ser Ser Asp Trp Thr
                165                 170                 175 cca agg cca cgg ata ggt cca tat act ttt gtt cag caa cat ctt atg      632
Pro Arg Pro Arg Ile Gly Pro Tyr Thr Phe Val Gln Gln His Leu Met
                180                 185                 190 att ggc aca gat cct cga aca att ctt aaa gat tta ttg ccg gaa aca      680
Ile Gly Thr Asp Pro Arg Thr Ile Leu Lys Asp Leu Leu Pro Glu Thr
195                 200                 205 ata cct cca cct gag ttg gat gat atg aca ctg tgg cag att gtt att      728
Ile Pro Pro Pro Glu Leu Asp Asp Met Thr Leu Trp Gln Ile Val Ile
210                 215                 220                 225 aat atc ctt tca gaa cca cca aaa agg aaa aaa aga aaa gat att aat      776
Asn Ile Leu Ser Glu Pro Pro Lys Arg Lys Lys Arg Lys Asp Ile Asn
                230                 235                 240 aca att gaa gat gct gtg aaa tta ctg caa gag tgc aaa aaa att ata      824
Thr Ile Glu Asp Ala Val Lys Leu Leu Gln Glu Cys Lys Lys Ile Ile
                245                 250                 255 gtt cta act gga gct ggg gtg tct gtt tca tgt gga ata cct gac ttc      872
Val Leu Thr Gly Ala Gly Val Ser Val Ser Cys Gly Ile Pro Asp Phe
            260                 265                 270 agg tca agg gat ggt att tat gct cgc ctt gct gta gac ttc cca gat      920
Arg Ser Arg Asp Gly Ile Tyr Ala Arg Leu Ala Val Asp Phe Pro Asp
275                 280                 285 ctt cca gat cct caa gcg atg ttt gat att gaa tat ttc aga aaa gat      968
Leu Pro Asp Pro Gln Ala Met Phe Asp Ile Glu Tyr Phe Arg Lys Asp
290                 295                 300                 305 cca aga cca ttc ttc aag ttt gca aag gaa ata tat cct gga caa ttc     1016
Pro Arg Pro Phe Phe Lys Phe Ala Lys Glu Ile Tyr Pro Gly Gln Phe
                310                 315                 320 cag cca tct ctc tgt cac aaa ttc ata gcc ttg tca gat aag gaa gga     1064
Gln Pro Ser Leu Cys His Lys Phe Ile Ala Leu Ser Asp Lys Glu Gly
            325                 330                 335 aaa cta ctt cgc aac tat acc cag aac ata gac acg ctg gaa cag gtt     1112
Lys Leu Leu Arg Asn Tyr Thr Gln Asn Ile Asp Thr Leu Glu Gln Val
            340                 345                 350 gcg gga atc caa agg ata att cag tgt cat ggt tcc ttt gca aca gca     1160
Ala Gly Ile Gln Arg Ile Ile Gln Cys His Gly Ser Phe Ala Thr Ala
355                 360                 365
```

```
tct tgc ctg att tgt aaa tac aaa gtt gac tgt gaa gct gta cga gga       1208
Ser Cys Leu Ile Cys Lys Tyr Lys Val Asp Cys Glu Ala Val Arg Gly
370                 375                 380                 385 gat att ttt aat cag gta gtt cct cga tgt cct agg tgc cca gct gat       1256
Asp Ile Phe Asn Gln Val Val Pro Arg Cys Pro Arg Cys Pro Ala Asp
            390                 395                 400 gaa ccg ctt gct atc atg aaa cca gag att gtg ttt ttt ggt gaa aat       1304
Glu Pro Leu Ala Ile Met Lys Pro Glu Ile Val Phe Phe Gly Glu Asn
                405                 410                 415 tta cca gaa cag ttt cat aga gcc atg aag tat gac aaa gat gaa gtt       1352
Leu Pro Glu Gln Phe His Arg Ala Met Lys Tyr Asp Lys Asp Glu Val
        420                 425                 430 gac ctc ctc att gtt att ggg tct tcc ctc aaa gta aga cca gta gca       1400
Asp Leu Leu Ile Val Ile Gly Ser Ser Leu Lys Val Arg Pro Val Ala
435                 440                 445 cta att cca agt tcc ata ccc cat gaa gtg cct cag ata tta att aat       1448
Leu Ile Pro Ser Ser Ile Pro His Glu Val Pro Gln Ile Leu Ile Asn
450                 455                 460                 465 aga gaa cct ttg cct cat ctg cat ttt gat gta gag ctt ctt gga gac       1496
Arg Glu Pro Leu Pro His Leu His Phe Asp Val Glu Leu Leu Gly Asp
            470                 475                 480 tgt gat gtc ata att aat gaa ttg tgt cat agg tta ggt ggt gaa tat       1544
Cys Asp Val Ile Ile Asn Glu Leu Cys His Arg Leu Gly Gly Glu Tyr
                485                 490                 495 gcc aaa ctt tgc tgt aac cct gta aag ctt tca gaa att act gaa aaa       1592
Ala Lys Leu Cys Cys Asn Pro Val Lys Leu Ser Glu Ile Thr Glu Lys
        500                 505                 510 cct cca cga aca caa aaa gaa ttg gct tat ttg tca gag ttg cca ccc       1640
Pro Pro Arg Thr Gln Lys Glu Leu Ala Tyr Leu Ser Glu Leu Pro Pro
515                 520                 525 aca cct ctt cat gtt tca gaa gac tca agt tca cca gaa aga act tca       1688
Thr Pro Leu His Val Ser Glu Asp Ser Ser Ser Pro Glu Arg Thr Ser
530                 535                 540                 545 cca cca gat tct tca gtg att gtc aca ctt tta gac caa gca gct aag       1736
Pro Pro Asp Ser Ser Val Ile Val Thr Leu Leu Asp Gln Ala Ala Lys
            550                 555                 560 agt aat gat gat tta gat gtg tct gaa tca aaa ggt tgt atg gaa gaa       1784
Ser Asn Asp Asp Leu Asp Val Ser Glu Ser Lys Gly Cys Met Glu Glu
                565                 570                 575 aaa cca cag gaa gta caa act tct agg aat gtt gaa agt att gct gaa       1832
Lys Pro Gln Glu Val Gln Thr Ser Arg Asn Val Glu Ser Ile Ala Glu
        580                 585                 590 cag atg gaa aat ccg gat ttg aag aat gtt ggt tct agt act ggg gag       1880
Gln Met Glu Asn Pro Asp Leu Lys Asn Val Gly Ser Ser Thr Gly Glu
595                 600                 605 aaa aat gaa aga act tca gtg gct gga aca gtg aga aaa tgc tgg cct       1928
Lys Asn Glu Arg Thr Ser Val Ala Gly Thr Val Arg Lys Cys Trp Pro
610                 615                 620                 625 aat aga gtg gca aag gag cag att agt agg cgg ctt gat ggt aat cag       1976
Asn Arg Val Ala Lys Glu Gln Ile Ser Arg Arg Leu Asp Gly Asn Gln
            630                 635                 640 tat ctg ttt ttg cca cca aat cgt tac att ttc cat ggc gct gag gta       2024
Tyr Leu Phe Leu Pro Pro Asn Arg Tyr Ile Phe His Gly Ala Glu Val
                645                 650                 655 tat tca gac tct gaa gat gac gtc tta tcc tct agt tct tgt ggc agt       2072
Tyr Ser Asp Ser Glu Asp Asp Val Leu Ser Ser Ser Ser Cys Gly Ser
        660                 665                 670 aac agt gat agt ggg aca tgc cag agt cca agt tta gaa gaa ccc atg       2120
Asn Ser Asp Ser Gly Thr Cys Gln Ser Pro Ser Leu Glu Glu Pro Met
```

```
                      675                 680                 685
gag gat gaa agt gaa att gaa gaa ttc tac aat ggc tta gaa gat gag      2168
Glu Asp Glu Ser Glu Ile Glu Glu Phe Tyr Asn Gly Leu Glu Asp Glu
    690                 695                 700                 705 cct gat gtt cca gag aga gct gga gga gct gga ttt ggg act gat gga      2216
Pro Asp Val Pro Glu Arg Ala Gly Gly Ala Gly Phe Gly Thr Asp Gly
                710                 715                 720 gat gat caa gag gca att aat gaa gct ata tct gtg aaa cag gaa gta      2264
Asp Asp Gln Glu Ala Ile Asn Glu Ala Ile Ser Val Lys Gln Glu Val
            725                 730                 735 aca gac atg aac tat cca tca aac aaa tca tag gtaataatt gtgcaggtac    2317
Thr Asp Met Asn Tyr Pro Ser Asn Lys Ser
        740                 745 aggaattgtt ccaccagcat taggaacttt agcatgtcaa aatgaatgtt tacttgtgaa    2377
ctcgatagag caaggaaacc agaaaggtgt aatatttata ggttggtaaa atagattgtt    2437
tttcatggat aattttttaac ttcattattt ctgtacttgt acaaactcaa cactaacttt   2497
ttttttttta aaaaaaaaaa ggtactaagt atcttcaatc agctgttggt caagactaac    2557
tttcttttaa aggttcattt gtatgataaa ttcatatgtg tatatataat ttttttttgtt  2617 ttgtctagtg agtttcaaca tttttaaagt tttcaaaaag ccatcggaat gttaaattaa    2677
tgtaaaggga cagctaatct agaccaaaga atggtatttt cacttttctt tgtaacattg    2737
aatggtttga agtactcaaa atctgttacg ctaaactttt gattctttaa cacaattatt   2797
tttaaacact ggcattttcc aaaactgtgg cagctaactt tttaaaatct caaatgacat    2857
gcagtgtgag tagaaggaag tcaacaatat gtggggagag cactcggttg tctttacttt    2917
taaaagtaat acttggtgct aagaatttca ggattattgt atttacgttc aaatgaagat    2977
ggcttttgta cttcctgtgg acatgtagta atgtctatat tggctcataa aactaacctg    3037
aaaaacaaat aaatgctttg gaatgtttc agttgcttta gaaacattag tgcctgcctg    3097 gatccccta gttttgaaat atttgccatt gttgtttaaa tacctatcac tgtggtagag    3157
cttgcattga tcttttccac aagtattaaa ctgccaaaat gtgaatatgc aaagcctttc   3217
tgaatctata ataatggtac ttctactggg gagagtgtaa tattttggac tgctgttttc    3277
cattaatgag gagagcaaca ggccccctgat tatacagttc caaagtaata agatgttaat   3337
tgtaattcag ccagaaagta catgtctccc attgggagga tttggtgtta aataccaaac    3397
tgctagccct agtattatgg agatgaacat gatgatgtaa cttgtaatag cagaatagtt    3457
aatgaatgaa actagttctt ataatttatc tttatttaaa agcttagcct gccttaaaac    3517
tagagatcaa ctttctcagc tgcaaaagct tctagtcttt caagaagttc atactttatg    3577
aaattgcaca gtaagcattt attttttcaga ccatttttga acatcactcc taaattaata   3637
aagtattcct ctgttgcttt agtatttatt acaataaaaa gggtttgaaa tatagctgtt   3697
ctttatgcat aaaacaccca gctaggacca ttactgccag agaaaaaaat cgtattgaat    3757
ggccatttcc ctacttataa gatgtctcaa tctgaattta tttggctaca ctaaagaatg    3817
cagtatattt agttttccat ttgcatgatg tttgtgtgct atagatgata ttttaaattg    3877
aaaagtttgt tttaaattat tttacagtg aagactgttt tcagctcttt ttatattgta    3937
catagtcttt tatgtaattt actggcatat gttttgtaga ctgtttaatg actgatatc    3997 ttccttcaac ttttgaaata caaaaccagt gttttttact tgtacactgt tttaaagtct   4057
attaaaattg tcatttgact ttttttctgtt aaaaaaaaaa aaaaaaaaaa             4107
```

```
<210> SEQ ID NO 2
<211> LENGTH: 747
<212> TYPE: PRT
<213> ORGANISM: Homo sapiens

<400> SEQUENCE: 2

Met Ala Asp Glu Ala Ala Leu Ala Leu Gln Pro Gly Gly Ser Pro Ser
1               5                   10                  15

Ala Ala Gly Ala Asp Arg Glu Ala Ser Ser Pro Ala Gly Glu Pro
            20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
            115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
            195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380
```

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
            405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
            435                 440                 445

Ala Leu Ile Pro Ser Ser Ile Pro His Glu Val Pro Gln Ile Leu Ile
450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
            515                 520                 525

Pro Thr Pro Leu His Val Ser Glu Asp Ser Ser Pro Glu Arg Thr
530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
            595                 600                 605

Glu Lys Asn Glu Arg Thr Ser Val Ala Gly Thr Val Arg Lys Cys Trp
            610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Val Leu Ser Ser Ser Cys Gly
            660                 665                 670

Ser Asn Ser Asp Ser Gly Thr Cys Gln Ser Pro Ser Leu Glu Glu Pro
            675                 680                 685

Met Glu Asp Glu Ser Glu Ile Glu Glu Phe Tyr Asn Gly Leu Glu Asp
            690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745

<210> SEQ ID NO 3
<211> LENGTH: 369
<212> TYPE: PRT
<213> ORGANISM: Homo sapiens

<400> SEQUENCE: 3

Met Pro Leu Ala Glu Cys Pro Ser Cys Arg Cys Leu Ser Ser Phe Arg
1               5                   10                  15

-continued

Ser Val Asp Phe Leu Arg Asn Leu Phe Ser Gln Thr Leu Ser Leu Gly
         20                  25                  30

Ser Gln Lys Glu Arg Leu Leu Asp Glu Leu Thr Leu Glu Gly Val Ala
     35                  40                  45

Arg Tyr Met Gln Ser Glu Arg Cys Arg Val Ile Cys Leu Val Gly
     50                  55                  60

Ala Gly Ile Ser Thr Ser Ala Gly Ile Pro Asp Phe Arg Ser Pro Ser
 65                  70                  75                  80

Thr Gly Leu Tyr Asp Asn Leu Glu Lys Tyr His Leu Pro Tyr Pro Glu
                 85                  90                  95

Ala Ile Phe Glu Ile Ser Tyr Phe Lys Lys His Pro Glu Pro Phe Phe
            100                 105                 110

Ala Leu Ala Lys Glu Leu Tyr Pro Gly Gln Phe Lys Pro Thr Ile Cys
        115                 120                 125

His Tyr Phe Met Arg Leu Leu Lys Asp Lys Gly Leu Leu Leu Arg Cys
    130                 135                 140

Tyr Thr Gln Asn Ile Asp Thr Leu Glu Arg Ile Ala Gly Leu Glu Gln
145                 150                 155                 160

Glu Asp Leu Val Glu Ala His Gly Thr Phe Tyr Thr Ser His Cys Val
                165                 170                 175

Ser Ala Ser Cys Arg His Glu Tyr Pro Leu Ser Trp Met Lys Glu Lys
            180                 185                 190

Ile Phe Ser Glu Val Thr Leu Lys Cys Glu Asp Cys Gln Ser Leu Val
        195                 200                 205

Lys Pro Asp Ile Val Phe Phe Gly Glu Ser Leu Pro Ala Arg Phe Phe
    210                 215                 220

Ser Cys Met Gln Ser Asp Phe Leu Lys Val Asp Leu Leu Leu Val Met
225                 230                 235                 240

Gly Thr Ser Leu Gln Val Gln Pro Phe Ala Ser Leu Ile Ser Lys Ala
                245                 250                 255

Pro Leu Ser Thr Pro Arg Leu Leu Ile Asn Lys Glu Lys Ala Gly Gln
            260                 265                 270

Ser Asp Pro Phe Leu Gly Met Ile Met Gly Leu Gly Gly Gly Met Asp
        275                 280                 285

Phe Asp Ser Lys Lys Ala Tyr Arg Asp Val Ala Trp Leu Gly Glu Cys
    290                 295                 300

Asp Gln Gly Cys Leu Ala Leu Ala Glu Leu Leu Gly Trp Lys Lys Glu
305                 310                 315                 320

Leu Glu Asp Leu Val Arg Arg Glu His Ala Ser Ile Asp Ala Gln Ser
                325                 330                 335

Gly Ala Gly Val Pro Asn Pro Ser Thr Ser Ala Ser Pro Lys Lys Ser
            340                 345                 350

Pro Pro Pro Ala Lys Asp Glu Ala Arg Thr Thr Glu Arg Glu Lys Pro
        355                 360                 365

Gln

<210> SEQ ID NO 4
<211> LENGTH: 562
<212> TYPE: PRT
<213> ORGANISM: Saccharomyces cerevisiae

<400> SEQUENCE: 4

Met Thr Ile Pro His Met Lys Tyr Ala Val Ser Lys Thr Ser Glu Asn
 1               5                  10                  15

-continued

```
Lys Val Ser Asn Thr Val Ser Pro Thr Gln Asp Lys Asp Ala Ile Arg
             20                  25                  30
Lys Gln Pro Asp Asp Ile Ile Asn Asn Asp Glu Pro Ser His Lys Lys
         35                  40                  45
Ile Lys Val Ala Gln Pro Asp Ser Leu Arg Glu Thr Asn Thr Thr Asp
     50                  55                  60
Pro Leu Gly His Thr Lys Ala Ala Leu Gly Glu Val Ala Ser Met Glu
 65                  70                  75                  80
Leu Lys Pro Thr Asn Asp Met Asp Pro Leu Ala Val Ser Ala Ala Ser
                 85                  90                  95
Val Val Ser Met Ser Asn Asp Val Leu Lys Pro Glu Thr Pro Lys Gly
            100                 105                 110
Pro Ile Ile Ile Ser Lys Asn Pro Ser Asn Gly Ile Phe Tyr Gly Pro
            115                 120                 125
Ser Phe Thr Lys Arg Glu Ser Leu Asn Ala Arg Met Phe Leu Lys Tyr
            130                 135                 140
Tyr Gly Ala His Lys Phe Leu Asp Thr Tyr Leu Pro Glu Asp Leu Asn
145                 150                 155                 160
Ser Leu Tyr Ile Tyr Tyr Leu Ile Lys Leu Leu Gly Phe Glu Val Lys
                165                 170                 175
Asp Gln Ala Leu Ile Gly Thr Ile Asn Ser Ile Val His Ile Asn Ser
            180                 185                 190
Gln Glu Arg Val Gln Asp Leu Gly Ser Ala Ile Ser Val Thr Asn Val
            195                 200                 205
Glu Asp Pro Leu Ala Lys Lys Gln Thr Val Arg Leu Ile Lys Asp Leu
        210                 215                 220
Gln Arg Ala Ile Asn Lys Val Leu Cys Thr Arg Leu Arg Leu Ser Asn
225                 230                 235                 240
Phe Phe Thr Ile Asp His Phe Ile Gln Lys Leu His Thr Ala Arg Lys
                245                 250                 255
Ile Leu Val Leu Thr Gly Ala Gly Val Ser Thr Ser Leu Gly Ile Pro
            260                 265                 270
Asp Phe Arg Ser Ser Glu Gly Phe Tyr Ser Lys Ile Lys His Leu Gly
        275                 280                 285
Leu Asp Asp Pro Gln Asp Val Phe Asn Tyr Asn Ile Phe Met His Asp
    290                 295                 300
Pro Ser Val Phe Tyr Asn Ile Ala Asn Met Val Leu Pro Pro Glu Lys
305                 310                 315                 320
Ile Tyr Ser Pro Leu His Ser Phe Ile Lys Met Leu Gln Met Lys Gly
                325                 330                 335
Lys Leu Leu Arg Asn Tyr Thr Gln Asn Ile Asp Asn Leu Glu Ser Tyr
            340                 345                 350
Ala Gly Ile Ser Thr Asp Lys Leu Val Gln Cys His Gly Ser Phe Ala
        355                 360                 365
Thr Ala Thr Cys Val Thr Cys His Trp Asn Leu Pro Gly Glu Arg Ile
    370                 375                 380
Phe Asn Lys Ile Arg Asn Leu Glu Leu Pro Leu Cys Pro Tyr Cys Tyr
385                 390                 395                 400
Lys Lys Arg Arg Glu Tyr Phe Pro Glu Gly Tyr Asn Asn Lys Val Gly
            405                 410                 415
Val Ala Ala Ser Gln Gly Ser Met Ser Glu Arg Pro Pro Tyr Ile Leu
        420                 425                 430
```

-continued

```
Asn Ser Tyr Gly Val Leu Lys Pro Asp Ile Thr Phe Phe Gly Glu Ala
        435                 440                 445

Leu Pro Asn Lys Phe His Lys Ser Ile Arg Glu Asp Ile Leu Glu Cys
    450                 455                 460

Asp Leu Leu Ile Cys Ile Gly Thr Ser Leu Lys Val Ala Pro Val Ser
465                 470                 475                 480

Glu Ile Val Asn Met Val Pro Ser His Val Pro Gln Val Leu Ile Asn
                485                 490                 495

Arg Asp Pro Val Lys His Ala Glu Phe Asp Leu Ser Leu Leu Gly Tyr
            500                 505                 510

Cys Asp Ile Ala Ala Met Val Ala Gln Lys Cys Gly Trp Thr Ile
        515                 520                 525

Pro His Lys Lys Trp Asn Asp Leu Lys Asn Lys Asn Phe Lys Cys Gln
    530                 535                 540

Glu Lys Asp Lys Gly Val Tyr Val Val Thr Ser Asp Glu His Pro Lys
545                 550                 555                 560

Thr Leu

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (6)
<223> OTHER INFORMATION: Ac-modified residue

<400> SEQUENCE: 5

Lys Gln Thr Ala Arg Lys
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (6)
<223> OTHER INFORMATION: Ac-modified residue

<400> SEQUENCE: 6

Lys Ser Thr Gly Gly Lys
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (2)
<223> OTHER INFORMATION: PO3-modified residue
<220> FEATURE:
<221> NAME/KEY: MOD_RES
<222> LOCATION: (6)
<223> OTHER INFORMATION: Ac-modified residue

<400> SEQUENCE: 7

Lys Ser Thr Gly Gly Lys
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (5)
<223> OTHER INFORMATION: Ac-modified residue

<400> SEQUENCE: 8

Lys Ala Pro Arg Lys
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Ac-modified residue

<400> SEQUENCE: 9

Ser Gly Arg Gly Lys
  1               5

<210> SEQ ID NO 10
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: Ac-modified residue
<220> FEATURE:
<223> OTHER INFORMATION: Description of Artificial Sequence: Synthetic
      peptide

<400> SEQUENCE: 10

Lys Gly Gly Ala Lys
  1               5

<210> SEQ ID NO 11
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (5)
<223> OTHER INFORMATION: Ac-modified residue

<400> SEQUENCE: 11

Lys Gly Gly Ala Lys
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ac-modified residue

<400> SEQUENCE: 12

Gln Pro Lys Lys
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-modified residue
<220> FEATURE:
<221> NAME/KEY: MOD_RES
<222> LOCATION: (4)
<223> OTHER INFORMATION: Ac-modified residue

<400> SEQUENCE: 13

Lys Ser Lys Lys
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ac-modified residue

<400> SEQUENCE: 14

Arg His Lys Lys
 1

<210> SEQ ID NO 15
<211> LENGTH: 4
```

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Ac-modified residue
<220> FEATURE:
<221> NAME/KEY: MOD_RES
<222> LOCATION: (4)
<223> OTHER INFORMATION: Ac-modified residue

<400> SEQUENCE: 15

Arg His Lys Lys
 1
```